(12) United States Patent
Zhao et al.

(10) Patent No.: US 10,294,259 B2
(45) Date of Patent: May 21, 2019

(54) PHENYL C-GLUCOSIDE DERIVATIVE CONTAINING DEOXYGLUCOSE STRUCTURE, PREPARATION METHOD AND USE THEREOF

(71) Applicant: Tianjin Institute of Pharmaceutical Research, Tianjin (CN)

(72) Inventors: Guilong Zhao, Tianjin (CN); Yuli Wang, Tianjin (CN); Bingni Liu, Tianjin (CN); Yafei Xie, Tianjin (CN); Yuqiang Liu, Tianjin (CN); Peng Liu, Tianjin (CN); Jiang Wu, Tianjin (CN); Jiajia Hou, Tianjin (CN); Wei Wei, Tianjin (CN); Wen Du, Tianjin (CN); Weiren Xu, Tianjin (CN); Lida Tang, Tianjin (CN); Meixiang Zou, Tianjin (CN)

(73) Assignee: Tianjin Institute of Pharmaceutical Research, Tianjin (CN)

( * ) Notice: Subject to any disclaimer, the term of this patent is extended or adjusted under 35 U.S.C. 154(b) by 0 days.

(21) Appl. No.: 15/349,040

(22) Filed: Nov. 11, 2016

(65) Prior Publication Data
US 2017/0057989 A1    Mar. 2, 2017

Related U.S. Application Data

(63) Continuation of application No. 14/652,225, filed as application No. PCT/CN2013/088633 on Dec. 5, 2013, now Pat. No. 9,505,734.

(30) Foreign Application Priority Data

Dec. 17, 2012   (CN) .......................... 2012 1 0553525
Mar. 15, 2013   (CN) .......................... 2013 1 0083945
Apr. 1, 2013    (CN) .......................... 2013 1 0109527
May 31, 2013    (CN) .......................... 2013 1 0213608
Jun. 17, 2013   (CN) .......................... 2013 1 0237558

(51) Int. Cl.
| | |
|---|---|
| A61K 47/22 | (2006.01) |
| C07H 19/01 | (2006.01) |
| C07D 309/06 | (2006.01) |
| C07D 309/10 | (2006.01) |
| C07D 335/02 | (2006.01) |
| C07D 407/12 | (2006.01) |
| C07D 409/10 | (2006.01) |
| C07D 493/08 | (2006.01) |
| C07D 493/10 | (2006.01) |

(52) U.S. Cl.
CPC ............. *C07H 19/01* (2013.01); *A61K 47/22* (2013.01); *C07D 309/06* (2013.01); *C07D 309/10* (2013.01); *C07D 335/02* (2013.01); *C07D 407/12* (2013.01); *C07D 409/10* (2013.01); *C07D 493/08* (2013.01); *C07D 493/10* (2013.01)

(58) Field of Classification Search
None
See application file for complete search history.

(56) References Cited

U.S. PATENT DOCUMENTS

| | | |
|---|---|---|
| 2006/0009400 A1 | 1/2006 | Eckhardt |
| 2006/0074031 A1 | 4/2006 | Eckhardt |

FOREIGN PATENT DOCUMENTS

| | | |
|---|---|---|
| CN | 1802366 A | 7/2006 |
| CN | 1829729 A | 9/2006 |
| EP | 1 609 785 A1 | 12/2005 |
| WO | 2005/012326 A1 | 2/2005 |

OTHER PUBLICATIONS

Chiara, J.L., et al., "Cascade Reaction of 6-Deoxy-6-iodohexopyranosides Promoted by Samarium Diiodide: A New Ring Contraction of Carbohydrate Derivatives," Journal of Organic Chemistry 61(19):6488-6489, Sep. 1996.

(Continued)

*Primary Examiner* — Layla D Berry
(74) *Attorney, Agent, or Firm* — Christensen O'Connor Johnson Kindness PLLC

(57) ABSTRACT

The present invention provides a phenyl C-glucoside derivative containing a deoxyglucose structure as represented by formula I, preparation method thereof, a pharmaceutical composition comprising the same, and uses thereof in the preparation of medicaments for treating diabetes, wherein substituents $R^1$-$R^7$ are as defined in the specification. The present invention also provides a method for synthesizing the phenyl C-glucoside derivative containing a deoxyglucose structure and an intermediate product. The method has advantages of being simple to manage and of low cost, which is suitable for large-scale industrial production. The present invention further provides a cocrystal of (1S)-1-[4-chloro-3-(4-ethoxybenzyl)phenyl]-1,6-dideoxy-D-glucose and L-proline, and preparation method and uses thereof.

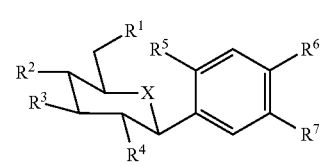

14 Claims, 7 Drawing Sheets

(56) References Cited

OTHER PUBLICATIONS

Shi, Y., et al., "A Facile Synthesis of 6-Deoxydapagliflozin," Monatshefte für Chemie—Chemical Monthly 144(12):1903-1910, Dec. 2013.

Smith, A.B., III, et al., "Phyllanthoside—Phyllanthostatin Synthetic Studies. 8. Total Synthesis of (+)-Phyllanthoside. Development of the Mitsunobu Glycosyl Ester Protocol," Journal of the American Chemical Society 113(6):2092-2112, Mar. 1991.

PHENYL C-GLUCOSIDE DERIVATIVE CONTAINING DEOXYGLUCOSE STRUCTURE, PREPARATION METHOD AND USE THEREOF

CROSS-REFERENCES TO RELATED APPLICATIONS

This application is a continuation of U.S. patent application Ser. No. 14/652,225, filed Oct. 13, 2015, which is a 371 National Phase of International Application No. PCT/CN2013/088633, filed Dec. 5, 2013, which claims the benefit of Chinese Application No. 201310237558.7 filed Jun. 17, 2013, Chinese Application No. 201310213608.8, filed May 31, 2013, Chinese Application No. 201310109527.3, filed Apr. 1, 2013, Chinese Application No. 201310083945.X, filed Mar. 15, 2013, and Chinese Application No. 201210553525.9, filed Dec. 17, 2012. Each application is incorporated herein by reference in its entirety.

TECHNICAL FIELD

The present invention relates to pharmaceutical field associated with diabetes. Specifically, the present invention relates to sodium glucose cotransporter 2 (SGLT2) inhibitors of phenyl C-glucoside derivative containing a deoxyglucose structure which have a therapeutic effect on diabetes, and a preparation method thereof, as well as a pharmaceutical composition comprising the same. The present invention also relates to a method for industrially synthesizing the phenyl C-glucoside derivative containing a deoxyglucose structure and an intermediate product. The present invention further relates to a cocrystal of the phenyl C-glucoside derivative containing a deoxyglucose structure and L-proline, as well as a preparation method and uses thereof.

BACKGROUND ART

So far there are approximately 0.17 billion patients with diabetes throughout the world, the vast majority of which are the patients with type II (i.e. non-insulin dependent) diabetes. Currently, the antidiabetic drugs used in clinical are primarily metformins, sulfonylureas, insulins, thiazolidinediones, alpha-glucosidase inhibitors, and dipeptidyl peptidase IV inhibitors. These drugs exhibit good therapeutic effects, but lead to safety issues when being administered in long-term, e.g. liver toxicity, and some drugs have problems such as weight gain and the like. Moreover, in many cases, it is difficult to achieve ideal target for blood glucose control even if combined use of drugs is given. Therefore, there is an urgent need for a diabetes drug with a novel action mechanism.

Sodium glucose cotransporter 2 (SGLT2) is a new target discovered in recent years for treating diabetes. SGLT2 is mainly distributed in renal proximal tubule, with the effect of absorbing the glucose in urine and returning them back into the blood. The method that the concentration of glucose in the blood can be lowered provided that SGLT2 is inhibited, has lowered the blood glucose levels in ever different ways. When the function of SGLT2 is blocked, there are more glucoses secreted to urine, which will help the patients with diabetes to maintain normal blood glucose level. Since SGLT2 inhibitors are not involved in the glucose metabolism, this kind of blood glucose lowering drugs are believed to have good safety.

The Chinese patent CN200610093189.9 disclosed a compound with the following structure as a SGLT2 inhibitor:

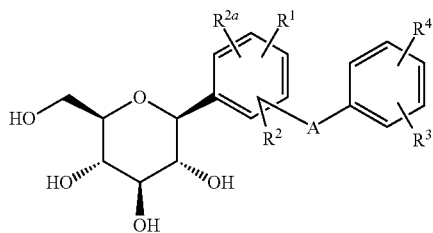

wherein A is O, S, NH or $(CH_2)_n$, and wherein n=0-3.

The Chinese patent CN200380110040.1 disclosed a compound with the following structure as a SGLT2 inhibitor:

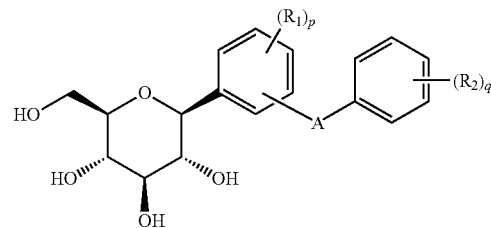

wherein A is a covalent bond, O, S, NH or $(CH_2)_n$, and wherein n=1-3.

The Chinese patent CN200480006761.2 disclosed a compound with the following structure as a SGLT2 inhibitor:

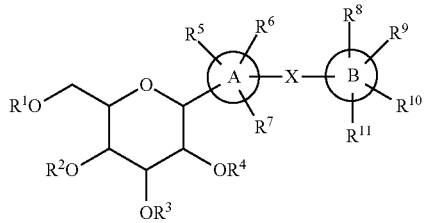

wherein X is a covalent bond or a lower alkylidene group.

The present invention disclosed a class of phenyl C-glucoside derivatives containing deoxyglucose structures as novel SGLT2 inhibitors, and these inhibitors can be used to prepare drugs for treating diabetes, particularly non-insulin dependent diabetes.

DISCLOSURE OF THE INVENTION

In order to overcome the deficiencies and shortcomings in the prior art, one object of the present invention is to provide a compound of general formula I or a pharmaceutically acceptable prodrug ester thereof which has good activity.

Another object of the present invention is to provide a method for preparing a compound of general formula I or a pharmaceutically acceptable prodrug ester thereof.

Yet another object of the present invention is to provide a pharmaceutical composition comprising a compound of general formula I or a pharmaceutically acceptable prodrug ester thereof as an active ingredient, and one or more pharmaceutically acceptable carriers, excipients or diluents, as well as its use in the treatment of diabetes.

The disclosure of the present invention is now described in detail in combination with the objects of the invention.

The present invention provides a compound having a structure of general formula I:

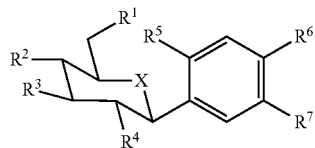

wherein X is selected from O and S;
$R^1$, $R^2$, $R^3$ and $R^4$ are independently selected from H and OH, and at least one of $R^1$, $R^2$, $R^3$ and $R^4$ is H;
$R^5$ is selected from H, $C_{1-3}$ alkyl, —$OCH_3$ and —$OC_2H_5$;
$R^6$ is selected from halogen and $C_{1-3}$ alkyl;
$R^7$ is selected from

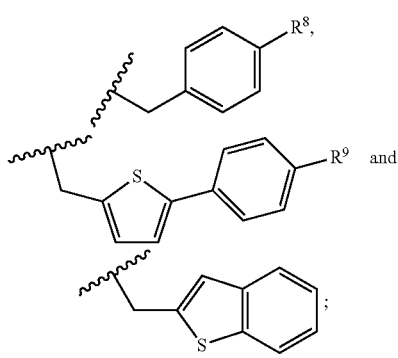

wherein, $R^8$ is selected from $C_{1-3}$ alkyl, $C_{1-3}$ alkoxy group and

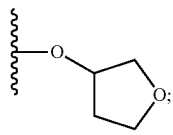 [SMILES: *OC1CCOC1]

$R^9$ is selected from halogen and $C_{1-3}$ alkyl;
optionally, X, the two carbon atoms adjacent to X, and —$CH_2$—O— form a five-membered ring; or the two carbon atoms forming the glycosidic bond, the unsubstituted carbon atoms on the benzene ring adjacent to the glycosidic bond carbon atoms, and —$CH_2$—O— form a five-membered ring.

In some embodiments of the present invention, the compound having the structure of general formula I may includes I-A and I-B, wherein the general formula of I-A is G1-G2.

G1 is selected from the following two groups:

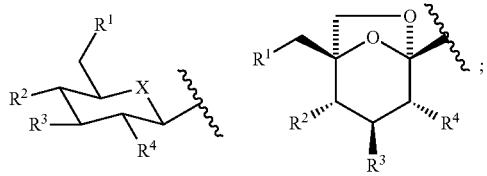

G2 is selected from the following five groups:

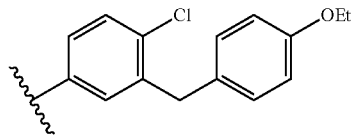

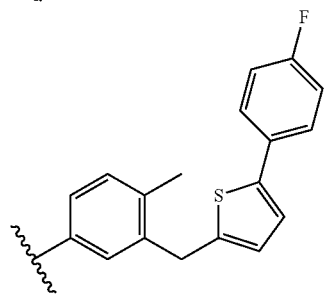

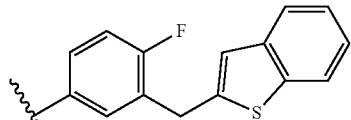

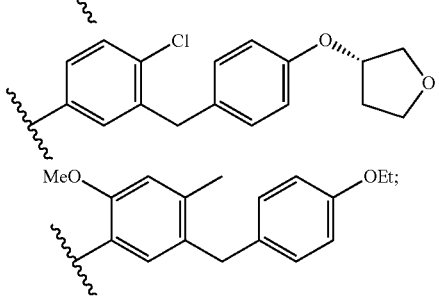

the I-B has the following structure:

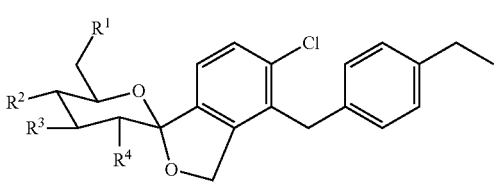

wherein X is selected from O and S;
$R^1$, $R^2$, $R^3$ and $R^4$ are as defined in any one selected from the following cases:
(1) $R^1$=H, $R^2$=OH, $R^3$=OH, $R^4$=OH;
(2) $R^1$=OH, $R^2$=H, $R^3$=OH, $R^4$=OH;
(3) $R^1$=OH, $R^2$=OH, $R^3$=H, $R^4$=OH;
(4) $R^1$=OH, $R^2$=OH, $R^3$=OH, $R^4$=H;
(5) $R^1$=H, $R^2$=H, $R^3$=OH, $R^4$=OH;
(6) $R^1$=H, $R^2$=OH, $R^3$=H, $R^4$=OH;
(7) $R^1$=H, $R^2$=OH, $R^3$=OH, $R^4$=H;
(8) $R^1$=OH, $R^2$=H, $R^3$=H, $R^4$=OH;
(9) $R^1$=OH, $R^2$=H, $R^3$=OH, $R^4$=H;
(10) $R^1$=OH, $R^2$=OH, $R^3$=H, $R^4$=H;
(11) $R^1$=H, $R^2$=H, $R^3$=H, $R^4$=OH;
(12) $R^1$=H, $R^2$=H, $R^3$=OH, $R^4$=H;
(13) $R^1$=H, $R^2$=OH, $R^3$=H, $R^4$=H;
(14) $R^1$=OH, $R^2$=H, $R^3$=H, $R^4$=H;
(15) $R^1$=H, $R^2$=H, $R^3$=H, $R^4$=H.

In a preferred embodiment of the present invention, the compound having general formula I is of one of the following structures:
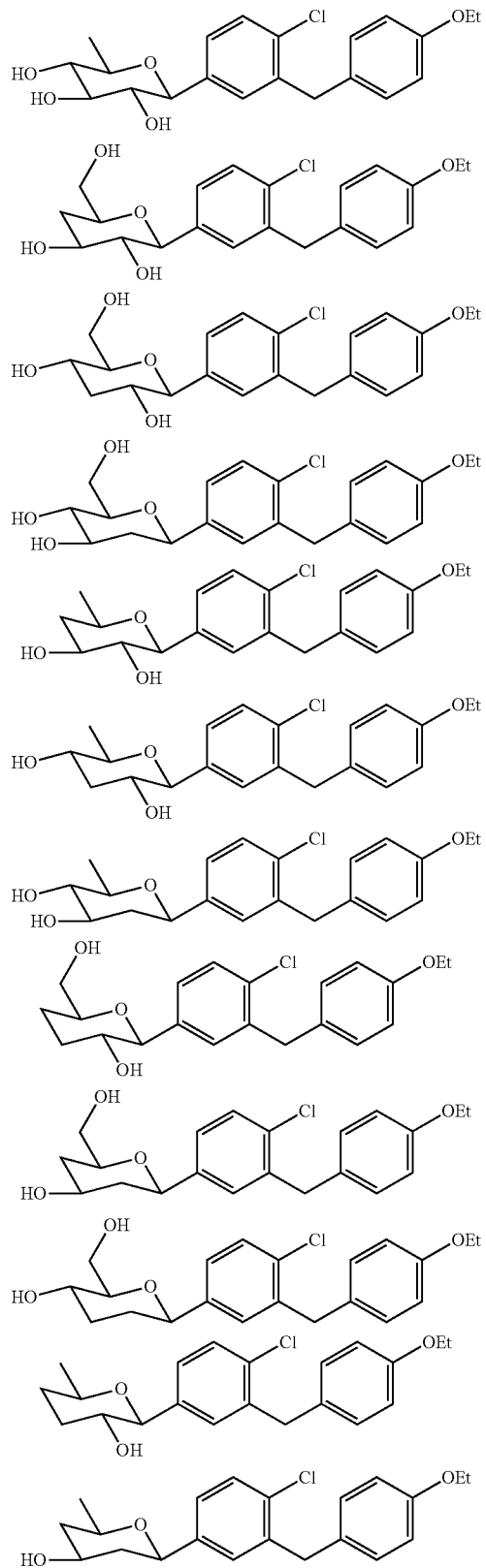
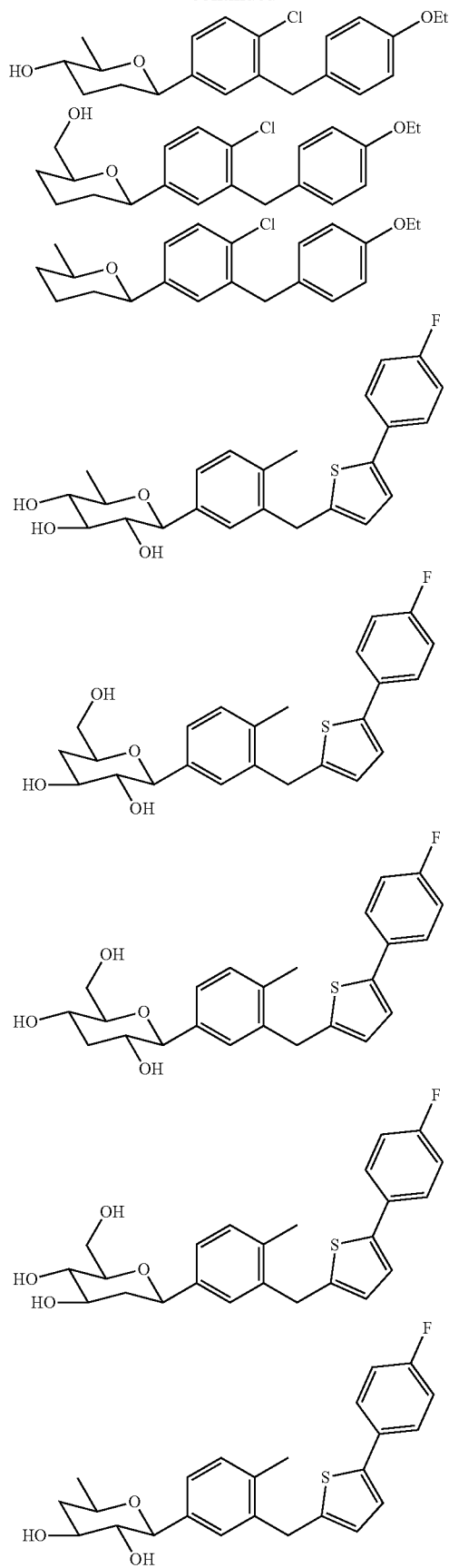

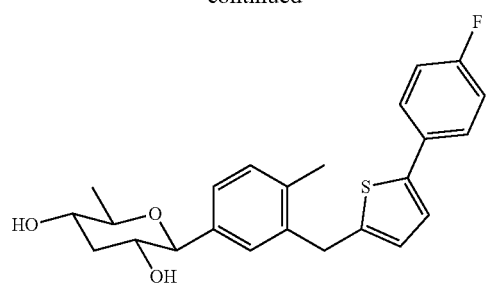
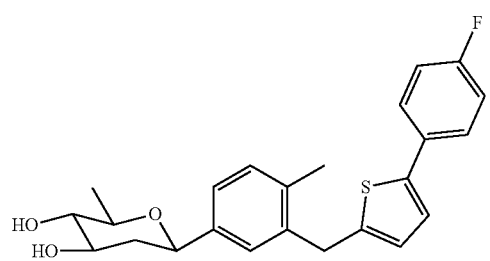
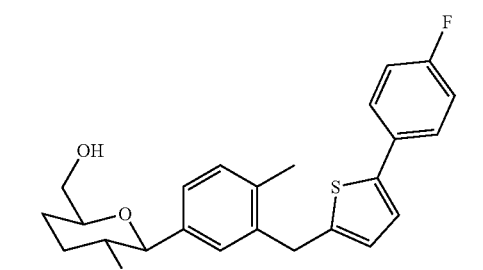
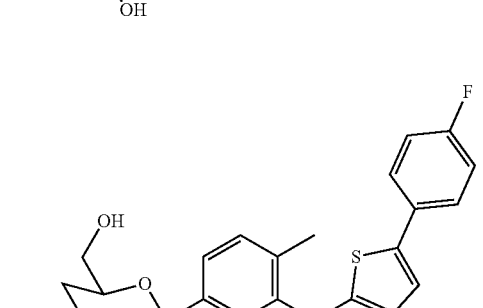
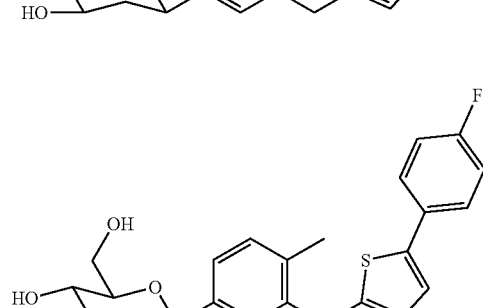
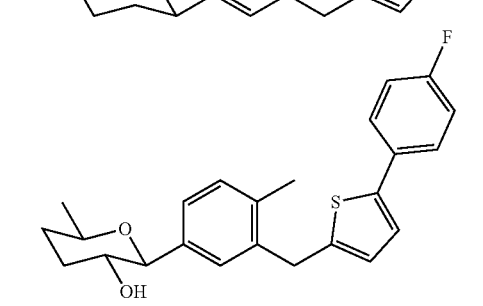
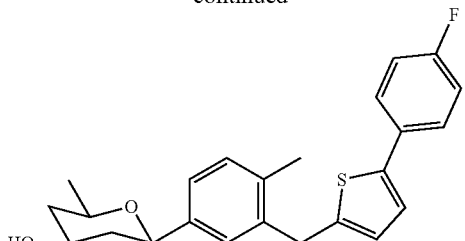
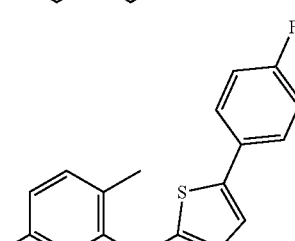
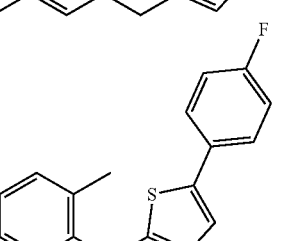
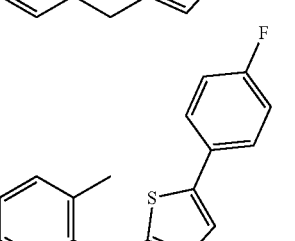
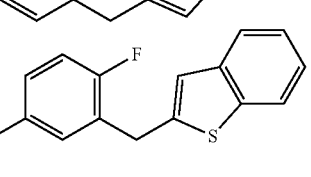
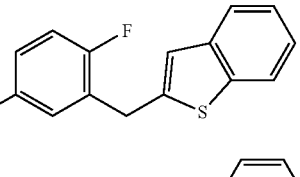
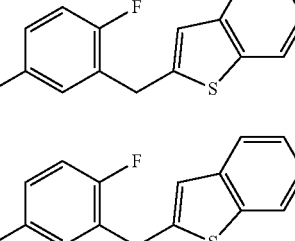
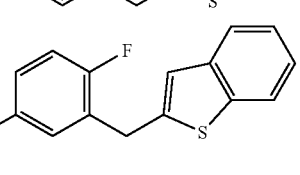

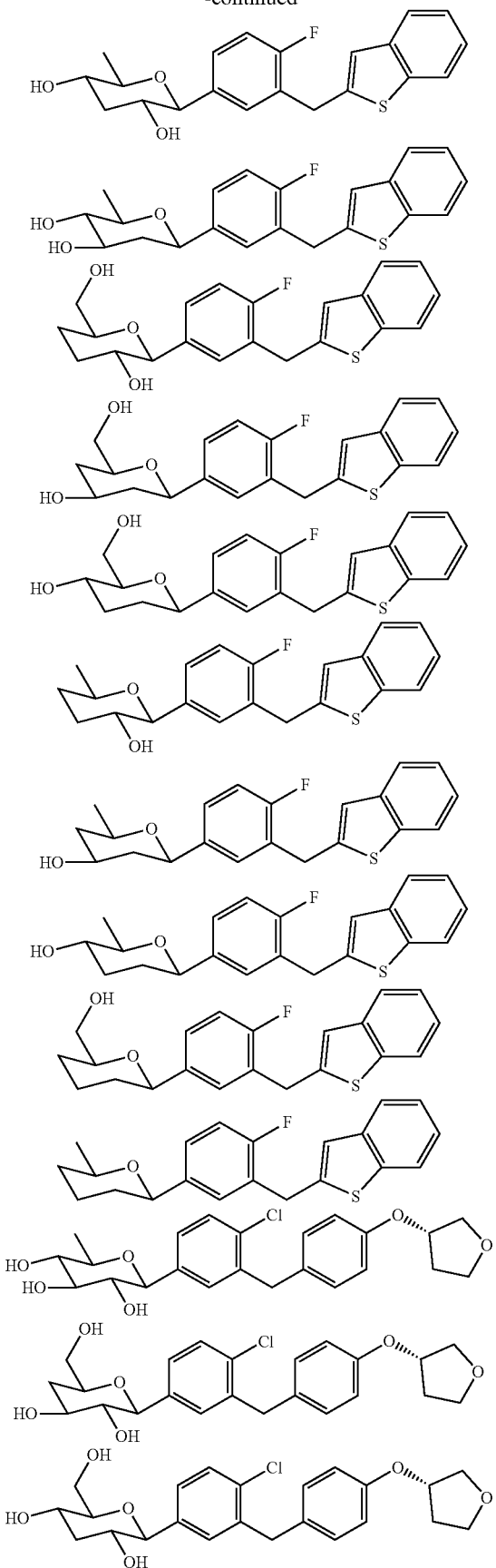
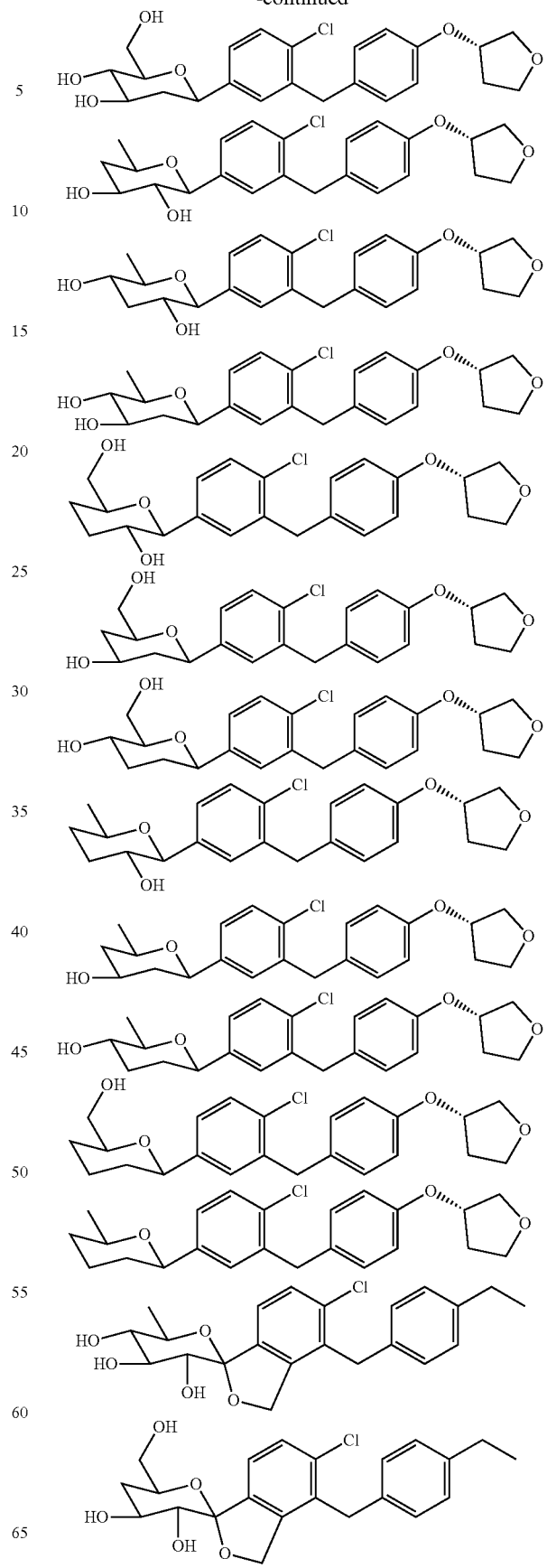

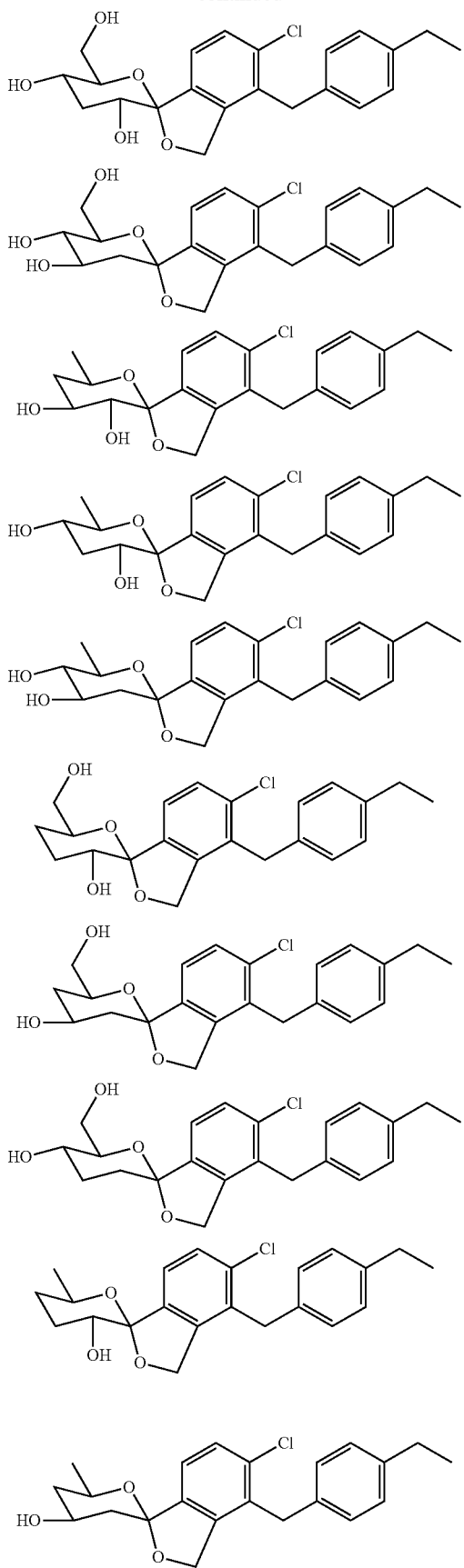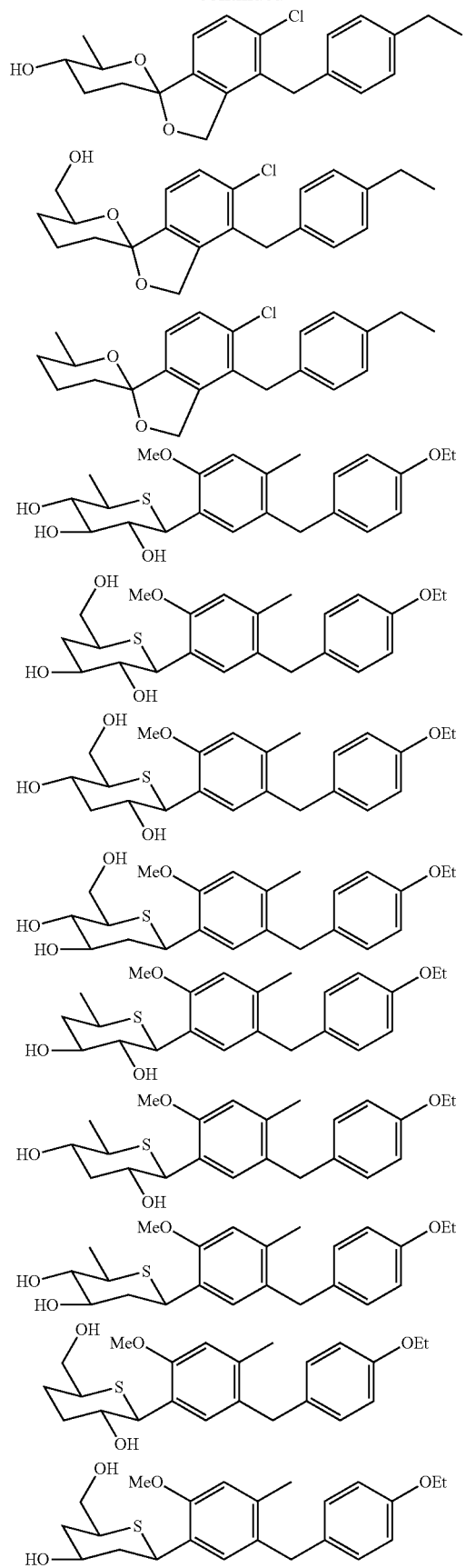

-continued
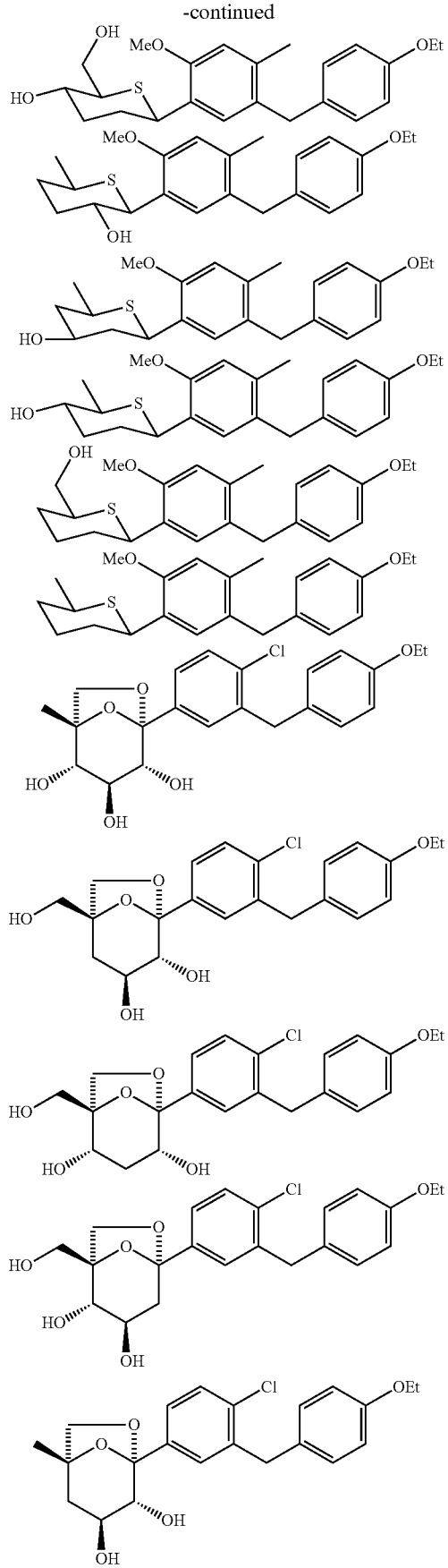
-continued
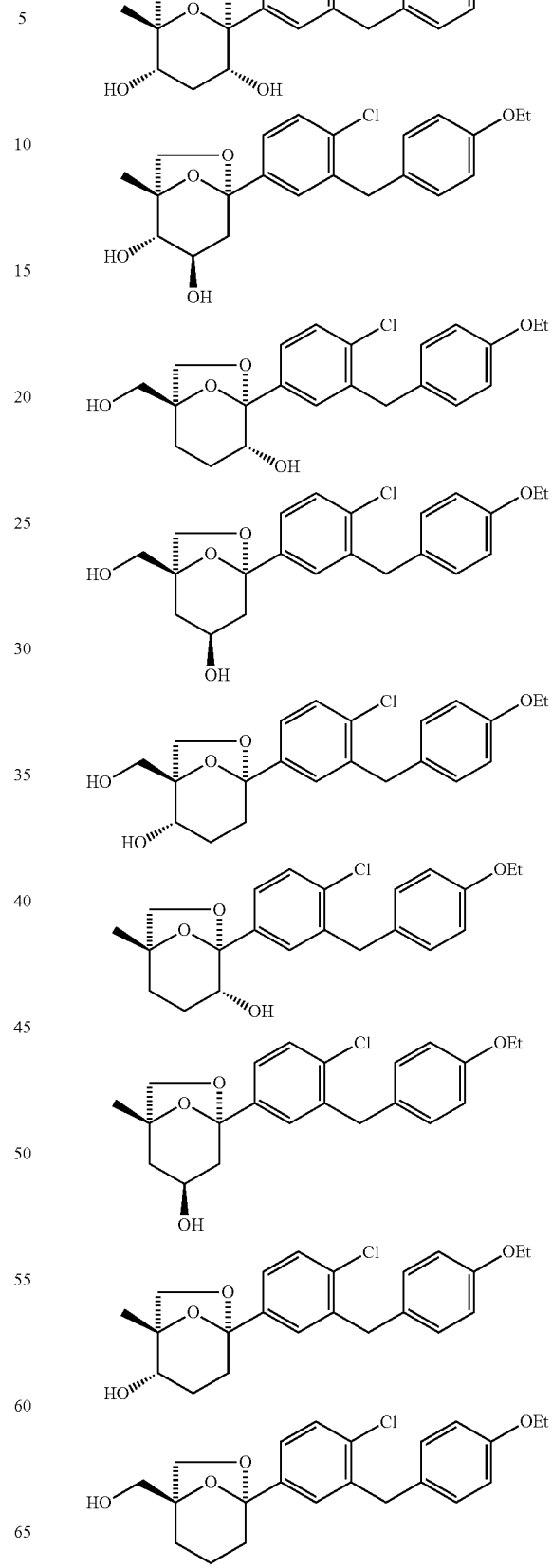

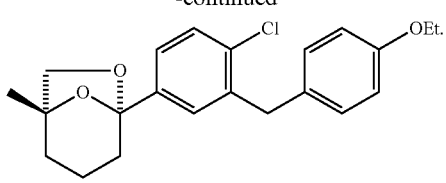
In a more preferred embodiment of the present invention, the compound having general formula I is of one of the following structures:
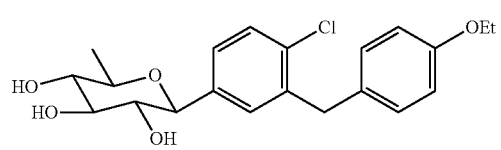
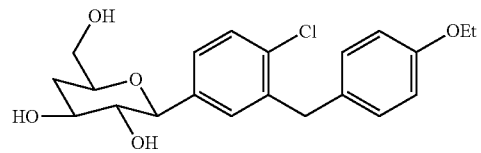
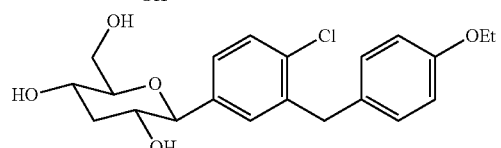
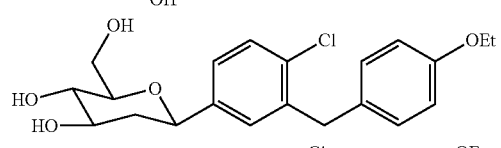
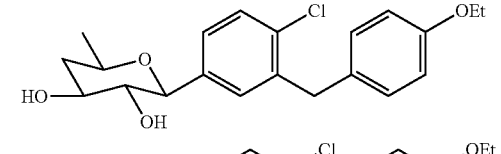
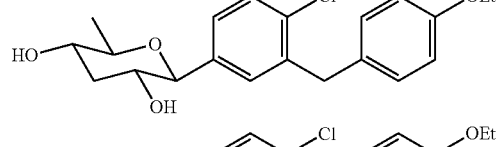
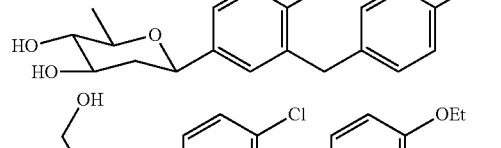
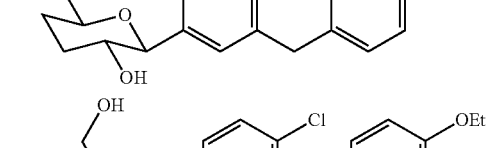
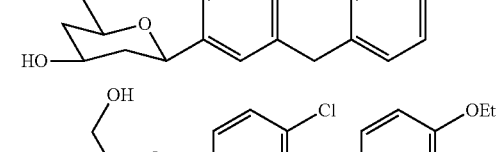
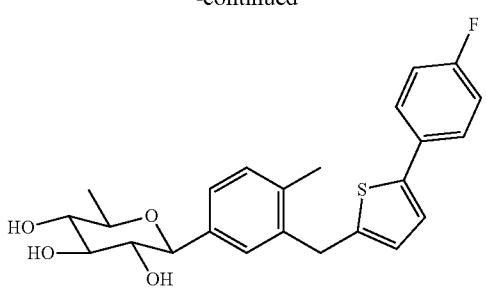
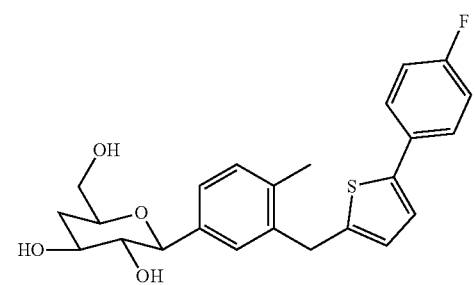
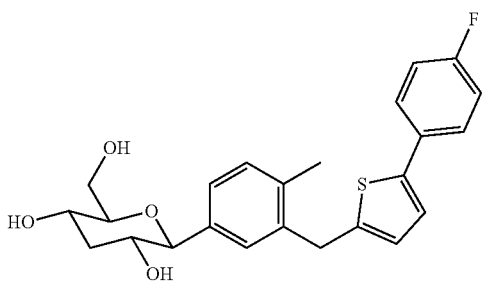
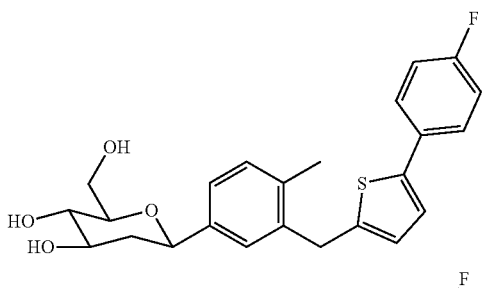
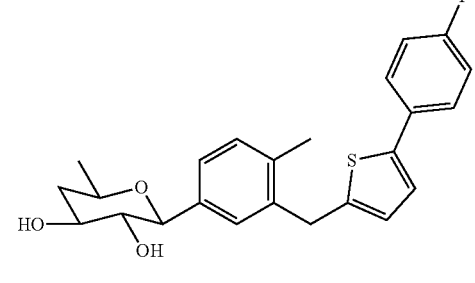
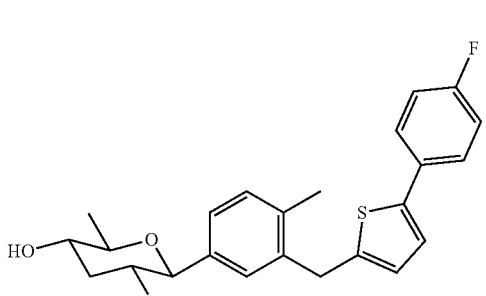

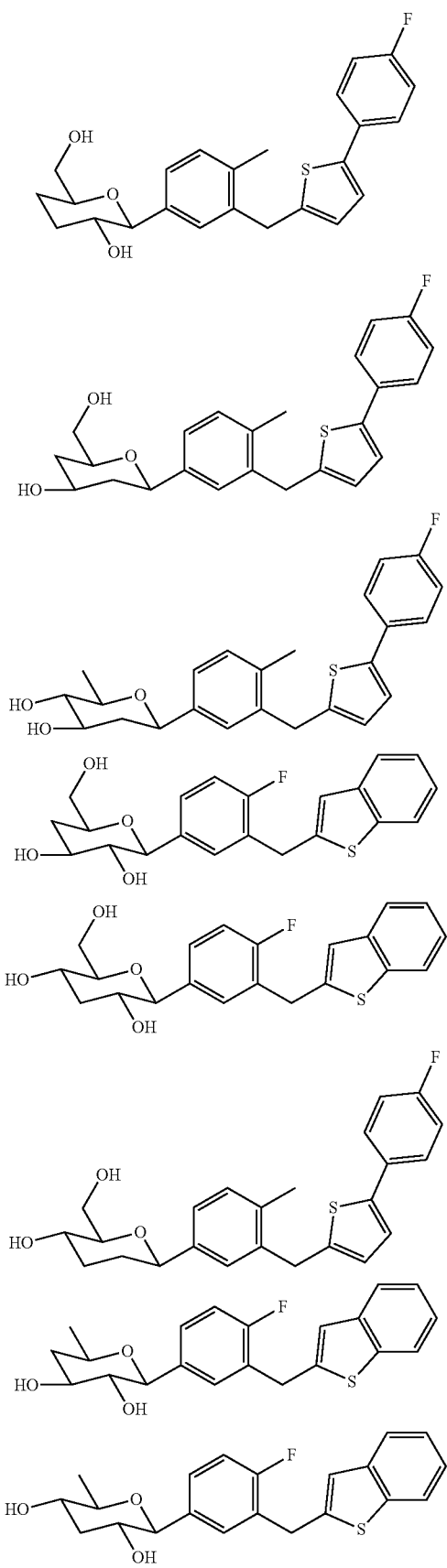
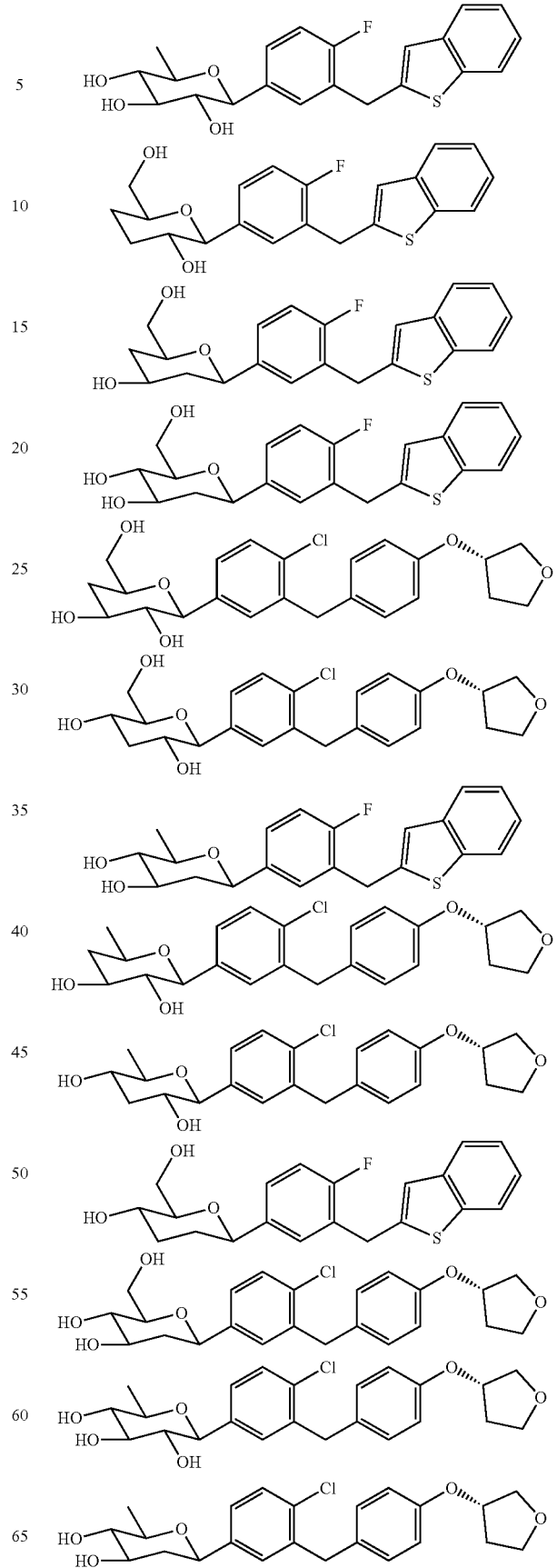

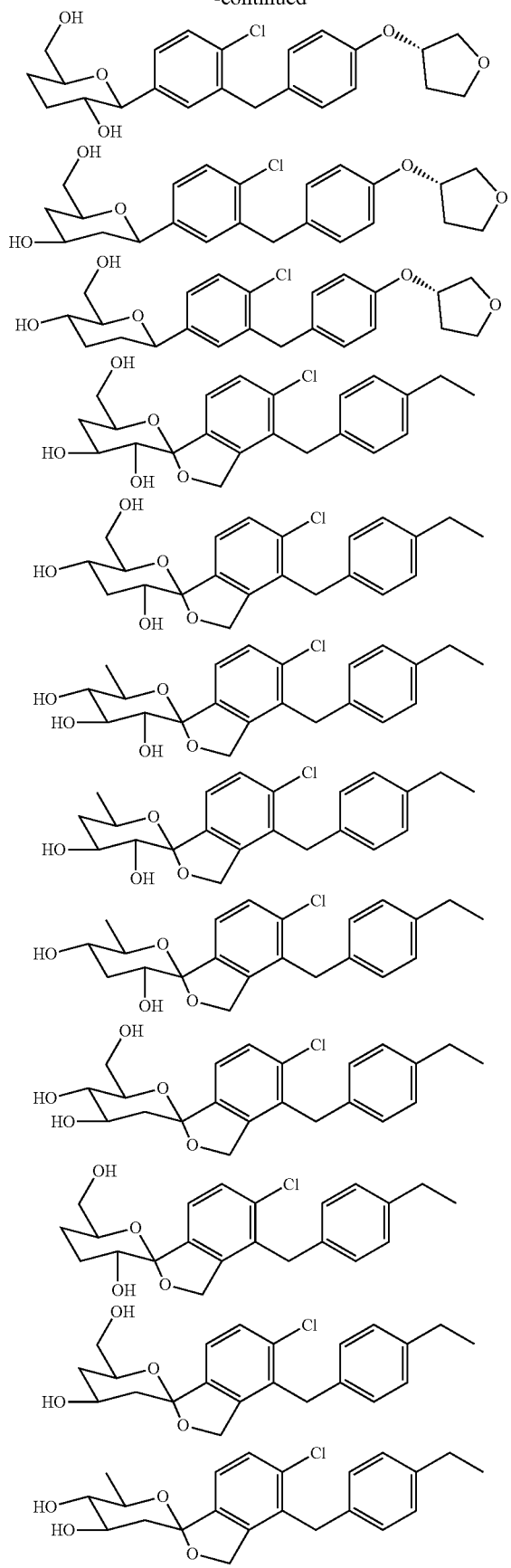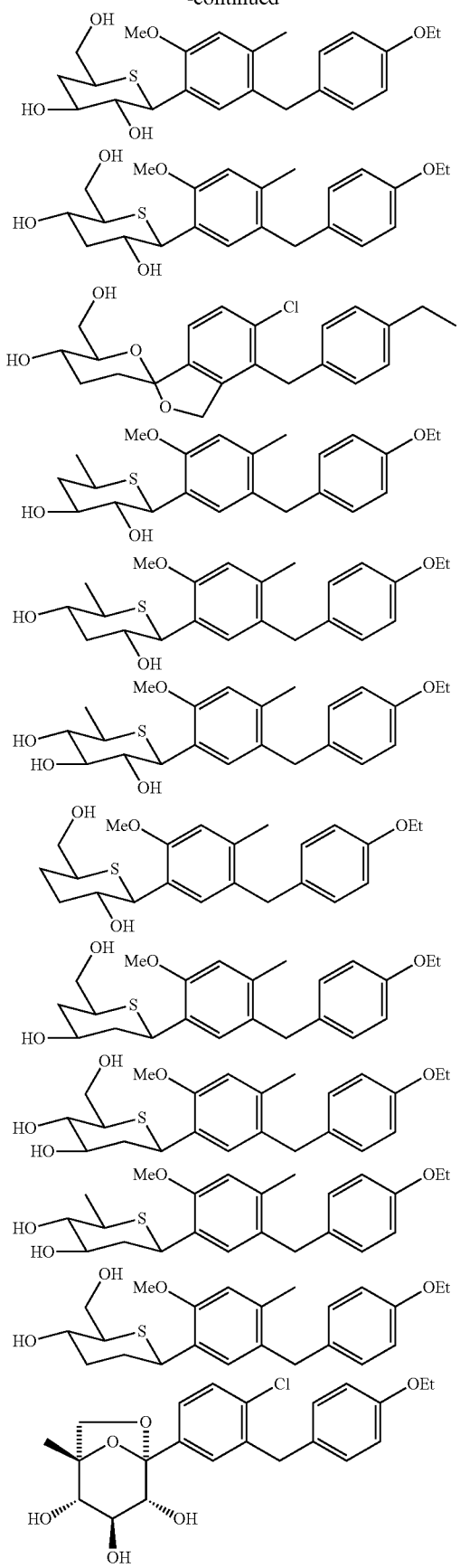

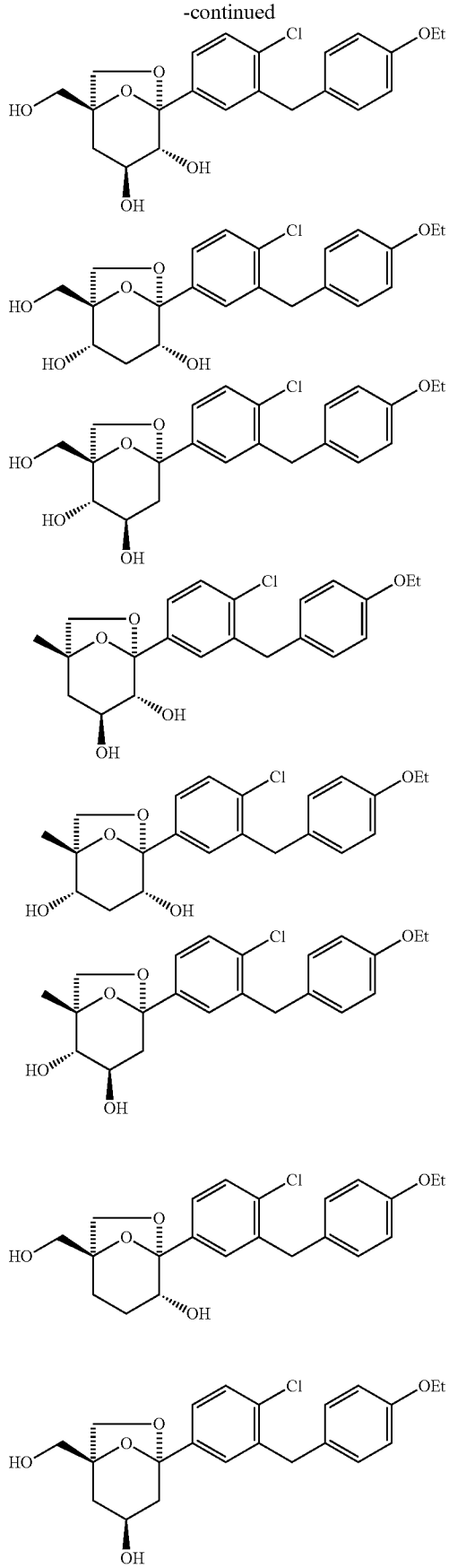
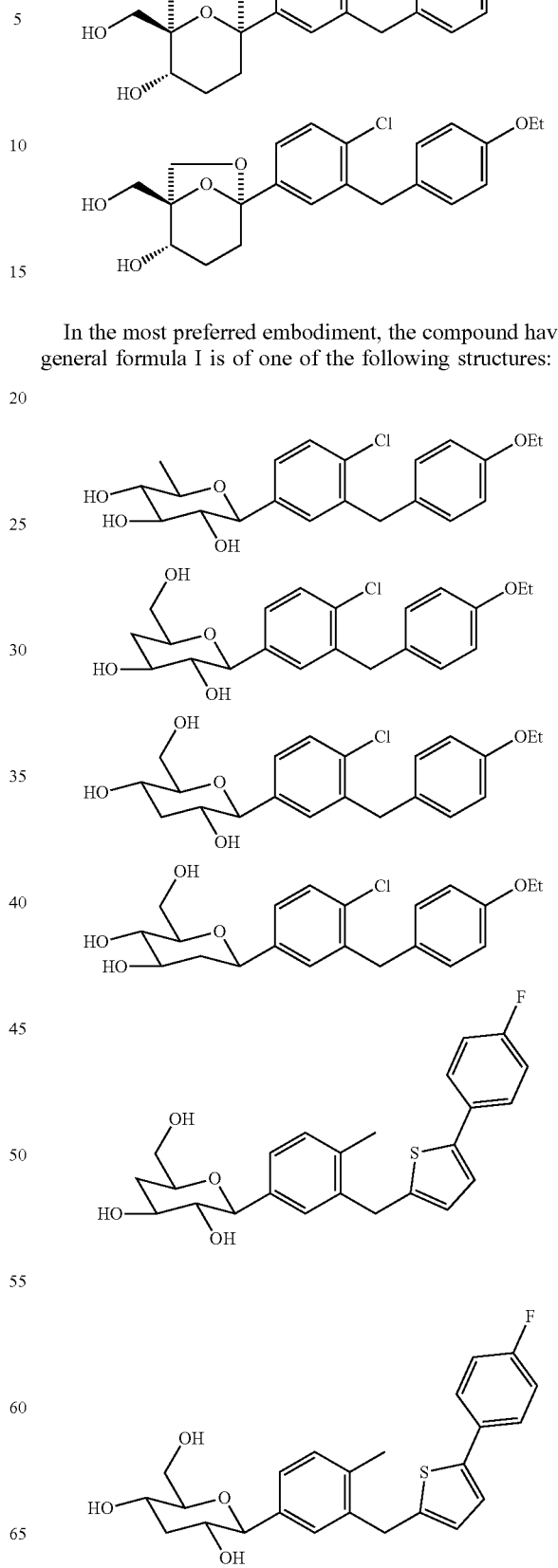
In the most preferred embodiment, the compound having general formula I is of one of the following structures:

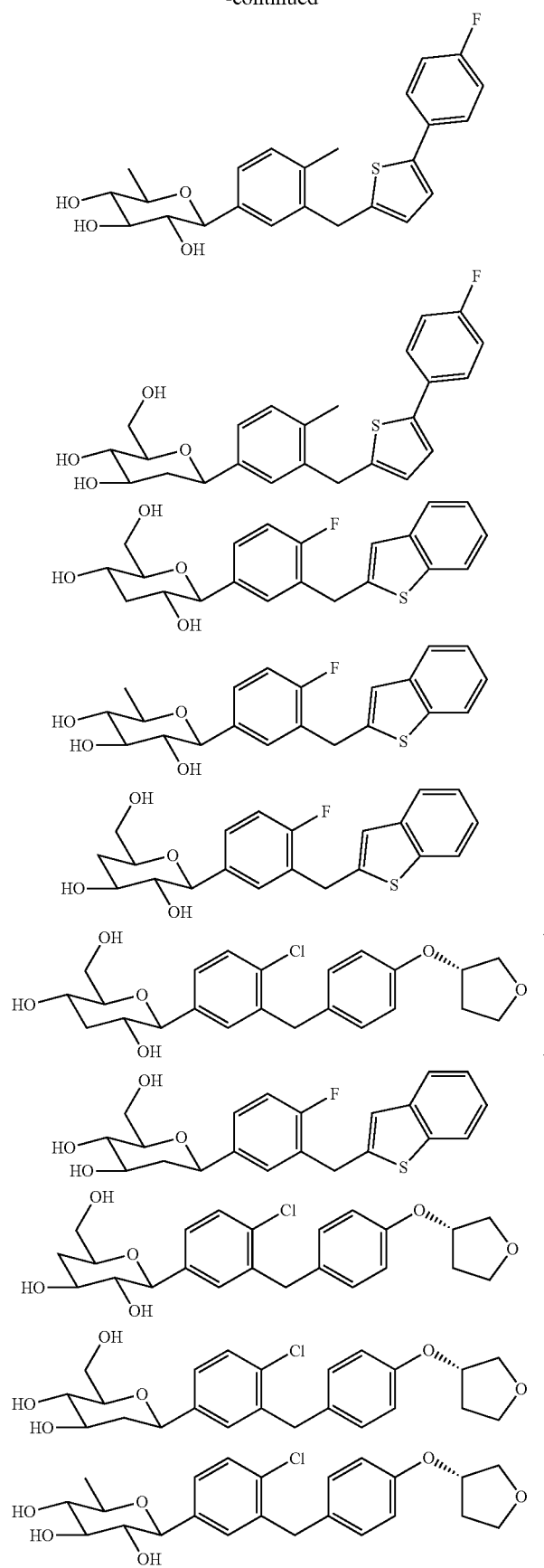
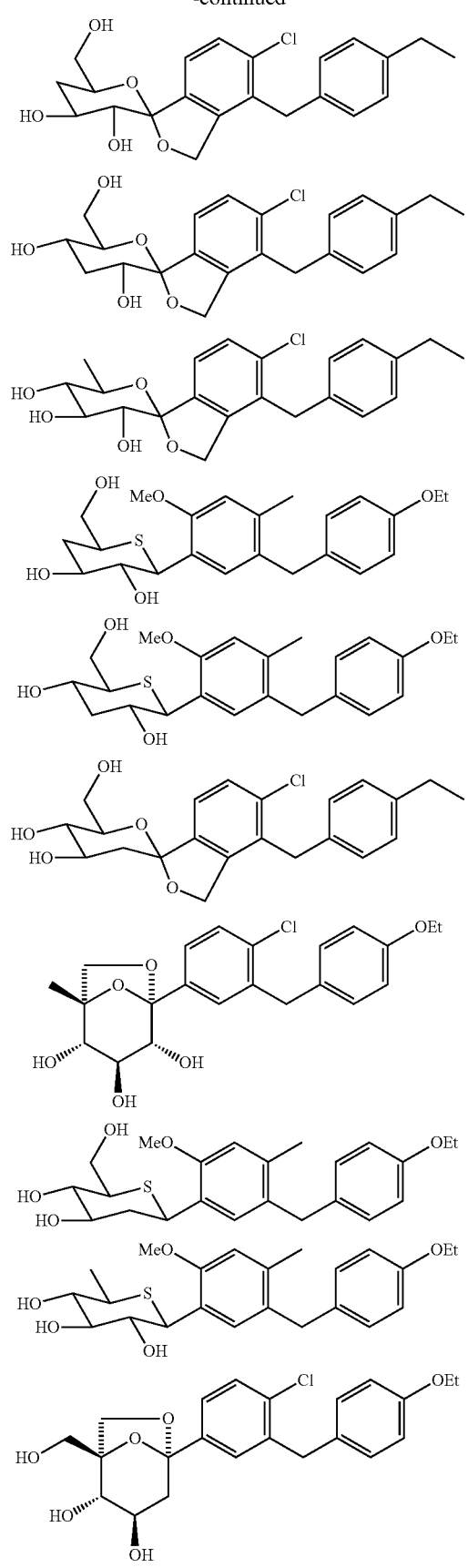

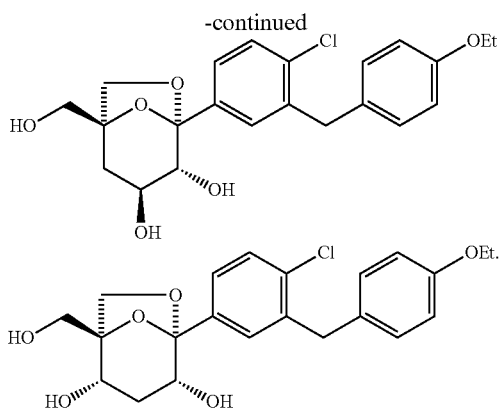

The present invention further provides a method for preparing a compound of general formula I, the method comprises using an un-deoxidized phenyl C-glucoside having the same structure as that of the target product as raw materials.

When the target product is a fully-deoxidized phenyl C-glucoside, the method comprises: converting all the hydroxyl groups on the sugar ring into iodine with an iodizating reagent, and then removing the iodine on the sugar ring via reduction, so as to obtain the target product.

When the target product is a—partially-deoxidized phenyl C-glucoside, the method comprises the steps as follows:

(1) hydroxyl protection: protecting the hydroxyl to be retained on the sugar ring with a hydroxyl protecting reagent;

(2) dehydroxylation: converting the hydroxyls to be removed on the sugar ring into iodine with an iodizating reagent, and then reducing the iodine on the sugar ring, so as to remove the hydroxyls to be removed; and (3) deprotection: removing the hydroxyl protecting group in the compound obtained in the above step, so as to obtain the target product.

It needs to be noted that the preparation method provided in the present invention only involves conversion of hydroxyls on the sugar ring or derivative thereof, and does not involve in the conversions of the other portions except for hydroxyls in the raw material molecules. Unless otherwise indicated, in the present invention, when describing a certain agent, the symbol "/" between compounds means "and".

According to the preparation method as provided by the present invention, wherein various reagents used during the preparation are not especially limited, as long as the compound of formula I can be obtained from said reagents according to the steps of the present invention, that is to say, as long as hydroxyls needed to be removed can be removed without changing other portions except the hydroxyl groups.

According to the preparation method as provided by the present invention, wherein the un-deoxidized phenyl C-glucoside refers to the case that all of $R^1$, $R^2$, $R^3$ and $R^4$ in the compound of general formula I are OH.

According to the preparation method as provided by the present invention, wherein the iodizating reagent may be $I_2$/triphenylphosphine/imidazole reagent (i.e., the combination of $I_2$, triphenylphosphine and imidazole). Method of removing the iodines on the sugar ring via reduction may be palladium-catalyzed hydrogenation or reducing with n-Bu$_3$SnH/AIBN reagent (wherein AIBN is azodiisobutyronitrile).

According to the preparation method of the present invention, wherein the hydroxyl-protecting reagent may select from one or more of acetic anhydride, acetyl chloride, tert-butyldimethylsilyl chloride (TBDMSCl), tert-butyldiphenylsilyl chloride (TBDPSCl), benzoyl chloride, p-methyl benzoyl chloride, pivaloyl chloride, (dimethoxymethyl)benzene (PhCH(OMe)$_2$), benzoic acid, 1,1,2,2-tetramethoxy cyclohexane/trimethyl orthoformate, chloroacetyl chloride and bromoacetyl chloride.

Since hydroxyls at different positions have different reactivity, different hydroxyl-protecting reagents and different protection processes can be used depending on the positions on which the hydroxyls will be retained. In practice, some ancillary steps are sometimes needed to add beyond the basic steps described in steps (1)-(3), e.g. multiple protection-deprotection strategy are sometimes needed to selectively protect the hydroxyls to be retained, and the purpose of performing such multiple protection-deprotection strategy is to distinguish hydroxyls to be retained from hydroxyls to be removed. The present invention discloses some typical examples below to illustrate the techniques of protection-deprotection described above (see the description of the synthetic schemes of 1-D-6 to 1-D-2, 3, 4, 6 below, and the more detailed description of 1-D1-6 to 1-D1-2, 3, 4, 6 in the Examples).

According to the preparation method of the present invention, wherein the reagents used in the deprotection steps are selected according to the hydroxyl-protecting reagents used, and specific selection principles are well known to one skilled in the art. For example, when acetic anhydride, acetyl chloride, benzoyl chloride or the like are used for hydroxyl protection, deprotection reagent may be MeONa/MeOH, NaOH/MeOH/H$_2$O, KOH/MeOH/H$_2$O, NaOH/EtOH/H$_2$O or KOH/EtOH/H$_2$O; when TBDMSCl or TBDPSCl is used for hydroxyl protection, deprotection reagent may be tetra-n-butylammonium fluoride or acetic acid; when PhCH(OMe)$_2$ is used for hydroxyl protection under acid condition, the acid may be any one of hydrochloric acid, sulfuric acid, methanesulfonic acid, camphorsulfonic acid, trifluoroacetic acid and p-toluene sulfonic acid, and deprotection reagent may also be an acid, such as hydrochloric acid, sulfuric acid, methanesulfonic acid, camphorsulfonic acid, trifluoroacetic acid and p-toluene sulfonic acid.

For example, (1) in certain embodiments, the hydroxyl to be removed is 6-hydroxyl (i.e., hydroxyl to be removed is the hydroxyl on $R^1$ position in general formula I). The preparation method may be: first converting 6-hydroxyl into TBDMSO- with reagents such as tert-butyldimethylsilyl chloride (TBDMSCl), followed by acetylating all the retaining hydroxyl with acetylation reagent, and then removing the 6-TBDMS, so as to achieve the protection of the hydroxyl to be retained; converting the 6-hydroxyl into I with iodizating reagent and reducing to remove the 6-hydroxyl; and finally removing acetyl to obtain a phenyl C-glucoside with the 6-hydroxyl removed. (One specific example of this embodiment can be seen below in synthetic process of 1-D-6)

(2) In certain embodiments, the hydroxyl to be removed is 4-hydroxyl (i.e., hydroxyl to be removed is the hydroxyl on $R^2$ position in general formula I). The preparation method may be: first forming a ring using a benzylidene formed by PhCH(OMe)$_2$ or benzaldehyde with the 4- and 6-hydroxyl under acid catalyzing, followed by acetylating the 2- and 3-hydroxyl with an acetylation reagent; and then treating it with acid to remove the benzylidene protecting group, and selectively protecting the primary alcohol (i.e., 6-hydroxyl) therein with benzoyl chloride or pivaloyl chloride; converting 4-hydroxyl into I with iodizating reagent and reducing it to remove the 4-hydroxyl; and finally removing the protecting groups acetyl and benzoyl or pivaloyl to obtain a phenyl C-glucoside with 4-hydroxyl removed. (One specific example of this embodiment can be seen below in synthetic process of 1-D-4)

(3) In certain embodiments, the hydroxyl to be removed is 3-hydroxyl (i.e., hydroxyl to be removed is the hydroxyl on $R^3$ position in general formula I). The preparation method may be: first forming a ring using a benzylidene formed by PhCH(OMe)$_2$ or benzaldehyde with the 4- and 6-hydroxyl under acid catalyzing, followed by converting the 3-hydroxyl into TBDMSO- with reagents such as TBDMSCl, and then acetylating the 2-hydroxyl with acetylation reagent, after which removing the 3-TBDMS; converting the 3-hydroxyl into I with iodizating reagent and reducing it to remove the 3-hydroxyl; and finally removing the protecting groups acetyl and benzylidene to obtain a phenyl C-glucoside with the 3-hydroxyl removed. (One specific example of this embodiment can be seen below in synthetic process of 1-D-3)

(4) In certain embodiments, hydroxyl to be removed is the 2-hydroxyl (i.e., hydroxyl to be removed is the hydroxyl on $R^4$ position in general formula I). The preparation method may be: first forming a ring using a benzylidene formed by PhCH(OMe)$_2$ or benzaldehyde with the 4- and 6-hydroxyl under acid catalyzing, followed by selectively protecting the primary alcohol (i.e., the 3-hydroxyl) therein with benzoyl chloride; converting the 2-hydroxyl into I with iodizating reagent and reducing it to remove the 2-hydroxyl; and finally removing the protecting groups benzoyl and benzylidene to obtain a phenyl C-glucoside with the 2-hydroxyl removed. (One specific example of this embodiment can be seen below in synthetic process of 1-D-2)

(5) In certain embodiments, hydroxyls to be removed are the 4- and 6-hydroxyls (i.e., hydroxyl to be removed is the hydroxyls on $R^1$ and $R^2$ position in general formula I). The preparation method may be: first forming a ring using a benzylidene formed by PhCH(OMe)$_2$ or benzaldehyde with the 4- and 6-hydroxyls under acid catalyzing, followed by acetylating all the retaining hydroxyls with a acetylation reagent, and then removing the 4- and 6-benzyl protecting groups so as to achieve the protection of the hydroxyls to be retained; converting the 4- and 6-hydroxyls into I with iodizating reagent and reducing it to remove the 4 and 6-hydroxyls; and finally removing the acetyl to obtain a phenyl C-glucoside with the 4- and 6-hydroxyls removed. (One specific example of this embodiment can be seen below in synthetic process of 1-D-4,6)

(6) In certain embodiments, hydroxyls to be removed are the 3- and 6-hydroxyls (i.e., hydroxyls to be removed are hydroxyls on the $R^1$ and $R^3$ positions in general formula I). The preparation method may be: first reacting the raw material with 1,1,2,2-tetramethoxy cyclohexane and trimethyl orthoformate under acid condition to give a product with the 3- and 4-positions being protected (the acid used is selected from hydrochloric acid, sulfuric acid, methanesulfonic acid, camphorsulfonic acid, trifluoroacetic acid or p-toluene sulfonic acid), followed by converting the 6-hydroxyl into TBDMSO- with reagents such as TBDMSCl, and then acetylating the 2-hydroxyl with acetylation reagent, after which treating it with acid to remove the 3- and 4-protecting groups and the 6-protecting group (the acid used is selected from acetic acid or trifluoroacetic acid); converting the 6-hydroxyl into TBDMSO- with reagents such as TBDMSCl again, converting the 3-hydroxyl into TBDMSO- with reagents such as TBDMSCl again, and acetylating the 4-hydroxyl with acetylation reagent again; and then treating it with tetra-n-butylammonium fluoride or acetic acid to remove the 3- and 6-TBDMS-; converting the 3- and 6-hydroxyls into I with iodizating reagent and reducing it to remove the 3- and 6-hydroxyls; and finally removing the acetyl protecting group to obtain a phenyl C-glucoside with the 3- and 6-hydroxyls removed. (One specific example of this embodiment can be seen below in synthetic process of 1-D-3,6)

(7) In certain embodiments, hydroxyls to be removed are the 2- and 6-hydroxyls (i.e., hydroxyls to be removed are hydroxyls on the $R^1$ and $R^4$ positions in general formula I). The preparation method may be: first reacting the raw material with 1,1,2,2-tetramethoxy cyclohexane and trimethyl orthoformate under acid condition to give a product with the 3- and 4-positions being protected; converting the 2- and 6-hydroxyls into I with iodizating reagent and reducing to remove the 2- and 6-hydroxyls; and finally treating it with acid to remove the 3- and 4-protecting groups to obtain a phenyl C-glucoside with the 3- and 4-hydroxyls removed. (One specific example of this embodiment can be seen below in synthetic process of 1-D-2,6)

(8) In certain embodiments, hydroxyls to be removed are the 3- and 4-hydroxyls (i.e., hydroxyls to be removed are the hydroxyls on $R^2$ and $R^3$ positions in general formula I). The preparation method may be: reacting raw material with 1,1,2,2-tetramethoxy cyclohexane and trimethyl orthoformate under acid condition, to give a product with the 3- and 4-positions being protected; and then acetylating the 2- and 6-hydroxyls with acetylation reagent; after which treating it with acid to remove the 3- and 4-protecting groups; converting the 3- and 4-hydroxyls into I with iodizating reagent and reducing it to remove the 3- and 4-hydroxyls; and finally removing the 2- and 6-acetyls to obtain a phenyl C-glucoside with the 3- and 4-hydroxyls removed. (One specific example of this embodiment can be seen below in synthetic process of 1-D-3,4)

(9) In certain embodiments, hydroxyls to be removed are the 2- and 4-hydroxyls (i.e., hydroxyls to be removed are the hydroxyls on $R^2$ and $R^4$ positions in general formula I). The preparation method may be: reacting raw material with 1,1,2,2-tetramethoxy cyclohexane and trimethyl orthoformate under acid condition to give a product with the 3- and 4-positions being protected; selectively protecting the 6-hydroxyl with benzoyl chloride; after which treating it with acid to remove the 3- and 4-protecting groups; selectively protecting the 6-hydroxyl with benzoyl chloride again; then converting the 2- and 4-hydroxyls into I with iodizating reagent and reducing it to remove the 2- and 4-hydroxyls; and finally removing the 3- and 6-benzoyls to obtain a phenyl C-glucoside with the 2- and 4-hydroxyls removed. (One specific example of this embodiment can be seen below in synthetic process of 1-D-2,4)

(10) In certain embodiments, hydroxyls to be removed are the 2- and 3-hydroxyls (i.e., hydroxyls to be removed are the hydroxyls on $R^1$ and $R^4$ positions in general formula I). The preparation method may be: first forming a ring using a benzylidene formed by PhCH(OMe)$_2$ or benzaldehyde with the 4- and 6-hydroxyls under acid catalyzing, followed by converting the 2- and 3-hydroxyls into I with iodizating reagent and reducing it to remove the 2 and 3-hydroxyls; and finally treating with acid to remove protecting groups on positions 4- and 6- to obtain a phenyl C-glucoside with the 2- and 3-hydroxyls removed. (One specific example of this embodiment can be seen in below synthetic process of 1-D-2,3)

(11) In certain embodiments, hydroxyls to be removed are the 3-, 4- and 6-hydroxyls (i.e., hydroxyls to be removed are the hydroxyls on $R^1$, $R^2$ and $R^3$ positions in general formula I). The preparation method may be: first forming a ring using a benzylidene formed by PhCH(OMe)₂ or benzaldehyde with the 4- and 6-hydroxyls under acid catalyzing, followed by converting the 3-hydroxyl into TBDMSO- with reagents such as TBDMSCl, and then acetylating the 2-hydroxyl with acetylation reagent; after which removing benzylidene and TBDMS-protecting groups under acid condition; and then converting the 3-, 4- and 6-hydroxyls into I with iodizating reagent and reducing it to remove the 3-, 4- and 6-hydroxyls; and finally removing the 2-acetyl to obtain a phenyl C-glucoside with the 3-, 4- and 6-hydroxyls removed. (One specific example of this embodiment can be seen below in synthetic process of 1-D-3, 4, 6)

(12) In certain embodiments, hydroxyls to be removed are the 2-, 4- and 6-hydroxyls (i.e., hydroxyls to be removed are the hydroxyls on $R^1$, $R^2$ and $R^4$ positions in general formula I). The preparation method may be: first forming a ring using a benzylidene formed by PhCH(OMe)₂ or benzaldehyde with the 4- and 6-hydroxyls under acid catalyzing, followed by selectively protecting the 3-hydroxyl with benzoyl chloride etc., and then removing the benzylidene under acid condition; converting the 2-, 4- and 6-hydroxyls into I with iodizating reagent and reducing it to remove the 2-, 4- and 6-hydroxyls; and finally removing the 3-benzoyl to obtain a phenyl C-glucoside with the 2-, 4- and 6-hydroxyls removed. (One specific example of this embodiment can be seen below in synthetic process of 1-D-2, 4, 6)

(13) In certain embodiments, hydroxyls to be removed are the 2-, 3- and 6-hydroxyls (i.e., hydroxyls to be removed are the hydroxyls on $R^1$, $R^3$ and $R^4$ positions in general formula I). The preparation method may be: first forming a ring using a benzylidene formed by PhCH(OMe)₂ or benzaldehyde with the 4- and 6-hydroxyls under acid catalyzing, followed by protecting the 2- and 3-hydroxyls with chloroacetyl chloride or bromoacetyl chloride etc., and then removing the benzylidene under acid condition; converting the 6-hydroxyl into TBDMSO- with reagents such as TBDMSCl, after which acetylating the 4-hydroxyl with acetylation reagent; removing the protecting groups on positions 2- and 3-under weak alkaline conditions, and treating it with tetra-n-butylammonium fluoride or acetic acid to remove the protecting group on position 6-; converting the 2-, 3- and 6-hydroxyls into I with iodizating reagent and reducing it to remove the 2-, 3- and 6-hydroxyls; and finally removing the 4-acetyl to obtain a phenyl C-glucoside with the 2-, 3- and 6-hydroxyls removed. (One specific example of this embodiment can be seen below in synthetic process of 1-D-2, 3, 6)

(14) In certain embodiments, hydroxyls to be removed are the 2-, 3- and 4-hydroxyls (i.e., hydroxyls to be removed are the hydroxyls on $R^2$, $R^3$ and $R^4$ positions in general formula I). The preparation method may be: protecting the 6-hydroxyl with benzoyl chloride, p-methyl benzoyl chloride or pivaloyl chloride; and then converting the 2-, 3- and 4-hydroxyls into I with iodizating reagent and reducing it to remove the 2-, 3- and 4-hydroxyls; and finally removing the protecting group on position 6- to obtain a phenyl C-glucoside with the 2-, 3- and 4-hydroxyls removed. (One specific example of this embodiment can be seen below in synthetic process of 1-D-2, 3, 4). The preparation method of the present invention will be described in more detail using some preferred compounds of formula I of the present invention as examples below.

The following compounds can be used as raw materials to prepare preferred compounds having general formula I of the present invention:

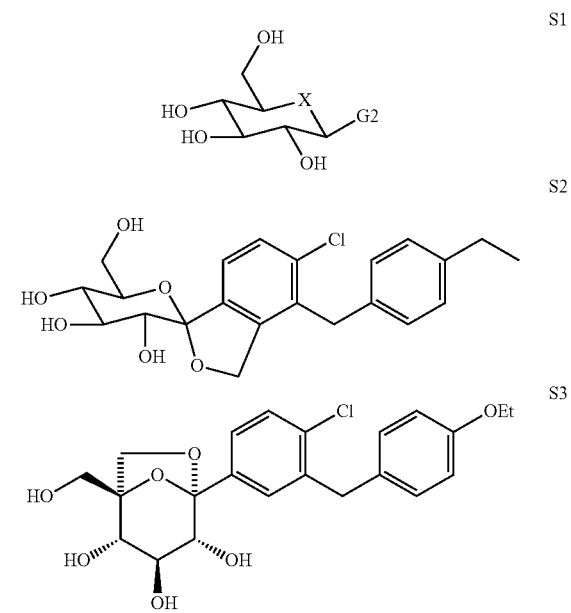

wherein X is selected from O or S; G2 is selected from the following groups:

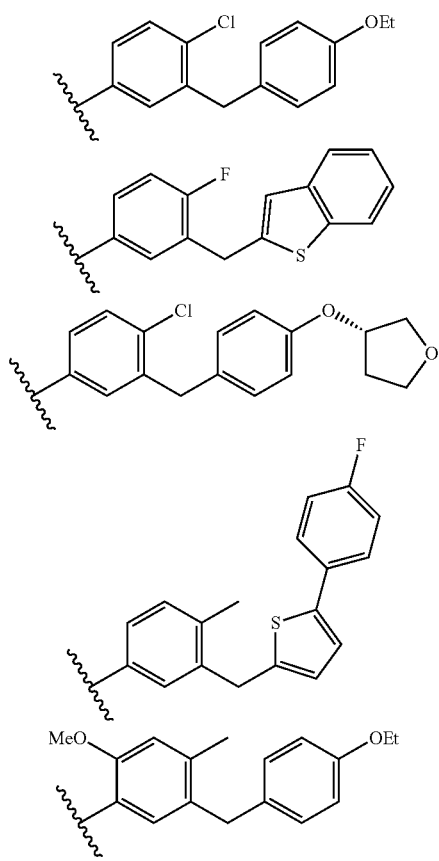

When compounds of general formula I described in the present invention are synthesized with S1-S3 as raw materials, the synthetic procedures only involve the conversion of hydroxyl groups on the sugar ring and derivative thereof and do not involve any change of the other portions except hydroxyl groups in the raw material molecules. Therefore, when the raw materials are S1-S3, the synthetic route from S1-S3 to the compounds of general formula I described in the present invention is illustrated by using the following general formula G to represent S1-S3.

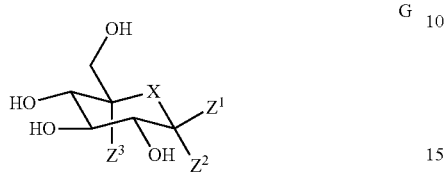

G wherein X is selected from O or S, definitions of $Z^1$-$Z^3$ have the following cases:

(1) $Z^1$=G2, $Z^2$=$Z^3$=H: then G=S1;

(2) $Z^1$ and $Z^2$ form a ring as shown in S2, $Z^3$=H: then G=S2;

(3) $Z^2$ and $Z^3$ form a ring as shown in S3, $Z^1$ are the groups as follows: then G=S3,

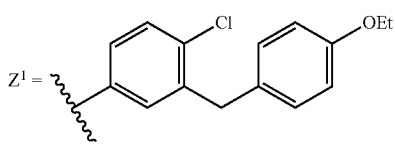 [SMILES: *c1ccc(Cl)c(Cc2ccc(OCC)cc2)c1]

Synthesizing the representative compounds of general formula I from raw materials may have several cases as follows:

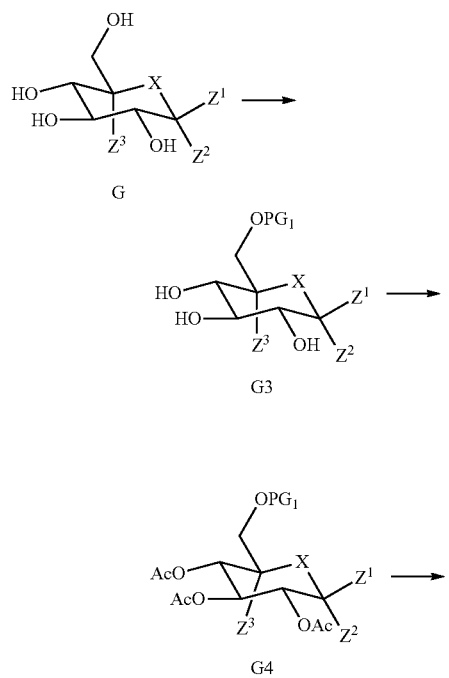

(1)

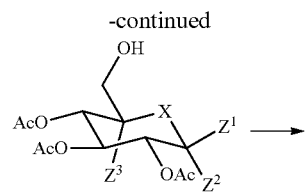

G5

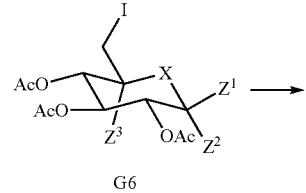

G6

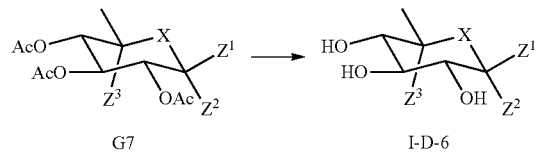

G7    I-D-6

Treating raw material G with 1 equivalent of protective reagent to convert it into G3, such protective reagent is selected from TBDMSCl or TBDPSCl etc., and corresponding PG$_1$ is selected from TBDMS or TBDPS; acetylazing G3 to convert it into G4, the acetylation reagent is selected from acetic anhydride or acetyl chloride; treating G4 to remove the protecting group PG$_1$ to give G5, the reagent is selected from tetra-n-butylammonium fluoride or acetic acid; converting G5 into G6 with iodizating reagent, the reagent is I$_2$/PPh$_3$/imidazole; converting G6 into G7 under reducing condition, the condition is selected from palladium-catalyzed hydrogenation or n-Bu$_3$SnH/AIBN, wherein AIBN is azodiisobutyronitrile; and finally removing the acetyl on G7 to give I-D-6, the conditions are selected from MeONa/MeOH, NaOH/MeOH/H$_2$O, KOH/MeOH/H$_2$O, NaOH/EtOH/H$_2$O or KOH/EtOH/H$_2$O; wherein X is selected from O or S, $Z^1$-$Z^3$ are defined as above, I-D-6 is one of the compounds having general formula I described in the present invention.

(2)

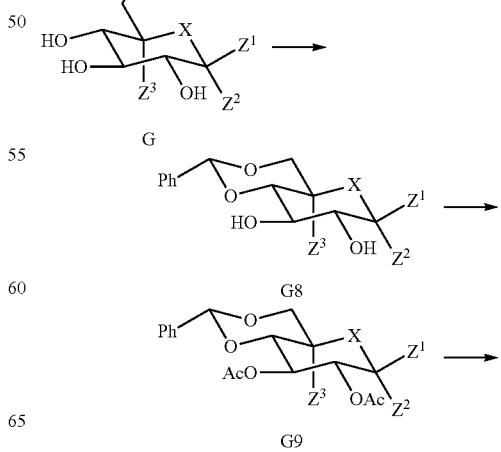

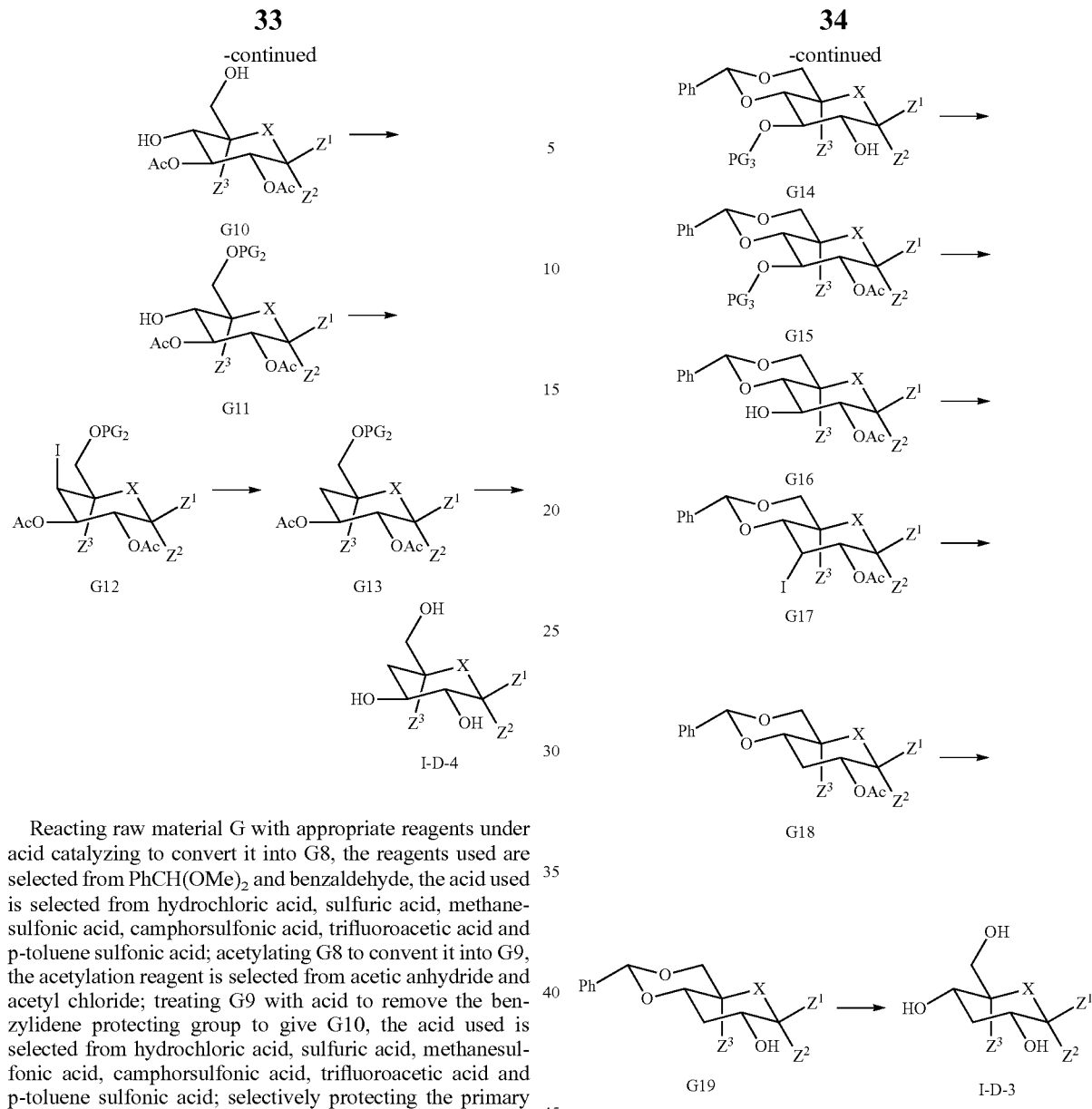

Reacting raw material G with appropriate reagents under acid catalyzing to convert it into G8, the reagents used are selected from PhCH(OMe)$_2$ and benzaldehyde, the acid used is selected from hydrochloric acid, sulfuric acid, methanesulfonic acid, camphorsulfonic acid, trifluoroacetic acid and p-toluene sulfonic acid; acetylating G8 to convent it into G9, the acetylation reagent is selected from acetic anhydride and acetyl chloride; treating G9 with acid to remove the benzylidene protecting group to give G10, the acid used is selected from hydrochloric acid, sulfuric acid, methanesulfonic acid, camphorsulfonic acid, trifluoroacetic acid and p-toluene sulfonic acid; selectively protecting the primary alcohol group in G10 with a protecting group of benzoyl chloride or pivaloyl chloride to give G11, PG$_2$ is selected from benzoyl and pivaloyl; converting G11 into G12 with iodizating reagent, the reagent is I$_2$/PPh$_3$/imidazole; converting G12 into G13 under reducing condition, the condition is selected from palladium-catalyzed hydrogenation or n-Bu$_3$SnH/AIBN, wherein AIBN is azodiisobutyronitrile; and finally removing the acetyl on G13 to give I-D-4, the conditions are selected from MeONa/MeOH, NaOH/MeOH/H$_2$O, KOH/MeOH/H$_2$O, NaOH/EtOH/H$_2$O or KOH/EtOH/H$_2$O; wherein X is selected from O or S, Z$^1$-Z$^3$ are defined as above, I-D-4 is one of the compounds having general formula I described in the present invention.

(3)

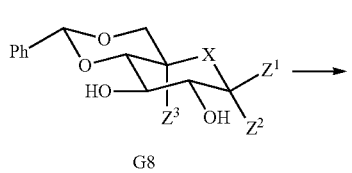

Protecting G8 with TBDMSCl or TBDPSCl to give G14, PG$_3$ is selected from TBDMS, TBDPS; acetylating G14 to convert it into G15, the acetylation reagent is selected from acetic anhydride or acetyl chloride; treating G15 to remove the protecting group PG$_3$ to give G16, the reagent is tetra-n-butylammonium fluoride; converting G16 into G17 with iodizating reagent, the reagent is I$_2$/PPh$_3$/imidazole; converting G17 into G18 under reducing condition, the condition is selected from palladium-catalyzed hydrogenation or n-Bu$_3$SnH/AIBN, wherein AIBN is azodiisobutyronitrile; removing the acetyl on G18 to give G19, the condition is selected from MeONa/MeOH, NaOH/MeOH/H$_2$O, KOH/MeOH/H$_2$O, NaOH/EtOH/H$_2$O or KOH/EtOH/H$_2$O; and finally treating G19 with acid to remove the benzylidene protecting group to give I-D-3, the acid used is selected from hydrochloric acid, sulfuric acid, methanesulfonic acid, camphorsulfonic acid, trifluoroacetic acid or p-toluene sulfonic acid; wherein X is selected from O or S, Z$^1$-Z$^3$ are defined as above, I-D-3 is one of the compounds having general formula I described in the present invention.

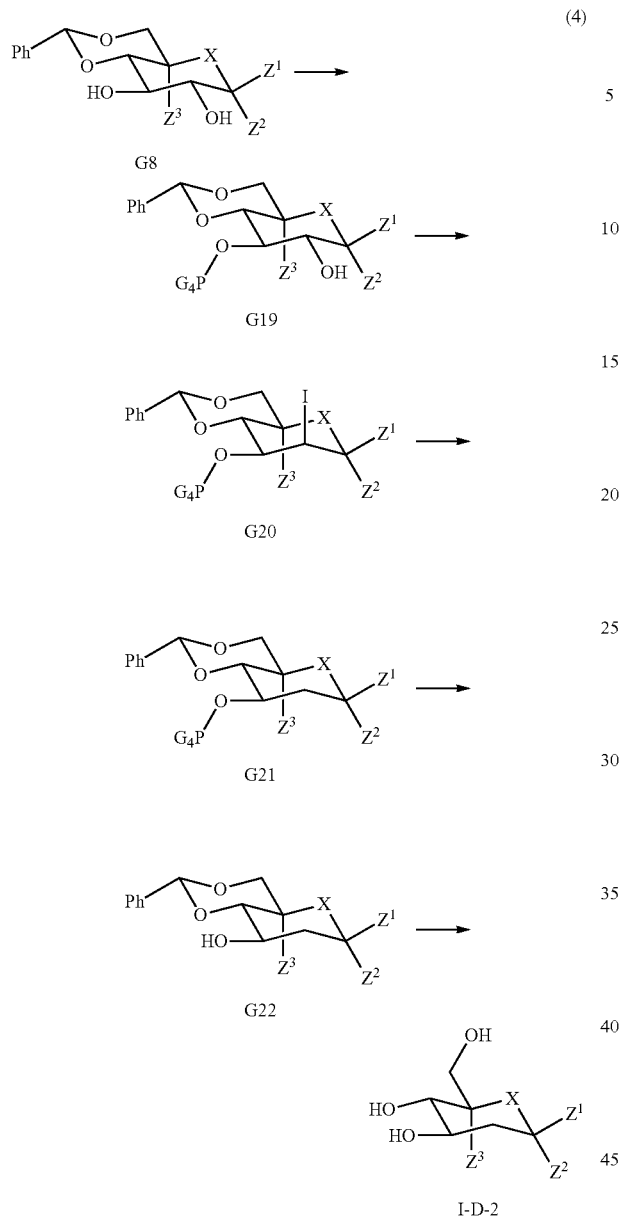

(4)

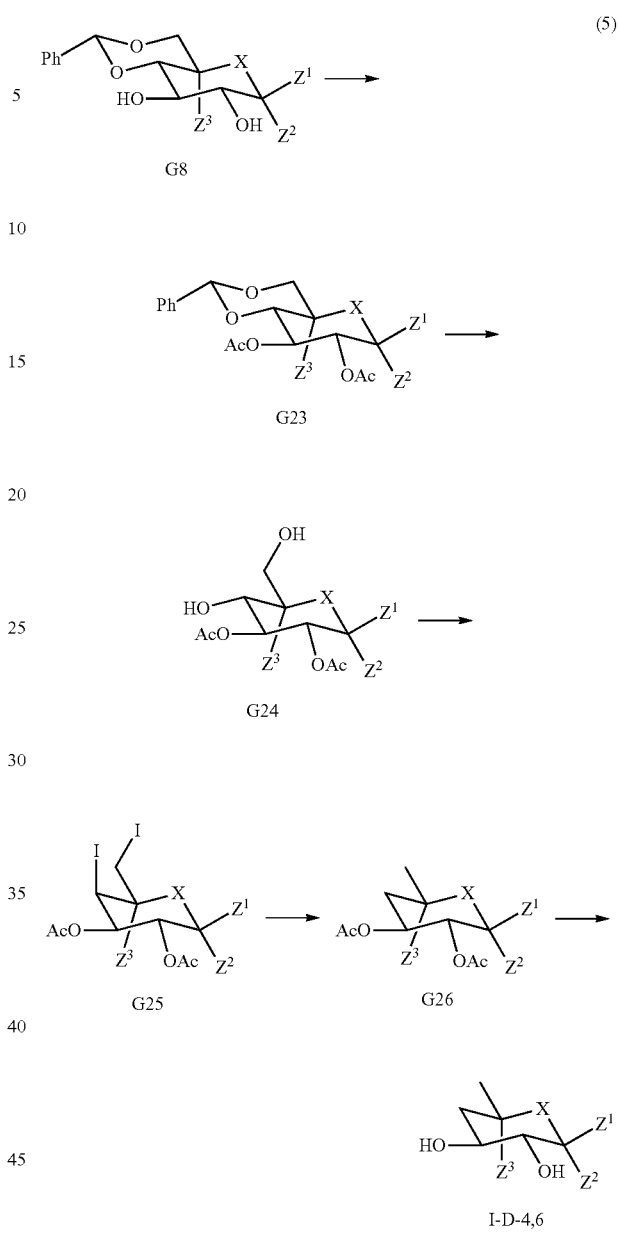

(5)

Protecting compound G8 with benzoyl chloride or p-methyl benzoyl chloride to give compound G19, PG$_4$ is selected from benzoyl or p-methyl benzoyl; converting G19 into G20 with iodizating reagent, the reagent is I$_2$/PPh$_3$/imidazole; converting G20 into G21 under reducing condition, the condition is selected from palladium-catalyzed hydrogenation or n-Bu$_3$SnH/AIBN, wherein AIBN is azodiisobutyronitrile; removing the benzoyl or p-methyl benzoyl on G21 to give G22, the condition is selected from MeONa/MeOH, NaOH/MeOH/H$_2$O, KOH/MeOH/H$_2$O, NaOH/EtOH/H$_2$O or KOH/EtOH/H$_2$O; and finally treating G22 with acid to remove the benzylidene protecting group to give I-D-2, the acid used is selected from hydrochloric acid, sulfuric acid, methanesulfonic acid, camphorsulfonic acid, trifluoroacetic acid or p-toluene sulfonic acid; wherein X is selected from O or S, Z$^1$-Z$^3$ are defined as above, I-D-2 is one of the compounds having general formula I described in the present invention.

Acetylating compound G8 to convert it into G23, the acetylation reagent is selected from acetic anhydride or acetyl chloride; and finally treating G23 with acid to remove the benzylidene protecting group to give G24, the acid used is selected from hydrochloric acid, sulfuric acid, methanesulfonic acid, camphorsulfonic acid, trifluoroacetic acid and p-toluene sulfonic acid; converting G24 into G25 with iodizating reagent, the reagent is I$_2$/PPh$_3$/imidazole; converting G25 into G26 under reducing condition, the condition is selected from palladium-catalyzed hydrogenation or n-Bu$_3$SnH/AIBN, wherein AIBN is azodiisobutyronitrile; removing acetyl on G26 to give I-D-4,6, the condition is selected from MeONa/MeOH, NaOH/MeOH/H$_2$O, KOH/MeOH/H$_2$O, NaOH/EtOH/H$_2$O or KOH/EtOH/H$_2$O; wherein X is selected from O or S, Z$^1$-Z$^3$ are defined as above, I-D-4,6 is one of the compounds having general formula I described in the present invention.

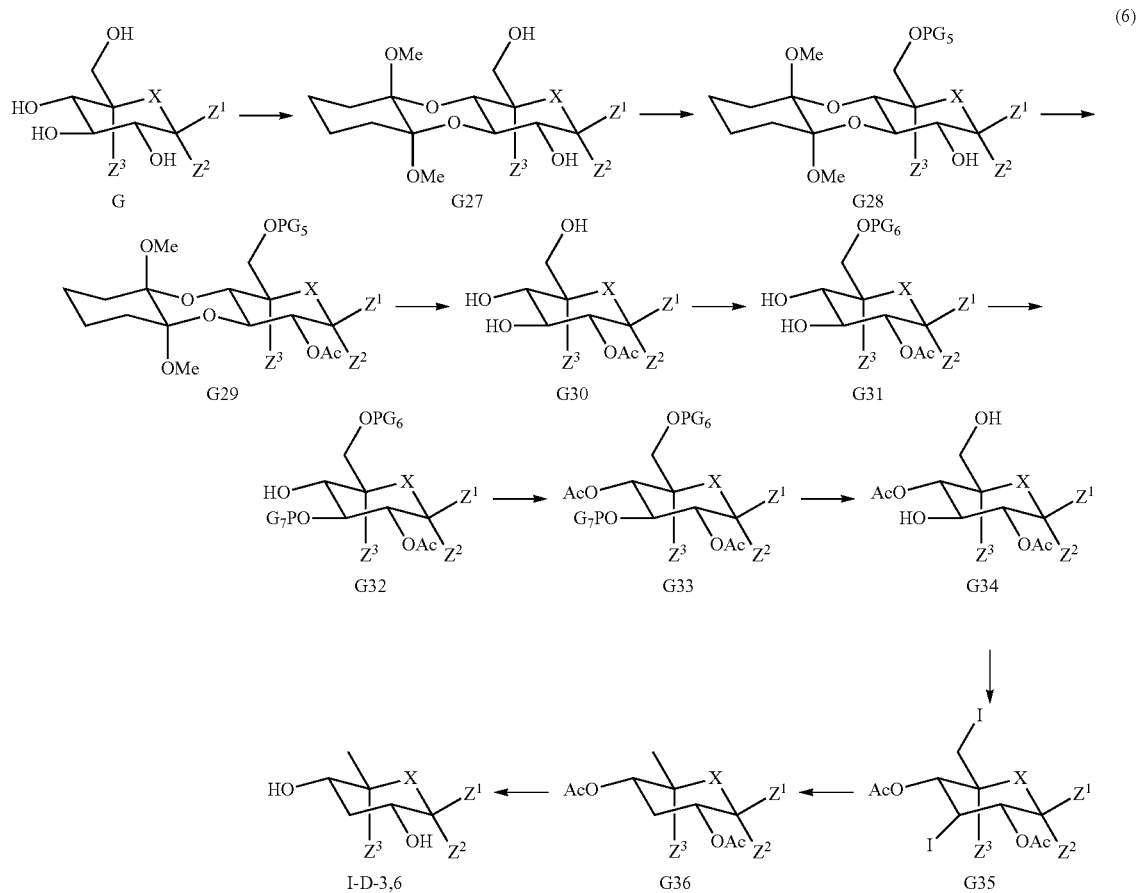

(6)

Reacting compound G with 1,1,2,2-tetramethoxy cyclohexane and trimethyl orthoformate under acid condition to give G27, the acid used is selected from hydrochloric acid, sulfuric acid, methanesulfonic acid, camphorsulfonic acid, trifluoroacetic acid or p-toluene sulfonic acid; protecting G27 with TBDMSCl or TBDPSCl to give G28, $PG_5$ is selected from TBDMS or TBDPS; acetylating compound G28 to convert it into G29, the acetylation reagent is selected from acetic anhydride or acetyl chloride; treating G29 with acid to remove the protecting groups to give G30, the acid used is selected from acetic acid or trifluoroacetic acid; protecting G30 with TBDMSCl or TBDPSCl to give G31, $PG_6$ is selected from TBDMS or TBDPS; protecting G31 with TBDMSCl or TBDPSCl to give G32, $PG_7$ is selected from TBDMS or TBDPS; acetylating compound G32 to convert it into G33, the acetylation reagent is selected from acetic anhydride or acetyl chloride; removing $PG_6$ and $PG_7$ on G33 to give G34, the reagent is selected from tetra-n-butylammonium fluoride or acetic acid; converting G34 into G35 with iodizating reagent, the reagent is $I_2/PPh_3$/imidazole; converting G35 into G36 under reducing condition, the condition is selected from palladium-catalyzed hydrogenation or n-Bu$_3$SnH/AIBN, AIBN is azodiisobutyronitrile; and finally removing the acetyl on G36 to give I-D-3,6, the condition is selected from MeONa/MeOH, NaOH/MeOH/H$_2$O, KOH/MeOH/H$_2$O, NaOH/EtOH/H$_2$O or KOH/EtOH/H$_2$O; wherein X is selected from O or S, $Z^1$-$Z^3$ are defined as above, I-D-3,6 is one of the compounds having general formula I described in the present invention.

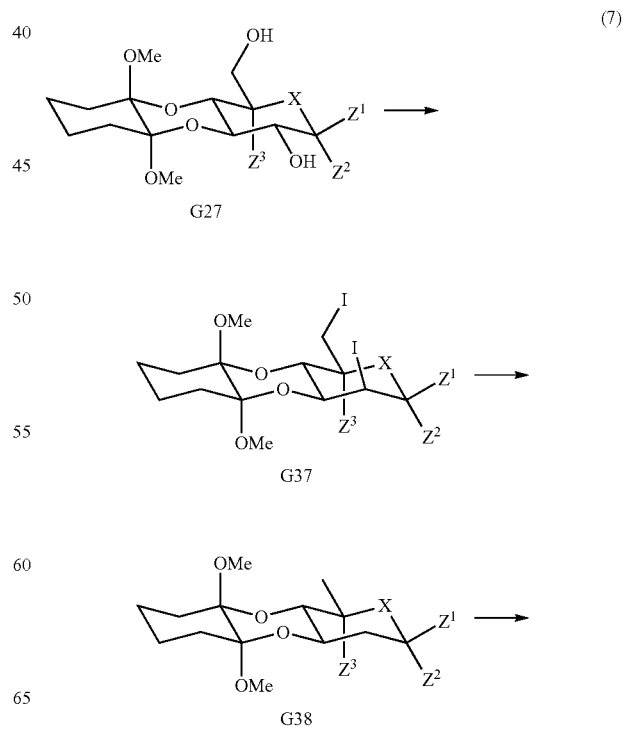

(7)

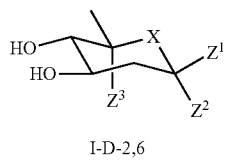

I-D-2,6

Converting compound G27 into G37 with iodizating reagent, the reagent is $I_2$/$PPh_3$/imidazole; converting G37 into G38 under reducing condition, the condition is selected from palladium-catalyzed hydrogenation or n-$Bu_3$SnH/AIBN, wherein AIBN is azodiisobutyronitrile; and finally removing the protecting groups on G38 under acid condition to give I-D-2,6, the acid used is selected from acetic acid or trifluoroacetic acid; wherein X is selected from O or S, $Z^1$-$Z^3$ are defined as above, I-D-2,6 is one of the compounds having general formula I described in the present invention.

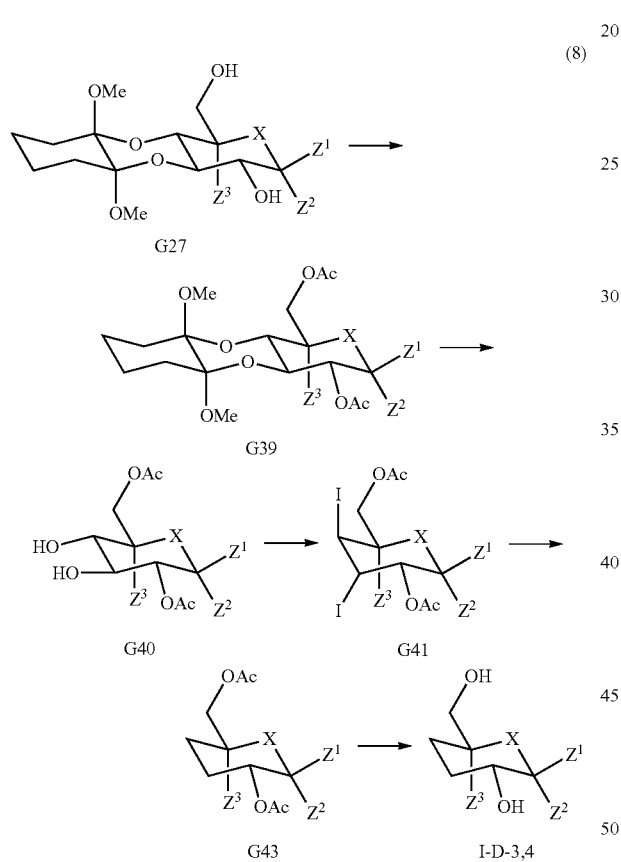

Acetylating compound G27 to convert it into G39, the acetylation reagent is selected from acetic anhydride or acetyl chloride; removing the protecting groups on G39 under acid condition to give G40, the acid used is selected from acetic acid or trifluoroacetic acid; converting G40 into G41 with iodizating reagent, the reagent is $I_2$/$PPh_3$/imidazole; converting G41 into G43 under reducing condition, the condition is selected from any one of a) $H_2$, Pd/C, b) $H_2$, Pd(OH)/C and c) $HCO_2NH_4$, Pd/C; and finally removing the acetyl on G43 to give I-D-3,4, the condition is selected from MeONa/MeOH, NaOH/MeOH/$H_2O$, KOH/MeOH/$H_2O$, NaOH/EtOH/$H_2O$ or KOH/EtOH/$H_2O$; wherein X is selected from O or S, $Z^1$-$Z^3$ are defined as above, I-D-3,4 is one of the compounds having general formula I described in the present invention.

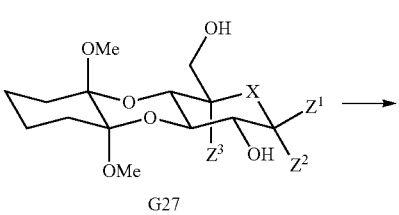

G27

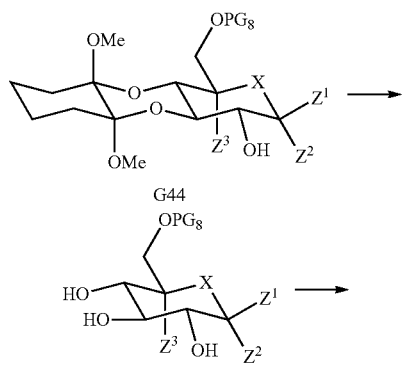

G44

G45

G46

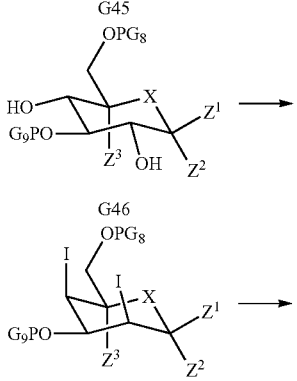

G47

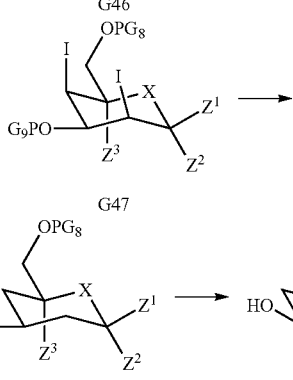

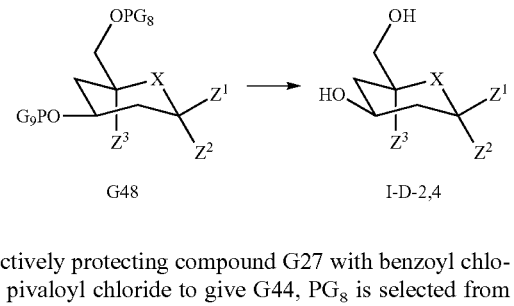

G48    I-D-2,4

Selectively protecting compound G27 with benzoyl chloride or pivaloyl chloride to give G44, $PG_8$ is selected from benzoyl or pivaloyl; removing the protecting groups on G44 under acid condition to give G45, the acid used is selected from acetic acid or trifluoroacetic acid; selectively protecting G45 with benzoyl chloride or pivaloyl chloride to give G46, $PG_9$ is selected from benzoyl or pivaloyl; converting G46 into G47 with iodizating reagent, the reagent is $I_2$/$PPh_3$/imidazole; converting G47 into G48 under reducing condition, the condition is selected from palladium-catalyzed hydrogenation or n-$Bu_3$SnH/AIBN, AIBN is azodiisobutyronitrile; and finally removing the two protecting groups $PG_8$ and $PG_9$ on G48 to give I-D-2,4, the condition is selected from MeONa/MeOH, NaOH/MeOH/$H_2O$, KOH/MeOH/$H_2O$, NaOH/EtOH/$H_2O$ or KOH/EtOH/$H_2O$; wherein X is selected from O or S, $Z^1$-$Z^3$ are defined as above, I-D-2,4 is one of the compounds having general formula I described in the present invention.

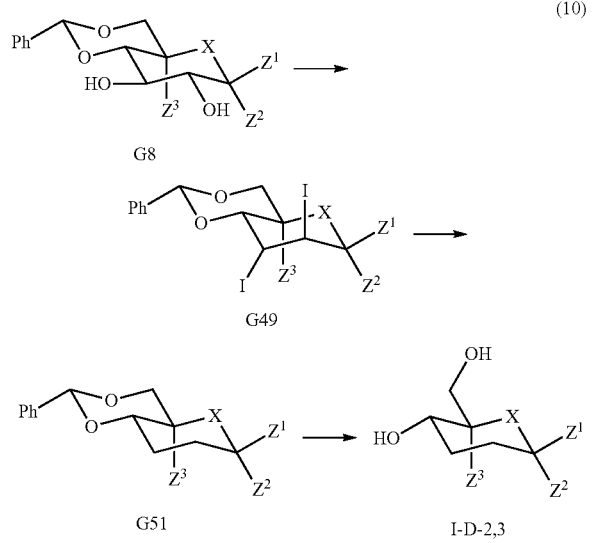

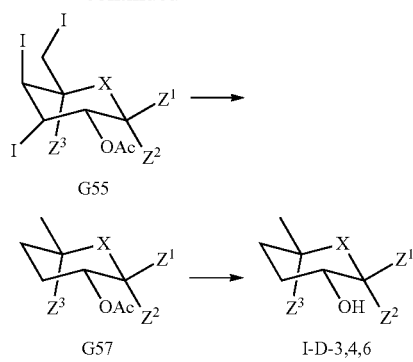

Converting G8 into G49 with iodizating reagent, the reagent is I$_2$/PPh$_3$/imidazole; converting G49 into G51 under reducing condition, the condition is selected from any one of a) H$_2$, Pd/C, b) H$_2$, Pd(OH)$_2$/C and c) HCO$_2$NH$_4$, Pd/C; and finally removing the protecting groups on G51 under acid condition to give I-D-2,3, the acid used is selected from hydrochloric acid, sulfuric acid, methanesulfonic acid, camphorsulfonic acid, trifluoroacetic acid or p-toluene sulfonic acid; wherein X is selected from O or S, Z$^1$-Z$^3$ are defined as above, I-D-2,3 is one of the compounds having general formula I described in the present invention.

Selectively protecting compound G8 with TBDMSCl, TIPSCl or TBDPSCl to give G52, PG$_{10}$ is selected from TBDMS, TIPS or TBDPS; acetylating G52 to convert it into G53, the acetylation reagent is selected from acetic anhydride or acetyl chloride; removing the benzylidene and PG$_{10}$ on G53 under acid condition to give G54, the acid used is selected from hydrochloric acid, sulfuric acid, methanesulfonic acid, camphorsulfonic acid, trifluoroacetic acid or p-toluene sulfonic acid; converting G54 into G55 with iodizating reagent, the reagent is I$_2$/PPh$_3$/imidazole; converting G55 into G57 under reducing condition, the condition is selected from any one of a) H$_2$, Pd/C, b) H$_2$, Pd(OH)$_2$/C and c) HCO$_2$NH$_4$, Pd/C; and finally removing the acetyl on G57 to give I-D-3, 4, 6, the condition is selected from MeONa/MeOH, NaOH/MeOH/H$_2$O, KOH/MeOH/H$_2$O, NaOH/EtOH/H$_2$O or KOH/EtOH/H$_2$O; wherein X is selected from O or S, Z$^1$-Z$^3$ are defined as above, I-D-3, 4, 6 is one of the compounds having general formula I described in the present invention.

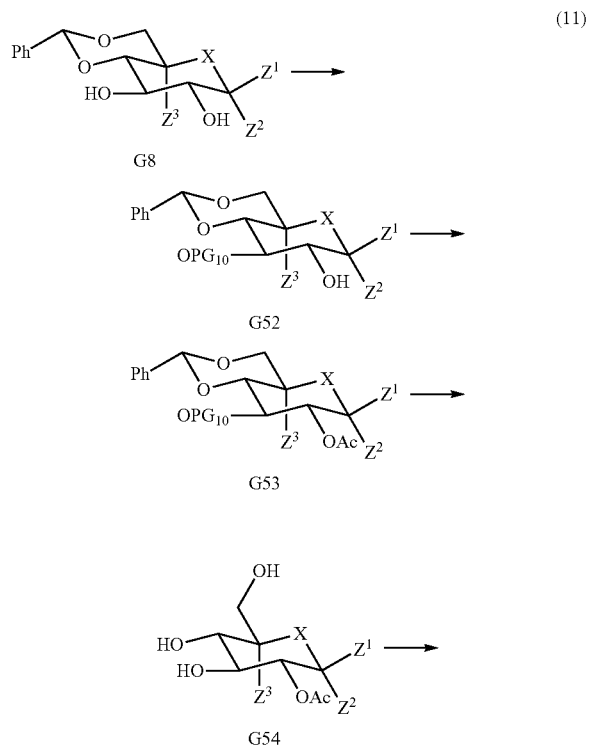

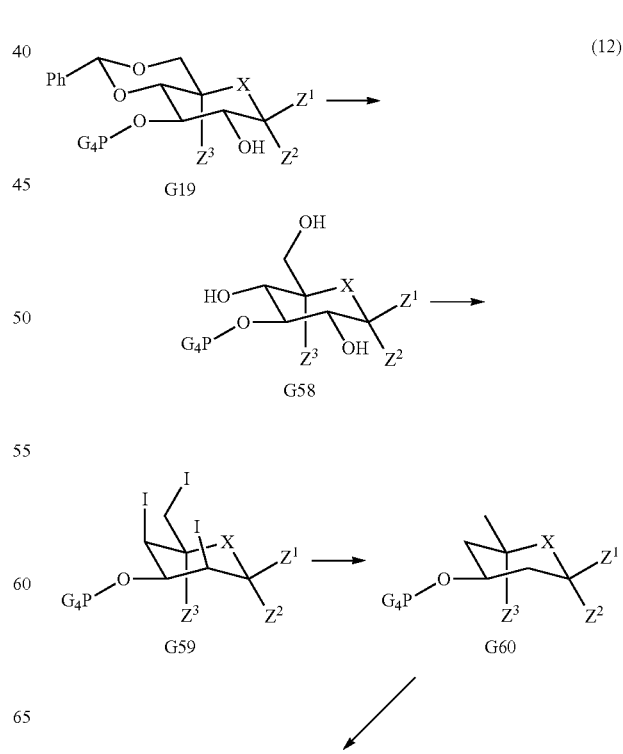

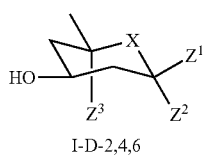

I-D-2,4,6

Removing the benzylidene on compound G19 under acid condition to give G58, the acid used is selected from hydrochloric acid, sulfuric acid, methanesulfonic acid, camphorsulfonic acid, trifluoroacetic acid or p-toluene sulfonic acid; converting G58 into G59 with iodizating reagent, the reagent is $I_2$/$PPh_3$/imidazole; converting G59 into G60 under reducing condition, the condition is selected from palladium-catalyzed hydrogenation or n-$Bu_3$SnH/AIBN, wherein AIBN is azodiisobutyronitrile; and finally removing the protecting group $PG_4$ on G60 to give I-D-2, 4, 6, the condition is selected from MeONa/MeOH, NaOH/MeOH/$H_2O$, KOH/MeOH/$H_2O$, NaOH/EtOH/$H_2O$ or KOH/EtOH/$H_2O$; wherein X is selected from O or S, $Z^1$-$Z^3$ are defined as above, I-D-2, 4, 6 is one of the compounds having general formula I described in the present invention.

(13)

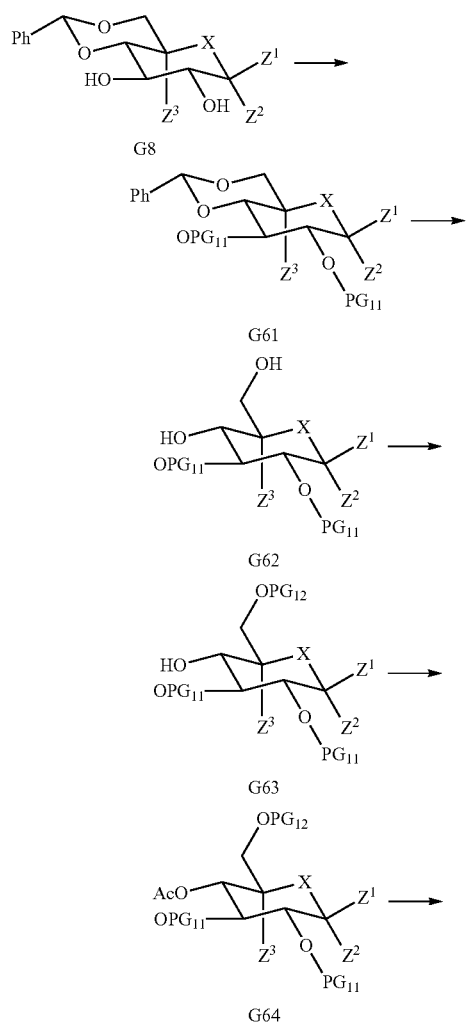

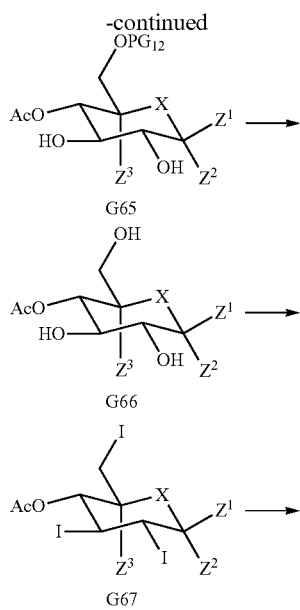

Protecting compound G8 with chloroacetyl chloride or bromoacetyl chloride to give G61, $PG_{11}$ is selected from chloracetyl or bromoacetyl; removing the benzylidene on G61 under acid condition to give G62, the acid used is selected from hydrochloric acid, sulfuric acid, methanesulfonic acid, camphorsulfonic acid, trifluoroacetic acid or p-toluene sulfonic acid; protecting G62 with TBDMSCl or TBDPSCl to give G63, $PG_{12}$ is selected from TBDMS or TBDPS; acetylating G63 to convert it into G64, the acetylation reagent is selected from acetic anhydride or acetyl chloride; treating G64 under weak alkaline condition to give G65, the weak alkaline condition is selected from NaHCO$_3$/EtOH, NaHCO$_3$/MeOH, NaOAc/EtOH or NaOAc/MeOH; treating G65 with tetra-n-butylammonium fluoride or acetic acid to remove the protecting group $PG_{12}$ to give G66; converting G66 into G67 with iodizating reagent, the reagent is $I_2$/$PPh_3$/imidazole; converting G67 under reducing condition into G69, the condition is selected from any one of a) $H_2$, Pd/C, b) $H_2$, Pd(OH)$_2$/C and c) HCO$_2$NH$_4$, Pd/C; finally removing acetyl on G69 to give I-D-2, 3, 6, the condition is selected from MeONa/MeOH, NaOH/MeOH/$H_2O$, KOH/MeOH/$H_2O$, NaOH/EtOH/$H_2O$ or KOH/EtOH/$H_2O$; wherein X is selected from O or S, $Z^1$-$Z^3$ are defined as above, I-D-2, 3, 6 is one of the compounds having general formula I described in the present invention.

(14)

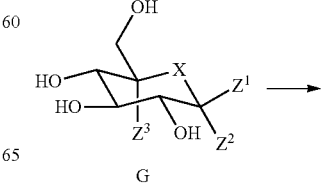

G

-continued

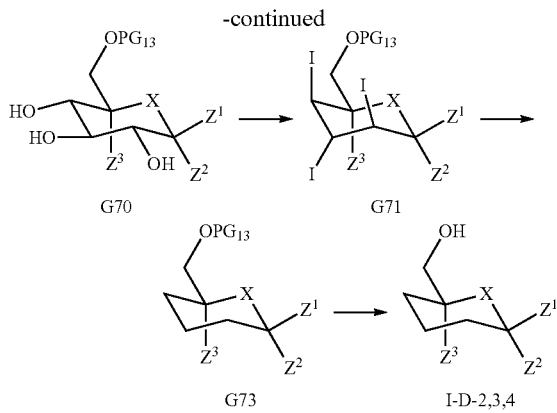

Protecting compound G with benzoyl chloride, p-methyl benzoyl chloride or pivaloyl chloride to give G70, $PG_{13}$ is selected from benzoyl, p-methyl benzoyl or pivaloyl; converting G70 with iodizating reagent into G71, the reagent is $I_2$/$PPh_3$/imidazole; converting G71 into G73 under reducing condition, the condition is selected from a) $H_2$, Pd/C, b) $H_2$, $Pd(OH)_2$/C or c) $HCO_2NH_4$, Pd/C; and finally removing the $PG_{13}$ on G73 to give I-D-2, 3, 4, the condition is selected from MeONa/MeOH, NaOH/MeOH/$H_2O$, KOH/MeOH/$H_2O$, NaOH/EtOH/$H_2O$ or KOH/EtOH/$H_2O$; wherein X is selected from O or S, $Z^1$-$Z^3$ are defined as above, I-D-2, 3, 4 is one of the compounds having general formula I described in the present invention.

(15)

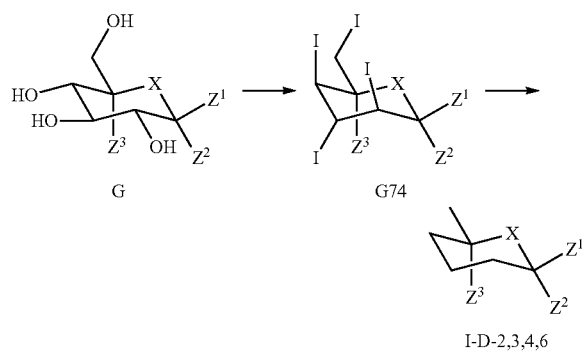

Converting compound G with iodizating reagent into G74, the reagent is $I_2$/$PPh_3$/imidazole; successively treating G74 under two different reducing conditions and ultimately getting I-D-2, 3, 4, 6, the reducing condition 1 is selected from palladium-catalyzed hydrogenation or n-$Bu_3SnH$/AIBN, wherein AIBN is azodiisobutyronitrile, and the reducing condition 2 is selected from any one of a) $H_2$, Pd/C, b) $H_2$, $Pd(OH)_2$/C, c) $HCO_2NH_4$, Pd/C; wherein X is selected from O or S, $Z^1$-$Z^3$ are defined as above, I-D-2, 3, 4, 6 is one of the compounds having general formula I described in the present invention.

The present invention also provides a pharmaceutically acceptable prodrug ester of the compound of formula I, comprising esters formed by any one or more hydroxyl groups on the molecule with acetyl, pivaloyl, various phosphoryl, aminocarbonyl, alkoxycarbonyl or the like.

The present invention also provides a pharmaceutical composition comprising a compound having general formula I or pharmaceutically acceptable prodrug ester thereof of the present invention, and one or more pharmaceutically acceptable carriers, excipients or diluents. The compound of formula I of the present invention can be formulated into a pharmaceutical composition by combining with one or more pharmaceutically acceptable carriers, excipients or diluents. The pharmaceutical composition can be formulated into solid oral preparations, liquid oral preparations, injections, and the like. The solid and liquid oral preparations include: tablets, dispersible tablets, sugar-coated tablets, granules, dry powders, capsules, and solutions. The injections include small volume injections, large infusions, lyophilized powder injections, and the like.

The pharmaceutical composition of the present invention, wherein the pharmaceutically or bromatologically acceptable adjuvants are selected from the group consisting of fillers, disintegrants, lubricants, flow aids, effervescing agents, flavoring agents, preservatives, coating materials or the other excipients.

The pharmaceutical composition of the present invention, the pharmaceutically or bromatologically acceptable adjuvants. The fillers comprise one or more of lactose, sucrose, dextrin, starch, pregelatinized starch, mannitol, sorbitol, calcium hydrophosphate, calcium sulfate, calcium carbonate, microcrystalline cellulose and combinations thereof; the adhesives comprise one or more of sucrose, starch, povidone, sodium carboxymethylcellulose, hydroxypropylmethyl cellulose, hydroxypropyl cellulose, methyl cellulose, polyglycol, ethanol for medical use, water and combinations thereof; the disintegrants comprise one or more of starch, crosslinked povidone, crosslinked sodium carboxymethyl cellulose, low substituted hydroxypropyl cellulose, sodium carboxymethyl cellulose, effervescent disintegrant and combinations thereof.

The present invention also provides use of a compound of general formula I or pharmaceutically acceptable prodrug esters thereof in the preparation of drugs for inhibiting SGLT2 enzyme. The present invention also provides use of a compound of general formula I or pharmaceutically acceptable prodrug esters thereof in the preparation of drugs for treating diabetes. The compound of general formula I of the present invention have inhibitory effect on SGLT2 enzyme, and can be used as an active ingredient for preparing drugs for treating diabetes. The activity of the compound of general formula I of the present invention is verified by a model for urine glucose excretion.

The present invention also provides a method for treating diabetes, the method comprises administering the compound having general formula I or the pharmaceutically acceptable prodrug ester thereof of the present invention to a patient in need of treatment. The compound of general formula I of the present invention is effective in a broad range of dosage. For example, the daily dosage is in a range of about 1 mg-500 mg/person, either in a single dose or multiple doses.

The actual administered dosage of the compound of the general formula I of the present invention can be determined by doctors according to the related conditions. Such conditions include the physical status of the subjects being treated, the administration routes, ages, weights, personal reaction to the drugs, the severity of the symptoms and the like.

The present inventors found in the further studies that the method for preparing compound (1S)-1-[4-chloro-3-(4-ethoxybenzyl)phenyl]-1,6-dideoxy-D-glucose (for convenient description, hereinafter referred to as I-D1-6) uses dapagliflozin as raw material (shown as the formula below). Such route is of high cost in the industrialized scale due to the high price of dapagliflozin.

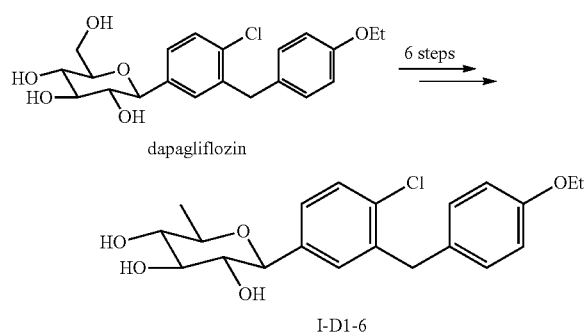

dapagliflozin

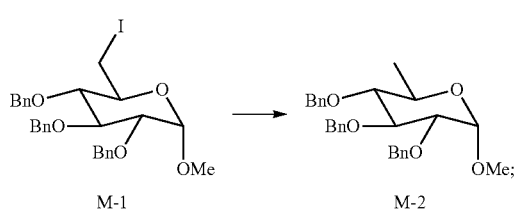

I-D1-6

Therefore, the present invention also provides a new method for synthesizing the compound I-D1-6. The method has advantages of being simple to manage and having low cost, which is suitable for large-scale industrial production of I-D1-6.

The present invention provides a method for synthesizing (1S)-1-[4-chloro-3-(4-ethoxybenzyl)phenyl]-1,6-dideoxy-D-glucose, the method comprises:

(1) using compound M-1 as a starting material, removing the iodine on compound M-1 to obtain compound M-2,

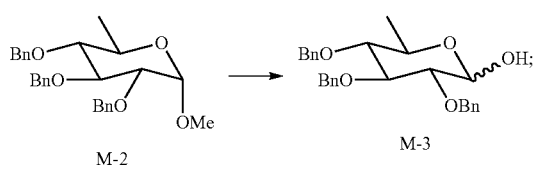

(2) acidic hydrolyzing compound M-2 to remove the methyl to give compound M-3,

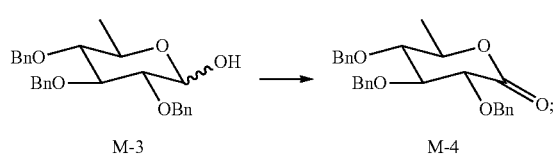

(3) oxidizing compound M-3 to give compound M-4,

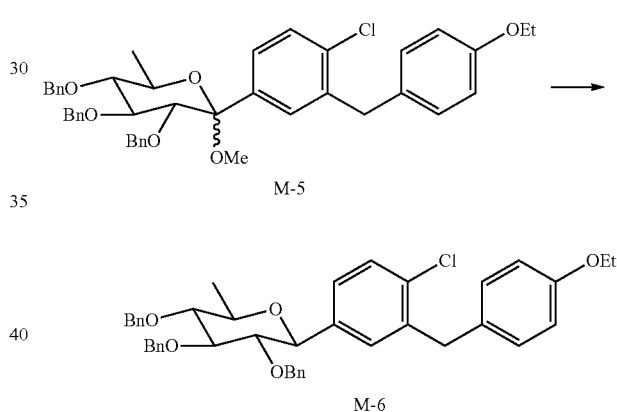

(4) treating (2-chloro-5-bromophenyl)(4-ethoxyphenyl) methane with alkyl lithium reagent or metal magnesium to give corresponding aryllithium or arylmagnesium, and then reacting it with compound M-4 to give an addition product M-5', reacting compound M-5' with methanol under acid catalyzing to give compound M-5,

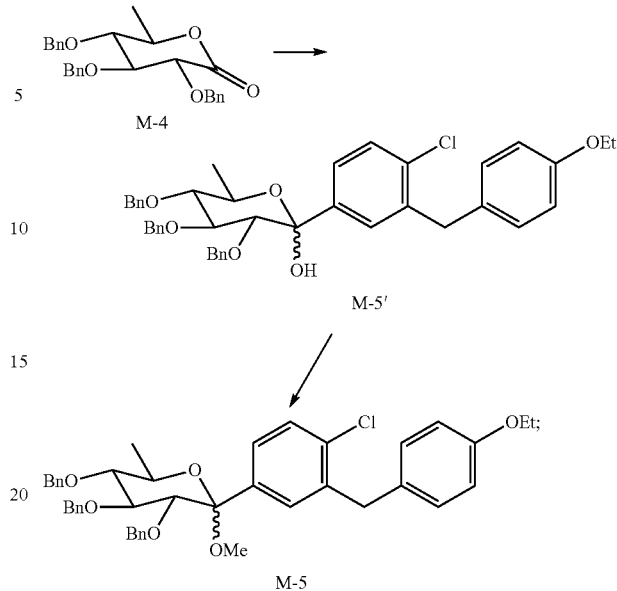

(5) reducing compound M-5 to give compound M-6,

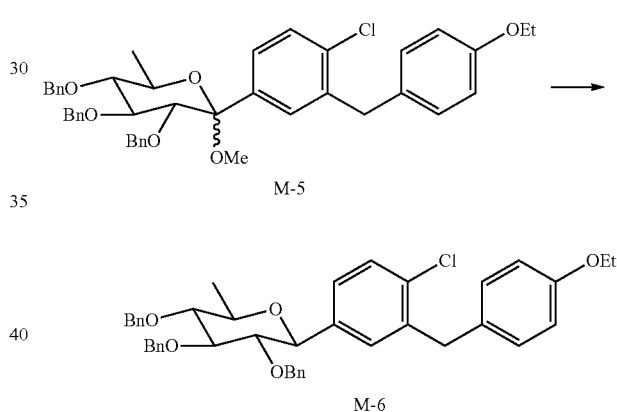

(6) acetolyzing compound M-6 to convert it into compound M-7,

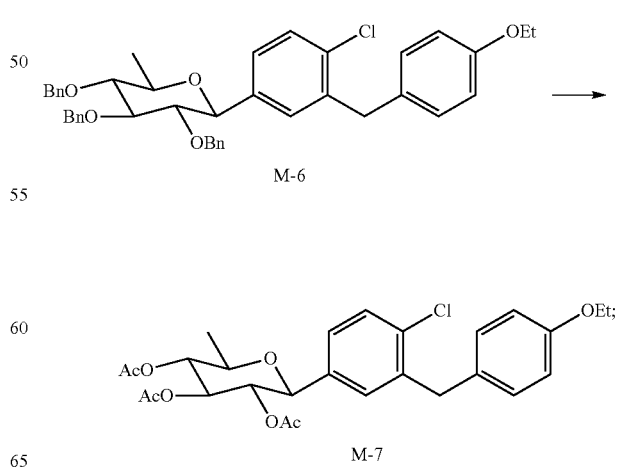

(7) deacetylating compound M-7 to give a product of I-D1-6,

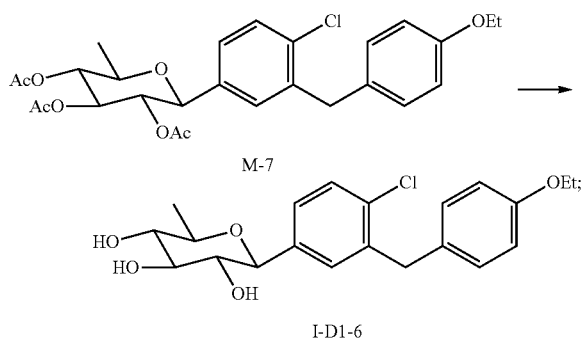

wherein, optionally, the steps (6) and (7) can be replaced by steps (6') and (7'):

(6') debenzylating compound M-6 to convert it into crude I-D1-6,

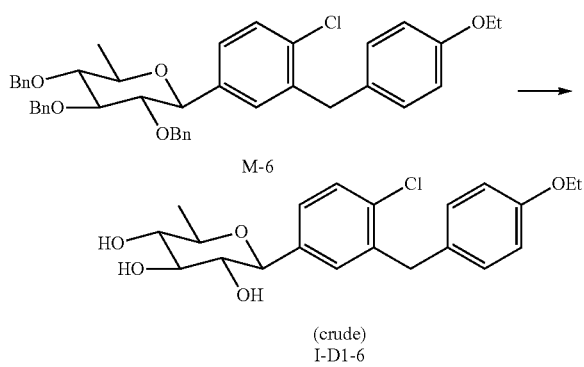

(7') acylating the crude I-D1-6 to give compound M-7', and then deacylating compound M-7' to give product I-D1-6, wherein $R^2$ in formula M-7' represents acetyl, benzoyl, or p-methylbenzoyl.

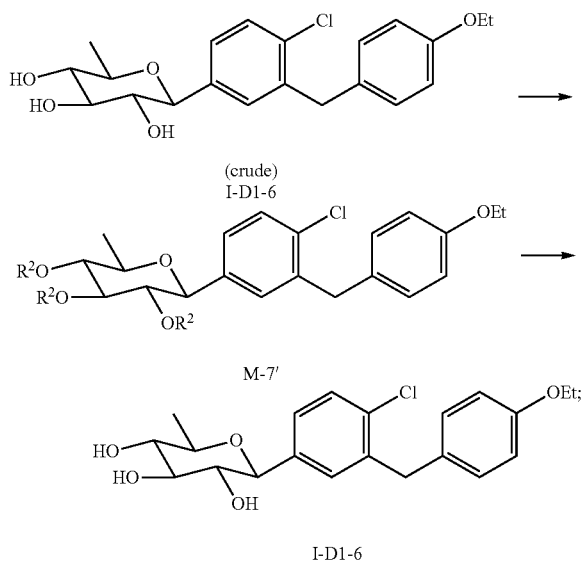

optionally, the step (7') can be replaced by step (7"):

(7") directly purifying the crude product of I-D1-6 to give product I-D1-6, wherein Bn in the formulae M-1, M-2, M-3, M-4, M-5, M-5' and M-6 represents benzyl, Me in the formulae M-1, M-2 and M-5 represents methyl, Et in the formulae M-5, M-5', M-6, M-7 and I-D1-6 represents ethyl, Ac in the formula M-7 represents acetyl.

According to the synthetic method provided by the present invention, wherein removing the iodine in step (1) is performed under the conditions selected from: (a) n-Bu$_3$SnH/AIBN, wherein n-Bu$_3$SnH is a reducing agent with an amount of 1.0-20 equivalent, AIBN is a catalyst with an amount of 0.1-10.0 equivalent, wherein AIBN is azodiisobutyronitrile; (b) TMS$_3$SiH/AIBN, wherein TMS$_3$SiH is a reducing agent with an amount of 1.0-20 equivalent, AIBN is a catalyst with an amount of 0.1-10.0 equivalent, wherein AIBN is azodiisobutyronitrile; (c) LiAlH$_4$, the amount of which is 1.0-20 equivalent; and (d) catalytic hydrogenation, the catalyst used is selected from Pd/C and Pd(OH)$_2$, the hydrogen source is selected from hydrogen gas, formic acid, ammonium formate and cyclohexene, preferably a catalytic hydrogenation using Pd/C as catalyst.

Preferably, the acidic hydrolyzing in step (2) is performed under the following conditions: heating M-2 in a solvent in the presence of an acid, the acid is selected from hydrochloric acid, hydrobromic acid, sulfuric acid, perchloric acid, trifluoroacetic acid, trichloroacetic acid, methanesulfonic acid and trifluoromethanesulfonic acid, preferably hydrochloric acid, the concentration of HCl in the final reaction solution is preferably 0.5-2.0 M; the solvent is selected from water, C$_1$-C$_5$ alcohols, acetic acid, acetone and butanone, preferably acetic acid.

Preferably, the oxidization in step (3) is performed under the conditions selected from: (a) Ac$_2$O/DMSO, wherein Ac$_2$O is 2.0-50 equivalent, DMSO is 5.0-50 equivalent, and equivalent of DMSO is more than that of Ac$_2$O; and (b) (COCl)$_2$/DMSO/Et$_3$N, has a equivalent ratio of (COCl)$_2$:DMSO:Et$_3$N=1:2:3-5, as a whole, the ratio of the three agents to the substrate is 1-5:1, preferably Ac$_2$O/DMSO, wherein DMSO is dimethyl sulfoxide.

Preferably, in step (4), the alkyl lithium is selected from n-butyl lithium, tert-butyl lithium, sec-butyl lithium and isobutyl lithium, the acid is selected from hydrochloric acid, hydrobromic acid, sulfuric acid, perchloric acid, trifluoroacetic acid, trichloroacetic acid, methanesulfonic acid and trifluoromethanesulfonic acid.

Preferably, the reducing condition in step (5) is reducing the M-5 compound with Et$_3$SiH in the presence of a lewis acid which is selected from BF$_3$-Et$_2$O, AlCl$_3$, SnCl$_2$, SnCl$_4$, ZnCl$_2$ and trimethylsilyl trifluoromethanesulfonate (TMSOTf), preferably BF$_3$-Et$_2$O.

Preferably, the reaction condition in step (6) is lewis acid/Ac$_2$O, wherein the lewis acid is selected from BF$_3$-Et$_2$O and TMSOTf. That is, acetolyzing the compound of formula M-6 with Ac$_2$O in the presence of BF$_3$-Et$_2$O or TMSOTf.

Preferably, the deacetylating in step (7) is performed under the conditions selected from: (a) MOH/protic solvent/H$_2$O, wherein MOH is selected from NaOH, KOH and LiOH; protic solvent is selected from MeOH, EtOH, isopropanol and propanol; (b) NaOR/ROH, wherein R is selected from Me, EtOH, n-Pr and i-Pr; and (c) R$^1$NH$_2$/protic solvent, wherein R$^1$ is selected from H, Me and Et, the protic solvent is selected from MeOH, EtOH, isopropanol, n-propanol and tert-butanol.

Preferably, the debenzylating in step (6') is performed under the conditions selected from: (a) AlCl₃/anisole (the solvent is anisole, and the reagent is AlCl₃); (b) trifluoromethanesulfonic acid/trifluoroacetic acid/dimethyl sulfide/m-cresol/1,2-ethanedithiol; (c) iodotrimethylsilane; (d) BCl₃; and (e) catalytic hydrogenation, the catalyst is selected from Pd/C and Pd(OH)₂.

Preferably, the acylating in step (7') is performed under the conditions selected from: (a) Ac₂O/pyridine, optionally adding DMAP (4-dimethylaminopyridine) as a catalyst; (b) AcONa/Ac₂O; (c) AcCl (acetyl chloride)/organic base; (d) benzoyl chloride/organic base; and (e) p-methyl benzoyl chloride/organic base, wherein the organic base is selected from triethylamine, pyridine, methylpyridine, dimethyl pyridine and trimethyl pyridine.

Preferably, the deacylating in step (7') is performed under the conditions selected from: (a) MOH/protic solvent/H₂O, wherein MOH is selected from NaOH, KOH and LiOH, the protic solvent is selected from MeOH, EtOH, isopropanol and propanol; (b) NaOR/ROH, R is selected from Me, EtOH, n-Pr and i-Pr; and (c) R¹NH₂/protic solvent, wherein R¹ is selected from H, Me and Et, the protic solvent is selected from MeOH, EtOH, isopropanol, n-propanol and tert-butanol.

Preferably, the method for purification in step (7") is selected from recrystallization, column chromatography and combination of recrystallization and column chromatography.

Unless otherwise specified, in the present invention, when describing a certain reagent, symbol "/" between various materials represents a relation of "and".

Unless otherwise stated, in the present invention, the abbreviations of substituents used have common meanings in the art, wherein Bn represents benzyl, Me represents methyl, Et represents ethyl, Ac represents acetyl, n-Pr represents n-propyl, i-Pr represents isopropyl, n-Bu represents n-butyl, and TMS represents trimethylsily.

Specifically, the flow chart of the synthetic method of the present invention may be represented as follows:

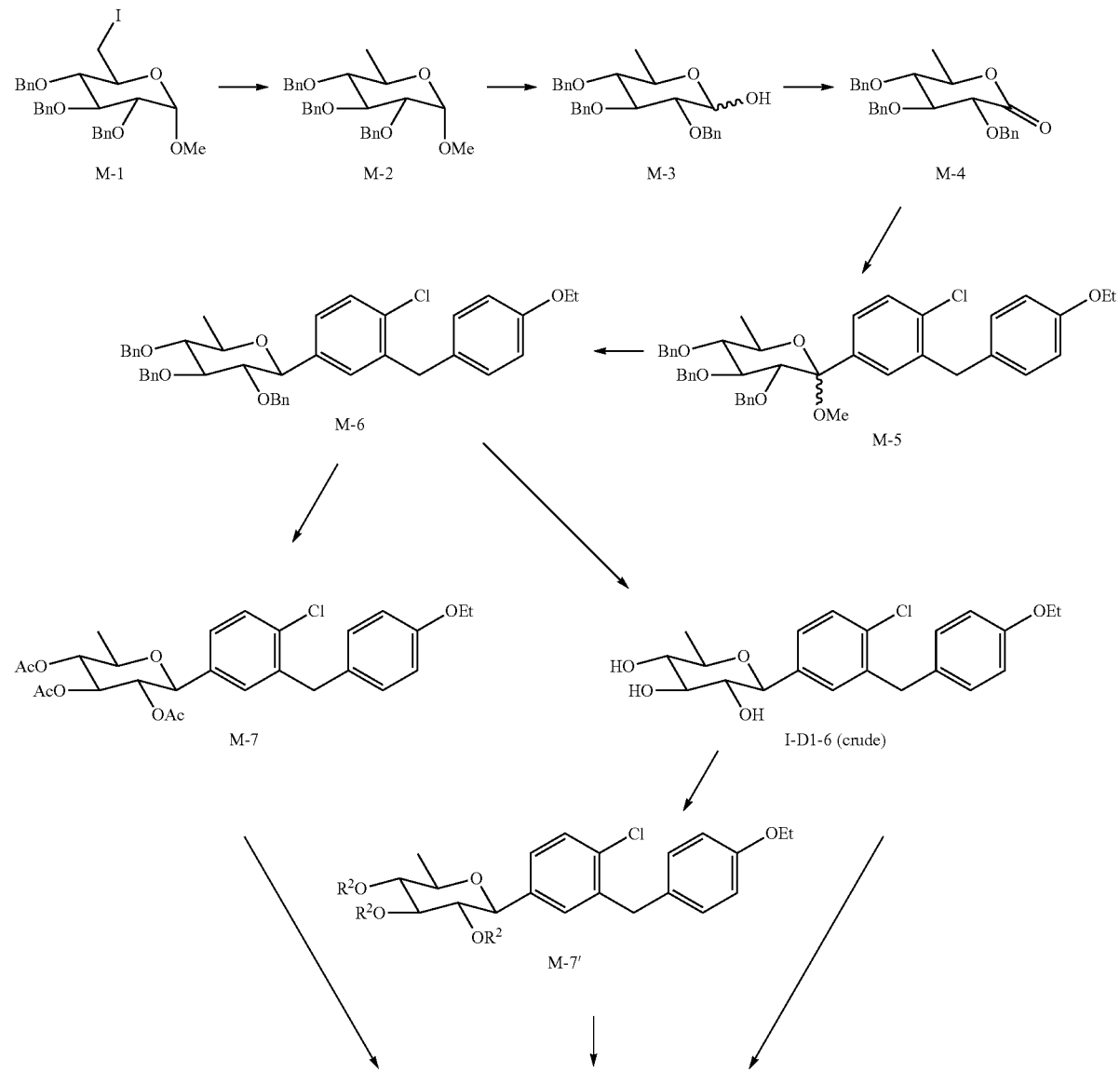

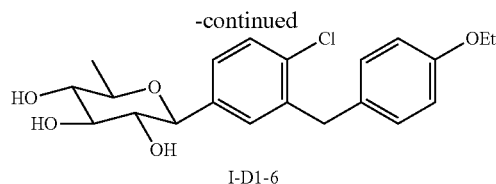
I-D1-6

Each step of reaction of the route for synthesizing I-D1-6 as illustrated above is described as follows:
(1) Step 1:

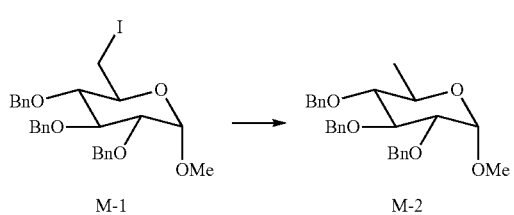

The raw material of this route is compound M-1, which is a known compound and can be synthesized according to the method in the literature (*Synthesis*, 2002, 1721-1727; *Synthesis*, 2000, 1027-1033; *Tetrahedron Lett.*, 1982, 23, 5327-5330).

After removing the iodine on M-1, compound M-2 is obtained. The condition of removing the iodine is selected from: 1) n-Bu$_3$SnH/AIBN, AIBN is azodiisobutyronitrile; 2) TMS$_3$SiH/AIBN; 3) LiAlH$_4$; 4) catalytic hydrogenation, the catalyst is selected from Pd/C and Pd(OH)$_2$, and the hydrogen source is selected from hydrogen gas, formic acid, ammonium formate, cyclohexene and the like. The reducing condition described above is preferably a catalytic hydrogenation using Pd/C as catalyst.

(2) Step 2:

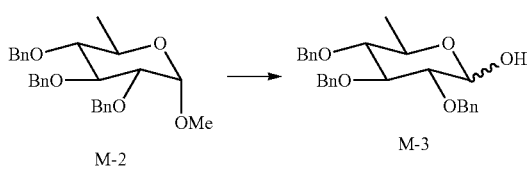

M-2 is acidic hydrolyzed to remove the methyl to give M-3. The acidic hydrolyzing condition is heating M-2 in a solvent in the presence of acid, the acid is selected from hydrochloric acid, hydrobromic acid, sulfuric acid, perchloric acid, trifluoroacetic acid, trichloroacetic acid, methanesulfonic acid, trifluoromethanesulfonic acid and the like, preferably hydrochloric acid; the solvent is selected from water, C$_1$-C$_5$ alcohol, acetic acid, acetone, butanone, preferably acetic acid.

(3) Step 3:

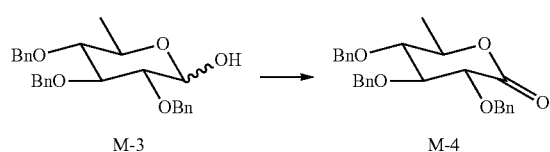

M-3 is oxidized into M-4. The oxidization condition is selected from: 1) Ac$_2$O/DMSO; 2) (COCl)$_2$/DMSO/Et$_3$N, preferably Ac$_2$O/DMSO.

(4) Step 4:

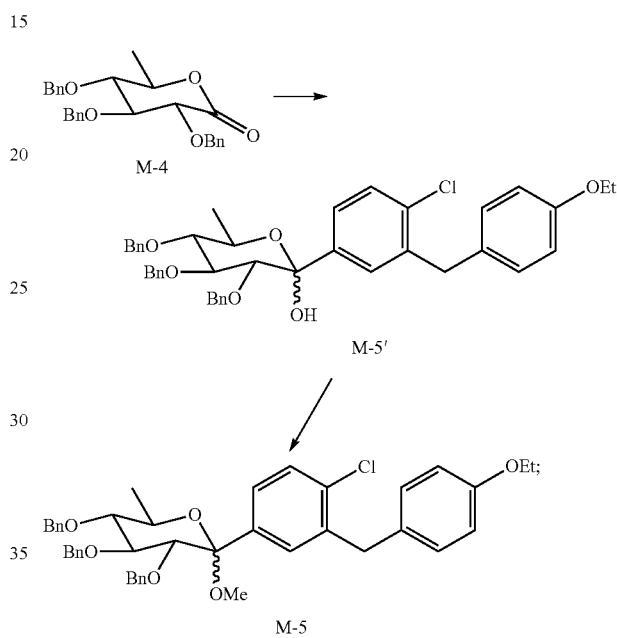

M-4 is converted into M-5. Firstly, (2-chloro-5-bromophenyl)(4-ethoxyphenyl)methane is treated with about 1 equivalent of alkyl lithium reagents or metal magnesium to give corresponding aryllithium or arylmagnesium, and then reacted with M-4 to give the addition product M-5', and the latter is reacted with methanol under acid catalyzing to give M-5. The alkyl lithium is selected from n-butyl lithium, tert-butyl lithium, sec-butyl lithium, isobutyl lithium.

(5) Step 5:

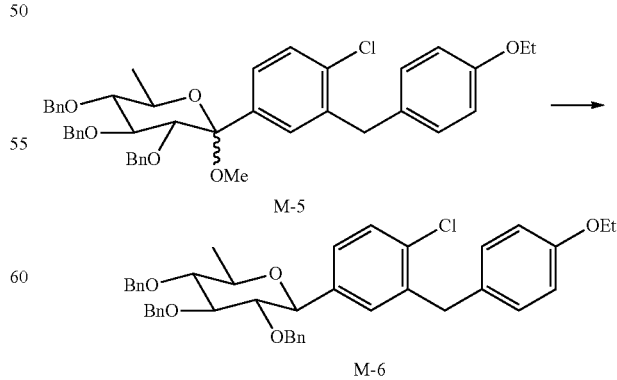

M-5 is reduced to give M-6. The reducing condition is reducing with Et$_3$SiH in the presence of a lewis acid which is selected from BF$_3$-Et$_2$O, AlCl$_3$, SnCl$_2$, SnCl$_4$, ZnCl$_2$, TMSOTf, preferably BF$_3$-Et$_2$O.

(6) Step 6:

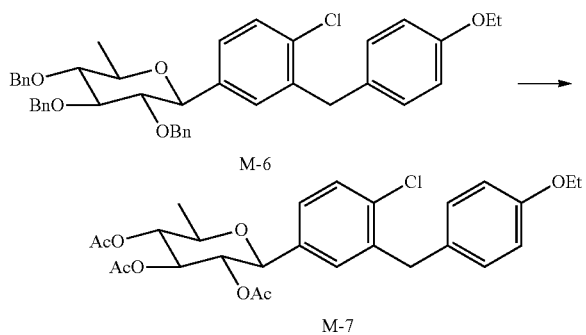

M-6 is acetolyzed to convert it into M-7. The reaction condition is under a lewis acid/Ac$_2$O, wherein the lewis acid is selected from BF$_3$-Et$_2$O and TMSOTf.

(7) Step 7:

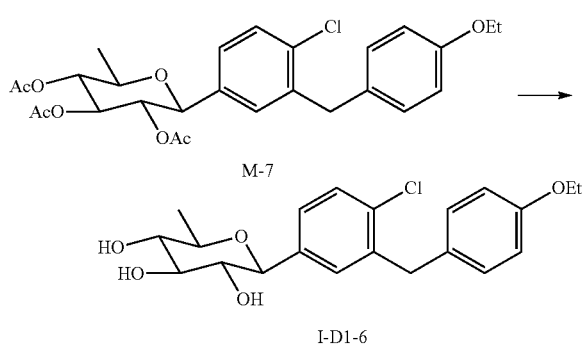

M-7 is deacetylated to give product I-D1-6. The deacetylation condition is selected from: 1) MOH/protic solvent/H$_2$O, wherein MOH is selected from NaOH, KOH, LiOH, the protic solvent is selected from MeOH, EtOH, isopropanol, propanol; 2) NaOR/ROH, R is selected from Me, EtOH, n-Pr and i-Pr; 3) R$^1$NH$_2$/protic solvent, wherein R$^1$ is selected from H, Me and Et, the protic solvent is selected from MeOH, EtOH, isopropanol, n-propanol and tert-butanol.

(8) Step 8:

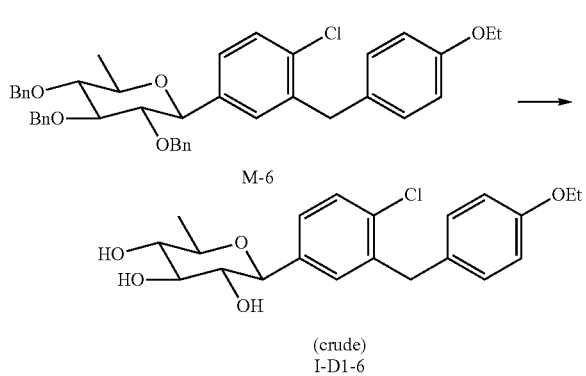

M-6 is debenzylated to convent it into crude I-D1-6. The debenzylation condition is selected from: 1) AlCl$_3$/anisole; 2) trifluoromethanesulfonic acid/trifluoroacetic acid/dimethyl sulfide/m-cresol/1,2-ethanedithiol; 3) iodotrimethylsilane; 4) BCl$_3$; 5) catalytic hydrogenation, the catalyst is selected from Pd/C and Pd(OH)$_2$. The crude I-D1-6 has more impurities than that of I-D1-6 prepared from pure M-7 in step (7). More creative work should be paid for the purification step.

(9) Step 9:

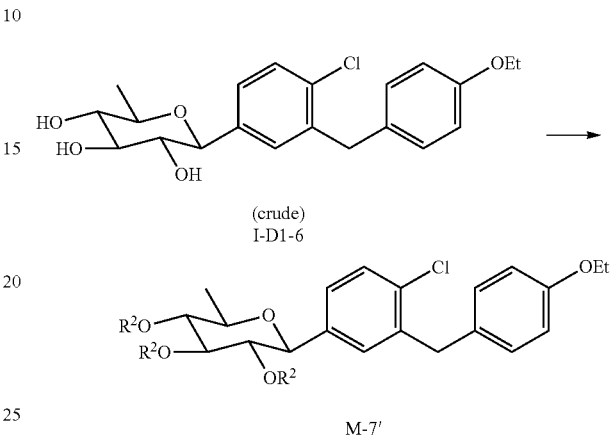

The crude I-D1-6 is acylated to give M-7', R$^2$ is selected from acetyl, benzoyl, p-methyl benzoyl and the like, the acylation condition is selected from: 1) Ac$_2$O/pyridine, DMAP (4-dimethylaminopyridine) etc. may be added as catalyst; 2) AcONa/Ac$_2$O; 3) AcCl/organic base; 4) benzoyl chloride/organic base; 5) p-methyl benzoyl chloride/organic base and the like. The organic base is selected from triethylamine, pyridine, methylpyridine, dimethyl pyridine and trimethyl pyridine and the like.

(10) Step 10:

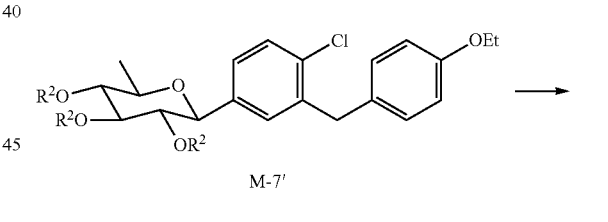

The product I-D1-6 may also be obtained by deacylating M-7'. The deacylation condition is selected from: 1) MOH/protic solvent/H$_2$O, wherein MOH is selected from NaOH, KOH, LiOH, the protic solvent is selected from MeOH, EtOH, isopropanol, propanol; 2) NaOR/ROH, R is selected from Me, EtOH, n-Pr and i-Pr; 3) R$^1$NH$_2$/protic solvent, wherein R$^1$ is selected from H, Me and Et, the protic solvent is selected from MeOH, EtOH, isopropanol, n-propanol, tert-butanol.

(11) Step 11:

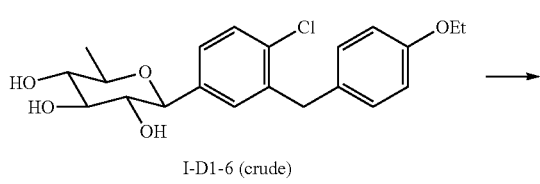

I-D1-6 (crude)

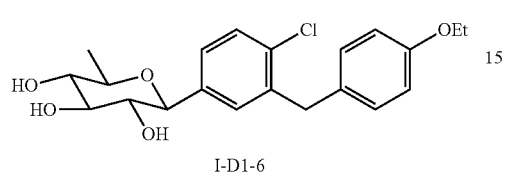

I-D1-6

The crude I-D1-6 is purified directly to give pure I-D1-6. The method for purification is selected from recrystallization, column chromatography, combination of recrystallization and column chromatography, and the like.

The present invention also provides intermediates for preparing the compound (1S)-1-[4-chloro-3-(4-ethoxybenzyl)phenyl]-1,6-dideoxy-D-glucose (I-D1-6).

Specifically, the present invention also provides a compound of formula M-7':

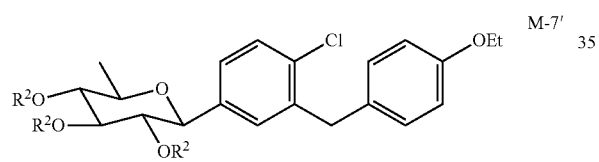

wherein $R^2$ is acetyl, benzoyl or p-methyl benzoyl.

According to the compound described above, wherein $R^2$ is preferably acetyl, the structural formula of the compound is shown as formula M-7:

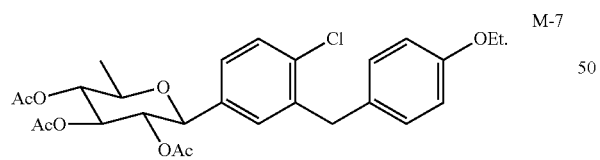

The present invention also provides a compound of formula M-6:

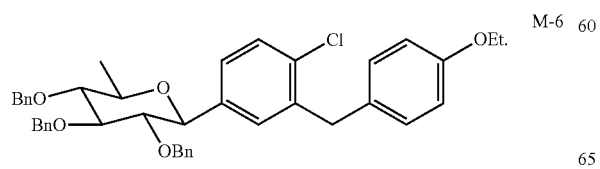

The present invention also provides a compound of formula M-5:

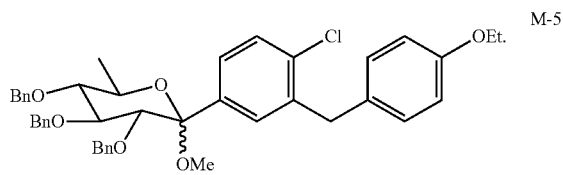 [SMILES: CCOc1ccc(Cc2cc(C3(OC)OC(C)C(OCc4ccccc4)C(OCc4ccccc4)C3OCc3ccccc3)ccc2Cl)cc1]

The present invention also provides a compound of formula M-5':

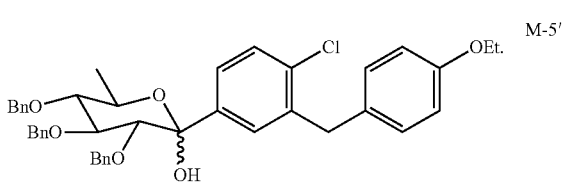 [SMILES: CCOc1ccc(Cc2cc(C3(O)OC(C)C(OCc4ccccc4)C(OCc4ccccc4)C3OCc3ccccc3)ccc2Cl)cc1]

The present invention also provides a compound of formula M-4:

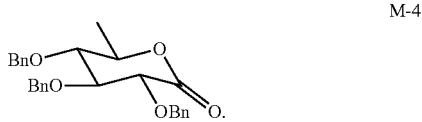 [SMILES: CC1OC(=O)C(OCc2ccccc2)C(OCc2ccccc2)C1OCc1ccccc1]

The present invention also provides a compound of formula M-3:

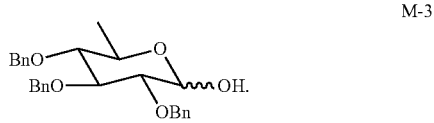 [SMILES: CC1OC(O)C(OCc2ccccc2)C(OCc2ccccc2)C1OCc1ccccc1]

The present invention also provides a compound of formula M-2:

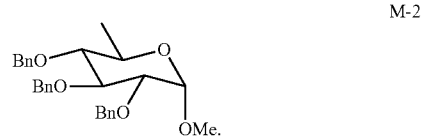 [SMILES: COC1OC(C)C(OCc2ccccc2)C(OCc2ccccc2)C1OCc1ccccc1]

The new synthetic method of compound I-D1-6 provided in the present invention has advantage of being simple to handle and of low cost, which is suitable for large-scale industrial production of I-D1-6.

The present inventors have done a lot of researches on (1S)-1-[4-chloro-3-(4-ethoxybenzyl)phenyl]-1,6-dideoxy-D-glucose (for convenient description, referred to as I-D1-6 hereinafter) as a Na+-glucose cotransporter 2 inhibitor. The compound may be used to prepare a pharmaceutical composition for treating diabetes.

During the study, the present inventors found that the later period of last step of preparing compound I-D1-6 as described above is isolating from the solution by evaporating solvents to dryness to obtain a product which is a solid substance in a form between white foam and white solid, and such state is unstable between various batches and is difficult to keep a constant appearance, thus is not suitable for being used directly as a raw medicine. Meanwhile, such compound usually exhibits some foam characteristic, thereby making further purification difficult, which brings about some difficulties in the preparation of raw medicine with high purity.

Therefore, the purpose of the present invention is to overcome the defects described above and provide a cocrystal of I-D1-6 and L-proline. The cocrystal has stable appearance status, which will help to further improve the purity of I-D1-6, and increase the storage stability, which can supply steadily for the preparation of the drug substance. Furthermore, the present invention also provides a preparation method and use of this crystal form, as well as a pharmaceutical composition comprising the crystal form.

The chemical structural formula of this cocrystal is as follows:

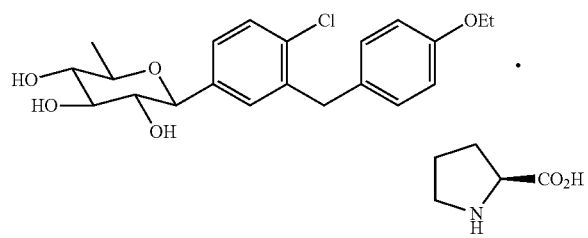

The present invention provides a cocrystal of (1S)-1-[4-chloro-3-(4-ethoxybenzyl) phenyl]-1,6-dideoxy-D-glucose (I-D1-6) and L-proline, the Powder X-ray Diffraction (PXRD) represented by 2θ angle has diffraction peaks near 4.74, 7.32, 9.74, 14.28, 16.46, 17.60, 18.70, 19.52, 20.62, 21.58, 23.02, 23.50, 26.30, 27.90.

According to the cocrystal of the present invention, wherein the Powder X-ray Diffraction of the cocrystal has diffraction peaks near the positions where the interplanar spacing d values are 18.63, 12.07, 9.07, 6.20, 5.38, 5.04, 4.74, 4.54, 4.30, 4.11, 3.86, 3.78, 3.39, 3.20 Å. Preferably, there may be following corresponding relations between the interplanar spacing d value and 2θ angle:

| 2θ (°) | d (Å) |
| --- | --- |
| 4.74 | 18.63 |
| 7.32 | 12.07 |
| 9.74 | 9.07 |
| 14.28 | 6.20 |
| 16.46 | 5.38 |
| 17.60 | 5.04 |
| 18.70 | 4.74 |
| 19.52 | 4.54 |
| 20.62 | 4.30 |
| 21.58 | 4.11 |
| 23.02 | 3.86 |
| 23.50 | 3.78 |
| 26.30 | 3.39 |
| 27.90 | 3.20 |

According to the cocrystal of the present invention, wherein the Differential Thermal Analysis (DTA) spectra of the cocrystal may have an endothermic peak at 170° C.

According to the cocrystal of the present invention, wherein the Powder X-Ray Diffraction spectra of the cocrystal is basically as shown in FIG. 2.

The present invention also provides a preparation method of the cocrystal described above, the method comprises: dissolving L-proline and water in ethanol to obtain a mixture solution containing L-proline, to which the solution of (1S)-1-[4-chloro-3-(4-ethoxybenzyl)phenyl]-1,6-dideoxy-D-glucose in ethanol is added under constant stirring until crystallization, collecting the crystals by suction filtration, after which drying to obtain the cocrystal.

According to the method of the present invention, wherein in the mixture solution containing L-proline, the mass-to-volume ratio (g/ml) of L-proline to water is 4: 0-4, preferably 4: 3-3.5; the mass-to-volume ratio (g/ml) of L-proline to ethanol is 4: 30-60, preferably 4: 33-40; preferably, in the solution of (1S)-1-[4-chloro-3-(4-ethoxybenzyl)phenyl]-1,6-dideoxy-D-glucose in ethanol, the mass-to-volume ratio (g/ml) of (1S)-1-[4-chloro-3-(4-ethoxybenzyl)phenyl]-1,6-dideoxy-D-glucose to ethanol is 1: 15-25, preferably 1:20; more preferably, the mass ratio (g/g) of (1S)-1-[4-chloro-3-(4-ethoxybenzyl)phenyl]-1,6-dideoxy-D-glucose to L-proline is 10: 3-6, preferably 10:6.

Preferably, all the operations above can be performed at room temperature, such as stirring constantly for crystallization at room temperature. The room temperature is for example 25-35° C., may be 25-27° C. and preferably 25° C.

Preferably, the drying operation is performed using vacuum oil pump, the drying time is 4-8 hours, preferably 5 hours.

The present invention also provides a pharmaceutical composition comprising therapeutically effective amount of the cocrystal of the present invention and one or more pharmaceutically acceptable adjuvants. The pharmaceutically acceptable adjuvants may be a matrix or adjuvant for keeping the drug dosage forms, selected and used according to different medicaments, and used according to different pharmaceutical compositions, and may selectively include carriers, excipients, diluents, fillers, adhesives, disintegrants, lubricants, flow aids, effervescing agents, flavoring agents, preservatives, coating materials and the like. The excipients include for example one or more of microcrystalline cellulose, lactose, pregelatinized starch, starch, dextrin, calcium phosphate, sucrose, dextran, mannitol, sorbitol, glucose, fructose, water, polyethylene glycol, propylene glycol, glycerol, cyclodextrin, cyclodextrin derivatives and combinations thereof. The fillers include for example one or more of lactose, sucrose, dextrin, starch, pregelatinized starch, mannitol, sorbitol, calcium hydrophosphate, calcium sulfate, calcium carbonate, microcrystalline cellulose and combinations thereof. The adhesives include for example one or more of sucrose, starch, povidone, sodium carboxymethylcellulose, hydroxypropylmethyl cellulose, hydroxypropyl cellulose, methyl cellulose, polyethylene glycol, ethanol for medical use, water and combinations thereof. The disintegrants include for example one or more of starch, crosslinked povidone, crosslinked sodium carboxymethyl cellulose, low substituted hydroxypropyl cellulose, sodium carboxymethyl cellulose, effervescent disintegrant and combinations thereof.

According to the pharmaceutical composition of the present invention, wherein the pharmaceutical composition can be solid oral formulations, liquid oral formulations or injections. Preferably, the solid oral formulations include dispersible tablets, enteric-coated tablets, chewing tablets, orally disintegrating tablets, capsules or granules; the liquid oral formulations include oral solutions; the injections include liquid for injection, lyophilized powder for injection, large infusions or small infusions.

The present invention also provides a cocrystal of the present invention or use of the cocrystal prepared according to the method of the present invention in the preparation of the pharmaceutical composition for treating diabetes. The present inventors found that I-D1-6 has inhibitory effect on SGLT2 enzyme, and can be used as an active ingredient for preparing drugs for treating diabetes. Furthermore, it has been demonstrated by inhibition of humanized SGLT2 in vitro and validation of model for rat urine glucose excretion that the cocrystal of I-D1-6 and L-proline of the present invention has higher SGLT2 enzyme inhibitory activity.

The present invention also provides the use of the cocrystal of the present invention or the cocrystal prepared by the method of the present invention in the preparation of sodium glucose cotransporter 2 inhibitor.

The present invention also provides the use of the cocrystal of the present invention or the cocrystal prepared by the method of the present invention as a medicament for treating diabetes.

The present invention also provides the use of the cocrystal of the present invention or cocrystal prepared by the method of the present invention as a sodium glucose cotransporter 2 inhibitor.

The present invention also provides a method for treating diabetes, the method comprises administering therapeutically effective amount of the cocrystal of the present invention or the cocrystal prepared by the method of the present invention to the patients.

The present invention also provides a method of treating diabetes by inhibiting the sodium glucose cotransporter 2, the method comprises administering therapeutically effective amount of the cocrystal of the present invention or the cocrystal prepared by the method of the present invention to the patients.

The cocrystal of I-D1-6 of the present invention is effective in a broad range of dosage. For example, the daily dosage is in a range of about 1 mg-300 mg/person, either in a single dose or multiple doses. The actual administered dosage of the cocrystal of I-D1-6 and L-proline of the present invention can be determined by the doctors according to the related conditions.

Such conditions include: the physical status of the subjects being treated, the administration routes, ages, weights, personal reaction to the drugs, the severity of the symptoms and the like.

As compared with the I-D1-6 sample which is prepared by ways such as directly evaporating the solution to dryness and which is in a form between foam and normal solid, the cocrystal of I-D1-6 and L-proline prepared by the present invention has good appearance stability (being a white solid, not with a foam-like characteristic to some degree) and reproducibility in batch to batch, and purity has been further improved. For example, through experiments, the present inventors found that the cocrystals, in the range of continuous preparation of 17 batches, have stable appearance, all of them are normal white solids, and every batch is stable cocrystal through PXRD and DTA analysis. In addition, through HPLC analysis, purities of the cocrystals in each batch are 99.49%-99.64% which are all significantly higher than the purity of I-D1-6 that is 99.20%, and the number of impurities are less than that of the raw materials (the raw materials have 7 impurities, all batches of cocrystals hold steady at 3 imputities). In the meanwhile, the $^1$H NMR tests of each batch show that all the mole ratios of I-D1-6 to L-proline in the cocrystals hold steady at 1:1.

Furthermore, the cocrystal of I-D1-6 and L-proline of the present invention also has good storage stability. For example, the present inventors testified by experiments that, in a two-week stability experiment of the cocrystal on light, heat, and steam, the impurities of the cocrystal do not increase apparently, and the mole ratios of I-D1-6 to L-proline in the cocrystals hold steady at 1:1, and thus have good storage stability.

Based on the above characteristics, the cocrystal of I-D1-6 and L-proline of the present invention can be used as a stable supply source of the I-D1-6 drug substance, which is more suitable for industrial production.

BRIEF DESCRIPTION OF THE DRAWINGS

The embodiments of the present invention are now illustrated in more detail with reference to the drawings, wherein.

BEST MODE FOR CARRYING OUT THE INVENTION

Figure 1:
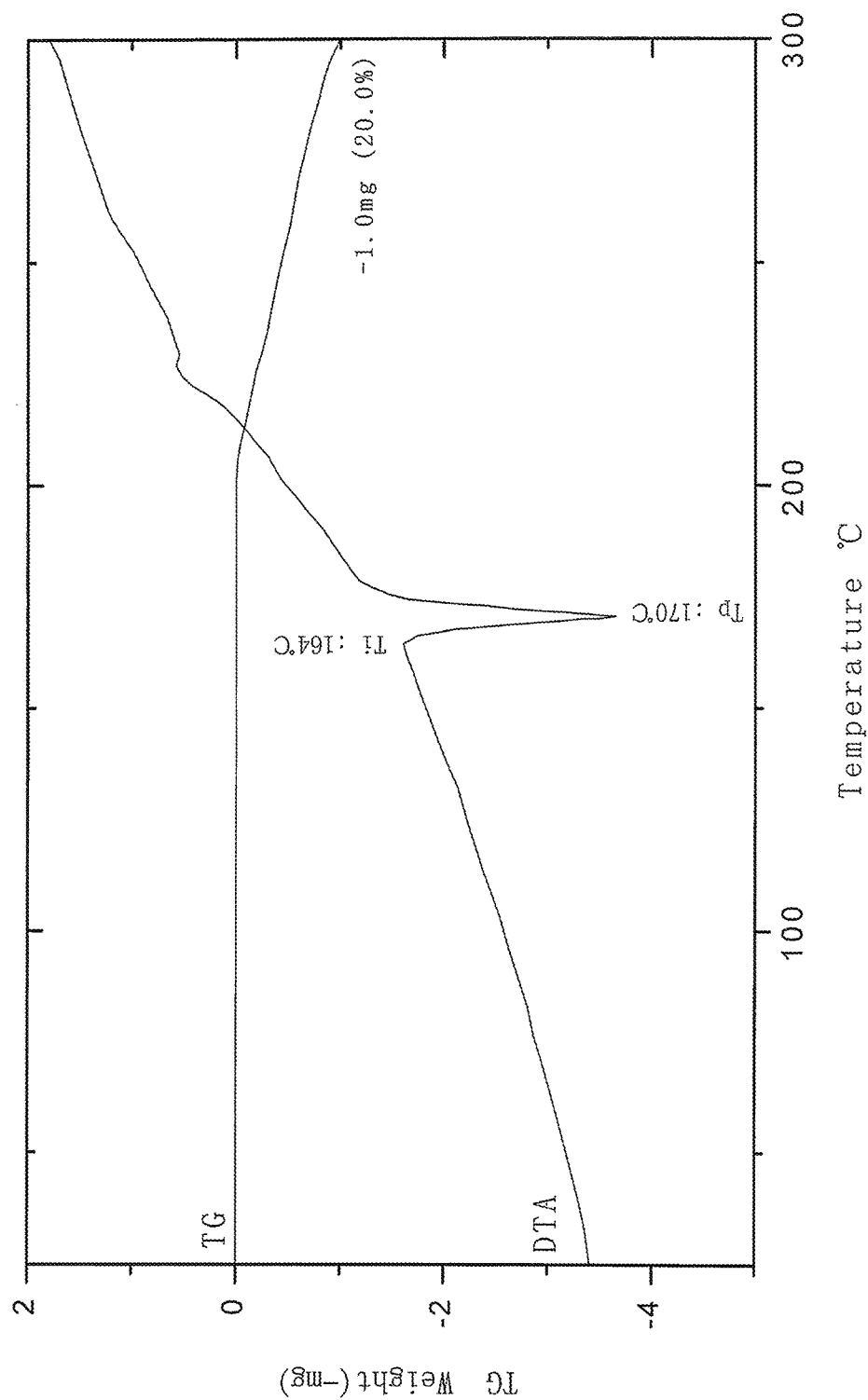
FIG. 1 illustrates the Differential Thermal Analysis (DTA) spectra of the cocrystal prepared in example 138.

The present invention will be further illustrated with reference to the examples below. It is necessary to state that, the examples below are only for illustration, but not for limitation of the present invention. Various alterations that are made by a person skilled in the art in accordance with teaching from the present invention should be within the scope claimed by the claims of the present invention.

Example 1

Preparation of (1S)-1-[4-chloro-3-(4-ethoxybenzyl) phenyl]-1,6-dideoxy-D-glucose (I-D1-6)

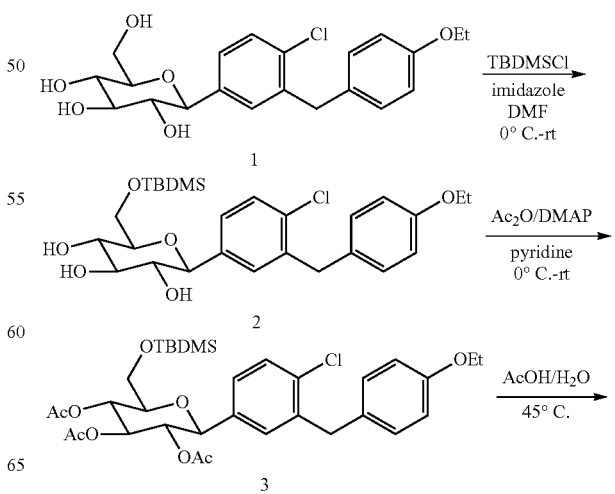

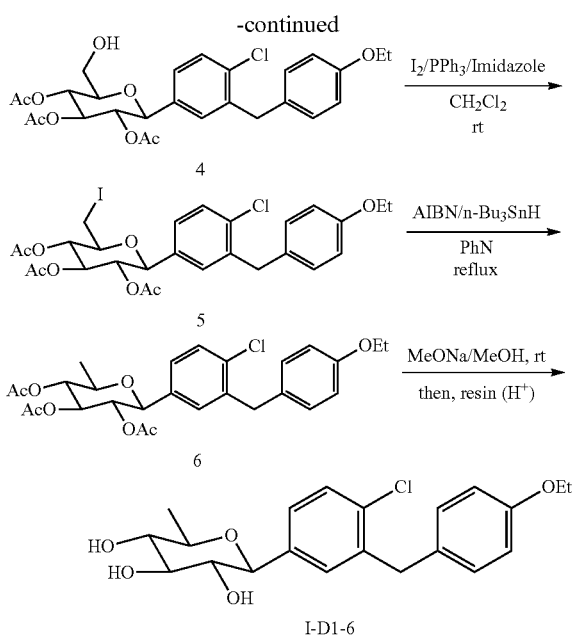

A.

4.09 g (10 mmol) of compound 1 is dissolved in 30 mL of dry DMF, stirred under cooling with an ice-water bath, 2.72 g (40 mmol) of imidazole is added, and then 1.66 g (11 mmol) of TBDMSCl (tert-butyldimethylsilyl chloride) is added dropwise slowly over 15 min. After the addition, the reaction compounds is stirred for another 3 hours at room temperature. The reaction mixture is diluted with 150 mL of dichloromethane, washed with 50 mL×3 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 2, a white foam-like solid. $^1$H NMR (DMSO-d$_6$, 400 MHz), δ 7.35 (d, 1H, J=8.0 Hz), 7.28 (d, 1H, J=2.0 Hz), 7.17 (dd, 1H, J=2.0 Hz and 8.4 Hz), 7.05 (d, 2H, J=8.8 Hz), 6.79 (d, 2H, J=8.8 Hz), 4.92-4.95 (m, 2H), 4.81 (d, 1H, J=6.0 Hz), 3.93-3.99 (m, 5H), 3.85 (d, 1H, J=10.4 Hz), 3.66 (dd, 1H, J=5.2 Hz and 11.6 Hz), 3.17-3.28 (m, 3H), 3.02-3.08 (m, 1H), 1.28 (t, 3H, J=7.0 Hz), 0.80 (s, 9H), −0.05 (s, 3H), −0.09 (s, 3H).

B.

4.19 g (8 mmol) of compound 2 is dissolved in 30 mL of pyridine, stirred under cooling with an ice-water bath. 15 mL of acetic anhydride is added dropwise slowly, and then 0.1 g of DMAP (4-dimethylaminopyridine) is added. After the addition, the reaction mixture is further stirred overnight at room temperature. The reaction mixture is dumped into 200 mL of ice water, stirred, and extracted with 50 mL×3 of dichloromethane. The organic phases are combined, washed successively with 50 mL 5% of diluted hydrochloric acid and 100 mL of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 3, a white solid, with a melting point of 101-102° C. $^1$H NMR (DMSO-d$_6$, 400 MHz), δ 7.41 (d, 1H, J=8.0 Hz), 7.19-7.22 (m, 2H), 7.03 (d, 2H, J=8.4 Hz), 6.80 (d, 2H, J=8.4 Hz), 5.30 (t, 1H, J=9.4 Hz), 5.06 (t, 1H, J=9.6 Hz), 4.83 (t, 1H, J=9.8 Hz), 4.61 (d, 1H, J=9.6 Hz), 3.90-4.00 (m, 4H), 3.81-3.84 (m, 1H), 3.60-3.71 (m, 2H), 1.99 (s, 3H), 1.90 (s, 3H), 1.69 (s, 3H), 1.28 (t, 3H, J=7.0 Hz), 0.82 (s, 9H), −0.03 (s, 3H), −0.08 (s, 3H).

C.

3.90 g (6 mmol) of compound 3 is dissolved in 50 mL 90% of acetic acid solution, stirred for 5 hours at 45° C., and then dumped into 200 mL of ice water, adjusted to pH=7-8 with saturated NaHCO$_3$ solution, and extracted with 50 mL×3 of dichloromethane. The organic phases are combined, washed with 100 mL of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 4, a white solid, melting point 120-121° C. $^1$H NMR (DMSO-d$_6$, 400 MHz), δ 7.38-7.41 (m, 1H), 7.26-7.30 (m, 1H), 7.20 (d, 1H, J=7.6 Hz), 7.05 (d, 2H, J=8.4 Hz), 6.81 (d, 2H, J=8.8 Hz), 5.29 (t, 1H, J=9.6 Hz), 5.02 (t, 1H, J=9.6 Hz), 4.90 (t, 1H, J=9.6 Hz), 4.75 (t, 1H, J=5.8 Hz), 4.59 (d, 1H, J=9.6 Hz), 3.92-4.01 (m, 3H), 3.74-3.78 (m, 1H), 3.48-3.53 (m, 1H), 3.39-3.43 (m, 1H), 1.99 (s, 3H), 1.91 (s, 3H), 1.68 (s, 3H), 1.28 (t, 3H, J=7.0 Hz).

D.

12.69 g (50 mmol) of iodine is dissolved in 50 mL of dry dichloromethane, stirred under cooling with an ice-water bath, 13.11 g (50 mmol) of triphenylphosphine is added slowly, after addition the reaction compounds are stirred for another 10 min. 13.62 g (200 mmol) of imidazole is then added slowly, and is stirred for another hour after the addition. 2.67 g (5 mmol) of compound 5 is added to the above resulting system, and after the addition the reaction compounds are stirred overnight at room temperature. The reaction mixture is diluted with 200 mL of dichloromethane, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product 5, a white solid, melting point 141-142° C. $^1$H NMR (DMSO-d$_6$, 400 MHz), δ 7.43 (d, 1H, J=8.4 Hz), 7.24 (dd, 1H, J=2.0 Hz and 8.4 Hz), 7.20 (d, 1H, J=2.0 Hz), 7.06 (d, 2H, J=8.8 Hz), 6.82 (d, 2H, J=8.4 Hz), 5.35 (t, 1H, J=9.4 Hz), 4.92 (t, 1H, J=9.4 Hz), 4.86 (t, 1H, J=9.8 Hz), 4.71 (d, 1H, J=10.0 Hz), 3.92-4.01 (m, 4H), 3.68-3.73 (m, 1H), 3.49 (dd, 1H, J=2.8 Hz and 11.2 Hz), 3.23-3.27 (m, 1H), 2.02 (s, 3H), 1.90 (s, 3H), 1.69 (s, 3H), 1.28 (t, 3H, J=7.0 Hz).

E.

1.93 g (3 mmol) of compound 5, 2.91 g (10 mmol) of n-Bu$_3$SnH and 0.49 g (3 mmol) of AIBN are dissolved in 20 mL of dry benzene, heated to reflux for 3 hours under nitrogen atmosphere. After cooling the reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 6, a white foam-like solid. $^1$H NMR (DMSO-d$_6$, 400 MHz), δ 7.39 (d, 1H, J=8.0 Hz), 7.23-7.26 (m, 2H), 7.04 (d, 2H, J=8.4 Hz), 6.81 (d, 2H, J=8.8 Hz), 5.26 (t, 1H, J=9.6 Hz), 4.94 (t, 1H, J=9.6 Hz), 4.83 (t, 1H, J=9.6 Hz), 4.57 (d, 1H, J=9.6 Hz), 3.92-4.01 (m, 4H), 3.80-3.87 (m, 1H), 2.02 (s, 3H), 1.91 (s, 3H), 1.67 (s, 3H), 1.28 (t, 3H, J=6.8 Hz), 1.12 (d, 3H, J=6.0 Hz). $^{13}$C NMR (DMSO-d$_6$, 100 MHz), δ 169.55, 169.49, 168.41, 156.91, 138.35, 136.52, 132.82, 130.92, 130.16, 129.50, 129.25, 126.57, 114.27, 77.52, 73.25, 73.01, 72.95, 72.65, 62.85, 37.37, 20.42, 20.26, 19.98, 17.33, 14.60.

F.

0.2 g of metallic sodium is added to 10 mL of dry absolute methanol, stirred under the protection of nitrogen at room temperature, until the metallic sodium disappears. Then 0.52 g (1 mmol) of compound 6 is added, and stirred for another 3 hours at room temperature. 2 g of strong acid cation exchange resin is added to the reaction system, stirred overnight at room temperature, until the reaction mixture's pH=7. The resin is removed by suction filtration, the filtrate is evaporated to dryness on the rotary evaporator, and the resulting residue is further dried on the vacuum oil pump to obtain the product I-D1-6, a white, foam-like solid. $^1$H NMR (DMSO-d$_6$, 400 MHz), δ 7.35 (d, 1H, J=8.0 Hz), 7.25 (d, 1H, J=2.0 Hz), 7.18 (dd, 1H, J=2.0 Hz and 8.0 Hz), 7.08 (d, 2H, J=8.8 Hz), 6.82 (d, 2H, J=8.8 Hz), 4.96 (d, 1H, J=5.2 Hz, D$_2$O-exchangeable), 4.91 (d, 1H, J=4.4 Hz, D$_2$O-exchangeable), 4.80 (d, 1H, J=5.6 Hz, D$_2$O-exchangeable), 3.92-4.01 (m, 5H), 3.26-3.32 (m, 1H), 3.18-3.25 (m, 1H), 3.09-3.15 (m, 1H), 2.89-2.95 (m, 1H), 1.28 (t, 3H, J=7.0 Hz), 1.15 (d, 3H, J=6.0 Hz). $^{13}$C NMR (DMSO-d$_6$, 100 MHz), δ 156.85, 139.65, 137.82, 131.83, 131.16, 130.58, 129.52, 128.65, 127.14, 114.26, 80.71, 77.98, 75.77, 75.51, 74.81, 62.84, 37.56, 18.19, 14.63. HR-ESI-MS, calcd for C$_{21}$H$_{29}$ClNO$_5$, 410.1734. found 410.1730 ([M+NH$_4$]$^+$).

Example 2

Preparation of (1S)-1-[4-chloro-3-(4-ethoxybenzyl) phenyl]-1,4-dideoxy-D-glucose (I-D1-4)

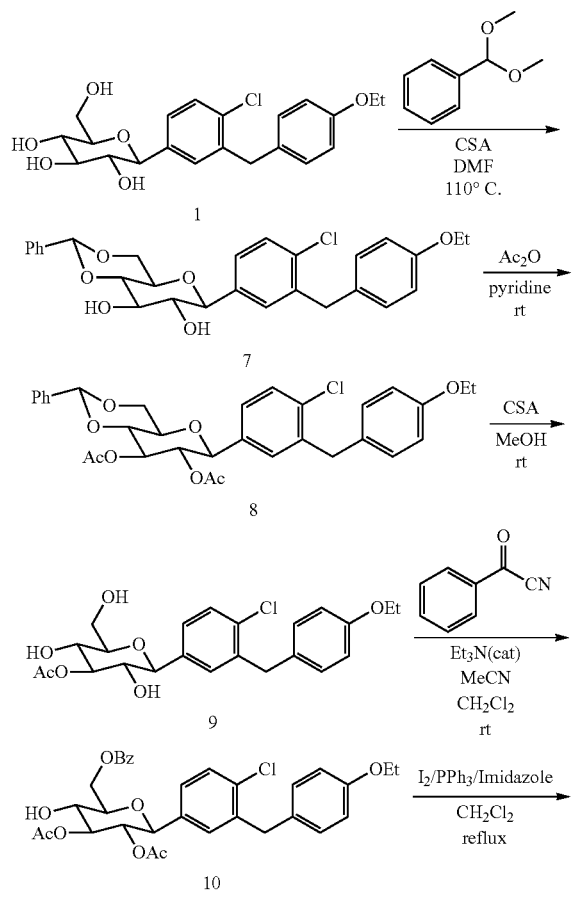

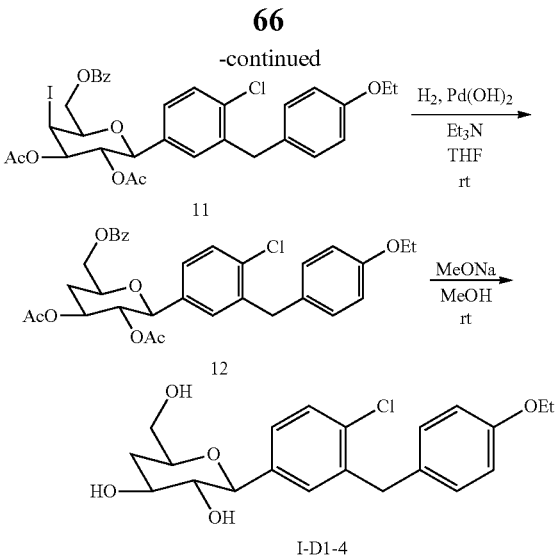

A.

4.09 g (10 mmol) of compound 1, 1.83 g (12 mmol) of benzaldehyde dimethyl acetal and 0.1 gram of CAS (camphorsulfonic acid) is dissolved in L of dry DMF, heated and stirred for 3 hours at 110° C. under nitrogen atmosphere. After cooling the reaction mixture is diluted with 150 mL of dichloromethane, washed successively with 20 mL of 5% sodium carbonate solution and saturated salt water, and dried with anhydrous sodium sulfate. The drying agent is removed by filtration, the solvent in the filtrate is removed on the rotary evaporator, and the resulting residue is purified by silica gel column chromatography to obtain the pure product 7, a white solid. Melting point 176-178° C. $^1$H NMR (DMSO-d$_6$, 400 MHz), δ 7.45-7.47 (m, 2H), 7.36-7.40 (m, 4H), 7.28 (d, 1H, J=1.6 Hz), 7.21 (dd, 1H, J=2.0 Hz and 8.4 Hz), 7.08 (d, 2H, J=8.8 Hz), 6.83 (d, 2H, J=8.4 Hz), 5.60 (s, 1H), 5.31 (d, 1H, J=3.6 Hz), 5.13 (d, 1H, J=5.6 Hz), 4.16-4.22 (m, 2H), 3.94-3.99 (m, 4H), 3.65-3.70 (m, 1H), 3.50-3.51 (m, 3H), 3.24-3.28 (m, 1H), 1.29 (t, 3H, J=6.8 Hz).

B.

3.98 g (8 mmol) of compound 7 is dissolved in 30 mL of pyridine, stirred under cooling with an ice-water bath. 15 mL of acetic anhydride is added dropwise slowly, and then 0.1 g of DMAP (4-dimethylaminopyridine) is added. After the addition, the reaction mixture is further stirred overnight at room temperature. The reaction mixture is dumped into 200 mL of ice water, stirred, and extracted with 50 mL×3 of dichloromethane. The organic phases are combined, washed successively with 50 mL of 5% diluted hydrochloric acid and 100 mL of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 8, a white, foam-like solid. $^1$H NMR (DMSO-d$_6$, 400 MHz), δ 7.36-7.42 (m, 6H), 7.23-7.26 (m, 2H), 7.04 (d, 2H, J=8.4 Hz), 6.82 (d, 2H, J=8.8 Hz), 5.66 (s, 1H), 5.37 (t, 1H, J=9.4 Hz), 4.97 (t, 1H, J=9.6 Hz), 2.55 (d, 1H, J=9.6 Hz), 4.25-4.26 (m, 1H), 3.93-4.02 (m, 5H), 3.78-3.82 (m, 2H), 1.96 (s, 3H), 1.70 (s, 3H), 1.29 (t, 3H, J=7.0 Hz).

C.

3.49 g (6 mmol) of compound 8 and 0.5 g of CAS are dissolved in 30 mL of methanol, and stirred overnight at room temperature. The reaction compounds are diluted with 100 mL of dichloromethane, washed successively with 50 mL of 2% sodium carbonate solution and saturated salt water, and dried with anhydrous sodium sulfate. The drying agent is removed by filtration, the solvent in the filtrate is removed on the rotary evaporator, the resulting residue is purified by silica gel column chromatography to obtain the pure product 9, a white, foam-like solid. $^1$H NMR (DMSO-$d_6$, 400 MHz), δ 7.37-7.39 (m, 1H), 7.25-7.27 (m, 2H), 7.03 (d, 2H, J=8.4 Hz), 6.81 (d, 2H, J=8.8 Hz), 5.47 (d, 1H, J=5.6 Hz, D$_2$O-exchangeable), 5.04 (t, 1H, J=9.2 Hz), 4.73 (t, 1H, J=9.6 Hz), 4.58 (t, 1H, J=5.8 Hz, D$_2$O-exchangeable), 4.46 (d, 1H, J=9.6 Hz), 3.91-4.00 (m, 4H), 3.71 (dd, 1H, J=5.2 Hz and 10.8 Hz), 3.49-3.56 (m, 2H), 3.43-3.47 (m, 1H), 1.95 (s, 3H), 1.62 (s, 3H), 1.28 (t, 3H, J=7.0 Hz).

D.

2.46 g (5 mmol) of compound 9 and 0.72 g (0.55 mmol) of benzoyl cyanide are dissolved in 20 mL of dry acetonitrile, and stirred at room temperature. 0.21 mL (0.15 g, 1.5 mmol) of triethylamine is added dropwise slowly with an injector. After the addition, the reaction compounds are stirred overnight at room temperature. The reaction mixture is dumped into 200 mL ice water, stirred, and extracted with 50 mL×3 of dichloromethane. The organic phases are combined, washed successively with 50 mL of 1% diluted hydrochloric acid and 100 mL of saturated salt water, and dried with anhydrous sodium sulfate. The drying agent is removed by filtration, the solvent in the filtrate is removed on the rotary evaporator, the resulting residue is purified by silica gel column chromatography to obtain the pure product 10, a white, foam-like solid. $^1$H NMR (DMSO-$d_6$, 400 MHz), δ 7.97-7.99 (m, 2H), 7.66 (t, 1H, J=7.4 Hz), 7.53 (t, 2H, J=7.6 Hz), 7.37 (d, 1H, J=9.2 Hz), 7.20-7.21 (m, 2H), 7.02 (d, 2H, J=8.8 Hz), 6.76 (d, 2H, J=8.4 Hz), 5.79 (d, 1H, J=6.0 Hz, D$_2$O-exchangeable), 5.12 (t, 1H, J=9.4 Hz), 4.82 (t, 1H, J=9.8 Hz), 4.56-4.59 (m, 2H), 4.42 (dd, 1H, J=5.2 Hz and 12.0 Hz), 3.86-3.97 (m, 5H), 3.71-3.77 (m, 1H), 1.97 (s, 3H), 1.67 (s, 3H), 1.27 (t, 3H, J=7.0 Hz).

E.

12.69 g (50 mmol) of iodine is dissolved in 50 mL of dry dichloromethane, stirred under cooling with an ice-water bath, 13.11 g (50 mmol) of triphenylphosphine is added slowly, After the addition, the reaction compounds are stirred for another 10 min. 13.62 g (200 mmol) of imidazole is then added, and stirred for another hour after the addition. To the above resulting system, 2.39 g (4 mmol) of compound 10 is added, after the addition the reaction compounds are stirred at reflux overnight under nitrogen atmosphere. The reaction mixture is diluted with 200 mL of dichloromethane, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product 11, a white, foam-like solid. $^1$H NMR (DMSO-$d_6$, 400 MHz), 7.92 (d, 2H, J=7.2 Hz), 7.66 (t, 1H, J=7.4 Hz), 7.52 (t, 2H, J=7.8 Hz), 7.44 (d, 1H, J=8.4 Hz), 7.25 (dd, 1H, J=2.0 Hz and 8.4 Hz), 7.15 (d, 1H, J=2.0 Hz), 7.04 (d, 2H, J=8.8 Hz), 6.81 (d, 2H, J=8.4 Hz), 5.17 (t, 1H, J=9.6 Hz), 4.94 (d, 1H, J=3.6 Hz), 4.82 (dd, 1H, J=4.0 Hz and 9.6 Hz), 4.65 (d, 1H, J=9.6 Hz), 4.42 (dd, 1H, J=6.8 Hz and 11.2 Hz), 4.29 (dd, 1H, J=4.4 Hz and 11.6 Hz), 3.91-4.01 (m, 4H), 3.83 (t, 1H, J=5.4 Hz), 2.03 (s, 3H), 1.72 (s, 3H), 1.28 (t, 3H, J=6.8 Hz).

F.

1.41 g (2 mmol) of compound 11 and 3 mL of triethylamine are dissolved in 10 mL THF, and then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 12, a white solid. Melting point 45-47° C. $^1$H NMR (DMSO-$d_6$, 400 MHz), δ 7.96 (d, 2H, J=7.6 Hz), 7.66 (t, 1H, J=7.2 Hz), 7.52 (t, 2H, J=7.4 Hz), 7.38 (d, 1H, J=8.0 Hz), 7.21-7.23 (m, 2H), 7.03 (d, 2H, J=8.0 Hz), 6.78 (d, 2H, J=8.4 Hz), 5.14-5.21 (m, 1H), 4.80 (t, 1H, J=9.4 Hz), 4.51 (d, 1H, J=9.6 Hz), 4.36-4.37 (m, 2H), 4.14-4.17 (m, 1H), 3.89-3.99 (m, 4H), 2.21-2.24 (m, 1H), 1.95 (s, 3H), 1.69 (s, 3H), 1.28 (t, 3H, J=6.8 Hz). $^{13}$C NMR (DMSO-$d_6$, 100 MHz), δ 169.64, 168.67, 165.46, 156.89, 138.25, 136.98, 133.40, 132.64, 130.91, 130.06, 129.48, 129.39, 129.20, 129.14, 128.77, 126.47, 114.25, 77.75, 73.35, 72.58, 71.03, 65.98, 62.84, 37.38, 32.48, 20.61, 20.09, 14.59.

G.

0.58 g (1 mmol) of compound 12 is dissolved in 10 mL of ethanol, stirred, and 1 mL of 50% NaOH solution is added. The reaction mixture is heated to reflux for 1 hour, dumped into water after cooling, adjusted with concentrated hydrochloric acid to pH=3, and extracted with 50 mL×3 of dichloromethane. The organic phases are combined, washed successively with 50 mL of 5% sodium carbonate solution and saturated salt water, and dried with anhydrous sodium sulfate. The drying agent is removed by filtration, the solvent in the filtrate is removed on the rotary evaporator, the resulting residue is purified by silica gel column chromatography to obtain the pure product I-D1-4, a white, foam-like solid. $^1$H NMR (DMSO-$d_6$, 400 MHz), δ 7.35 (d, 1H, J=8.0 Hz), 7.28 (d, 1H, J=1.6 Hz), 7.20 (dd, 1H, J=1.8 Hz and 8.2 Hz), 7.08 (d, 2H, J=8.4 Hz), 6.82 (d, 2H, J=8.8 Hz), 4.82 (d, 1H, J=4.8 Hz), 4.75 (d, 1H, J=5.6 Hz), 4.59 (t, 1H, J=5.8 Hz), 3.92-4.01 (m, 5H), 3.46-3.51 (m, 2H), 3.31-3.42 (m, 2H), 2.99-3.05 (m, 1H), 1.89 (dd, 1H, J=4.8 Hz and 11.6 Hz), 1.23-1.30 (m, 4H). $^{13}$C NMR (DMSO-$d_6$, 400 MHz), 156.84, 139.83, 137.72, 131.76, 131.16, 130.76, 129.51, 128.58, 127.31, 114.25, 80.97, 76.57, 76.24, 71.97, 64.04, 62.83, 37.57, 36.28, 14.62.

Example 3

Preparation of (1S)-1-[4-chloro-3-(4-ethoxybenzyl) phenyl]-1,3-dideoxy-D-glucose (I-D1-3)

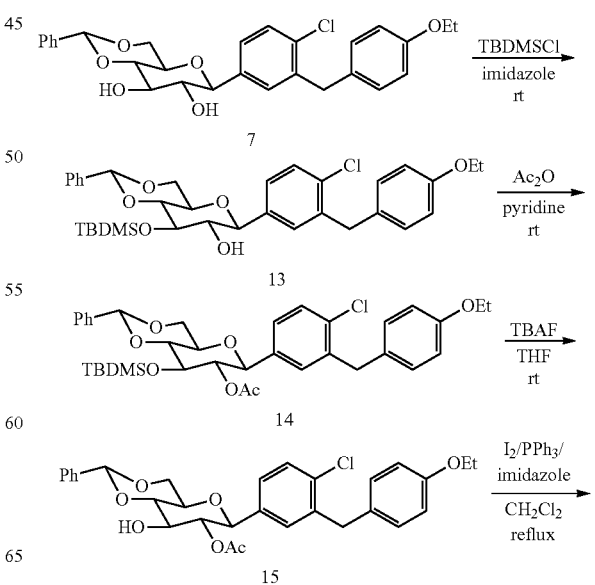

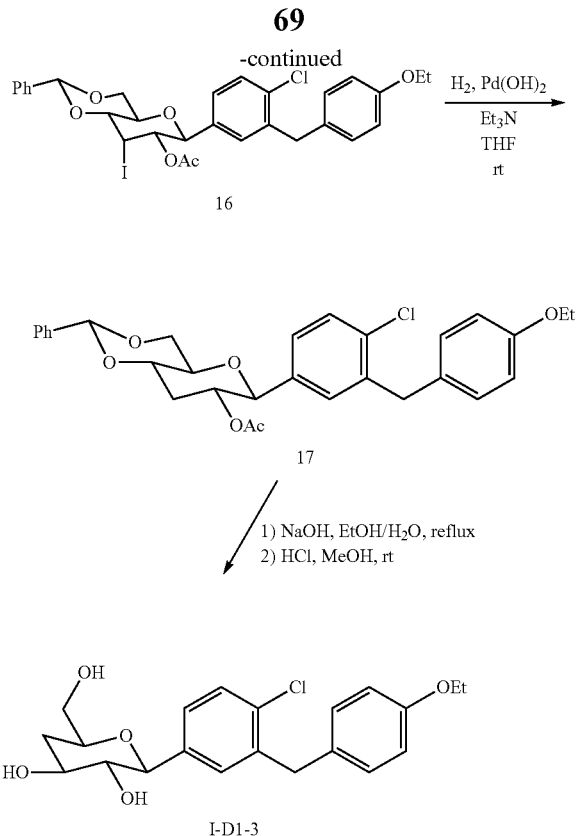

A.

4.97 g (10 mmol) of compound 7 is dissolved in 30 mL of dry DMF, stirred under cooling with an ice-water bath, 2.72 g (40 mmol) of imidazole is added, and then 1.66 g (11 mmol) of TBDMSCl (tert-butyldimethylsilyl chloride) is added dropwise slowly over 15 min. After the addition, the reaction compounds are stirred for another 3 hours at room temperature. The reaction mixture is diluted with 150 mL of dichloromethane, washed with 50 mL×3 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 13, a white, foam-like solid. ESI-MS, m/z=628 ([M+NH$_4$]$^+$).

B.

4.89 g (8 mmol) of compound 13 is dissolved in 30 mL of pyridine, and stirred under cooling with an ice-water bath. 10 mL of acetic anhydride is added dropwise slowly, and then 0.1 g of DMAP (4-dimethylaminopyridine) is added. After the addition, the reaction mixture is further stirred overnight at room temperature. The reaction mixture is dumped into 200 mL of ice water, stirred, and extracted with 50 mL×3 of dichloromethane. The organic phases are combined, washed successively with 50 mL of 5% diluted hydrochloric acid and 100 mL of saturated salt water, and dried with anhydrous sodium sulfate. The drying agent is removed by filtration, the solvent in the filtrate is removed on the rotary evaporator, the resulting residue is purified by silica gel column chromatography to obtain the pure product 14, a white, foam-like solid. ESI-MS, m/z=670 ([M+NH$_4$]$^+$).

C.

3.92 g (6 mmol) of compound 14 is dissolved in 40 mL of dry THF, stirred under cooling with an ice-water bath, 0.37 g (6 mmol) of glacial acetic acid is added, and then 6 mL (6 mmol, 1 M of THF solution) of TBAF (tetra-n-butylammonium fluoride) solution is added dropwise. The reaction compounds are stirred overnight at room temperature, dumped into 200 mL of ice water, stirred, and extracted with 50 mL×3 of dichloromethane, The organic phases are combined, washed with the saturated salt water, and dried with anhydrous sodium sulfate. The drying agent is removed by filtration, the solvent in the filtrate is removed on the rotary evaporator, the resulting residue is purified by silica gel column chromatography to obtain the pure product 15, a white, foam-like solid. ESI-MS, m/z=561 ([M+Na]$^+$).

D.

12.69 g (50 mmol) of iodine is dissolved in 50 mL of dry dichloromethane, stirred under cooling with an ice-water bath, and 13.11 g (50 mmol) of triphenylphosphine is added slowly, after the addition the reaction compounds are stirred for another 10 min. 13.62 g (200 mmol) of imidazole is then added slowly, and stirred for another hour after the addition. To the above resulting system, 2.70 g (5 mmol) of compound 15 is added, after the addition the reaction compounds are stirred to reflux overnight under nitrogen atmosphere. The reaction mixture is diluted with 200 mL of dichloromethane, washed with the saturated salt water, and dried with anhydrous sodium sulfate. The drying agent is removed by filtration, the solvent in the filtrate is removed on the rotary evaporator, the resulting residue is purified by silica gel column chromatography to obtain the pure product 16, a white, foam-like solid. ESI-MS, m/z=671 ([M+Na]$^+$).

E.

1.95 g (3 mmol) of compound 16 and 3 mL of triethylamine are dissolved in 10 mL of THF, 0.3 g of Pd(OH)$_2$ is then added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 17, a white solid. ESI-MS, m/z=545 ([M+Na]$^+$).

F.

1.05 g (2 mmol) of compound 17 is dissolved in 10 mL of ethanol, 1 mL 50% of NaOH solution is added, heated to reflux for 1 hour, after cooling to room temperature, the pH is adjusted with the concentrated hydrochloric acid to pH=2, heated to continue to reflux for half an hour. The reaction compounds are dumped into 100 mL saturated salt water, stirred, and extracted with 50 mL×3 of dichloromethane, The organic phases are combined, washed with the saturated salt water, and dried with anhydrous sodium sulfate. The drying agent is removed by filtration, the solvent in the filtrate is removed on the rotary evaporator, the resulting residue is purified by silica gel column chromatography to obtain the pure product I-D1-3, a white, foam-like solid. ESI-MS, m/z=415 ([M+Na]$^+$). $^1$H NMR (DMSO-d$_6$, 400 MHz), δ 7.35 (d, 1H, J=8.4 Hz), 7.30 (d, 1H, J=1.6 Hz), 7.22 (dd, 1H, J=1.8 Hz and 8.2 Hz), 7.08 (d, 2H, J=8.8 Hz), 6.81 (d, 2H, J=8.4 Hz), 4.82 (d, 1H, J=5.6 Hz), 4.73 (d, 1H, J=6.4 Hz), 4.38 (t, 1H, J=5.8 Hz), 3.92-4.01 (m, 4H), 3.85 (d, 1H, J=9.2 Hz), 3.67-3.72 (m, 1H), 3.27-3.45 (m, 3H), 3.07-3.10 (m, 1H), 2.20-2.25 (m, 1H), 1.43 (q, 1H, J=11.5 Hz), 1.28 (t, 3H, J=6.8 Hz). $^{13}$C NMR (DMSO-d$_6$, 100 MHz), δ 156.83, 139.91, 137.66, 131.78, 131.17, 130.73, 129.48, 128.55, 127.18, 114.24, 83.29, 82.92, 69.20, 64.67, 62.83, 61.22, 42.81, 37.60, 14.62.

Example 4

Preparation of (1S)-1-[4-chloro-3-(4-ethoxybenzyl)phenyl]-1,2-dideoxy-D-glucose (I-D1-2)

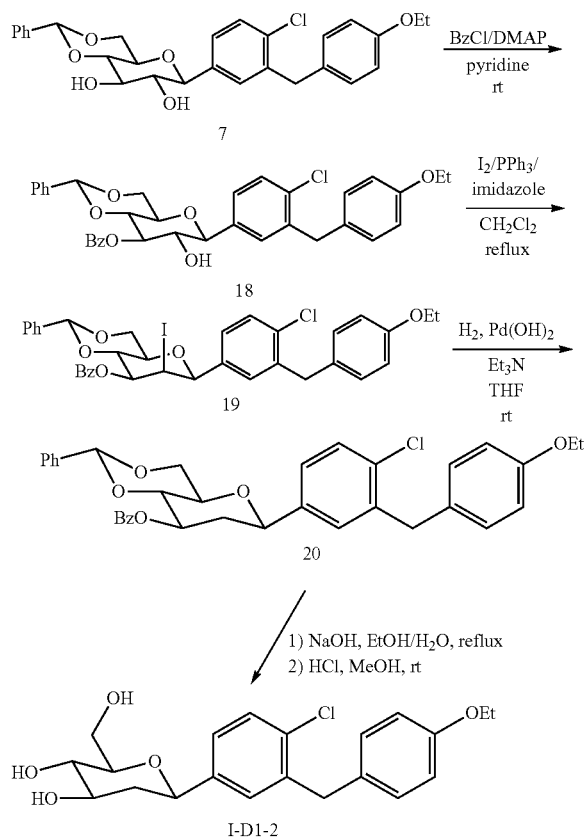

A.

4.97 g (10 mmol) of compound 7 and 0.2 g of DMAP are dissolved in 20 mL dry pyridine, stirred under cooling with an ice-water bath, 1.55 g (11 mmol) of benzoyl chloride is added dropwise. After the addition, the reaction compounds are stirred overnight at room temperature. The reaction mixture is diluted with 150 mL of dichloromethane, washed successively with 100 mL 5% of diluted hydrochloric acid and 50 mL×2 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 18, a white, foam-like solid. ESI-MS, m/z=623 ([M+Na]$^+$).

B.

12.69 g (50 mmol) of iodine is dissolved in 50 mL of dry dichloromethane, stirred under cooling with an ice-water bath, and 13.11 g (50 mmol) of triphenylphosphine is added slowly, After the addition, the reaction compounds are stirred for another 10 min. 13.62 g (200 mmol) of imidazole is then added slowly, and stirred for another hour after the addition. To the above resulting system, 3.01 g (5 mmol) of compound 18 is added, after the addition the reaction compounds are stirred to reflux overnight under nitrogen atmosphere. The reaction mixture is diluted with 200 mL of dichloromethane, washed with the saturated salt water, and dried with anhydrous sodium sulfate. The drying agent is removed by filtration, the solvent in the filtrate is removed on the rotary evaporator, the resulting residue is purified by silica gel column chromatography to obtain the pure product 19, a white, foam-like solid. ESI-MS, m/z=733 ([M+Na]$^+$).

C.

2.13 g (3 mmol) of compound 19 and 3 mL of triethylamine are dissolved in 10 mL of THF, 0.3 g of Pd(OH)$_2$ is then added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 20, a white solid. ESI-MS, m/z=607 ([M+Na]$^+$).

D.

1.17 g (2 mmol) of compound 20 is dissolved in 10 mL of ethanol, 1 mL 50% of NaOH solution is added, heated to reflux for 1 hour, after cooling to room temperature the pH is adjusted with the concentrated hydrochloric acid to pH=2, heated to continue to reflux for half an hour. The reaction compounds are dumped into 100 mL of saturated salt water, stirred, and extracted with 50 mL×3 of dichloromethane. The organic phases are combined, washed with the saturated salt water, and dried with anhydrous sodium sulfate. The drying agent is removed by filtration, the solvent in the filtrate is removed on the rotary evaporator, and the resulting residue is purified by silica gel column chromatography to obtain the pure product I-D1-2, a white, foam-like solid. ESI-MS, m/z=410 ([M+NH$_4$]$^+$). $^1$H NMR (DMSO-d$_6$, 400 MHz), 7.36 (d, 1H, J=8.4 Hz), 7.34 (d, 1H, J=1.6 Hz), 7.25 (dd, 1H, J=2.0 Hz and 8.4 Hz), 7.07 (d, 2H, J=8.4 Hz), 6.82 (d, 2H, J=8.4 Hz), 4.88 (d, 1H, J=5.2 Hz), 4.83 (d, 1H, J=4.8 Hz), 4.38-4.43 (m, 2H), 3.93-3.98 (m, 4H), 3.69-3.74 (m, 1H), 3.45-3.54 (m, 2H), 3.16-3.20 (m, 1H), 3.01-3.07 (m, 1H), 1.98-2.02 (m, 1H), 1.35 (q, 1H, J=12.0 Hz), 1.28 (t, 3H, J=7.0 Hz)

Example 5

Preparation of (1S)-1-[4-chloro-3-(4-ethoxybenzyl)phenyl]-1,4,6-trideoxy-D-glucose (I-D1-4,6)

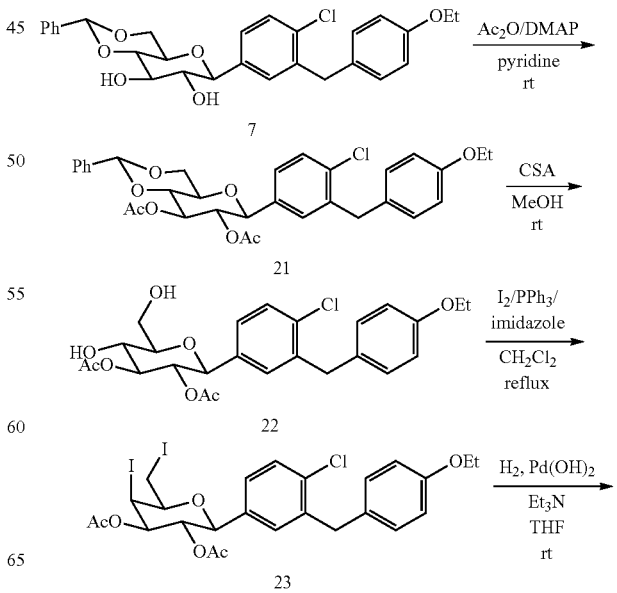

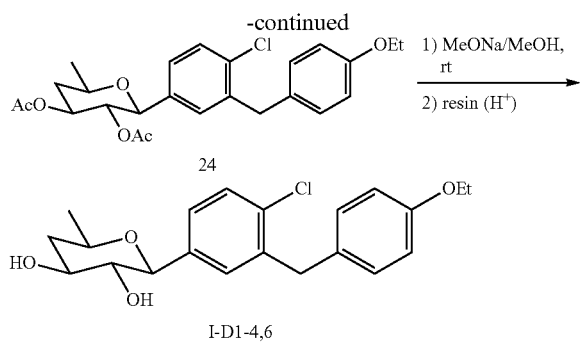

A.

4.97 g (10 mmol) of compound 7 and 0.2 g of DMAP are dissolved in 30 mL dry pyridine, stirred under cooling with an ice-water bath, 10 mL of acetic anhydride is added dropwise. After the addition, the reaction compounds are stirred overnight at room temperature. The reaction mixture is diluted with 150 mL of dichloromethane, washed successively with 100 mL 5% of diluted hydrochloric acid and 50 mL×2 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 21, a white, foam-like solid. ESI-MS, m/z=603 ([M+Na]$^+$).

B.

4.65 g (8 mmol) of compound 21 and 0.5 g of CAS are dissolved in 30 mL methanol, stirred overnight at room temperature. The reaction compounds are diluted with 100 mL dichloromethane, washed successively with 50 mL 2% of sodium carbonate solution and saturated salt water, and dried with anhydrous sodium sulfate. The drying agent is removed by filtration, the solvent in the filtrate is removed on the rotary evaporator, the resulting residue is purified by silica gel column chromatography to obtain the pure product 22, a white, foam-like solid. ESI-MS, m/z=493 ([M+H]$^+$).

C.

12.69 g (50 mmol) of iodine is dissolved in 50 mL of dry dichloromethane, stirred under cooling with an ice-water bath, 13.11 g (50 mmol) of triphenylphosphine is added slowly, After the addition, the reaction compounds are stirred for another 10 min. 13.62 g (200 mmol) of imidazole is then added slowly, and stirred for another hour after the addition. To the above resulting system, 2.46 g (5 mmol) of compound 22 is added, after the addition the reaction compounds are stirred to reflux overnight under nitrogen atmosphere. The reaction mixture is diluted with 200 mL of dichloromethane, washed with the saturated salt water, and dried with anhydrous sodium sulfate. The drying agent is removed by filtration, the solvent in the filtrate is removed on the rotary evaporator, the resulting residue is purified by silica gel column chromatography to obtain the pure product 23, a white, foam-like solid. ESI-MS, m/z=735 ([M+Na]$^+$).

D.

2.14 g (3 mmol) of compound 23 and 2 mL of triethylamine are dissolved in 10 mL of THF, 0.2 g of Pd(OH)$_2$ is then added, the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 24, a white solid. ESI-MS, m/z=483 ([M+Na]$^+$).

E.

To 10 mL of dry absolute methanol, 0.3 g of metallic sodium is added, stirred under the protection of nitrogen at room temperature, until the metallic sodium disappears. 0.46 g (1 mmol) of compound 24 is then added, and stirred for another 3 hours at room temperature. To the reaction system, 3 g of strong acid cation exchange resin is added, stirred overnight at room temperature, until the reaction mixture's pH=7. The resin is removed by suction filtration, the filtrate is evaporated to dryness on the rotary evaporator, and the resulting residue is further dried on the vacuum oil pump to obtain the product I-D1-4,6, a white, foam-like solid. ESI-MS, m/z=399 ([M+Na]$^+$).

Example 6

Preparation of (1S)-1-[4-chloro-3-(4-ethoxybenzyl)phenyl]-1,3,6-trideoxy-D-glucose (I-D1-3,6)

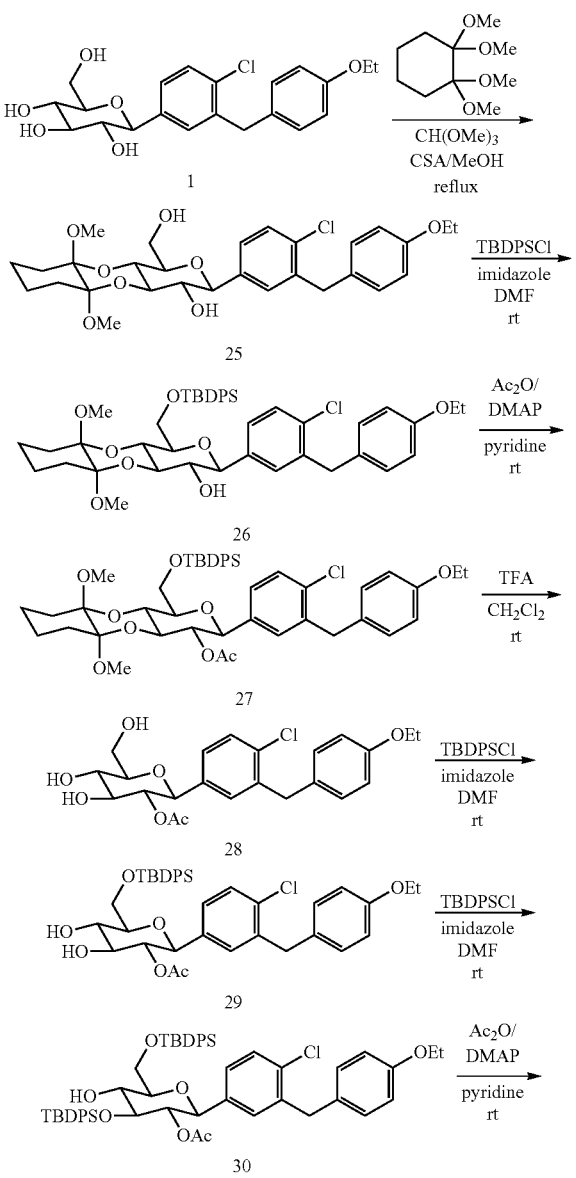

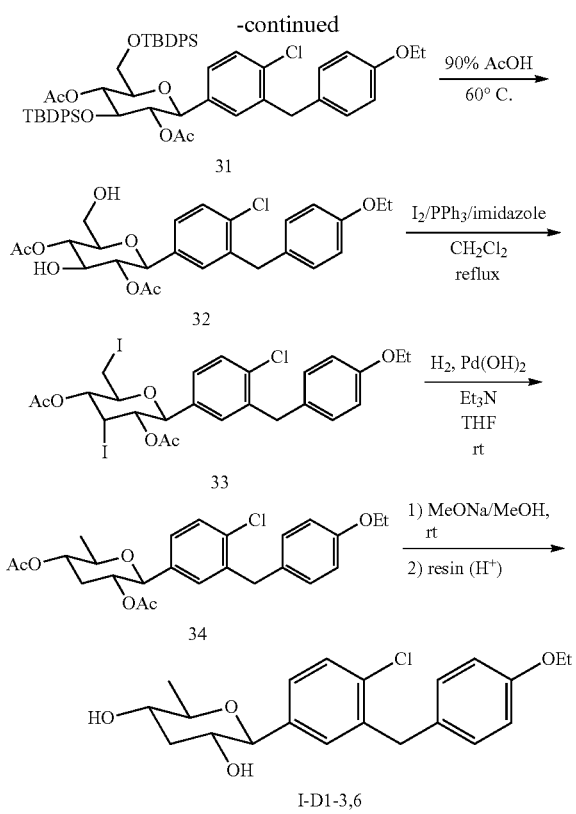

I-D1-3,6

A.

4.09 g (10 mmol) of compound 1, 3.06 g (15 mmol) of 1,1,2,2-tetramethoxy cyclohexane and 1 mL of trimethyl orthoformate are dissolved in 40 mL of dry methanol, 0.2 g of camphorsulfonic acid is added. The reaction mixture is heated to reflux overnight. After the reaction mixture is cooled to room temperature, 0.5 g of potassium carbonate is added, stirred at room temperature, until pH>7. The solid is removed by suction filtration, and then the solvent in the filtrate is removed on the rotary evaporator, the residue is purified directly by column chromatography to obtain the pure product 25, a white solid. ESI-MS, m/z=571 ([M+Na]$^+$).

B.

4.39 g (8 mmol) of compound 25 is dissolved in 30 mL of dry DMF, stirred under cooling with an ice-water bath, 2.72 g (40 mmol) of imidazole is added, and then 2.75 g (10 mmol) of TBDPSCl (tert-butyldiphenylsilyl chloride) is added dropwise slowly over 15 min. After the addition, the reaction compounds are stirred for another 3 hours at room temperature. The reaction mixture is diluted with 150 mL of dichloromethane, washed with 50 mL×3 of the saturated salt water, and dried with anhydrous sodium sulfate. The drying agent is removed by filtration, the solvent in the filtrate is removed on the rotary evaporator, and the resulting residue is purified by silica gel column chromatography to obtain the pure product 26, a white, foam-like solid. ESI-MS, m/z=809 ([M+Na]$^+$).

C.

4.72 g (6 mmol) of compound 26 and 0.2 g of DMAP are dissolved in 30 mL dry pyridine, stirred under cooling with an ice-water bath, and 10 mL of acetic anhydride is added dropwise. After the addition, the reaction compounds are stirred overnight at room temperature. The reaction mixture is diluted with 150 mL of dichloromethane, washed successively with 100 mL of 5% diluted hydrochloric acid and 50 mL×2 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 27, a white, foam-like solid. ESI-MS, m/z=851 ([M+Na]$^+$).

D.

4.15 g (5 mmol) of compound 27 is dissolved in the mixture composed of 10 mL of dichloromethane and 10 mL of trifluoroacetic acid (TFA), stirred overnight at room temperature. The reaction mixture is dumped into 100 mL of saturated salt water, stirred, and extracted with 50 mL×3 of dichloromethane. The organic phases are combined, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 28, a white, foam-like solid. ESI-MS, m/z=473 ([M+Na]$^+$).

E.

1.80 g (4 mmol) of compound 28 dissolved in 20 mL of dry DMF, stirred under cooling with an ice-water bath, 2.72 g (40 mmol) of imidazole is added, and then 1.37 g (5 mmol) of TBDPSCl (tert-butyldiphenylsilyl chloride) is added dropwise slowly over 15 min. After the addition, the reaction compounds are stirred for another 3 hours at room temperature. The reaction mixture is diluted with 150 mL of dichloromethane, washed with 50 mL×3 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 29, a white, foam-like solid. ESI-MS, m/z=711 ([M+Na]$^+$).

F.

2.76 g (4 mmol) of compound 29 is dissolved in 20 mL of dry DMF, stirred under cooling with an ice-water bath, 2.72 g (40 mmol) of imidazole is added, and then 1.37 g (5 mmol) of TBDPSCl (tert-butyldiphenylsilyl chloride) is added dropwise slowly over 15 min. After the addition, the reaction compounds are stirred for another 3 hours at room temperature. The reaction mixture is diluted with 150 mL of dichloromethane, washed with 50 mL×3 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 30, a white, foam-like solid. ESI-MS, m/z=949 ([M+Na]$^+$).

G.

2.78 g (3 mmol) of compound 30 and 0.15 g DMAP are dissolved in 20 mL dry pyridine, stirred under cooling with an ice-water bath, and 8 mL of acetic anhydride is added dropwise. After the addition, the reaction compounds are stirred overnight at room temperature. The reaction mixture is diluted with 150 mL of dichloromethane, washed successively with 100 mL of 5% diluted hydrochloric acid and 50 mL×2 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 31, a white, foam-like solid. ESI-MS, m/z=991 ([M+Na]$^+$).

H.

2.42 g (2.5 mmol) of compound 31 is dissolved in 20 mL of 90% aqueous acetic acid solution, heated up to 60° C., and stirred overnight. After cooling the reaction mixture is dumped into 100 mL of saturated salt water, adjusted to pH=6-7 with saturated NaHCO$_3$ solution, stirred, and extracted with 50 mL×3 of dichloromethane. The organic phases are combined, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 32, a white, foam-like solid. ESI-MS, m/z=515 ([M+Na]$^+$).

I.

6.35 g (25 mmol) of iodine is dissolved in 50 mL of dry dichloromethane, stirred under cooling with an ice-water bath, 6.56 g (25 mmol) of triphenylphosphine is added slowly, after the addition the reaction compounds are stirred for another 10 min. 6.81 g (100 mmol) of imidazole is then added slowly, and stirred for another hour after the addition. To the above resulting system, 0.99 g (2 mmol) of compound 32 is added, After the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 33, a white, foam-like solid. ESI-MS, m/z=735 ([M+Na]$^+$).

J.

0.93 g (1.3 mmol) of compound 33 and 1 mL of triethylamine are dissolved in 5 mL of THF, then 0.1 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 34, a white solid. ESI-MS, m/z=478 ([M+NH$_4$]$^+$).

K.

To 5 mL of dry absolute methanol, 0.1 g metallic sodium is added, stirred under the protection of nitrogen at room temperature, until the metallic sodium disappears. 0.46 g (1 mmol) of compound 34 is then added, and stirred for another 3 hours at room temperature. To the reaction system, 1 g of strong acid cation exchange resin is added, stirred overnight at room temperature, until the reaction mixture's pH=7. The resin is removed by suction filtration, the filtrate is evaporated to dryness on the rotary evaporator, and the resulting residue is further dried on the vacuum oil pump to obtain the product I-D1-3,6, a white, foam-like solid. ESI-MS, m/z=399 ([M+Na]$^+$).

Example 7

Preparation of (1S)-1-[4-chloro-3-(4-ethoxybenzyl)phenyl]-1,2,6-trideoxy-D-glucose (I-D1-2,6)

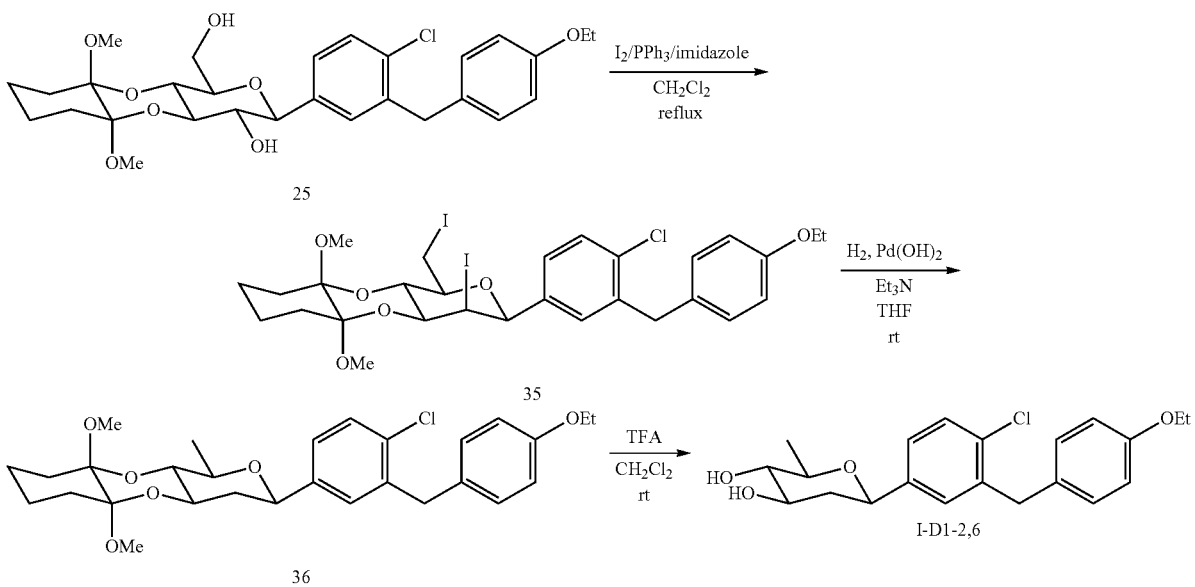

A.

12.69 g (50 mmol) of iodine is dissolved in 50 mL of dry dichloromethane, stirred under cooling with an ice-water bath, 13.11 g (50 mmol) of triphenylphosphine is added slowly, after the addition, the reaction compounds are stirred for another 10 min. 13.62 g (200 mmol) of imidazole is then added slowly, and stirred for another hour after the addition. To the above resulting system, 2.75 g (5 mmol) of compound 25 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 35, a white, foam-like solid. ESI-MS, m/z=791 ([M+Na]$^+$).

B.

1.54 g (3 mmol) of compound 35 and 2 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 36, a white solid. ESI-MS, m/z=539 ([M+Na]$^+$).

C.

0.52 g (1 mmol) of compound 36 is dissolved in a mixture composed of 6 mL of dichloromethane and 6 mL of trifluoroacetic acid (TFA), and stirred overnight at room temperature. The reaction mixture is dumped into 100 mL of saturated salt water, stirred, and extracted with 50 mL×3 of dichloromethane. The organic phases are combined, washed with the saturated salt water, and dried with anhydrous sodium sulfate. The drying agent is removed by filtration, the solvent in the filtrate is removed on the rotary evaporator, and the resulting residue is purified by silica gel column chromatography to obtain the pure product I-D1-2,6, a white, foam-like solid. ESI-MS, m/z=393 ([M+NH$_4$]$^+$).

Example 8

Preparation of (1S)-1-[4-chloro-3-(4-ethoxybenzyl) phenyl]-1,3,4-trideoxy-D-glucose (I-D1-3,4)

and 50 mL×2 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 37, a white, foam-like solid. ESI-MS, m/z=655 ([M+Na]$^+$).

B.

3.80 g (6 mmol) of compound 37 is dissolved in a mixture composed of 10 mL of dichloromethane and 10 mL of trifluoroacetic acid (TFA), and stirred overnight at room temperature. The reaction mixture is dumped into 100 mL of saturated salt water, stirred, and extracted with 100 mL×3 of dichloromethane. The organic phases are combined, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 38, a white, foam-like solid. ESI-MS, m/z=493 ([M+H]$^+$).

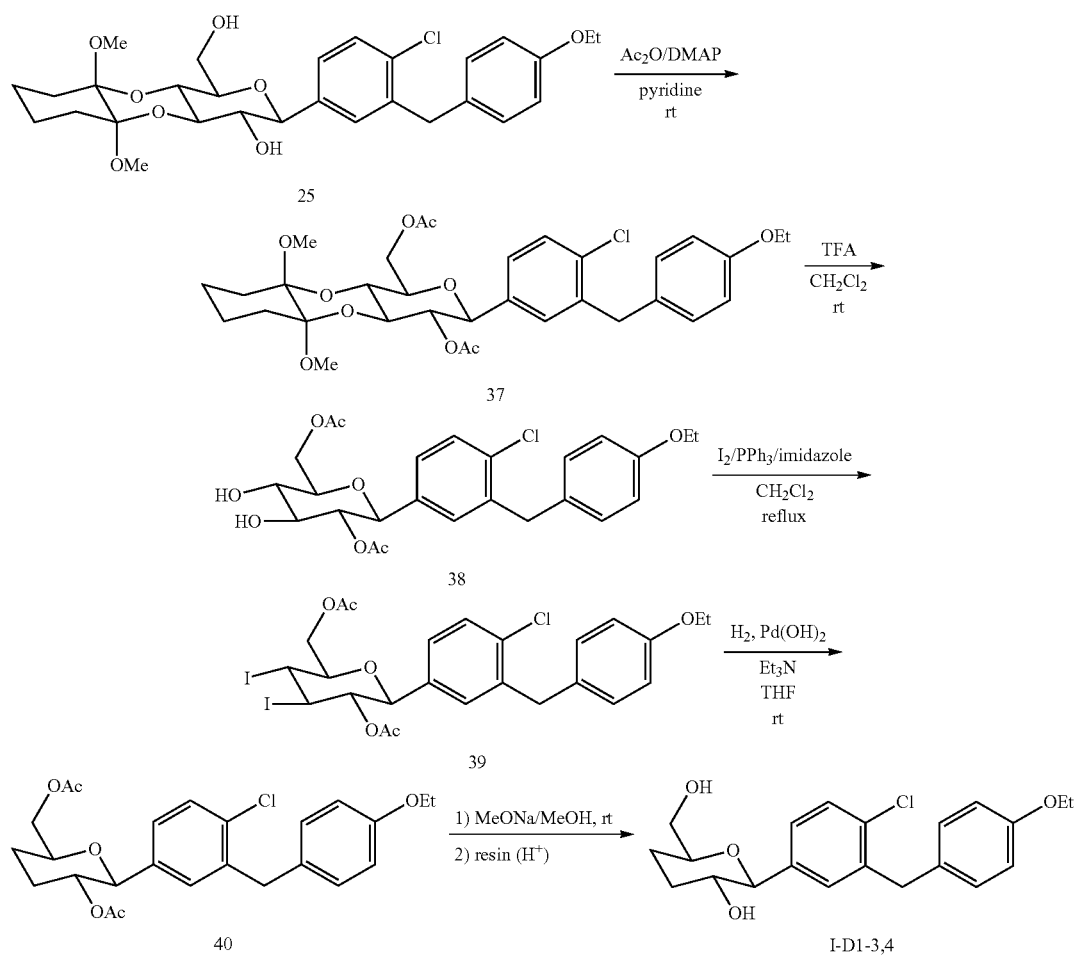

A.

5.49 g (10 mmol) of compound 25 and 0.30 g DMAP are dissolved in 30 mL of dry pyridine, stirred under cooling with an ice-water bath, and 15 mL of acetic anhydride is added dropwise. After the addition, the reaction compounds are stirred overnight at room temperature. The reaction mixture is diluted with 150 mL of dichloromethane, washed successively with 100 mL of 5% diluted hydrochloric acid

C.

12.69 g (50 mmol) of iodine is dissolved in 50 mL of dry dichloromethane, stirred under cooling with an ice-water bath, 13.11 g (50 mmol) of triphenylphosphine is added slowly, after the addition the reaction compounds are stirred for another 10 min. 13.62 g (200 mmol) of imidazole is then added slowly, and stirred for another hour after the addition. To the above resulting system, 2.46 g (5 mmol) of compound 38 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 39, a white, foam-like solid. ESI-MS, m/z=735 ([M+Na]$^+$).

D.

2.14 g (3 mmol) of compound 39 and 2 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 40, a white, foam-like solid. ESI-MS, m/z=483 ([M+Na]$^+$).

E.

To 5 mL of dry absolute methanol, 0.1 g of metallic sodium is added, stirred under the protection of nitrogen at room temperature, until the metallic sodium disappearing. 0.46 g (1 mmol) of compound 40 is then added, stirred for another 3 hours at room temperature. To the reaction system, 1 g of strong acid cation exchange resin is added, stirred overnight at room temperature, until the pH of the reaction mixture is pH=7. The resin is removed by suction filtration, the filtrate is evaporated to dryness on the rotary evaporator, and the resulting residue is further dried on the vacuum oil pump to obtain the product I-D1-3,4, a white, foam-like solid. ESI-MS, m/z=394 ([M+NH$_4$]$^+$).

Example 9

Preparation of (1S)-1-[4-chloro-3-(4-ethoxybenzyl)phenyl]-1,2,4-trideoxy-D-glucose (I-D1-2,4)

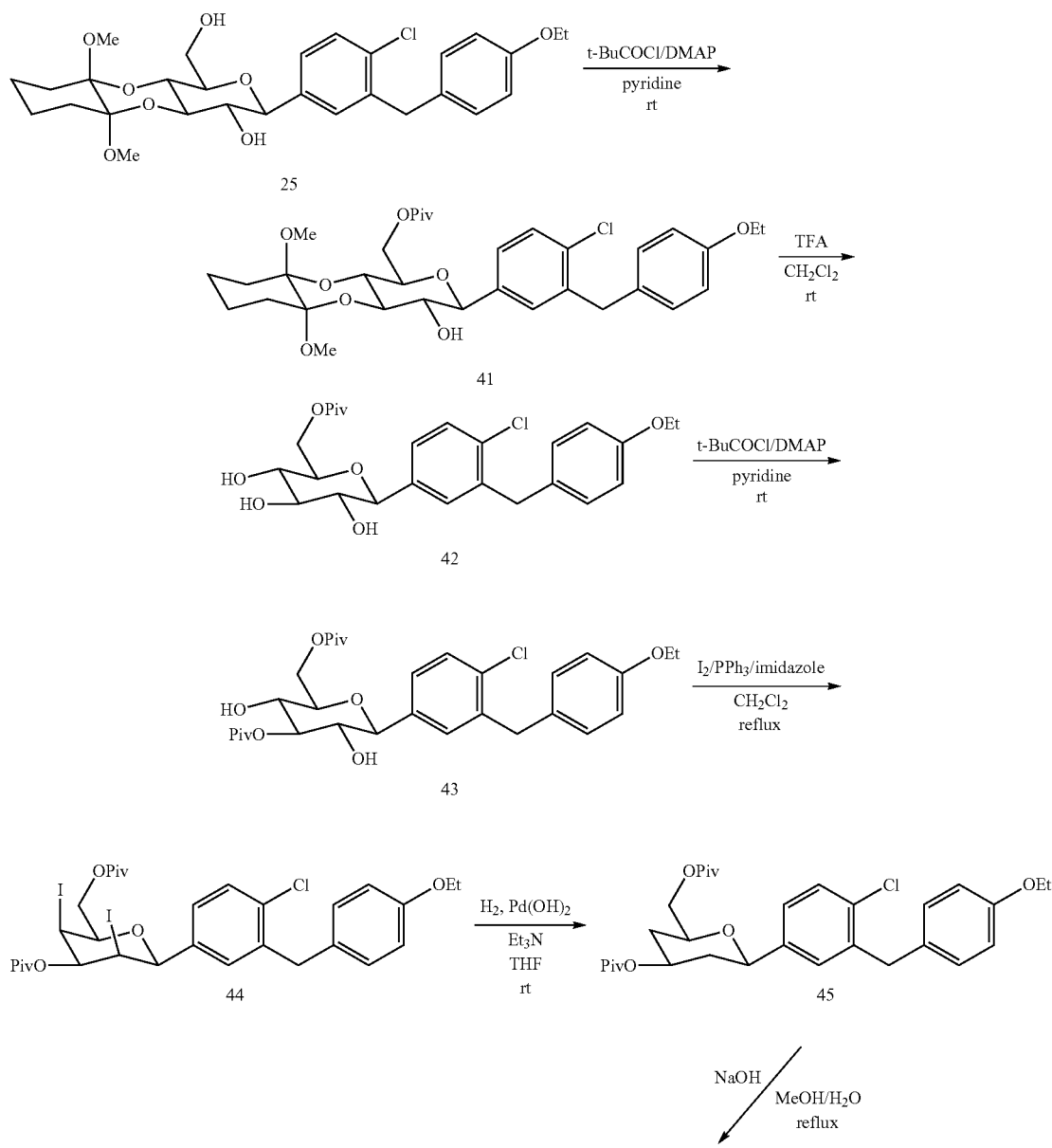

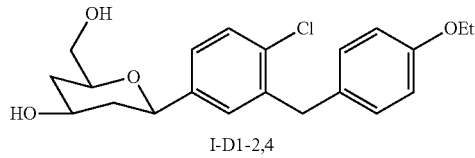

I-D1-2,4

A.

5.49 g (10 mmol) of compound 25 and 0.5 g of DMAP are dissolved in 20 mL of dry pyridine, stirred under cooling with an ice-water bath, and 1.33 g (11 mmol) of pivaloyl chloride is added dropwise. After the addition, the reaction compounds are stirred overnight at room temperature. The reaction mixture is diluted with 150 mL of dichloromethane, washed successively with 100 mL of 5% diluted hydrochloric acid and 50 mL×2 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 41, a white, foam-like solid. ESI-MS, m/z=655 ([M+Na]$^+$).

B.

5.07 g (8 mmol) of compound 41 is dissolved in a mixture composed of 10 mL of dichloromethane and 10 mL of trifluoroacetic acid (TFA), and stirred overnight at room temperature. The reaction mixture is dumped into 200 mL of saturated salt water, stirred, and extracted with 100 mL×3 of dichloromethane. The organic phases are combined, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 42, a white, foam-like solid. ESI-MS, m/z=510 ([M+NH$_4$]$^+$).

C.

2.96 g (6 mmol) of compound 42 and 0.3 g of DMAP are dissolved in 20 mL of dry pyridine, stirred under cooling with an ice-water bath, 0.96 g (8 mmol) of pivaloyl chloride is added dropwise. After the addition, the reaction compounds are stirred overnight at room temperature. The reaction mixture is diluted with 150 mL of dichloromethane, washed successively with 100 mL of 5% diluted hydrochloric acid and 50 mL×2 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 43, a white, foam-like solid. ESI-MS, m/z=599 ([M+Na]$^+$).

D.

12.69 g (50 mmol) of iodine is dissolved in 50 mL of dry dichloromethane, stirred under cooling with an ice-water bath, 13.11 g (50 mmol) of triphenylphosphine is added slowly, after the addition the reaction compounds are stirred for another 10 min. 13.62 g (200 mmol) of imidazole is then added slowly, and stirred for another hour after the addition. To the above resulting system, 2.89 g (5 mmol) of compound 43 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product 44, a white, foam-like solid. ESI-MS, m/z=797 ([M+H]$^+$).

E.

2.39 g (3 mmol) of compound 44 and 2 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, the resulting residue is purified by column chromatography to obtain the pure product 45, a white, foam-like solid. ESI-MS, m/z=567 ([M+Na]$^+$).

F.

0.55 (1 mmol) of compound 45 is dissolved in 10 mL of methanol, stirred, and 1 mL of 50% NaOH solution is added, heated to reflux for half an hour. The reaction compounds are dumped into water after cooling, adjusted with the concentrated hydrochloric acid to pH=4, and extracted with 50 mL×3 of dichloromethane. The organic phases are combined, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product I-D1-2,4, a white, foam-like solid. ESI-MS, m/z=377 ([M+H]$^+$).

Example 10

Preparation of (1S)-1-[4-chloro-3-(4-ethoxybenzyl)phenyl]-1,2,3-trideoxy-D-glucose (I-D1-2,3)

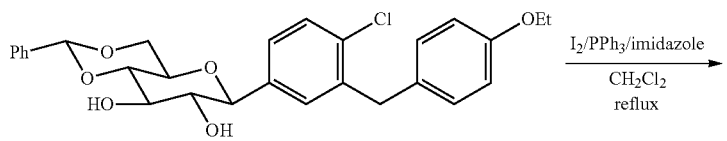

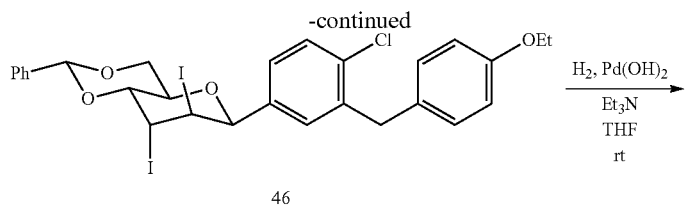

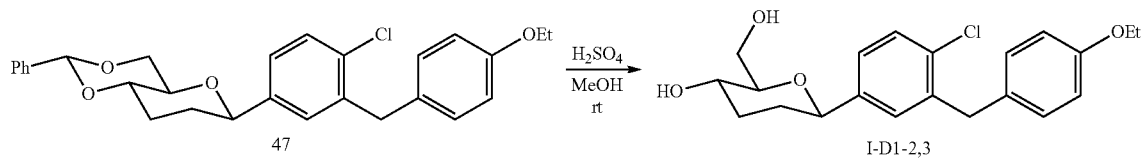

A.

12.69 g (50 mmol) of iodine is dissolved in 50 mL of dry dichloromethane, stirred under cooling with an ice-water bath, 13.11 g (50 mmol) of triphenylphosphine is added slowly, after the addition the reaction compounds are stirred for another 10 min. 13.62 g (200 mmol) of imidazole is then added slowly, and stirred for another hour after the addition. To the above resulting system, 2.48 g (5 mmol) of compound 7 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 46, a white, foam-like solid. ESI-MS, m/z=734 ([M+NH$_4$]$^+$).

B.

1.43 g (2 mmol) of compound 46 and 2 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 47, a white, foam-like solid. ESI-MS, m/z=487 ([M+Na]$^+$).

C.

0.46 g (1 mmol) of compound 47 dissolved in 5 mL of methanol containing 3 drops of concentrated sulfuric acid, stirred overnight at room temperature. The reaction mixture is dumped into 100 mL saturated salt water, stirred, and extracted with 100 mL×3 dichloromethane. The organic phases are combined, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product I-D1-2,3, a white, foam-like solid. ESI-MS, m/z=394 ([M+NH$_4$]$^+$).

Example 11

Preparation of (1S)-1-[4-chloro-3-(4-ethoxybenzyl)phenyl]-1,3,4,6-tetradeoxy-D-glucose (I-D1-3, 4, 6)

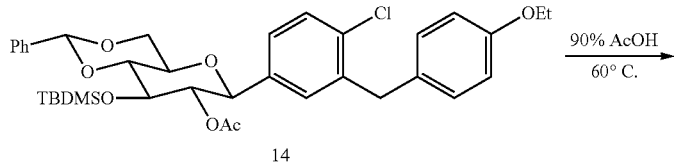

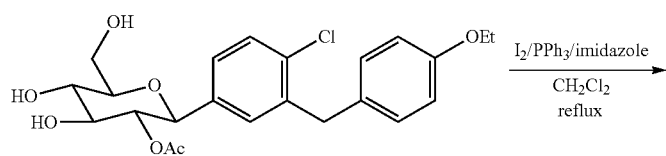

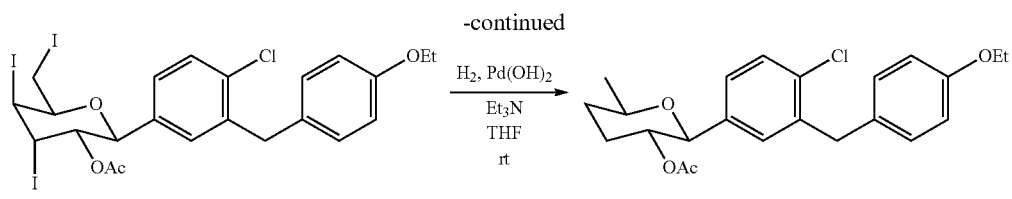

A.

6.53 g (10 mmol) of compound 14 is dissolved in 50 mL of 90% acetic acid solution, stirred overnight at 60° C., dumped into 200 mL of ice water after cooling slightly, adjusted to pH=7-8 with saturated NaHCO$_3$, and extracted with 50 mL×3 of dichloromethane. The organic phases are combined, washed with 100 mL of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 48, a white, foam-like solid. ESI-MS, m/z=468 ([M+NH$_4$]$^+$).

B.

12.69 g (50 mmol) of iodine is dissolved in 50 mL of dry dichloromethane, stirred under cooling with an ice-water bath, 13.11 g (50 mmol) of triphenylphosphine is added slowly, after the addition, the reaction compounds are stirred for another 10 min. 13.62 g (200 mmol) of imidazole is then added slowly, and stirred for another hour after the addition. To the above resulting system, 2.25 g (5 mmol) of compound 48 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 49, a white, foam-like solid. ESI-MS, m/z=803 ([M+Na]$^+$).

C.

1.56 g (2 mmol) of compound 49 and 2 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 50, a white, foam-like solid. ESI-MS, m/z=425 ([M+Na]$^+$).

D.

To 5 mL of dry absolute methanol, 0.1 g of metallic sodium is added, stirred under the protection of nitrogen at room temperature, until the metallic sodium disappeared. 0.40 g (1 mmol) of compound 50 is then added, and stirred for another 3 hours at room temperature. To the reaction system, 1 g of strong acid cation exchange resin is added, stirred overnight at room temperature, until the pH of the reaction mixture is pH=7. The resin is removed by suction filtration, the filtrate is evaporated to dryness on the rotary evaporator, the resulting residue is further dried on the vacuum oil pump to obtain the product I-D1-3, 4, 6, a white, foam-like solid. ESI-MS, m/z=378 ([M+NH$_4$]$^+$).

Example 12

Preparation of (1S)-1-[4-chloro-3-(4-ethoxybenzyl) phenyl]-1,2,4,6-tetradeoxy-D-glucose (I-D1-2, 4, 6)

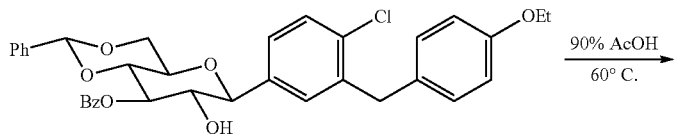

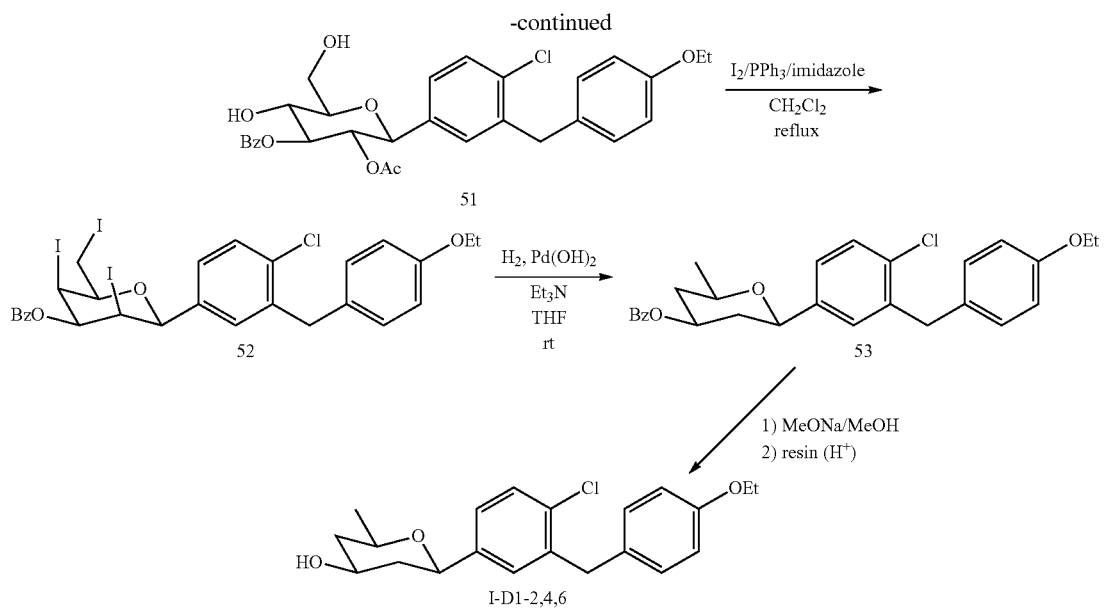

A.

6.01 g (10 mmol) of compound 18 is dissolved in 50 mL of 90% acetic acid solution, stirred overnight at 60° C., dumped into 200 mL of ice water after cooling slightly, adjusted to pH=7-8 with saturated NaHCO$_3$, and extracted with 50 mL×3 of dichloromethane. The organic phases are combined, washed with 100 mL of saturated salt water, and dried with anhydrous sodium sulfate. The drying agent is removed by filtration, the solvent in the filtrate is removed on the rotary evaporator, the resulting residue is purified by silica gel column chromatography to obtain the pure product 51, a white, foam-like solid. ESI-MS, m/z=535 ([M+Na]$^+$).

B.

12.69 g (50 mmol) of iodine is dissolved in 50 mL of dry dichloromethane, stirred under cooling with an ice-water bath, 13.11 g (50 mmol) of triphenylphosphine is added slowly, after the addition, the reaction compounds are stirred for another 10 min. 13.62 g (200 mmol) of imidazole is then added slowly, and stirred for another hour after the addition. To the above resulting system, 2.05 g (4 mmol) of compound 51 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 52, a white, foam-like solid. ESI-MS, m/z=864 ([M+Na]$^+$).

C.

1.56 g (2 mmol) of compound 52 and 2 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 53, a white, foam-like solid. ESI-MS, m/z=487 ([M+Na]$^+$).

D.

To 5 mL of dry absolute methanol, 0.1 g of metallic sodium is added, stirred under the protection of nitrogen at room temperature, until the metallic sodium disappeared. 0.47 g (1 mmol) of compound 53 is then added, and stirred for another 3 hours at room temperature. To the reaction system, 1 g of strong acid cation exchange resin is added, stirred overnight at room temperature, until the reaction mixture's pH=7. The resin is removed by suction filtration, the filtrate is evaporated to dryness on the rotary evaporator, the resulting residue is further dried on the vacuum oil pump to obtain the product I-D1-2, 4, 6, a white, foam-like solid. ESI-MS, m/z=361 ([M+H]$^+$).

Example 13

Preparation of (1S)-1-[4-chloro-3-(4-ethoxybenzyl) phenyl]-1,2,3,6-tetradeoxy-D-glucose (I-D1-2, 3, 6)

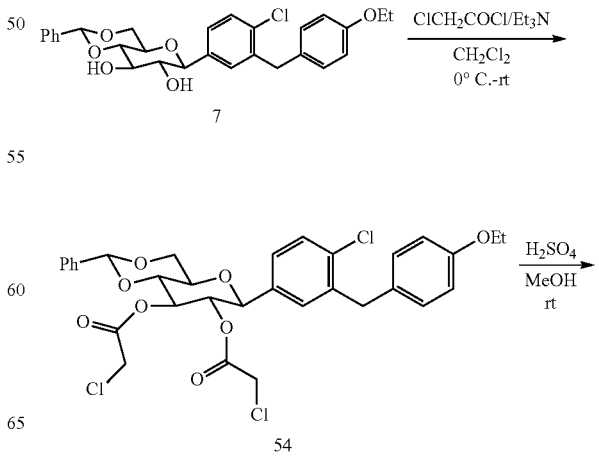

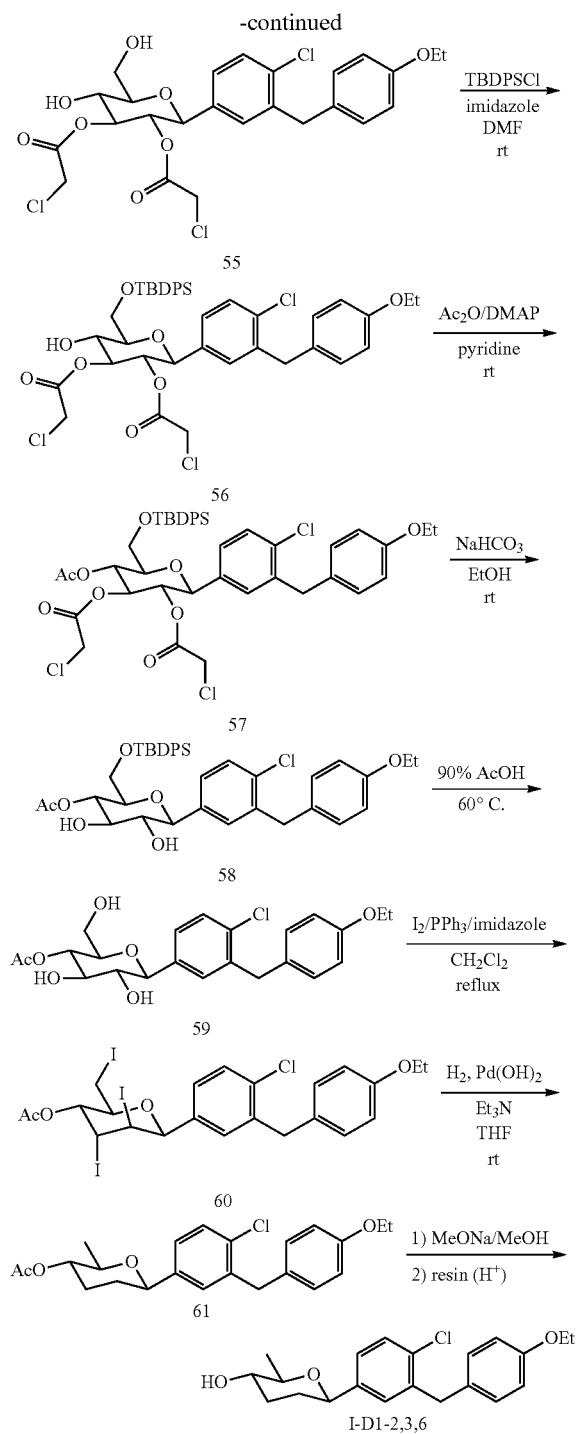

residue is purified by silica gel column chromatography to obtain the pure product 54, a white, foam-like solid. ESI-MS, m/z=671 and 673 ([M+Na]+).

B.

5.20 g (8 mmol) of compound 54 is dissolved in 40 mL of methanol containing 5 drops of concentrated sulfuric acid, stirred overnight at room temperature. The reaction mixture is dumped into 200 mL of saturated salt water, stirred, and extracted with 100 mL×3 of dichloromethane. The organic phases are combined, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 55, a white, foam-like solid. ESI-MS, m/z=578 and 580 ([M+NH4]+).

C.

3.37 g (6 mmol) of compound 55 is dissolved in 20 mL of dry DMF, stirred under cooling with an ice-water bath, 2.72 g (40 mmol) of imidazole is added, and then 2.20 g (8 mmol) of TBDPSCl (tert-butyldiphenylsilyl chloride) is added dropwise slowly over 15 min. After the addition, the reaction compounds are stirred for another 3 hours at room temperature. The reaction mixture is diluted with 150 mL of dichloromethane, washed with 50 mL×3 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 56, a white, foam-like solid. ESI-MS, m/z=821 and 823 ([M+Na]+).

D.

4.00 g (5 mmol) of compound 56 and 0.30 g of DMAP are dissolved in 30 mL of dry pyridine, stirred under cooling with an ice-water bath, and 15 mL of acetic anhydride is added dropwise. After the addition, the reaction compounds are stirred overnight at room temperature. The reaction mixture is diluted with 150 mL of dichloromethane, washed successively with 100 mL of 5% diluted hydrochloric acid and 50 mL×2 of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 57, a white, foam-like solid. ESI-MS, m/z=863 and 865 ([M+Na]+).

E.

3.37 g (4 mmol) of compound 57 is dissolved in 30 mL of absolute ethanol, stirred at room temperature, 1.68 g (20 mmol) of NaHCO3 solid is added, and further stirred overnight at room temperature. The reaction mixture is dumped into 200 mL of saturated salt water, stirred, and extracted with 100 mL×3 of dichloromethane. The organic phases are combined, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product 58, a white, foam-like solid. ESI-MS, m/z=706 ([M+NH4]+).

F.

2.07 g (3 mmol) of compound 58 is dissolved in 20 mL of 90% aqueous acetic acid solution, stirred overnight at 60° C., dumped into 200 mL of ice water after cooling slightly, adjusted to pH=7-8 with saturated NaHCO3, and extracted with 50 mL×3 of dichloromethane. The organic phases are combined, washed with 100 mL of saturated salt water, and dried with anhydrous sodium sulfate. The drying agent is

A.

4.97 g (10 mmol) of compound 7 and 6.07 g (60 mmol) of triethylamine are dissolved in 50 mL of dry dichloromethane, stirred under cooling with an ice-water bath. 3.39 g (30 mmol) of chloroacetyl chloride is added dropwise slowly. After the addition, the reaction mixture is stirred overnight at room temperature. The reaction mixture is diluted with 150 mL of dichloromethane, washed successively with saturated salt water, 2% diluted hydrochloric acid and saturated salt water, and dried with anhydrous sodium sulfate. The drying agent is removed by filtration, the solvent in the filtrate is removed on the rotary evaporator, and the resulting removed by filtration, the solvent in the filtrate is removed on the rotary evaporator, the resulting residue is purified by silica gel column chromatography to obtain the pure product 59, a white, foam-like solid. ESI-MS, m/z=473 ([M+Na]$^+$).

G.

12.69 g (50 mmol) of iodine is dissolved in 50 mL of dry dichloromethane, stirred under cooling with an ice-water bath, 13.11 g (50 mmol) of triphenylphosphine is added slowly, after the addition, the reaction compounds are stirred for another 10 min. 13.62 g (200 mmol) of imidazole is then added slowly, and stirred for another hour after the addition. To the above resulting system, 0.90 g (2 mmol) of compound 59 is added, after addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration,

I.

To 5 mL of dry absolute methanol, 0.1 g of metallic sodium is added, stirred under the protection of nitrogen at room temperature, until the metallic sodium disappeared. 0.40 g (1 mmol) of compound 61 is then added, and stirred for another 3 hours at room temperature. To the reaction system, 1 g of strong acid cation exchange resin is added, stirred overnight at room temperature, until the reaction mixture's pH=7. The resin is removed by suction filtration, the filtrate is evaporated to dryness on the rotary evaporator, and the resulting residue is further dried on the vacuum oil pump to obtain the product I-D1-2, 3, 6, a white, foam-like solid. ESI-MS, m/z=383 ([M+Na]$^+$).

Example 14

Preparation of (1S)-1-[4-chloro-3-(4-ethoxybenzyl) phenyl]-1,2,3,4-tetradeoxy-D-glucose (I-D1-2, 3, 4)

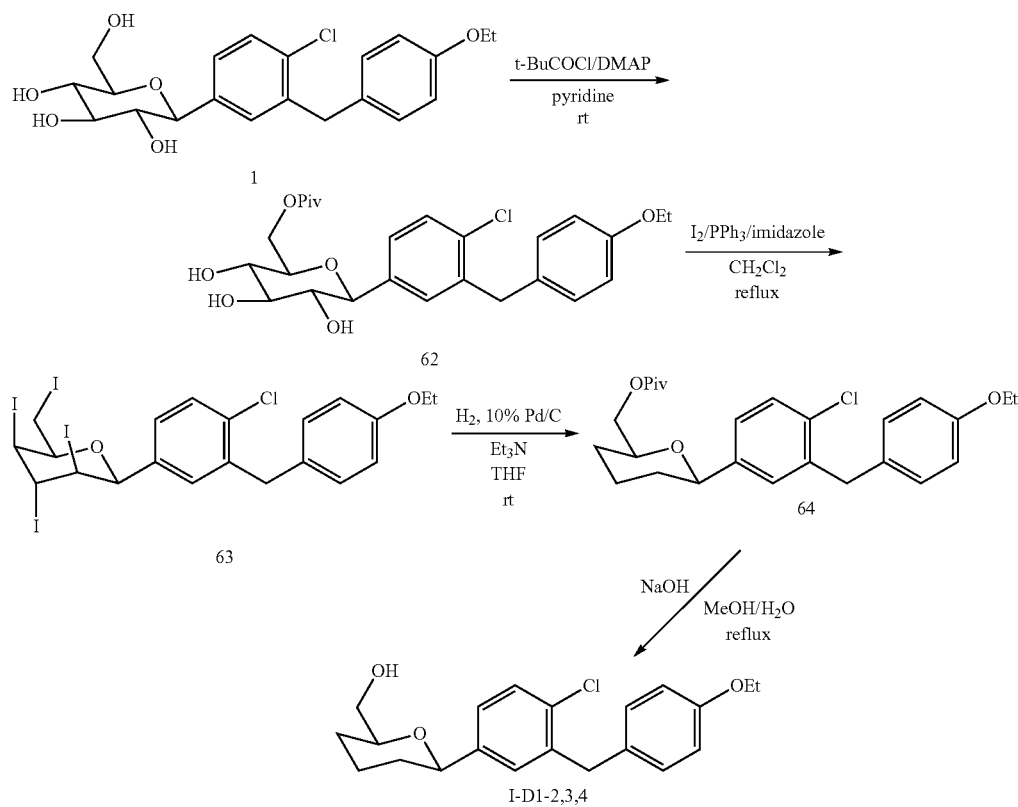

the solvent in the filtrate is removed on the rotary evaporator, the resulting residue is purified by silica gel column chromatography to obtain the pure product 60, a white, foam-like solid. ESI-MS, m/z=781 ([M+H]$^+$).

H.

1.17 g (1.5 mmol) of compound 60 and 1 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product 61, a white, foam-like solid. ESI-MS, m/z=425 ([M+Na]$^+$).

A.

4.09 g (10 mmol) of compound 1 and 0.5 g of DMAP are dissolved in 20 mL of dry pyridine, stirred under cooling with an ice-water bath, and 1.33 g (11 mmol) of pivaloyl chloride is added dropwise. After the addition, the reaction compounds are stirred overnight at room temperature. The reaction mixture is diluted with 150 mL of dichloromethane, washed successively with 100 mL of 5% diluted hydrochloric acid and 50 mL×2 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 62, a white, foam-like solid. ESI-MS, m/z=515 ([M+Na]$^+$).

B.

12.69 g (50 mmol) of iodine is dissolved in 50 mL of dry dichloromethane, stirred under cooling with an ice-water bath, 13.11 g (50 mmol) of triphenylphosphine is added slowly, after the addition the reaction compounds are stirred for another 10 min. 13.62 g (200 mmol) of imidazole is then added slowly, and stirred for another hour after the addition. To the above resulting system, 0.99 g (2 mmol) of compound 62 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product 63, a white, foam-like solid. ESI-MS, m/z=840 ([M+NH$_4$]$^+$).

C.

1.23 g (1.5 mmol) of compound 63 and 1 mL of triethylamine are dissolved in 10 mL of THF, then 0.2 g 10% of Pd/C is added, and the reaction mixture is hydrogenated overnight under the pressure of 0.3 MPa of hydrogen gas at room temperature. The reaction compounds are suction filtered to remove the catalyst, the filtrate is evaporated to dryness on the rotary evaporator, and the resulting residue is purified by column chromatography to obtain the pure product 64, a white, foam-like solid. ESI-MS, m/z=467 ([M+Na]$^+$).

D.

0.44 (1 mmol) of compound 65 is dissolved in 5 mL methanol, stirred, 0.5 mL 50% of NaOH solution is added, heated up to reflux for half an hour. The reaction compounds are dumped into water after cooling, adjusted with the concentrated hydrochloric acid to pH=4, and extracted with 50 mL×3 of dichloromethane. The organic phases are combined, washed with saturated salt water, and dried with anhydrous sodium sulfate. The drying agent is removed by filtration, the solvent in the filtrate is removed on the rotary evaporator, and the resulting residue is purified by silica gel column chromatography to obtain the pure product I-D1-2, 3, 4, a white, foam-like solid. ESI-MS, m/z=361 ([M+H]$^+$).

Example 15

Preparation of (1S)-1-[4-chloro-3-(4-ethoxybenzyl) phenyl]-1,2,3,4,6-pentadeoxy-D-glucose (I-D1-2, 3, 4, 6)

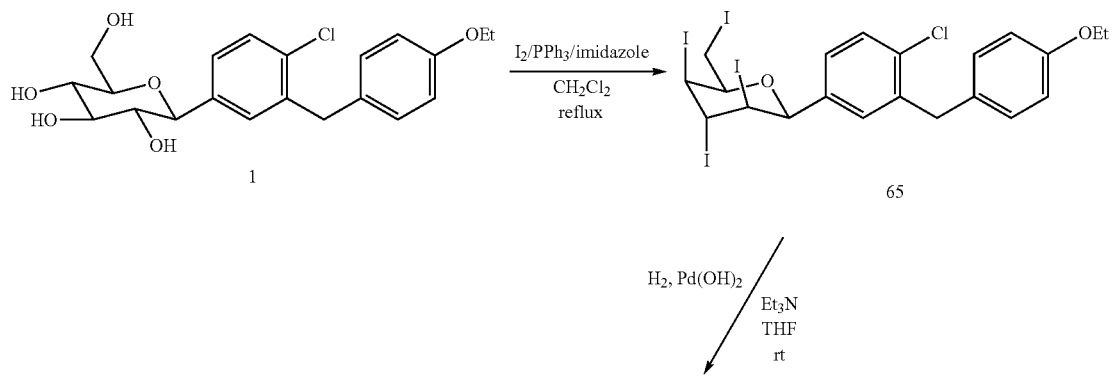

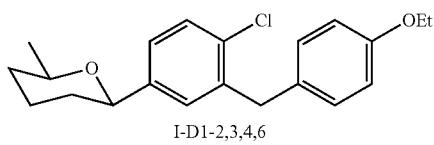

I-D1-2,3,4,6

A.

12.69 g (50 mmol) of iodine is dissolved in 50 mL of dry dichloromethane, stirred under cooling with an ice-water bath, 13.11 g (50 mmol) of triphenylphosphine is added slowly, after the addition, the reaction compounds are stirred for another 10 min. 13.62 g (200 mmol) of imidazole is then added slowly, and stirred for another hour after the addition. To the above resulting system, 0.98 g (2 mmol) of compound 1 is added, after the addition the reaction compounds are stirred at reflux overnight under nitrogen atmosphere. The reaction mixture is diluted with 100 mL of dichloromethane, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product 65, a white, foam-like solid. ESI-MS, m/z=870 ([M+Na]$^+$).

B.

0.85 g (1.5 mmol) of compound 65 and 1 mL of triethylamine are dissolved in 10 mL of THF, then 0.2 g of Pd(OH)$_2$ is added, and the reaction mixture is hydrogenated overnight at room temperature. The reaction compounds are suction filtered to remove the catalyst, the filtrate is evaporated to dryness on the rotary evaporator, and the resulting residue is purified by column chromatography to obtain the pure product I-D1-2, 3, 4, 6, a white, foam-like solid. ESI-MS, m/z=367 ([M+Na]$^+$).

Example 16-106

The following compounds having general formula I are prepared with the methods of Examples 1-15.

| Example | Structure | ESI-MS | Preparation method |
|---|---|---|---|
| 16 | 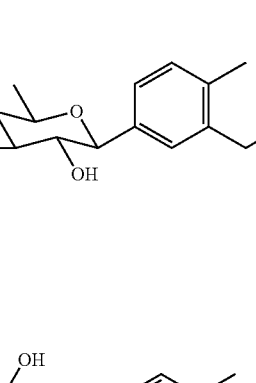 | 429 ([M + H]$^+$) | Example 1 |
| 17 | 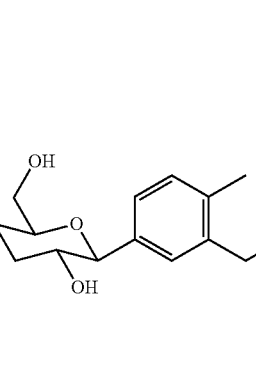 | 429 ([M + H]$^+$) | Example 2 |
| 18 | 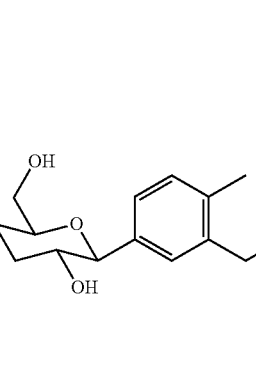 | 429 ([M + H]$^+$) | Example 3 |
| 19 | 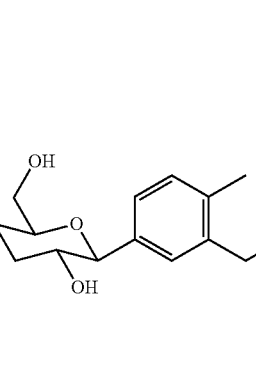 | 429 ([M + H]$^+$) | Example 4 |

-continued

| Example | Structure | ESI-MS | Preparation method |
|---|---|---|---|
| 21 | 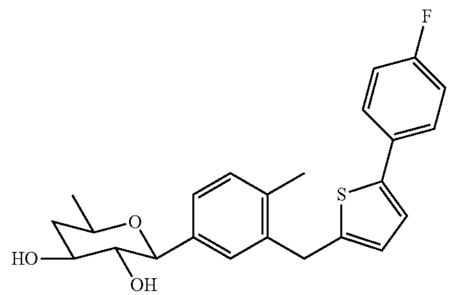 [SMILES: Cc1ccc(C2OC(C)CC(O)C2O)cc1Cc1ccc(-c2ccc(F)cc2)s1] | 413 ([M + H]$^+$) | Example 5 |
| 22 | 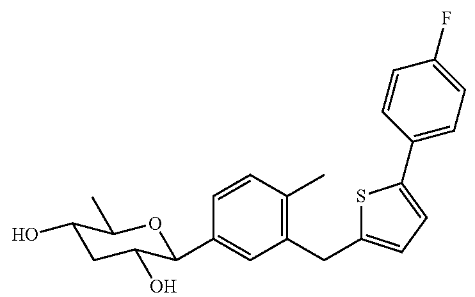 [SMILES: Cc1ccc(C2OC(C)C(O)CC2O)cc1Cc1ccc(-c2ccc(F)cc2)s1] | 413 ([M + H]$^+$) | Example 6 |
| 23 | 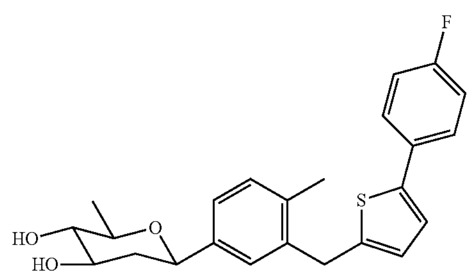 [SMILES: Cc1ccc(C2CC(O)C(O)C(C)O2)cc1Cc1ccc(-c2ccc(F)cc2)s1] | 413 ([M + H]$^+$) | Example 7 |
| 24 | 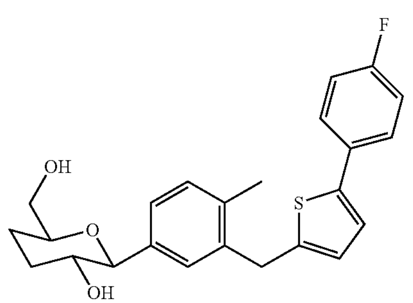 [SMILES: Cc1ccc(C2OC(CO)CCC2O)cc1Cc1ccc(-c2ccc(F)cc2)s1] | 413 ([M + H]$^+$) | Example 8 |
| 25 | 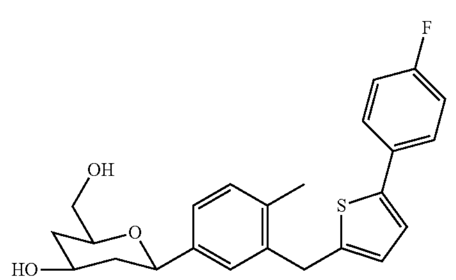 [SMILES: Cc1ccc(C2CC(O)CC(CO)O2)cc1Cc1ccc(-c2ccc(F)cc2)s1] | 413 ([M + H]$^+$) | Example 9 |

-continued

| Example | Structure | ESI-MS | Preparation method |
|---|---|---|---|
| 26 | 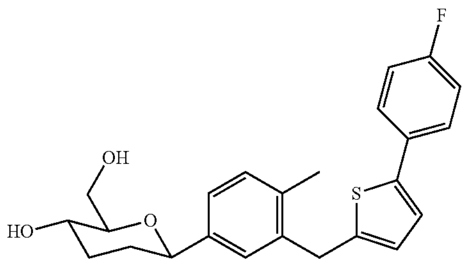 [SMILES: Cc1ccc(C2CCC(O)C(CO)O2)cc1Cc1ccc(-c2ccc(F)cc2)s1] | 413 ([M + H]$^+$) | Example 10 |
| 27 | 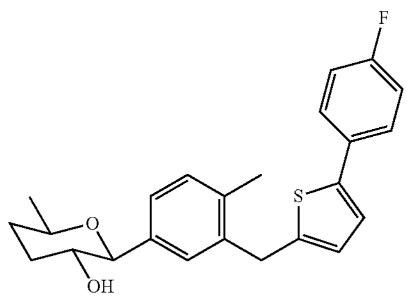 [SMILES: Cc1ccc(C2OC(C)CCC2O)cc1Cc1ccc(-c2ccc(F)cc2)s1] | 397 ([M + H]$^+$) | Example 11 |
| 28 | 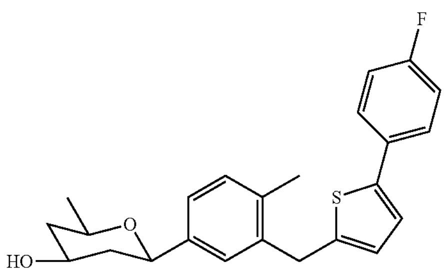 [SMILES: Cc1ccc(C2CC(O)CC(C)O2)cc1Cc1ccc(-c2ccc(F)cc2)s1] | 397 ([M + H]$^+$) | Example 12 |
| 29 | 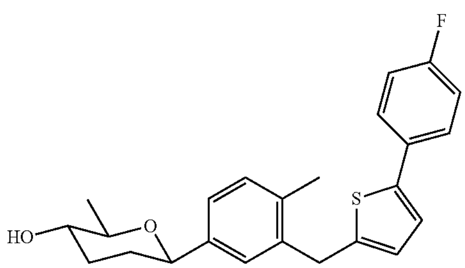 [SMILES: Cc1ccc(C2CCC(O)C(C)O2)cc1Cc1ccc(-c2ccc(F)cc2)s1] | 397 ([M + H]$^+$) | Example 13 |
| 30 | 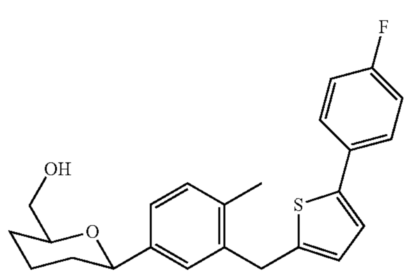 [SMILES: Cc1ccc(C2CCCC(CO)O2)cc1Cc1ccc(-c2ccc(F)cc2)s1] | 397 ([M + H]$^+$) | Example 14 |

-continued
| Example | Structure | ESI-MS | Preparation method |
|---|---|---|---|
| 31 | 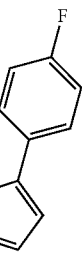 | 381 ([M + H]⁺) | Example 15 |
| 32 | 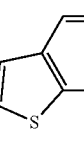 | 389 ([M + H]⁺) | Example 1 |
| 33 | 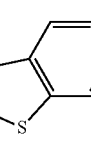 | 389 ([M + H]⁺) | Example 2 |
| 34 | 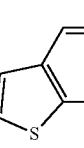 | 389 ([M + H]⁺) | Example 3 |
| 35 | 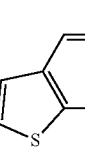 | 389 ([M + H]⁺) | Example 4 |
| 36 | 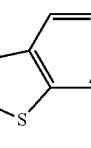 | 373 ([M + H]⁺) | Example 5 |
| 37 | 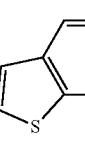 | 373 ([M + H]⁺) | Example 6 |
| 38 | 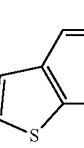 | 373 ([M + H]⁺) | Example 7 |
| 39 | 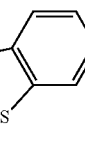 | 373 ([M + H]⁺) | Example 8 |

| Example | Structure | ESI-MS | Preparation method |
|---|---|---|---|
| 40 | 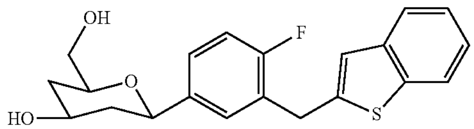 [SMILES: OCC1CC(O)CC(c2ccc(F)c(Cc3cc4ccccc4s3)c2)O1] | 373 ([M + H]+) | Example 9 |
| 41 | 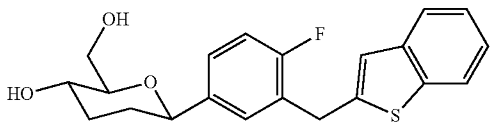 [SMILES: OCC1OC(c2ccc(F)c(Cc3cc4ccccc4s3)c2)CCC1O] | 373 ([M + H]+) | Example 10 |
| 42 | 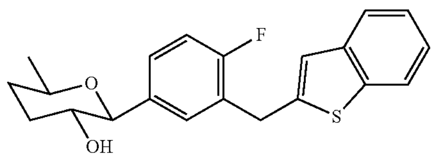 [SMILES: CC1CCC(O)C(c2ccc(F)c(Cc3cc4ccccc4s3)c2)O1] | 357 ([M + H]+) | Example 11 |
| 43 | 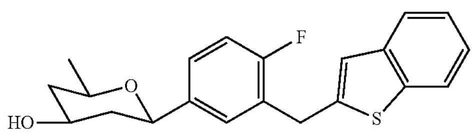 [SMILES: CC1CC(O)CC(c2ccc(F)c(Cc3cc4ccccc4s3)c2)O1] | 357 ([M + H]+) | Example 12 |
| 44 | 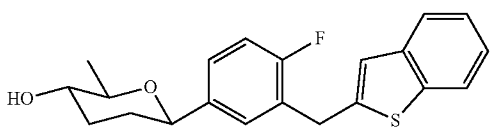 [SMILES: CC1OC(c2ccc(F)c(Cc3cc4ccccc4s3)c2)CCC1O] | 357 ([M + H]+) | Example 13 |
| 45 | 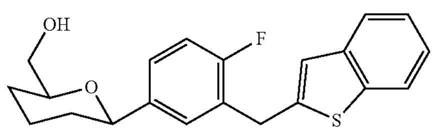 [SMILES: OCC1CCCC(c2ccc(F)c(Cc3cc4ccccc4s3)c2)O1] | 357 ([M + H]+) | Example 14 |
| 46 | 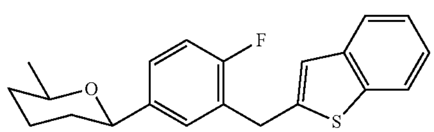 [SMILES: CC1CCCC(c2ccc(F)c(Cc3cc4ccccc4s3)c2)O1] | 341 ([M + H]+) | Example 15 |
| 47 | 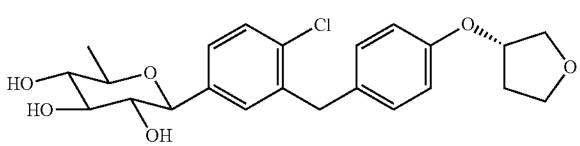 | 435 ([M + H]+) | Example 1 |
| 48 | 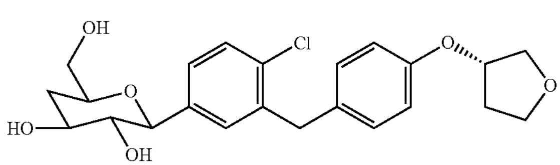 [SMILES: OCC1CC(O)C(O)C(c2ccc(Cl)c(Cc3ccc(O[C@H]4CCOC4)cc3)c2)O1] | 435 ([M + H]+) | Example 2 |
| 49 | 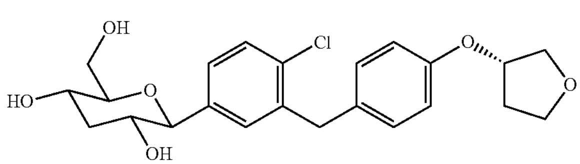 [SMILES: OCC1OC(c2ccc(Cl)c(Cc3ccc(O[C@H]4CCOC4)cc3)c2)C(O)CC1O] | 435 ([M + H]+) | Example 3 |

-continued

| Example | Structure | ESI-MS | Preparation method |
|---|---|---|---|
| 50 | 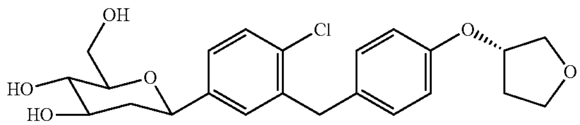 [SMILES: OCC1OC(c2ccc(Cl)c(Cc3ccc(O[C@H]4CCOC4)cc3)c2)CC(O)C1O] | 435 ([M + H]⁺) | Example 4 |
| 51 | 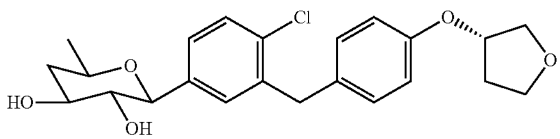 [SMILES: CC1CC(O)C(O)C(c2ccc(Cl)c(Cc3ccc(O[C@H]4CCOC4)cc3)c2)O1] | 419 ([M + H]⁺) | Example 5 |
| 52 | 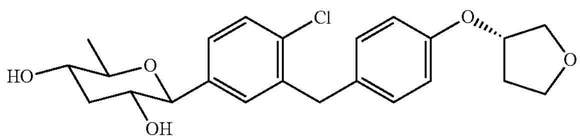 [SMILES: CC1OC(c2ccc(Cl)c(Cc3ccc(O[C@H]4CCOC4)cc3)c2)C(O)CC1O] | 419 ([M + H]⁺) | Example 6 |
| 53 | 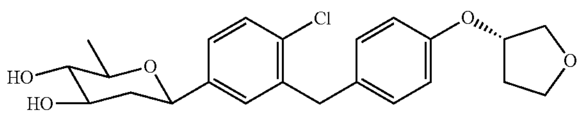 [SMILES: CC1OC(c2ccc(Cl)c(Cc3ccc(O[C@H]4CCOC4)cc3)c2)CC(O)C1O] | 419 ([M + H]⁺) | Example 7 |
| 54 | 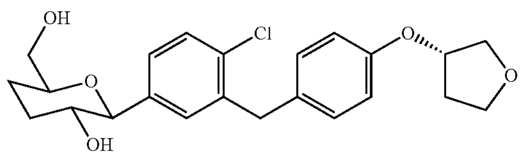 [SMILES: OCC1CCC(O)C(c2ccc(Cl)c(Cc3ccc(O[C@H]4CCOC4)cc3)c2)O1] | 419 ([M + H]⁺) | Example 8 |
| 55 | 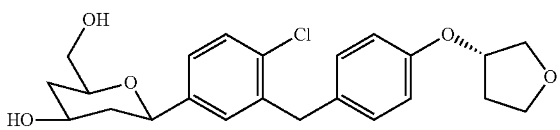 [SMILES: OCC1CC(O)CC(c2ccc(Cl)c(Cc3ccc(O[C@H]4CCOC4)cc3)c2)O1] | 419 ([M + H]⁺) | Example 9 |
| 56 | 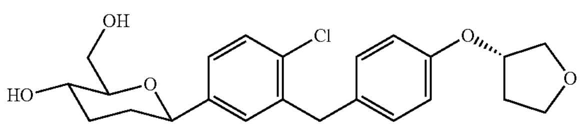 [SMILES: OCC1OC(c2ccc(Cl)c(Cc3ccc(O[C@H]4CCOC4)cc3)c2)CCC1O] | 419 ([M + H]⁺) | Example 10 |
| 57 | 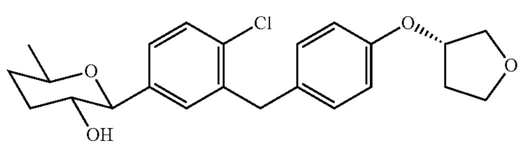 [SMILES: CC1CCC(O)C(c2ccc(Cl)c(Cc3ccc(O[C@H]4CCOC4)cc3)c2)O1] | 403 ([M + H]⁺) | Example 11 |
| 58 | 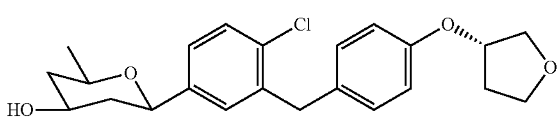 [SMILES: CC1CC(O)CC(c2ccc(Cl)c(Cc3ccc(O[C@H]4CCOC4)cc3)c2)O1] | 403 ([M + H]⁺) | Example 12 |
| 59 | 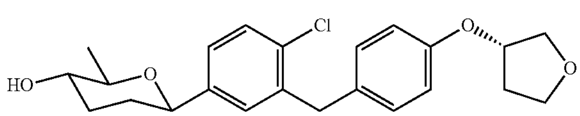 [SMILES: CC1OC(c2ccc(Cl)c(Cc3ccc(O[C@H]4CCOC4)cc3)c2)CCC1O] | 403 ([M + H]⁺) | Example 13 |
| 60 | 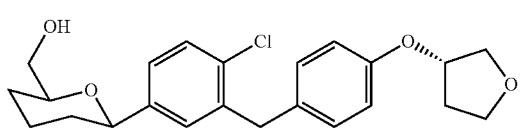 [SMILES: OCC1CCCC(c2ccc(Cl)c(Cc3ccc(O[C@H]4CCOC4)cc3)c2)O1] | 403 ([M + H]⁺) | Example 14 |

-continued

| Example | Structure | ESI-MS | Preparation method |
|---------|-----------|--------|--------------------|
| 61 | 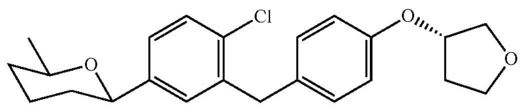 [SMILES: CC1CCCC(c2ccc(Cl)c(Cc3ccc(O[C@H]4CCOC4)cc3)c2)O1] | 387 ([M + H]⁺) | Example 15 |
| 62 | 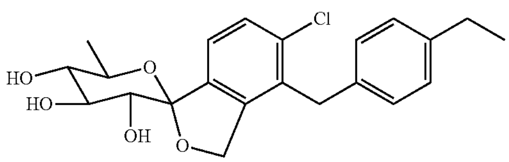 [SMILES: CCc1ccc(Cc2c(Cl)ccc3c2COC32OC(C)C(O)C(O)C2O)cc1] | 405 ([M + H]⁺) | Example 1 |
| 63 | 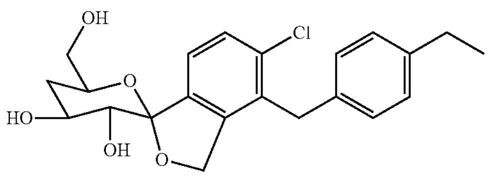 [SMILES: CCc1ccc(Cc2c(Cl)ccc3c2COC32OC(CO)CC(O)C2O)cc1] | 405 ([M + H]⁺) | Example 2 |
| 64 | 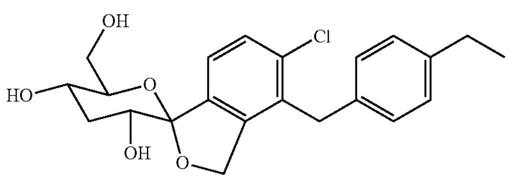 [SMILES: CCc1ccc(Cc2c(Cl)ccc3c2COC32OC(CO)C(O)CC2O)cc1] | 405 ([M + H]⁺) | Example 3 |
| 65 | 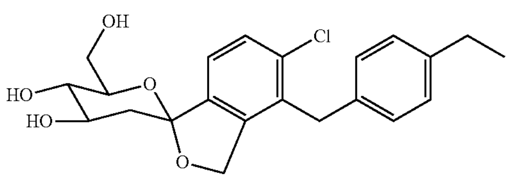 [SMILES: CCc1ccc(Cc2c(Cl)ccc3c2COC32CC(O)C(O)C(CO)O2)cc1] | 405 ([M + H]⁺) | Example 4 |
| 66 | 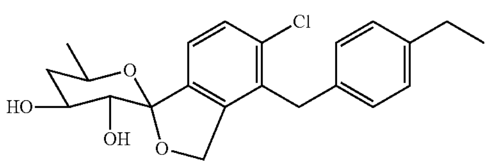 [SMILES: CCc1ccc(Cc2c(Cl)ccc3c2COC32OC(C)CC(O)C2O)cc1] | 389 ([M + H]⁺) | Example 5 |
| 67 | 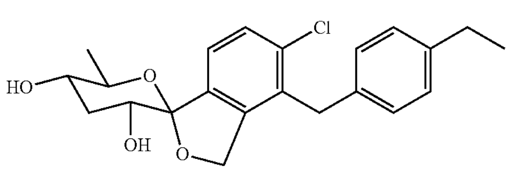 [SMILES: CCc1ccc(Cc2c(Cl)ccc3c2COC32OC(C)C(O)CC2O)cc1] | 389 ([M + H]⁺) | Example 6 |
| 68 | 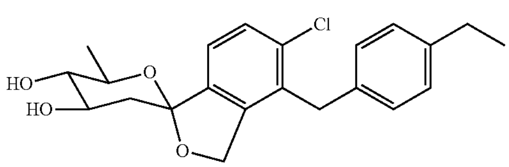 [SMILES: CCc1ccc(Cc2c(Cl)ccc3c2COC32CC(O)C(O)C(C)O2)cc1] | 389 ([M + H]⁺) | Example 7 |
| 69 | 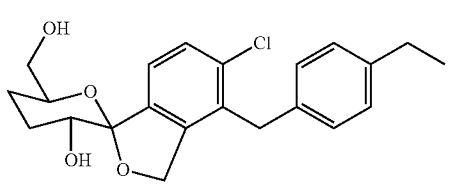 [SMILES: CCc1ccc(Cc2c(Cl)ccc3c2COC32OC(CO)CCC2O)cc1] | 389 ([M + H]⁺) | Example 8 |

-continued

| Example | Structure | ESI-MS | Preparation method |
|---|---|---|---|
| 70 | 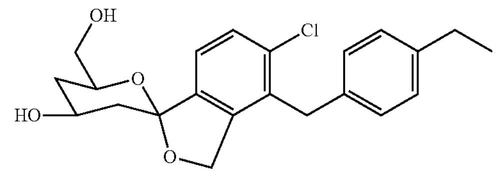 [SMILES: CCc1ccc(Cc2c(Cl)ccc3c2COC32CC(O)CC(CO)O2)cc1] | 389 ([M + H]+) | Example 9 |
| 71 | 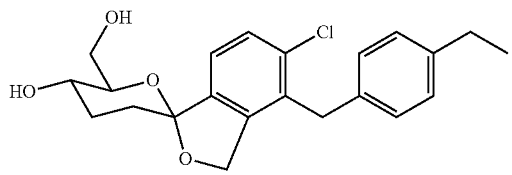 [SMILES: CCc1ccc(Cc2c(Cl)ccc3c2COC32CCC(O)C(CO)O2)cc1] | 389 ([M + H]+) | Example 10 |
| 72 | 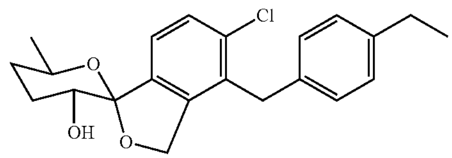 [SMILES: CCc1ccc(Cc2c(Cl)ccc3c2COC32OC(C)CCC2O)cc1] | 373 ([M + H]+) | Example 11 |
| 73 | 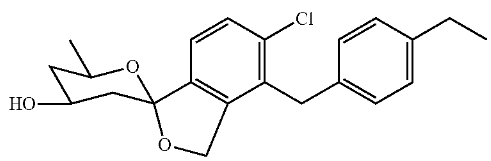 [SMILES: CCc1ccc(Cc2c(Cl)ccc3c2COC32CC(O)CC(C)O2)cc1] | 373 ([M + H]+) | Example 12 |
| 74 | 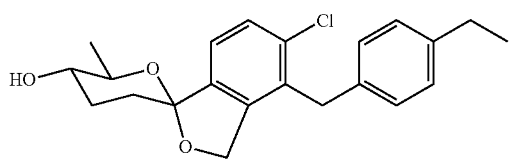 [SMILES: CCc1ccc(Cc2c(Cl)ccc3c2COC32CCC(O)C(C)O2)cc1] | 373 ([M + H]+) | Example 13 |
| 75 | 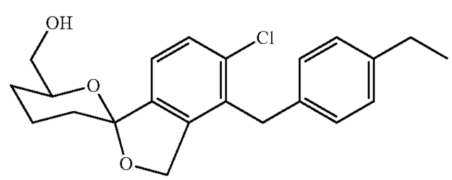 [SMILES: CCc1ccc(Cc2c(Cl)ccc3c2COC32CCCC(CO)O2)cc1] | 373 ([M + H]+) | Example 14 |
| 76 | 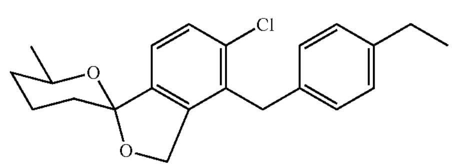 [SMILES: CCc1ccc(Cc2c(Cl)ccc3c2COC32CCCC(C)O2)cc1] | 357 ([M + H]+) | Example 15 |
| 77 | 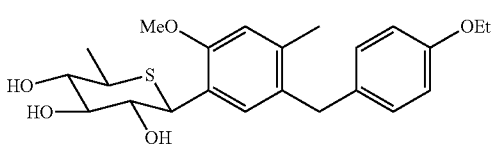 [SMILES: CCOc1ccc(Cc2cc(C3SC(C)C(O)C(O)C3O)c(OC)cc2C)cc1] | 419 ([M + H]+) | Example 1 |
| 78 | 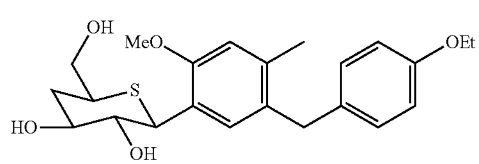 [SMILES: CCOc1ccc(Cc2cc(C3SC(CO)CC(O)C3O)c(OC)cc2C)cc1] | 419 ([M + H]+) | Example 2 |

-continued

| Example | Structure | ESI-MS | Preparation method |
|---|---|---|---|
| 79 | 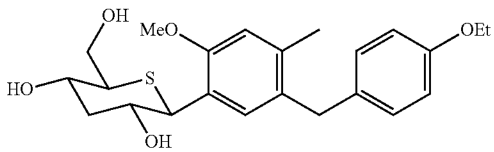 [SMILES: CCOc1ccc(Cc2cc(C3SC(CO)C(O)CC3O)c(OC)cc2C)cc1] | 419 ([M + H]⁺) | Example 3 |
| 80 | 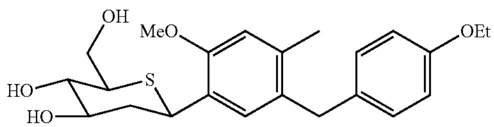 [SMILES: CCOc1ccc(Cc2cc(C3CC(O)C(O)C(CO)S3)c(OC)cc2C)cc1] | 419 ([M + H]⁺) | Example 4 |
| 81 | 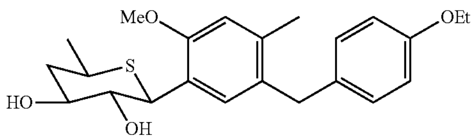 [SMILES: CCOc1ccc(Cc2cc(C3SC(C)CC(O)C3O)c(OC)cc2C)cc1] | 403 ([M + H]⁺) | Example 5 |
| 82 | 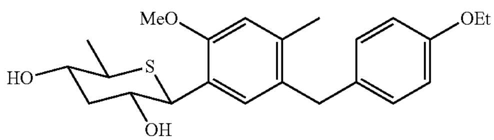 [SMILES: CCOc1ccc(Cc2cc(C3SC(C)C(O)CC3O)c(OC)cc2C)cc1] | 403 ([M + H]⁺) | Example 6 |
| 83 | 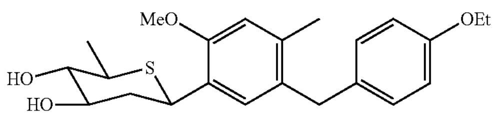 [SMILES: CCOc1ccc(Cc2cc(C3CC(O)C(O)C(C)S3)c(OC)cc2C)cc1] | 403 ([M + H]⁺) | Example 7 |
| 84 | 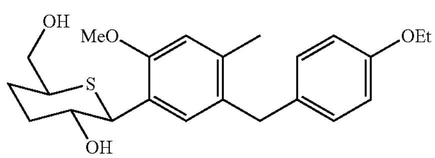 [SMILES: CCOc1ccc(Cc2cc(C3SC(CO)CCC3O)c(OC)cc2C)cc1] | 403 ([M + H]⁺) | Example 8 |
| 85 | 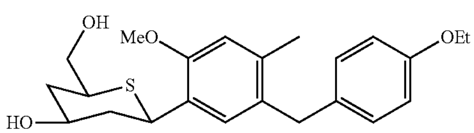 [SMILES: CCOc1ccc(Cc2cc(C3CC(O)CC(CO)S3)c(OC)cc2C)cc1] | 403 ([M + H]⁺) | Example 9 |
| 86 | 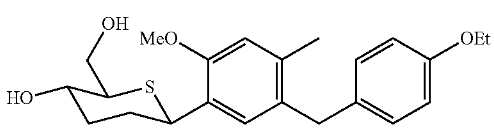 [SMILES: CCOc1ccc(Cc2cc(C3CCC(O)C(CO)S3)c(OC)cc2C)cc1] | 403 ([M + H]⁺) | Example 10 |
| 87 | 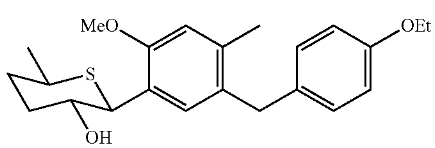 [SMILES: CCOc1ccc(Cc2cc(C3SC(C)CCC3O)c(OC)cc2C)cc1] | 387 ([M + H]⁺) | Example 11 |
| 88 | 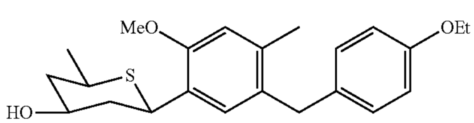 [SMILES: CCOc1ccc(Cc2cc(C3CC(O)CC(C)S3)c(OC)cc2C)cc1] | 387 ([M + H]⁺) | Example 12 |
| 89 | 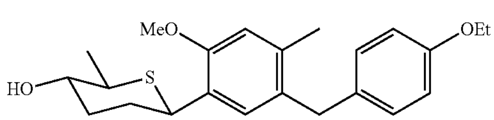 [SMILES: CCOc1ccc(Cc2cc(C3CCC(O)C(C)S3)c(OC)cc2C)cc1] | 387 ([M + H]⁺) | Example 13 |

-continued

| Example | Structure | ESI-MS | Preparation method |
|---|---|---|---|
| 90 | 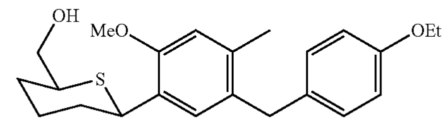 [SMILES: CCOc1ccc(Cc2cc(C3CCCC(CO)S3)c(OC)cc2C)cc1] | 387 ([M + H]+) | Example 14 |
| 91 | 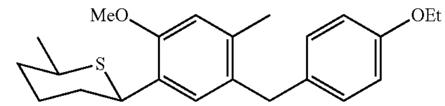 [SMILES: CCOc1ccc(Cc2cc(C3CCCC(C)S3)c(OC)cc2C)cc1] | 371 ([M + H]+) | Example 15 |
| 92 | 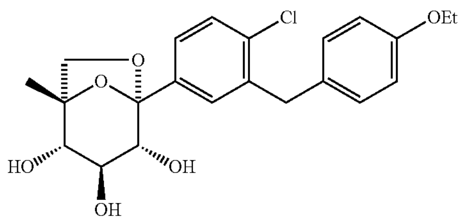 [SMILES: CCOc1ccc(Cc2cc([C@]34OC[C@](C)(O3)[C@@H](O)[C@H](O)[C@H]4O)ccc2Cl)cc1] | 421 ([M + H]+) | Example 1 |
| 93 | 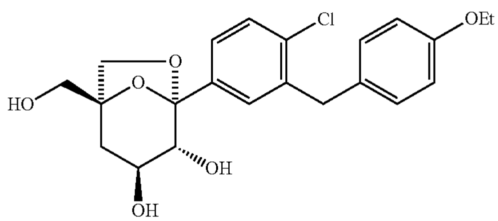 [SMILES: CCOc1ccc(Cc2cc([C@@]34OC[C@@](CO)(C[C@H](O)[C@H]3O)O4)ccc2Cl)cc1] | 421 ([M + H]+) | Example 2 |
| 94 | 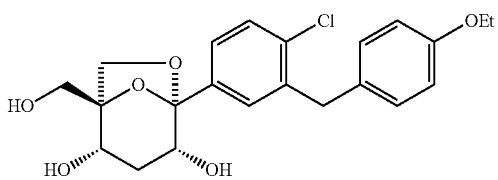 [SMILES: CCOc1ccc(Cc2cc([C@]34OC[C@](CO)(O3)[C@@H](O)C[C@H]4O)ccc2Cl)cc1] | 421 ([M + H]+) | Example 3 |
| 95 | 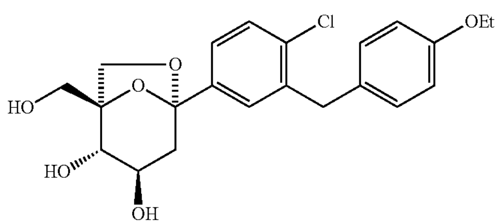 [SMILES: CCOc1ccc(Cc2cc([C@]34C[C@@H](O)[C@H](O)[C@](CO)(CO3)O4)ccc2Cl)cc1] | 421 ([M + H]+) | Example 4 |
| 96 | 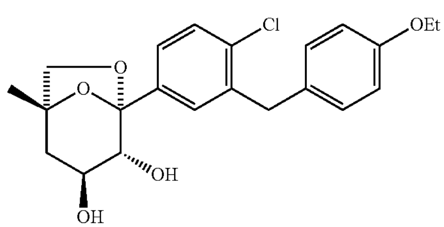 [SMILES: CCOc1ccc(Cc2cc([C@@]34OC[C@@](C)(C[C@H](O)[C@H]3O)O4)ccc2Cl)cc1] | 405 ([M + H]+) | Example 5 |
| 97 | 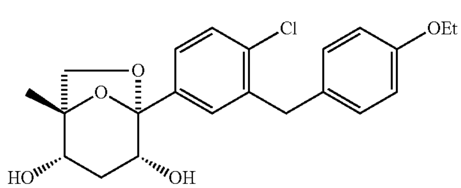 [SMILES: CCOc1ccc(Cc2cc([C@]34OC[C@](C)(O3)[C@@H](O)C[C@H]4O)ccc2Cl)cc1] | 405 ([M + H]+) | Example 6 |

-continued

| Example | Structure | ESI-MS | Preparation method |
|---|---|---|---|
| 98 | 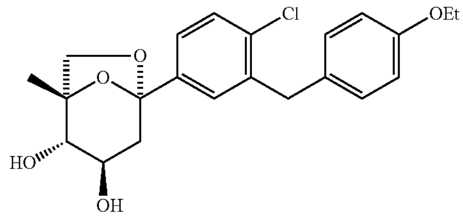 [SMILES: CCOc1ccc(Cc2cc([C@]34C[C@@H](O)[C@H](O)[C@](C)(CO3)O4)ccc2Cl)cc1] | 405 ([M + H]⁺) | Example 7 |
| 99 | 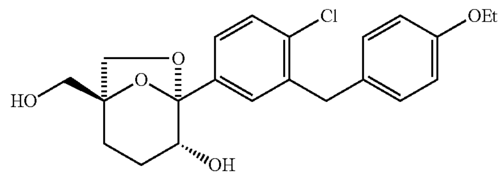 [SMILES: CCOc1ccc(Cc2cc([C@@]34OC[C@@](CO)(CC[C@H]3O)O4)ccc2Cl)cc1] | 405 ([M + H]⁺) | Example 8 |
| 100 | 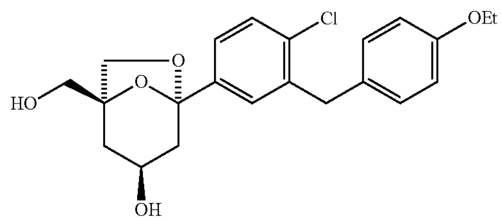 [SMILES: CCOc1ccc(Cc2cc([C@]34C[C@@H](O)C[C@](CO)(CO3)O4)ccc2Cl)cc1] | 405 ([M + H]⁺) | Example 9 |
| 101 | 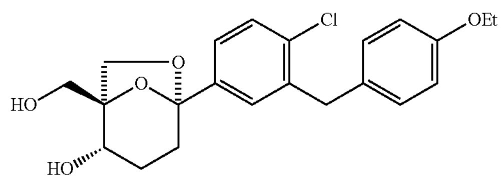 [SMILES: CCOc1ccc(Cc2cc([C@]34CC[C@H](O)[C@](CO)(CO3)O4)ccc2Cl)cc1] | 405 ([M + H]⁺) | Example 10 |
| 102 | 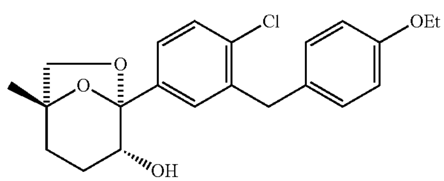 [SMILES: CCOc1ccc(Cc2cc([C@@]34OC[C@@](C)(CC[C@H]3O)O4)ccc2Cl)cc1] | 389 ([M + H]⁺) | Example 11 |
| 103 | 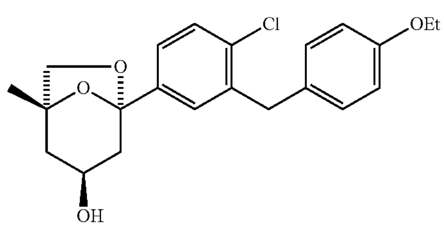 [SMILES: CCOc1ccc(Cc2cc([C@]34C[C@@H](O)C[C@](C)(CO3)O4)ccc2Cl)cc1] | 389 ([M + H]⁺) | Example 12 |
| 104 | 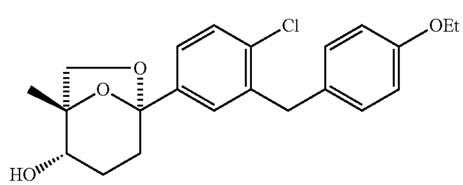 [SMILES: CCOc1ccc(Cc2cc([C@]34CC[C@H](O)[C@](C)(CO3)O4)ccc2Cl)cc1] | 389 ([M + H]⁺) | Example 13 |
| 105 | 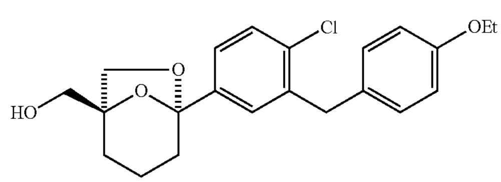 [SMILES: CCOc1ccc(Cc2cc([C@]34CCC[C@](CO)(CO3)O4)ccc2Cl)cc1] | 389 ([M + H]⁺) | Example 14 |

| Example | Structure | ESI-MS | Preparation method |
|---|---|---|---|
| 106 | 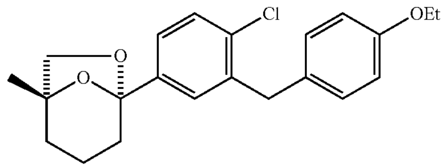 [SMILES: CCOc1ccc(Cc2cc([C@]34CCC[C@](C)(CO3)O4)ccc2Cl)cc1] | 373 ([M + H]+) | Example 15 |

Example 107

|  | amount/tablet |
|---|---|
| sample in Example 1 | 20 mg |
| microcrystalline cellulose | 80 mg |
| pregelatinized starch | 70 mg |
| polyvinyl pyrrolidone | 6 mg |
| sodium carboxymethyl starch | 5 mg |
| magnesium stearate | 2 mg |
| talc powders | 2 mg |

The active ingredient, pregelatinized starch and microcrystalline cellulose are sieved and mixed sufficiently, and then polyvinyl pyrrolidone solution is added and mixed to make soft materials. The soft materials are sieved to make wet granules, which are dried at 50-60° C. Sodium carboxymethyl starch, magnesium stearate and talc powders are pre-sieved, and then added to granules described above for tabletting.

Example 108

|  | amount/tablet |
|---|---|
| sample in Example 2 | 20 mg |
| microcrystalline cellulose | 80 mg |
| pregelatinized starch | 70 mg |
| polyvinyl pyrrolidone | 6 mg |
| sodium carboxymethyl starch | 5 mg |
| magnesium stearate | 2 mg |
| talc powders | 2 mg |

The active ingredient, pregelatinized starch and microcrystalline cellulose are sieved and mixed sufficiently, and then polyvinyl pyrrolidone solution is added and mixed to make soft materials. The soft materials are sieved to make wet granules, which are dried at 50-60° C. Sodium carboxymethyl starch, magnesium stearate and talc powders are pre-sieved, and then added to granules described above for tabletting.

Example 109

|  | amount/capsule |
|---|---|
| sample in Example 3 | 20 mg |
| microcrystalline cellulose | 30 mg |
| pregelatinized starch | 20 mg |
| polyvinyl pyrrolidone | 3 mg |
| magnesium stearate | 2 mg |
| talc powders | 1 mg |

The active ingredient, pregelatinized starch and microcrystalline cellulose are sieved and mixed sufficiently, and then polyvinyl pyrrolidone solution is added and mixed to make soft materials. The soft materials are sieved to make wet granules, which are dried at 50-60° C. Magnesium stearate and talc powders are pre-sieved, and then added to granules described above for capsulizing to obtain the final product.

Example 110

|  | amount/capsule |
|---|---|
| sample in Example 4 | 20 mg |
| microcrystalline cellulose | 30 mg |
| pregelatinized starch | 20 mg |
| polyvinyl pyrrolidone | 3 mg |
| magnesium stearate | 2 mg |
| talc powders | 1 mg |

The active ingredient, pregelatinized starch and microcrystalline cellulose are sieved and mixed sufficiently, and then polyvinyl pyrrolidone solution is added and mixed to make soft materials. The soft materials are sieved to make wet granules, which are dried at 50-60'C. Magnesium stearate and talc powders are pre-sieved, and then added to granules described above for capsulizing to obtain the final product.

Example 111

|  | amount/50 mL |
|---|---|
| sample in Example 5 | 20 mg |
| citric acid | 100 mg |
| NaOH | q.s. (to adjust pH to 4.0-5.0) |
| distilled water | 50 mL |

The distilled water and citric acid are firstly added into the distilled water. After stirring to dissolve, the sample is then added, and heated slightly for dissolving. pH value is adjusted to 4.0-5.0, and 0.2 g of the active carbon is added, stirred for 20 minutes at room temperature and then filtered. The filtrate, whose concentration is determined in a central-controlled manner, is batched into 5 mL per ampoule and sterilized for 30 minutes at high temperature to obtain the injection.

Example 112

|  | amount/50 mL |
|---|---|
| sample in Example 6 | 20 mg |
| citric acid | 100 mg |
| NaOH | q.s. (to adjust pH to 4.0-5.0) |
| distilled water | 50 mL |

The distilled water and citric acid are firstly added into the distilled water. After stirring to dissolve, the sample is then added, and heated slightly for dissolving. pH value is adjusted to 4.0-5.0, and 0.2 g of the active carbon is added in, stirred for 20 minutes at room temperature and then filtered. The filtrate, whose concentration is determined in a central-controlled manner, is batched into 5 mL per ampoule and sterilized for 30 minutes at high temperature to obtain the injection.

Example 113

| sample in Example 7 | 3.0 g |
|---|---|
| Poloxamer | 1.0 g |
| sodium hydroxide | 0.2 g |
| citric acid | QS |
| Mannitol | 26.0 g |
| Lactose | 23.0 g |
| water for injection | 100 mL |

Preparation process: To 80 mL of water for injection, the active ingredient, mannitol, lactose, Poloxamer are added, and stirred to dissolve, 1 mol/L of citric acid is added to adjust pH to 7.0-9.0, and then water is complemented to 100 mL. 0.5 g of active carbon is added and stirred for 20 minutes at the temperature of 30° C. The active carbon is removed, and filtered for sterilization by using micro-porous filtrating film. The filtrate is batched at 1 ml per piece. After pre-freezing for 2 hours, the samples are lyophilized for 12 hours under the reduced pressure. After the temperature of the samples reaches room temperature, they are dried for 5 hours again to make white loose bulks. After sealing, the final products are obtained.

Example 114

| Granules | 100 bags |
|---|---|
| sample in Example 8 | 30.0 g |
| Lactose | 55.0 g |
| Mannitol | 14.0 g |
| Aspartame | 0.05 g |
| Essence | 0.05 g |
| 2% hydroxypropylmethyl cellulose (formulated with pure water) | QS |

Preparation process: the active ingredient and adjuvants are sieved at 100 mesh respectively, and mixed sufficiently. Then, the prescribed amount of adjuvants and the active ingredient are weighted and mixed sufficiently. The adhesive is added to make the soft materials, sieved at 14 mesh to form granules, and dried at 55° C. The granules are sieved at 12 mesh, and then the bags are weighted for packaging.

Example 115

The health SD rats are injected intraperitoneally with multiple low doses of streptozotocin for modeling (type 2 diabetes model) after feeding with high-fat and high-sucrose diet, and the content of blood glucose is measured before and after modeling. After the modeling successful, the rats for modeling are randomly divided (8 rats/group) into one blank group (administering the same volume of 0.5% CMC sodium solution) and several groups for compounds to be tested (6 mg/kg) according to the content of 24-hour urine glucose and the body weight. Rats in each group are fasted for 16 hours before experiment. The experimental rats are administered intragastrically with glucose (2 g/kg) at 0.5 h after intragastrical administration with compounds to be tested. The urine is collected at the time-period of 0-12 h after administration, and the urine glucose values are measured at each time-period by glucose-oxidase method. The results are shown in Table 1 below.

TABLE 1

Urine glucose values measured by glucose-oxidase method at each time period

| Compound | Urine glucose excretion (mg/200 g body weight of the rat) |
|---|---|
| ![structure with OH, Cl, OEt groups on sugar-aryl-aryl scaffold] | 743 |

TABLE 1-continued
Urine glucose values measured by glucose-oxidase method at each time period
| Compound | Urine glucose excretion (mg/200 g body weight of the rat) |
|---|---|
| 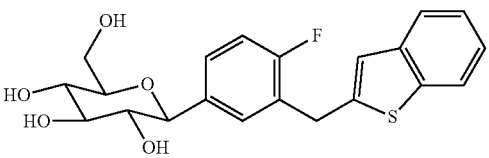 [SMILES: OCC1OC(c2ccc(F)c(Cc3cc4ccccc4s3)c2)C(O)C(O)C1O] | 621 |
| 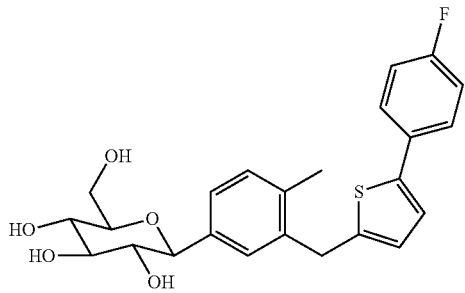 [SMILES: Cc1ccc(C2OC(CO)C(O)C(O)C2O)cc1Cc1ccc(-c2ccc(F)cc2)s1] | 655 |
| 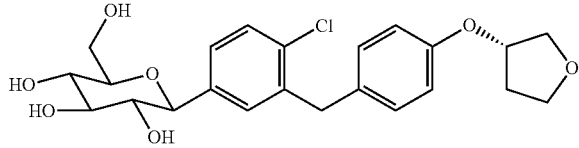 [SMILES: OCC1OC(c2ccc(Cl)c(Cc3ccc(O[C@H]4CCOC4)cc3)c2)C(O)C(O)C1O] | 643 |
| 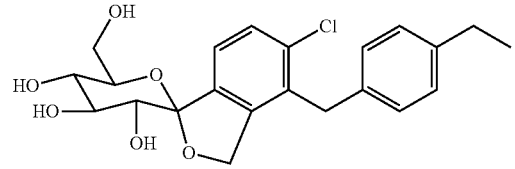 | 587 |
| 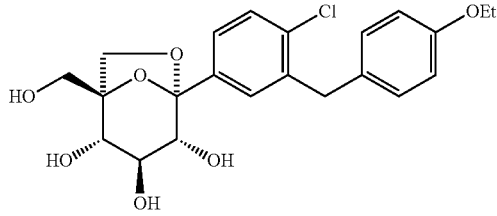 [SMILES: CCOc1ccc(Cc2cc([C@]34OC[C@](CO)(O3)[C@@H](O)[C@H](O)[C@H]4O)ccc2Cl)cc1] | 455 |
| 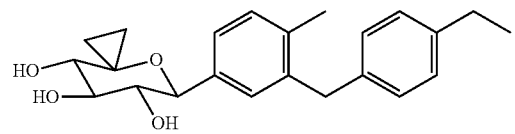 [SMILES: CCc1ccc(Cc2cc(C3OC4(CC4)C(O)C(O)C3O)ccc2C)cc1] | 609 |
| 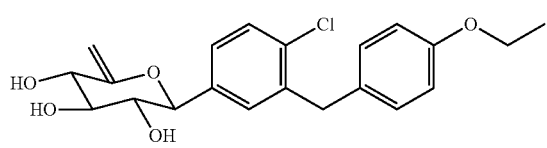 | 457 |

TABLE 1-continued
Urine glucose values measured by glucose-oxidase method at each time period
| Compound | Urine glucose excretion (mg/200 g body weight of the rat) |
|---|---|
| 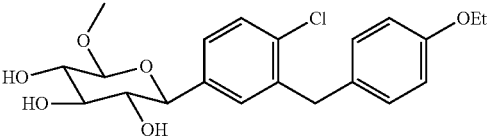 [SMILES: CCOc1ccc(Cc2cc(C3OC(OC)C(O)C(O)C3O)ccc2Cl)cc1] | 644 |
| 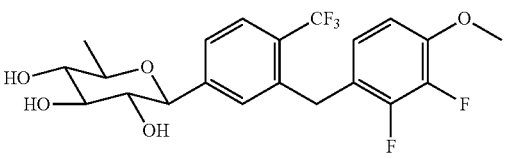 [SMILES: COc1ccc(Cc2cc(C3OC(C)C(O)C(O)C3O)ccc2C(F)(F)F)c(F)c1F] | 622 |
| 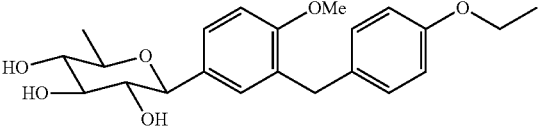 [SMILES: CCOc1ccc(Cc2cc(C3OC(C)C(O)C(O)C3O)ccc2OC)cc1] | 688 |
| 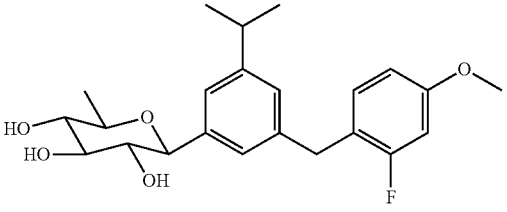 [SMILES: COc1ccc(Cc2cc(C(C)C)cc(C3OC(C)C(O)C(O)C3O)c2)c(F)c1] | 523 |
| 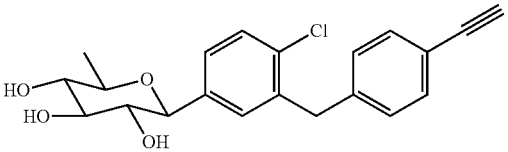 [SMILES: C#Cc1ccc(Cc2cc(C3OC(C)C(O)C(O)C3O)ccc2Cl)cc1] | 671 |
| 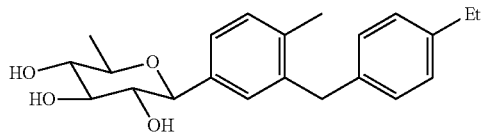 [SMILES: CCc1ccc(Cc2cc(C3OC(C)C(O)C(O)C3O)ccc2C)cc1] | 613 |
| 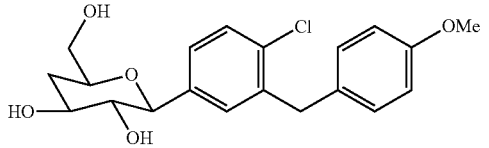 [SMILES: COc1ccc(Cc2cc(C3OC(CO)CC(O)C3O)ccc2Cl)cc1] | 310 |
| 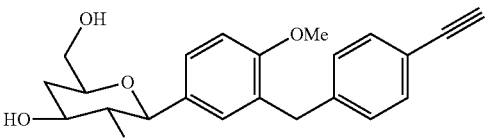 | 328 |

TABLE 1-continued
Urine glucose values measured by glucose-oxidase method at each time period
| Compound | Urine glucose excretion (mg/200 g body weight of the rat) |
|---|---|
| 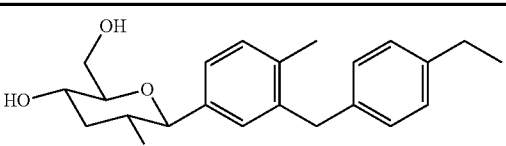 | 230 |
| 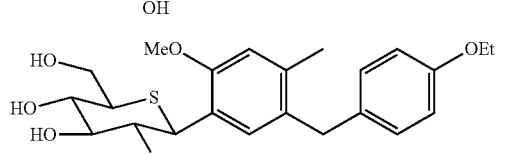 | 625 |
| 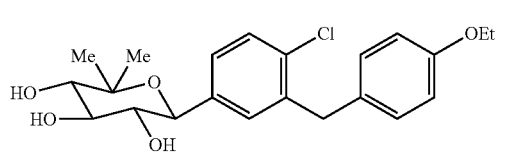 [SMILES: CCOc1ccc(Cc2cc(C3OC(C)(C)C(O)C(O)C3O)ccc2Cl)cc1] | 470 |
| 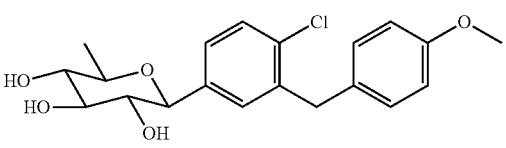 | 736 |
| 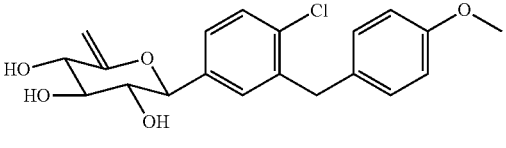 | 410 |
| 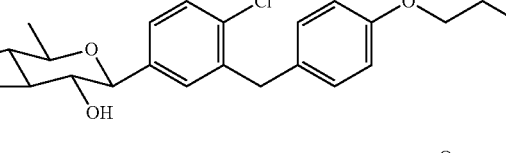 | 721 |
| 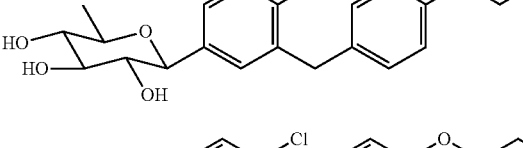 | 700 |
| 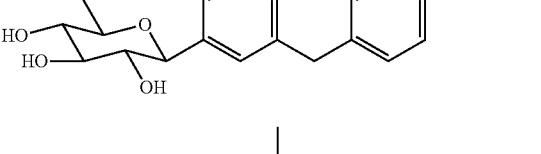 | 712 |
| 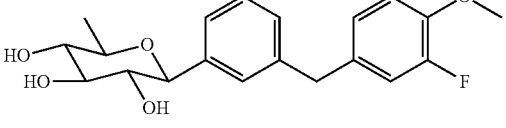 | 539 |

TABLE 1-continued
Urine glucose values measured by glucose-oxidase method at each time period
| Compound | Urine glucose excretion (mg/200 g body weight of the rat) |
|---|---|
| 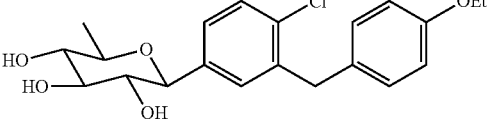 | 833 |
| 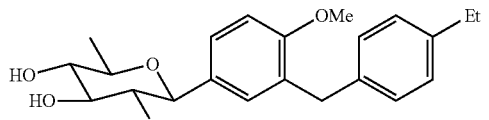 | 439 |
| 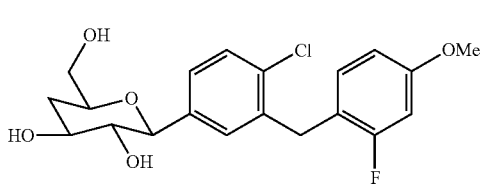 [SMILES: COc1ccc(Cc2cc(C3OC(CO)CC(O)C3O)ccc2Cl)c(F)c1] | 288 |
| 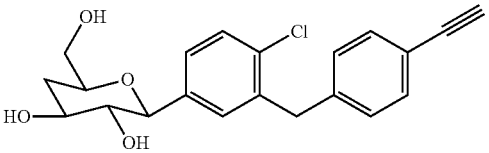 [SMILES: C#Cc1ccc(Cc2cc(C3OC(CO)CC(O)C3O)ccc2Cl)cc1] | 213 |
| 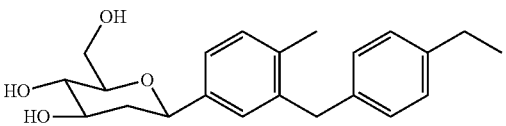 [SMILES: CCc1ccc(Cc2cc(C3CC(O)C(O)C(CO)O3)ccc2C)cc1] | 378 |
| 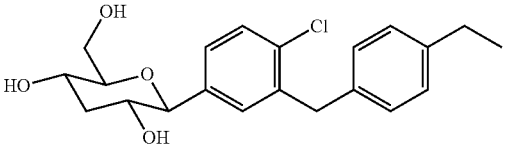 | 198 |
| 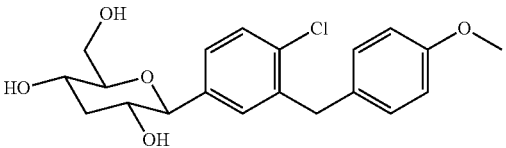 [SMILES: COc1ccc(Cc2cc(C3OC(CO)C(O)CC3O)ccc2Cl)cc1] | 235 |
| 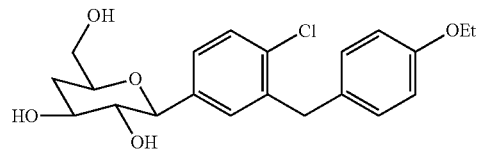 [SMILES: CCOc1ccc(Cc2cc(C3OC(CO)CC(O)C3O)ccc2Cl)cc1] | 880 |
| 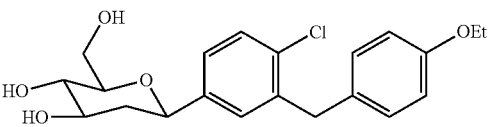 [SMILES: CCOc1ccc(Cc2cc(C3CC(O)C(O)C(CO)O3)ccc2Cl)cc1] | 811 |

TABLE 1-continued
Urine glucose values measured by glucose-oxidase method at each time period
| Compound | Urine glucose excretion (mg/200 g body weight of the rat) |
|---|---|
| 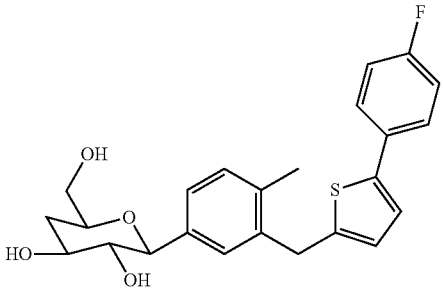 [SMILES: Cc1ccc(C2OC(CO)CC(O)C2O)cc1Cc1ccc(-c2ccc(F)cc2)s1] | 801 |
| 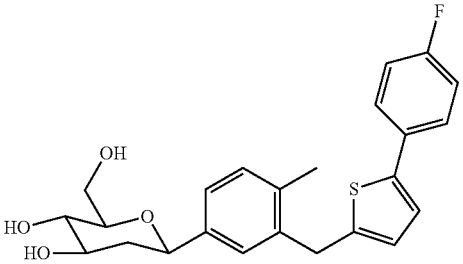 [SMILES: Cc1ccc(C2CC(O)C(O)C(CO)O2)cc1Cc1ccc(-c2ccc(F)cc2)s1] | 698 |
| 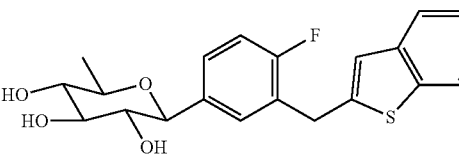 | 749 |
| 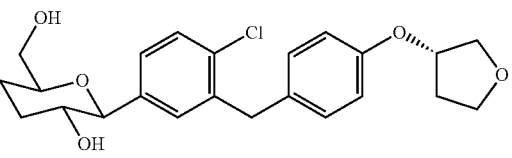 | 721 |
| 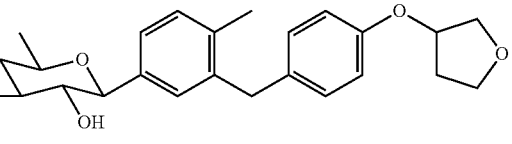 | 611 |
| 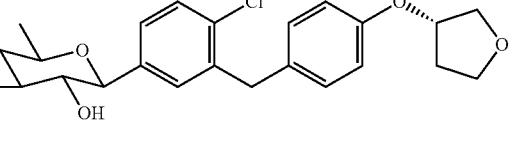 | 748 |
| 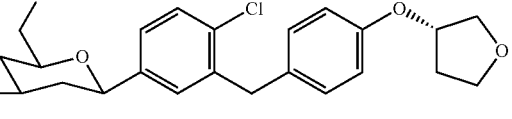 | 744 |

TABLE 1-continued
Urine glucose values measured by glucose-oxidase method at each time period
| Compound | Urine glucose excretion (mg/200 g body weight of the rat) |
|---|---|
| 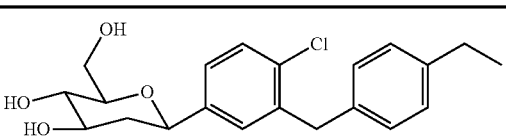 | 412 |
| 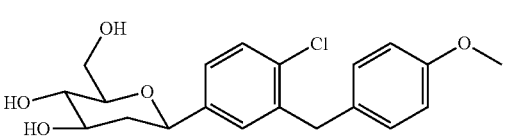 [SMILES: COc1ccc(Cc2cc(C3CC(O)C(O)C(CO)O3)ccc2Cl)cc1] | 426 |
| 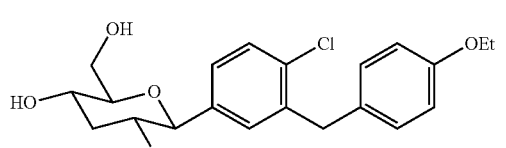 | 828 |
| 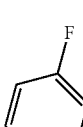 | 723 |
| 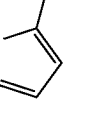 | 772 |
| 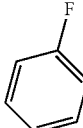 | 656 |
| 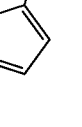 | 689 |

TABLE 1-continued
Urine glucose values measured by glucose-oxidase method at each time period
| Compound | Urine glucose excretion (mg/200 g body weight of the rat) |
|---|---|
| 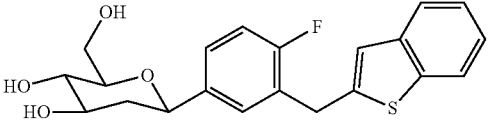 [SMILES: OCC1OC(c2ccc(F)c(Cc3cc4ccccc4s3)c2)CC(O)C1O] | 716 |
| 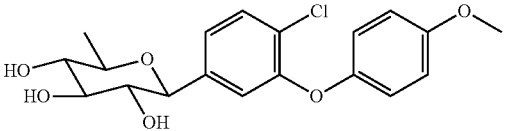 | 457 |
| 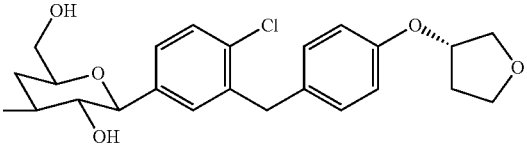 | 723 |
| 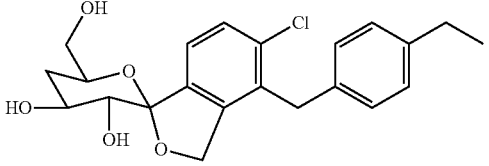 [SMILES: CCc1ccc(Cc2c(Cl)ccc3c2COC32OC(CO)CC(O)C2O)cc1] | 634 |
| 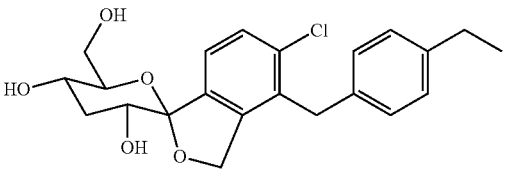 | 712 |
| 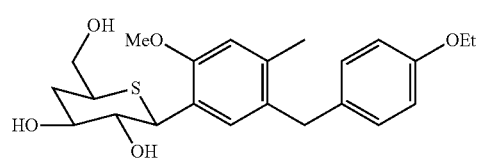 [SMILES: CCOc1ccc(Cc2cc(C3SC(CO)CC(O)C3O)c(OC)cc2C)cc1] | 677 |
| 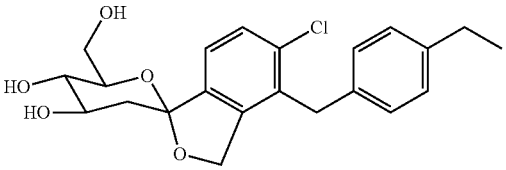 [SMILES: CCc1ccc(Cc2c(Cl)ccc3c2COC32CC(O)C(O)C(CO)O2)cc1] | 717 |
| 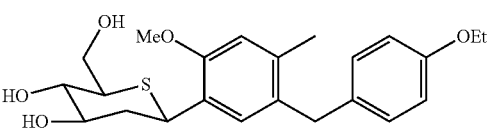 [SMILES: CCOc1ccc(Cc2cc(C3CC(O)C(O)C(CO)S3)c(OC)cc2C)cc1] | 786 |

TABLE 1-continued

Urine glucose values measured by glucose-oxidase method at each time period

| Compound | Urine glucose excretion (mg/200 g body weight of the rat) |
|---|---|
| (structure) | 665 |
| (structure) | 751 |
| (structure) | 765 |
| (structure) | 656 |
| (structure) | 677 |
| (structure) | 755 |
| (structure) | 766 |
| (structure) | 728 |

TABLE 1-continued

Urine glucose values measured by glucose-oxidase method at each time period

| Compound | Urine glucose excretion (mg/200 g body weight of the rat) |
|---|---|
| [structure with MeO, OEt, S-sugar] | 698 |
| [structure with Cl, OEt, bicyclic sugar] | 565 |
| [structure with Cl, OEt, bicyclic sugar] | 711 |
| [structure with F, thiophene, sugar] | 701 |
| [structure with Cl, tetrahydrofuran, sugar-OH] | 721 |
| [structure with MeO, OEt, S-sugar-OH] | 730 |

The above results show that the compounds having the structures of general formula I of the present invention have stronger urine glucose excreting ability than that of the corresponding compound having no deoxy on the sugar ring. In the series of 6-deoxy compounds of compound I (see Example 1), the product I-D1-6 recorded in Example 1 have stronger urine glucose excretion effect than that of the I-D1-6 analogues having combinations of the other substituents on the two benzene rings at the rightside of the molecule, suggesting that the combinations of the substituents on the two benzene rings at the rightside of the molecule of products I-D1-6 recorded in Example 1 of the present invention are optimal. In the series of 4-deoxy compounds of compound I (see Example 2), the products I-D1-4 recorded in example 2 have stronger urine glucose excretion effect than that of the I-D1-4 analogues having combinations of the other substituents on the two benzene rings at the rightside of the molecule, suggesting that the combinations of the substituents on the two benzene rings at the rightside of the molecule of products I-D1-4 as recorded in Example 2 of the present invention are optimal. In the series of 3-deoxy compounds of compound I (see Example 3), the products I-D1-3 recorded in example 3 have stronger urine glucose excretion effect than that of the I-D1-3 analogues having combinations of the other substituents on the two benzene rings at the rightside of the molecule, suggesting that the combinations of the substituents on the two benzene rings at the rightside of the molecule of products I-D1-3 as recorded in Example 3 of the present invention are optimal. Similarly, in the series of 2-deoxy compounds of compound I (see Example 4), the products I-D1-2 recorded in Example 4 have stronger urine glucose excretion effect than that of the I-D1-2 analogues having combinations of the other substituents on the two benzene rings at the rightside of the molecule, suggesting that the combinations of the substituents on the two benzene rings at the rightside of the molecule of products I-D1-2 as recorded in Example 4 of the present invention are optimal.

Example 116

Mice (18-20 g) with equal numbers of male and female are divided into groups (10 mice/group), after normal feeding for 3 days, fasted for 12 hours, and then administered intragastrically with a single dose of 750 mg/kg compound respectively. The mice are observed for the behaviors and deaths within one week after administration with compounds to be tested. The observed results are shown in Table 2 below.

TABLE 2

Behavior and deaths of the mice within one week after administration with compounds to be tested

| Compound | Behaviors after administration with the compound to be tested |
|---|---|
|  | 8 dead |
|  | 7 dead |
|  | 7 dead |
|  | 9 dead |
|  | 6 dead |
|  | 2 dead |

TABLE 2-continued
Behavior and deaths of the mice within one week after administration with compounds to be tested
| Compound | Behaviors after administration with the compound to be tested |
|---|---|
| 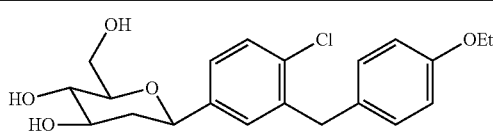 | 2 dead |
| 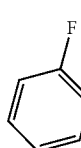 | 3 dead |
| 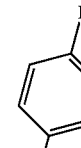 | 5 dead |
| 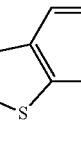 | 2 dead |
| 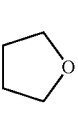 | 0 dead |
| 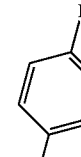 | 9 dead |

TABLE 2-continued
Behavior and deaths of the mice within one week after administration with compounds to be tested
| Compound | Behaviors after administration with the compound to be tested |
|---|---|
| 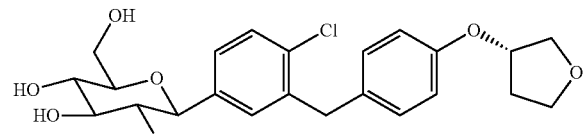 | 7 dead |
| 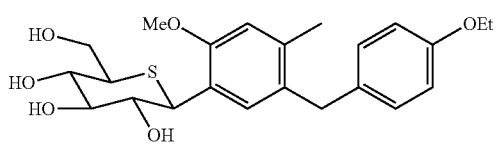 [SMILES: CCOc1ccc(Cc2cc(C3SC(CO)C(O)C(O)C3O)c(OC)cc2C)cc1] | 10 dead |
| 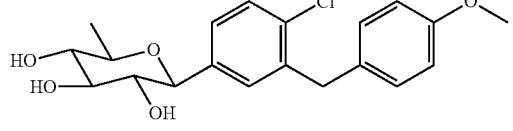 | 7 dead |
| 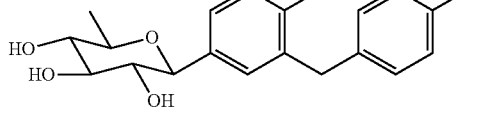 | 1 dead |
| 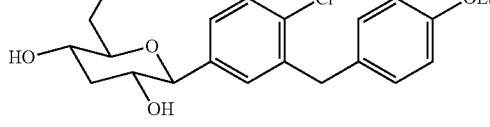 | 3 dead |
| 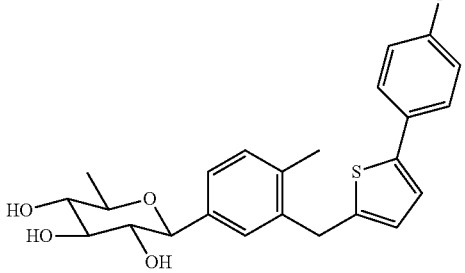 | 4 dead |
| 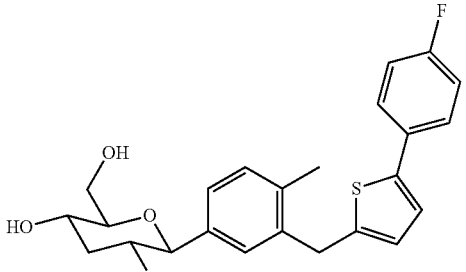 | 3 dead |

TABLE 2-continued
Behavior and deaths of the mice within one week after administration with compounds to be tested
| Compound | Behaviors after administration with the compound to be tested |
|---|---|
| 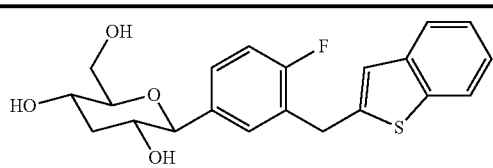 | 0 dead |
| 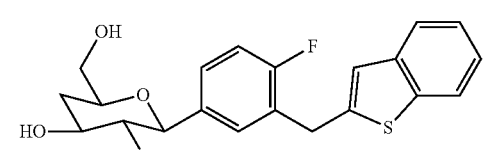 | 1 dead |
| 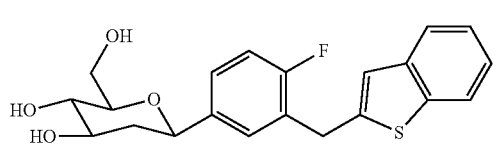 | 3 dead |
| 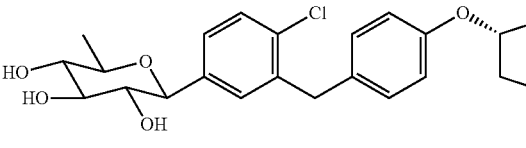 | 1 dead |
| 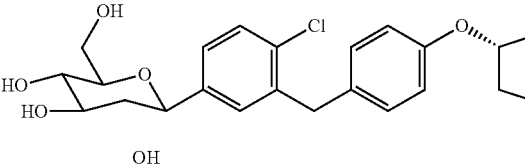 | 2 dead |
| 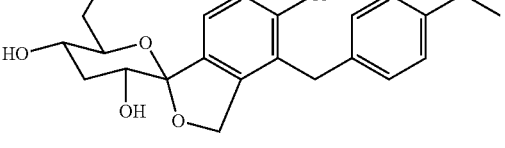 | 5 dead |
| 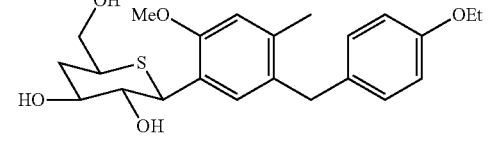 | 1 dead |
| 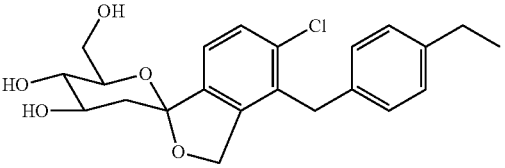 [SMILES: CCc1ccc(Cc2c(Cl)ccc3c2COC32CC(O)C(O)C(CO)O2)cc1] | 2 dead |
| 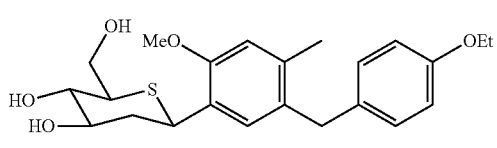 [SMILES: CCOc1ccc(Cc2cc(C3CC(O)C(O)C(CO)S3)c(OC)cc2C)cc1] | 3 dead |

TABLE 2-continued

Behavior and deaths of the mice within one week after administration with compounds to be tested

| Compound | Behaviors after administration with the compound to be tested |
|---|---|
| [structure] | 3 dead |
| [structure] | 4 dead |
| [structure] | 1 dead |
| [structure] | 1 dead |
| [structure] | 1 dead |
| [structure] | 2 dead |
| [structure] | 5 dead |
| [structure] | 3 dead |

TABLE 2-continued

Behavior and deaths of the mice within one week after administration with compounds to be tested

| Compound | Behaviors after administration with the compound to be tested |
|---|---|
| (structure) | 0 dead |
| (structure) | 3 dead |
| (structure) | 4 dead |
| (structure) | 2 dead |
| (structure) | 3 dead |
| (structure) | 0 dead |
| (structure) | 2 dead |

TABLE 2-continued

Behavior and deaths of the mice within one week after administration with compounds to be tested

| Compound | Behaviors after administration with the compound to be tested |
|---|---|
| (structure: 6-deoxy thioglucoside with CH₂OH, HO on sugar ring; S-linked to benzene ring bearing MeO and methyl substituents, connected via CH₂ to a second benzene ring with OEt) | 0 dead |

The above results show that the compounds with the structures of general formula I have less toxicity than that of the corresponding compounds having no deoxy on the sugar rings.

Example 117

IC$_{50}$ values of inhibition of some compounds described in the present invention and related compounds on SGLT2 and SGLT1 are determined according to the method similar to that recorded in the document (Meng, W. et al, *J. Med. Chem.*, 2008, 51, 1145-1149). The results are shown in Table 3 below.

The above results of determination of IC$_{50}$ show that, comparing with the molecule containing an methoxyl at the corresponding position and the molecule containing an methyl at the corresponding postion on the left benzene ring listed in Table 3, the derivative described above containing an ethoxyl at the right side of 6-deoxy glucoside molecule represented by 1-D1-6 prepared in example 1 has: (1) much stronger inhibition to SGLT2; (2) much less inhibition to SGLT1; (3) much better selectivity on SGLT1/SGLT2, suggesting that the combination of the substituents on the two benzene rings at the right side of the molecule of product I-D1-6 recorded in example 1 of the present invention is optimal.

TABLE 3

IC$_{50}$ values of some compounds against SGLT1 and SGLT2

| Compound | IC$_{50}$ (hSGLT2, nM) | IC$_{50}$ (hSGLT1, nM) | Selectivity IC$_{50}$ (hSGLT1)/IC$_{50}$ (hSGLT2) |
|---|---|---|---|
| (6-deoxy glucoside, Cl on left benzene ring, OMe on right benzene ring) | 3.3 | 86 | 26 |
| (6-deoxy glucoside, Cl on left benzene ring, OEt on right benzene ring) | 0.67 | 250.8 | 374 |
| (6-deoxy glucoside, methyl on left benzene ring, OEt on right benzene ring) | 7.8 | 187.3 | 24 |

Examples of the industrial synthetic method and intermediates of I-D1-6 are provided as follows.

Example 118: Synthesis of Compound M-2

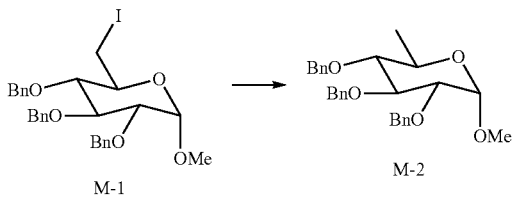

28.72 g (50 mmol) of compound M-1 is dissolved in 300 mL methanol, 15.18 g (150 mmol) of triethylamine and 3.00 g of Pd/C catalyst with the Pd mass fraction of 10% are added, and then the catalytic hydrogenation is conducted at room temperature and normal pressure, and the reaction process is monitored by thin layer chromatography (TLC), until the reaction completes. This process typically requires 12-24 hours.

After the reaction completes, the Pd/C catalyst is removed by suction filtration, the resulting filtrate is evaporated to dryness on the rotary evaporator, the resulting residue is dissolved with dichloromethane, and then washed with 0.1 mol/l of aqueous NaCl solution, and dried with anhydrous sodium sulfate. After that, the dichloromethane is removed on the rotary evaporator, and the resulting residue is purified by column chromatography to obtain the pure product M-2.

M-2 is a colourless oil, the $^1$H NMR (400 MHz, DMSO-$d_6$) of which is as follows: δ 7.26-7.34 (m, 15H), 4.83 (d, 1H, J=11.2 Hz), 4.77 (d, 1H, J=11.2 Hz), 4.74 (d, 1H, J=3.2 Hz), 4.69 (d, 1H, J=11.2 Hz), 4.60-4.67 (m, 2H), 4.59 (d, 1H, J=11.6 Hz), 3.71 (t, 1H, J=9.2 Hz), 3.54-3.58 (m, 1H), 3.47 (dd, 1H, J=3.6 Hz and 9.6 Hz), 3.28 (s, 3H), 3.10 (t, 1H, J=9.2 Hz), 1.16 (d, 3H, J=6.4 Hz).

Example 119: Synthesis of Compound M-2

28.72 g (50 mmol) of compound M-1 is dissolved in 200 mL of tetrahydrofuran (THF), 23.02 g (0.5 mol) of formic acid and 2.00 g of Pd/C catalyst with the Pd mass fraction of 10% are added, and then stirred in the nitrogen atmosphere at room temperature, and the reaction process is monitored by TLC, until the reaction substantially completes. This process typically requires 12-24 hours.

After the reaction completes, the Pd/C catalyst is removed by suction filtration, the resulting filtrate is dumped into 500 mL of water, the pH value is adjusted to pH=5-6 with saturated aqueous NaHCO$_3$ solution, and extracted with 100 mL×3 of dichloromethane. The organic phases are combined, washed with 0.1 mol/l aqueous NaCl solution, and dried with anhydrous sodium sulfate, evaporated on the rotary evaporator to remove the solvent, and the resulting residue is purified by column chromatography to obtain the pure product M-2. M-2 is a colourless oil, the $^1$H NMR spectra is the same as that of Example 118.

Example 120: Synthesis of Compound M-2

The raw materials and operations are essentially the same as Example 119, except that the formic acid in Example 119 is replaced by ammonium formate and cyclohexene respectively, and the pure products M-2 are prepared respectively, the $^1$H NMR spectra of which are the same as Example 118, and thus the conversion from M-1 to M-2 are achieved.

Example 121: Synthesis of Compound M-3

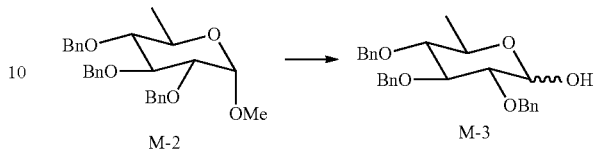

17.94 g (40 mmol) of compound M-2 is dissolved in 150 mL of glacial acetic acid, followed by adding 20 mL of hydrochloric acid with a concentration of 6 M, and then heated for 30 min under stirring in 85° C. water bath. At this moment, TLC shows that the reaction completes substantially. The reaction mixture is quickly cooled to room temperature, dumped into 500 mL of ice water, stirred, and the pH value is adjusted to pH=4-6 with saturated NaHCO$_3$ solution, and extracted with 100 mL×3 of dichloromethane. The organic phases are combined, washed with 0.1 mol/l aqueous NaCl solution, and dried with anhydrous sodium sulfate, evaporated to dryness on the rotary evaporator, and the resulting residue is purified by column chromatography to obtain the pure product M-3.

M-3 is a white solid, has a melting point of 92-94° C., and is analyzed with $^1$H NMR, which is shown as a mixture of a and 3 isomer.

Example 122: Synthesis of Compound M-3

The raw materials and operations are essentially the same as Example 121, except that the hydrochloric acid with a concentration of 6 M in Example 121 is replaced by sulfuric acid with a concentration of 3 M, and the pure product M-3 is prepared, the melting point of which is 92-94° C., and thus the conversion from M-2 to M-3 is achieved.

Example 123: Synthesis of Compound M-4

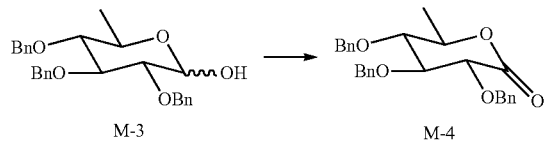

80 mL of dimethyl sulfoxide (DMSO) is added into a 250 mL of round-bottom flask, and cooled with ice water bath. 50 mL of acetic anhydride (Ac$_2$O) is added dropwise slowly under stirring, and stirred for another half an hour at this temperature after addition. After that, the solution prepared by dissolving 13.04 g (30 mmol) of M-3 in 20 mL of DMSO is added dropwise slowly, and then stirred at room temperature until the TLC shows that the reaction completes.

After the reaction completes, the reaction mixture is dumped into 500 mL of ice water, stirred for half an hour, the pH value is adjusted to pH=4-6 with saturated aqueous NaHCO$_3$ solution, and extracted with 100 mL×3 of dichloromethane. The organic phases are combined, washed with 0.1 mol/l aqueous NaCl solution, dried with anhydrous sodium sulfate, and evaporated to dryness on the rotary evaporator, the resulting residue is purified by column chromatography to obtain the pure product M-4.

M-4 is a white solid, has a melting point of 66-67° C., the $^1$H-NMR (400 MHz, CDCl$_3$) of which are as follows: δ 7.22-7.38 (m, 15H), 4.92 (d, 1H, J=11.2 Hz), 4.68 (d, 1H, J=11.2 Hz), 4.64 (d, 1H, J=11.6 Hz), 4.62 (d, 1H, J=11.6 Hz), 4.50-4.56 (m, 3H), 4.10 (d, 1H, J=4.8 Hz), 3.88 (t, 1H, J=5.4 Hz), 3.44 (dd, 1H, J=5.6 Hz and 8.8 Hz), 1.39 (d, 3H, J=6.4 Hz). Moreover, $^{13}$C-NMR (100 MHz, CDCl$_3$) of M-4 is as follows: δ 168.99, 137.36, 137.30, 136.77, 128.48, 128.45, 128.43, 128.34, 128.14, 127.99, 127.93, 81.36, 81.15, 77.29, 74.58, 73.48, 73.21, 72.97, 18.27.

Example 124: Synthesis of Compound M-5

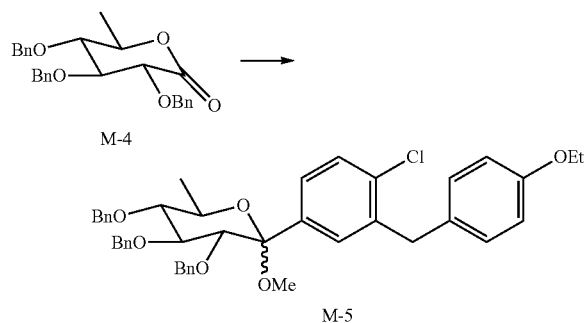

To a 250 mL of dry round-bottom flask, 6.51 g (20 mmol) of (2-chloro-5-bromophenyl) (4-ethoxyphenyl) methane and 60 mL of dry THF are added, and the magneton is added. After purging with nitrogen gas, the mouth of the round-bottom flask is sealed with a soft rubber plug. The flask is placed in a liquid nitrogen-ethanol system to cool to −78° C., and stirred. 12.5 mL of n-butyl lithium solution with a concentration of 1.6 M (20 mmol n-butyl lithium) is added slowly with a injector, and stirred for another half an hour at this temperature after the addition, and then the solution prepared by dissolving 8.65 g (20 mmol) of M-4 in 40 mL of dry THF is added slowly with a injector. After the addition, the reaction mixture is stirred for another 1 hour at this temperature. After which, at this temperature, the solution prepared by dissolving 4.81 g (50 mmol) of methanesulfonic acid in 20 mL of methanol is added slowly with a injector, and stirred at room temperature for 12 hours after the addition.

The reaction mixture is dumped into 400 mL of ice water, stirred, the pH value is adjusted to pH=4-6 with saturated NaHCO$_3$ solution, and extracted with 100 mL×3 of dichloromethane. The organic phases are combined, washed with 0.1 mol/l aqueous NaCl solution, and dried with anhydrous sodium sulfate, evaporated to dryness on the rotary evaporator, and the resulting residue is the crude product of M-5. The crude product of M-5 is analyzed using electrospray ionization-mass spectrometry (ESI-MS), the mass-charge ratio of which is m/z=693 ([M+H]$^+$). Wherein, the crude product can be used for the next step of reaction without purification.

Example 125: Synthesis of Compound M-5

To a 250 mL of dry round-bottom flask, 6.51 g (20 mmol) of (2-chloro-5-bromophenyl)(4-ethoxyphenyl)methane, 0.61 g (25 mmol) of metal magnesium and 20 mL of dry THF are added, the magneton is added, and stirred at room temperature. A small particle of iodine is added, and then heat the whole flask with hot water of 45° C.-65° C., until the reaction is initiated and most of the metal magnesium is used up. The flask is cooled with ice water, and to which a solution prepared by dissolving 8.65 g (20 mmol) of M-4 in 40 mL dry THF is added dropwise slowly through a dropping funnel. After the addition, the reaction mixture is stirred for another 1 hour at this temperature. The solution prepared by dissolving 4.81 g (50 mmol) of methanesulfonic acid in 20 mL of methanol is added dropwise slowly through a dropping funnel under cooling with ice water, and is stirred overnight at room temperature after addition.

The reaction mixture is dumped into 400 mL of ice water, stirred for half an hour, the pH value is adjusted to pH=4-6 with saturated NaHCO$_3$ solution, and extracted with 100 mL×3 of dichloromethane. The organic phases are combined, washed with 0.1 mol/l aqueous NaCl solution, and dried with anhydrous sodium sulfate, evaporated to dryness on the rotary evaporator, and the resulting residue is the crude product of M-5. The crude product of M-5 is analyzed using electrospray ionization-mass spectrometry (ESI-MS), the mass-charge ratio of which is m/z=693 ([M+H]$^+$). Wherein, the crude product can be used for the next step of reaction without purification.

Example 126: Synthesis of Compound M-6

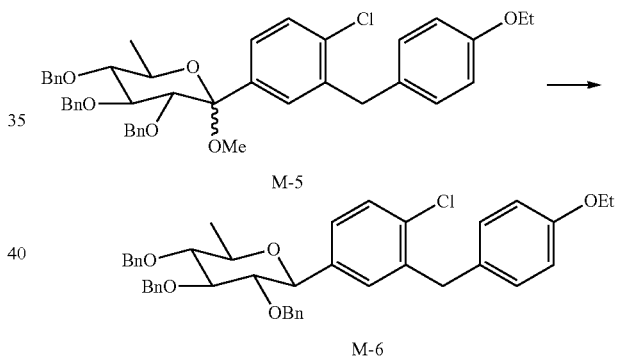

In a 250 mL of round-bottom flask, the crude product of compound M-5 prepared in Example 7 is dissolved in the mixture solvents of 100 mL of dry dichloromethane and 50 mL of acetonitrile, 5.81 g (50 mmol) of Et$_3$SiH is added, and stirred under cooling at −30° C. The solution prepared by dissolving 2.84 g (20 mmol) of boron trifluoride diethyl etherate in 10 mL of dry dichloromethane is added dropwise slowly through a dropping funnel. After the addition, the reaction mixture is heated up to room temperature, and stirred for another 5 hours at this room temperature, TLC shows that the reaction has completed. 20 mL of saturated sodium bicarbonate solution is carefully added into the reaction mixture, dumped into 400 mL of ice water after being stirred for another half an hour, stirred, and then extracted with 100 mL×3 of dichloromethane. The organic phases are combined, washed with 0.1 mol/l aqueous NaCl solution, dried with anhydrous sodium sulfate, and evaporated to dryness on the rotary evaporator. The resulting residue is purified by column chromatography to obtain the pure product of M-6.

M-6 has a melting point of 97-98° C., the $^1$H-NMR (DMSO-d$_6$, 400 MHz) of which is as follows: δ 7.41 (d, 1H, J=8.4 Hz), 7.22-7.35 (m, 12H), 7.14-7.20 (m, 3H), 7.03 (d, 2H, J=8.4 Hz), 6.83-6.85 (m, 3H), 6.73 (d, 2H, J=8.4 Hz), 4.76-4.82 (m, 3H), 4.66 (d, 1H, J=11.2 Hz), 4.35 (d, 1H, J=10.8 Hz), 4.23 (d, 1H, J=9.6 Hz), 3.89-4.01 (m, 4H), 3.78 (d, 1H, J=10.8 Hz), 3.69 (t, 1H, J=8.8 Hz), 3.47-3.55 (m, 2H), 3.27 (t, 1H, J=9.2 Hz), 1.27 (t, 3H, J=7.0 Hz), 1.20 (d, 3H, J=6.0 Hz).

Example 127: Synthesis of Compound M-7

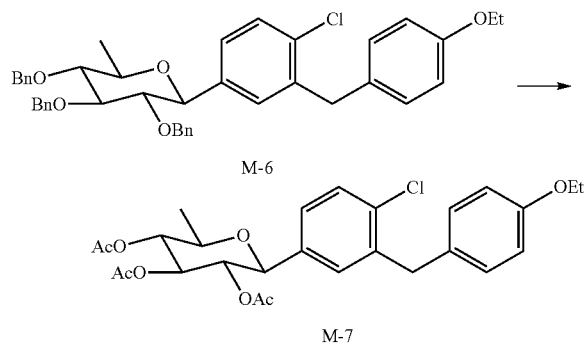

6.63 g (10 mmol) of compound M-6 is dissolved in 60 mL of redistilled acetic anhydride, stirred at a temperature of −10° C., 11.11 g (50 mmol) of trimethylsilyl trifluoromethanesulfonate (TMSOTf) is added dropwise slowly, and heat it up slowly to room temperature after the addition, and then stirred overnight. The reaction mixture is carefully dumped into 300 mL of ice water, stirred, and extracted with 100 mL×3 of dichloromethane. The organic phases are combined, washed with 0.1 mol/l aqueous NaCl solution, and dried with anhydrous sodium sulfate, evaporated to dryness on the rotary evaporator. The resulting residue is purified by column chromatography to obtain the pure product of M-7.

M-7 has a melting point of 130-131° C., the $^1$H-NMR (DMSO-$d_6$, 400 MHz) of which is as follows: δ 7.39 (d, 1H, J=8.0 Hz), 7.23-7.26 (m, 2H), 7.04 (d, 2H, J=8.4 Hz), 6.81 (d, 2H, J=8.8 Hz), 5.26 (t, 1H, J=9.6 Hz), 4.94 (t, 1H, J=9.6 Hz), 4.83 (t, 1H, J=9.6 Hz), 4.57 (d, 1H, J=9.6 Hz), 3.92-4.01 (m, 4H), 3.80-3.87 (m, 1H), 2.02 (s, 3H), 1.91 (s, 3H), 1.67 (s, 3H), 1.28 (t, 3H, J=6.8 Hz), 1.12 (d, 3H, J=6.0 Hz). and, M-7的 $^{13}$C-NMR (DMSO-$d_6$, 100 MHz), δ 169.55, 169.49, 168.41, 156.91, 138.35, 136.52, 132.82, 130.92, 130.16, 129.50, 129.25, 126.57, 114.27, 77.52, 73.25, 73.01, 72.95, 72.65, 62.85, 37.37, 20.42, 20.26, 19.98, 17.33, 14.60.

Example 128: Synthesis of Compound I-D1-6

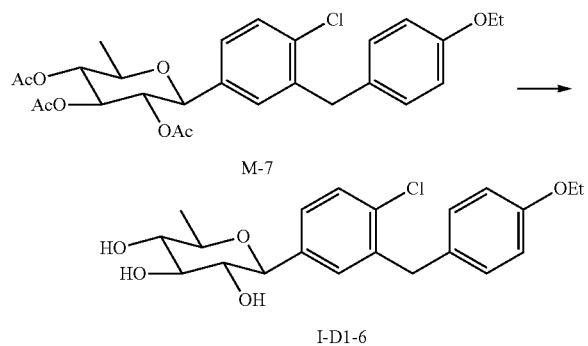

2.59 g (5 mmol) of compound M-7 is dissolved in 30 mL of methanol, stirred at room temperature, 3 mL of NaOH solution with a concentration of 30% is then added, and then heated to reflux for half an hour, TLC shows that the reaction has completed. The reaction mixture, after slightly cooling, is dumped into 300 mL of ice water, stirred, the pH value is adjusted with hydrochloric acid to pH=7, and extracted with 50 mL×3 of ethyl acetate. The organic phases are combined, washed with 0.1 mol/l aqueous NaCl solution, dried with anhydrous sodium sulfate, and evaporated to dryness on the rotary evaporator. The resulting residue is purified by column chromatography with a short silica gel column. The resulting product is recrystallized with ethyl acetate/petroleum ether to obtain the pure product of I-D1-6.

I-D1-6 has a melting point of 145° C., the $^1$H-NMR (DMSO-$d_6$, 400 MHz) of which is as follows: δ 7.35 (d, 1H, J=8.0 Hz), 7.25 (d, 1H, J=2.0 Hz), 7.18 (dd, 1H, J=2.0 Hz and 8.0 Hz), 7.08 (d, 2H, J=8.8 Hz), 6.82 (d, 2H, J=8.8 Hz), 4.96 (d, 1H, J=5.2 Hz, $D_2$O-exchangeable), 4.91 (d, 1H, J=4.4 Hz, $D_2$O-exchangeable), 4.80 (d, 1H, J=5.6 Hz, $D_2$O-exchangeable), 3.92-4.01 (m, 5H), 3.26-3.32 (m, 1H), 3.18-3.25 (m, 1H), 3.09-3.15 (m, 1H), 2.89-2.95 (m, 1H), 1.28 (t, 3H, J=7.0 Hz), 1.15 (d, 3H, J=6.0 Hz).

$^{13}$C-NMR (DMSO-$d_6$, 100 MHz) of I-D1-6 is as follows: δ 156.85, 139.65, 137.82, 131.83, 131.16, 130.58, 129.52, 128.65, 127.14, 114.26, 80.71, 77.98, 75.77, 75.51, 74.81, 62.84, 37.56, 18.19, 14.63.

The I-D1-6 as prepared in this Example is analyzed using electrospray ionization-mass spectrometry (HR-ESI-MS) at high resolution, wherein $C_{21}H_{29}ClNO_5$ ([M+NH$_4$]$^+$) is calculated as 410.1734, and measured as 410.1730.

Example 129: Synthesis of Compound I-D1-6

0.2 g of metallic sodium is added in 20 mL of absolute methanol, stirred at room temperature, until the metallic sodium disappears, then 2.59 g (5 mmol) of compound M-7 is added, and stirred for another 5 hours, by this time TLC shows that the reaction has completed. After the reaction completes, the dry model 732 strong acid cation exchange resin is added, stirred overnight at room temperature, until pH=7. The resin is removed by suction filtration, the resulting filtrate is evaporated to dryness on the rotary evaporator, and the resulting residue is purified by column chromatography with a short silica gel column. The resulting product is recrystallized with ethyl acetate/petroleum ether to obtain the pure product of I-D1-6.

The I-D1-6 as prepared in this Example has a melting point of 145° C., the $^1$H-NMR, $^{13}$C-NMR and HR-ESI-MS have the same data with the corresponding data in Example 128.

Example 130: Synthesis of Compound I-D1-6

2.59 g (5 mmol) of compound M-7 is dissolved in 30 mL of saturated NH$_3$/methanol, stirred overnight at room temperature, TLC shows that the reaction has completed. The reaction mixture, after slightly cooling, is dumped into 300 mL of ice water, stirred, and extracted with 50 mL×3 of ethyl acetate.

The organic phases are combined, washed with 0.1 mol/l aqueous NaCl solution, and dried with anhydrous sodium sulfate, evaporated to dryness on the rotary evaporator. The resulting residue is purified by column chromatography with a short silica gel column. The resulting product is recrystallized with ethyl acetate/petroleum to obtain the pure product of I-D1-6.

The I-D1-6 as prepared in this Example has a melting point of 145° C., the $^1$H-NMR, $^{13}$C-NMR and HR-ESI-MS have the same data with the corresponding data in Example 128.

Example 131: Synthesis of the Crude Product of Compound I-D1-6

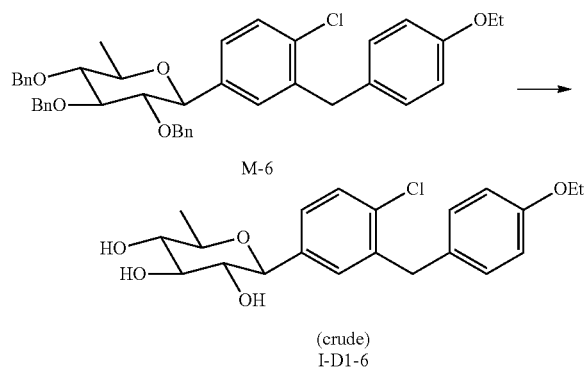

M-6

(crude)
I-D1-6

6.63 g (10 mmol) of compound M-6 is dissolved in 40 mL of dry anisole, stirred under cooling with ice-water bath, 6.67 g (50 mmol) of anhydrous AlCl$_3$ is added slowly, after the addition heat it up slowly to room temperature, and then stirred overnight, and TLC shows that the reaction substantially completes.

After the reaction completes, the reaction mixture, after slightly cooling, is dumped into 300 mL of ice water, stirred, and extracted with 50 mL×3 of ethyl acetate. The organic phases are combined, washed with 0.1 mol/l aqueous NaCl solution, dried with anhydrous sodium sulfate, and evaporated to dryness on the rotary evaporator. The resulting residue is the crude product of I-D1-6.

The crude product of I-D1-6 prepared in this Example is analyzed using electrospray ionization-mass spectrometry (HR-ESI-MS). Wherein C$_{21}$H$_{29}$ClNO$_5$ ([M+NH$_4$]$^+$) is calculated as 410.1734, and measured as 410.1732.

Since the crude product I-D1-6 has more impurities than the I-D1-6 prepared from the pure product M-7 in Example 128, it needs more creative work in the purification.

Example 132: Synthesis of the Crude Product of Compound I-D1-6

6.63 g (10 mmol) of compound M-6 is dissolved in 40 mL of dry acetonitrile, stirred under cooling with an ice-water bath, 10.00 g (50 mmol) of iodotrimethylsilane (TMSI) is added slowly, and heated up slowly to room temperature after the addition, stirred overnight at room temperature, and then heated up to reflux for 3 hours, and TLC shows that the reaction basically completes.

After the reaction completes, the reaction mixture, after slightly cooling, is dumped into 300 mL of ice water, stirred, and extracted with 50 mL×3 of ethyl acetate. The organic phases are combined, washed with 0.1 mol/l aqueous NaCl solution, dried with anhydrous sodium sulfate, and evaporated to dryness on the rotary evaporator. The resulting residue is the crude product of I-D1-6.

The crude product of I-D1-6 prepared in this Example is analyzed using electrospray ionization-mass spectrometry (HR-ESI-MS). Wherein C$_{21}$H$_{29}$ClNO$_5$ ([M+NH$_4$]$^+$) is calculated as 410.1734, and measured as 410.1732.

Example 133: Synthesis of Compound I-D1-6 Crude Product 6.63 g (10 mmol) of compound M-6 is dissolved in 20 mL of dry dichloromethane, cooled to −30° C., stirred, 50 mL (50 mmol) of BCl$_3$ in dichloromethane solution with a concentration of 1 M is added slowly, and heated up slowly to room temperature after the addition, stirred overnight at room temperature, and TLC shows that the reaction completes.

After the reaction completes, the reaction mixture, after slightly cooling, is dumped into 300 mL of ice water, stirred, and extracted with 50 mL×3 of ethyl acetate. The organic phases are combined, washed with 0.1 mol/l NaCl aqueous solution, dried with anhydrous sodium sulfate, and evaporated to dryness on the rotary evaporator. The resulting residue is the crude product of I-D1-6.

The crude product of I-D1-6 prepared in this Example is analyzed using electrospray ionization-mass spectrometry (HR-ESI-MS). Wherein C$_{21}$H$_{29}$ClNO$_5$ ([M+NH$_4$]$^+$) is calculated as 410.1734, and measured as 410.1736.

Example 134: Synthesis of the Crude Product of Compound I-D1-6

6.63 g (10 mmol) of compound M-6 is dissolved in 40 mL of THF, 0.5 g of Pd/C catalyst with a Pd mass fraction of 10% is added, catalytic hydrogenated overnight at room temperature, and TLC shows that the reaction substantially completes. After the reaction completes, the reaction mixture is filtered by suction, the filtrate is evaporated to dryness on the rotary evaporator, and the resulting residue is the crude product of I-D1-6.

The crude product of I-D1-6 prepared in this Example is analyzed using electrospray ionization-mass spectrometry (HR-ESI-MS). Wherein C$_{21}$H$_{29}$ClNO$_5$ ([M+NH$_4$]$^+$) is calculated as 410.1734, and measured as 410.1740.

Example 135: Synthesis of Compound M-7 from the Crude Product of I-D1-6

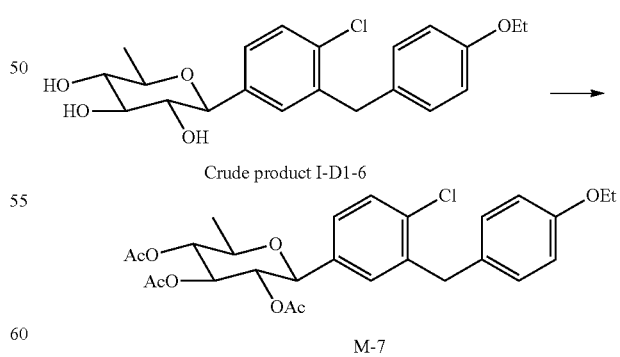

Crude product I-D1-6

M-7

3.93 g (10 mmol) of the crude product of compound I-D1-6 prepared in Example 131 is dissolved in 30 mL of pyridine, 0.5 g of dimethylaminopyridine (DMAP) is added, stirred under cooling with an ice-water bath, 20 mL of acetic anhydride is added dropwise slowly through a dropping funnel. After the addition, the reaction mixture is stirred overnight at room temperature, TLC shows that the reaction completes.

After the reaction completes, the reaction mixture is dumped into 300 mL of ice water, stirred, and extracted with 50 mL×3 of ethyl acetate. The organic phases are combined, washed with 100 mL of 5% hydrochloric acid and 0.1 mol/l aqueous NaCl solution respectively, dried with anhydrous sodium sulfate, and evaporated to dryness on the rotary evaporator. The resulting residue is purified by column chromatography to obtain the pure product of M-7.

The M-7 as prepared in this Example has a melting point of 130-131° C., the $^1$H-NMR and $^{13}$C-NMR HR-ESI-MS have the same data with the corresponding data in Example 127.

Example 136: Synthesis of Compound M-7 from the Crude Product of I-D1-6

3.93 g (10 mmol) of the crude product of compound I-D1-6 prepared in Example 132 and 0.5 g of anhydrous sodium acetate are suspended in 30 mL of acetic anhydride, heated up to reflux for half an hour, and TLC shows that the reaction completes. The reaction mixture, after slightly cooling, is dumped into 300 mL of ice water, stirred for 5 hours, and extracted with 50 mL×3 of ethyl acetate. The organic phases are combined, washed with 100 mL of saturated NaHCO$_3$ and 0.1 mol/l aqueous NaCl solution respectively, dried with anhydrous sodium sulfate, and evaporated to dryness on the rotary evaporator. The resulting residue is purified by column chromatography to obtain the pure product of M-7.

The M-7 as prepared in this Example has a melting point of 130-131° C., the $^1$H-NMR and $^{13}$C-NMR HR-ESI-MS have the same data with the corresponding data in Example 127.

Example 137: Directly Purification of the Crude Product of I-D1-6 to Obtain the Pure Product I-D1-6

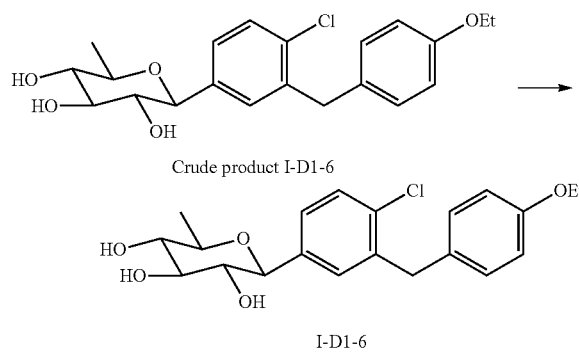

3.00 g of the crude product of compound I-D1-6 prepared in Example 133 is carefully purified by column chromatography: 3 cm×30 cm glass chromatography column, firstly eluting with 500 mL of ethyl acetate/petroleum ether (volume ratio 1/2) mixture solvent, and then eluting with pure ethyl acetate, and collecting the eluent. After that, the solvent is removed by evaporating on the rotary evaporator, the resulting residue is recrystallized with ethyl acetate/petroleum ether (volume ratio 1/1), to obtain the pure product I-D1-6.

The purity of the pure product I-D1-6 is analyzed by using high performance liquid chromatography (HPLC), and the purity is above 99.6%, individual impurity <0.2%, and determination of the heavy metal is eligible.

Examples of the Cocrystal of I-D1-6 and L-Proline are Provided Below.

The materials and experimental methods used in the experiment of the present invention are generally described in this Section. Although many materials and operation methods used for achieving the purpose of the present invention are well known in the art, they are described as much detail as possible in the present invention. A person skilled in the art understands that, unless otherwise indicated in the context, materials and operation methods used in the present invention are well known in the art.

In Combination with the Following Examples, the Determination Conditions of the Cocrystal in the Present Invention are as Follows:

Powder X-Ray Diffraction (PXRD) Condition:
Instrument: Model Rigaku D/Max-2500 18 kW
Diffractometer: polycrytalling powder diffractometer
Target: Cu-Kα radiation, λ=1.5405 Å, 2θ=3-50°
Tube voltage: 40 KV
Tube current: 100 mA
Scanning speed: 8° C./min
Crystal graphite monochromator
DS/SS=1°; RS: 0.3 mm
Differential Thermal Analysis (DTA) condition:
Instrument: Rigaku PTC-10A TG-DTA analyzer
Heating rate: 10° C./min
Scanning temperature range: 0-300° C.
Reference compound: Al$_2$O$_3$
Sample amount: 5.0 mg of cocrystal to be tested
High Performance Liquid Chromatography (HPLC) Condition:
Chromatographic column: C$_{18}$, 150 mm×4.6 mm, 5 um
Mobile phase: methanol:water:acetic acid=70:30:0.25
Wave length: 230 nm
Flow rate: 0.8 ml/min
Injection volume: 10 uL
Column temperature: 35° C.
Instrument: Purkinje General L6 liquid chromatograph; Hitachi L-7250 automatic injector; Purkinje General LC Win chromatograph work station
Nuclear Magnetic Resonance (NMR) Condition:
Instrument: Bruker AV400 Nuclear magnetic resonance spectrometer
Solvent: DMSO-d$_6$ Example 138

This Example is used for illustrating the cocrystal of I-D1-6 and L-proline of the present invention and preparation process thereof.

I-D1-6 is prepared as the raw material. The following processes can be referenced:

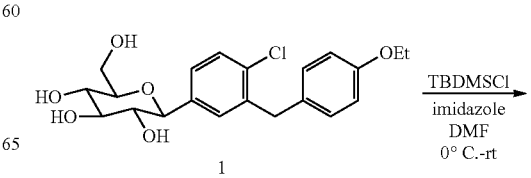

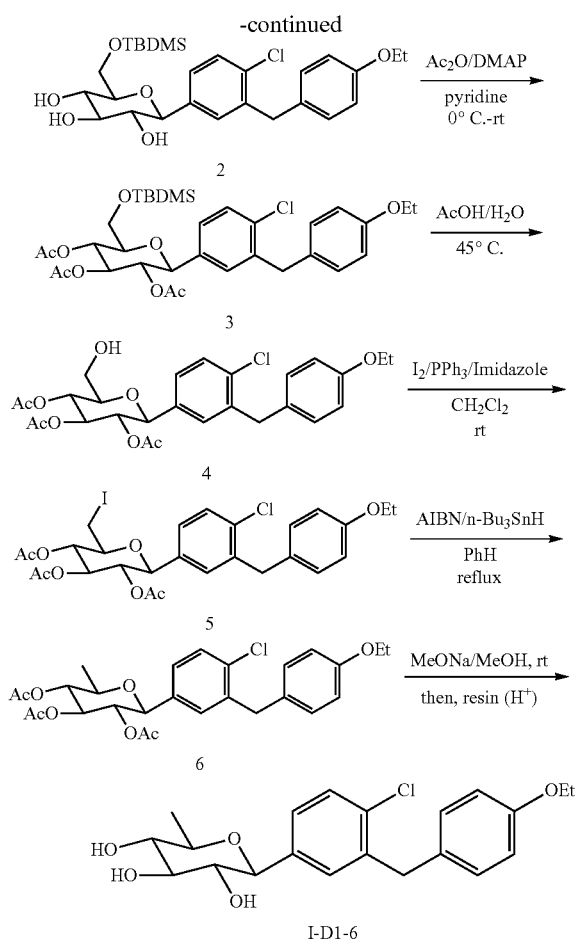

The specific preparation process is as follows:

40.9 g (100 mmol) of the above formula compound 1 is dissolved in 300 mL of dry DMF, stirred under cooling with an ice-water bath, 27.2 g (400 mmol) of imidazole is added, and then 16.6 g (110 mmol) of TBDMSCl (tert-butyldimethylsilyl chloride) is added dropwise slowly over 15 min. After the addition, the reaction compounds are stirred for another 3 hours at room temperature. The reaction mixture is diluted with 1500 mL of dichloromethane, washed with 500 mL×3 of saturated salt water, and dried with anhydrous sodium sulfate. The drying agent is removed by filtration, the solvent in the filtrate is removed on the rotary evaporator, the resulting residue is purified by silica gel column chromatography to obtain the pure product 2, which is a white, foamed solid.

41.9 g (80 mmol) of compound 2 is dissolved in 300 mL of pyridine, stirred under cooling with an ice-water bath. 150 mL of acetic anhydride is added dropwise slowly, and then 1 g of DMAP (4-dimethylaminopyridine) is added. After the addition, the reaction mixture is further stirred overnight at room temperature. The reaction mixture is dumped into 2000 mL of ice water, stirred, and extracted with 500 mL×3 of dichloromethane. The organic phases are combined, washed successively with 500 mL of 5% diluted hydrochloric acid and 1000 mL of saturated salt water, and dried with anhydrous sodium sulfate. The drying agent is removed by filtration; the solvent in the filtrate is removed on the rotary evaporator. The resulting residue is purified by silica gel column chromatography to obtain the pure product 3, which is a white solid and has a melting point of 101-102° C.

39.0 g (60 mmol) of compound 3 is dissolved in 500 mL of 90% aqueous acetic acid solution, stirred for 5 hours at 45° C., and then dumped into 2000 mL of ice water, adjusted the pH to pH=7-8 with saturated NaHCO$_3$, and extracted with 500 mL×3 of dichloromethane. The organic phases are combined, washed with 1000 mL of saturated salt water, and dried with anhydrous sodium sulfate. The drying agent is removed by filtration, the solvent in the filtrate is removed on the rotary evaporator, and the resulting residue is purified by silica gel column chromatography to obtain the pure product 4, which is a white solid and has a melting point of 120-121° C.

126.9 g (500 mmol) of iodine is dissolved in 500 mL of dry dichloromethane, stirred under cooling with an ice-water bath, 131.1 g (500 mmol) of triphenylphosphine is added slowly, after the addition the reaction compounds are stirred for another 10 min. 136.2 g (2 mol) of imidazole is then added slowly, stirred for another hour after the addition. To the above resulting system, 26.7 g (50 mmol) of compound 5 is added, after the addition the reaction compound is stirred overnight at room temperature. The reaction mixture is diluted with 2000 mL of dichloromethane, washed with saturated salt water, and dried with anhydrous sodium sulfate. The drying agent is removed by filtration, the solvent in the filtrate is removed on the rotary evaporator, the resulting residue is purified by silica gel column chromatography to obtain the pure product 5, which is a white solid and has a melting point of 141-142° C.

19.3 g (30 mmol) of compound 5, 29.1 g (100 mmol) of n-Bu$_3$SnH and 4.9 g (30 mmol) of AIBN are dissolved in 200 mL of dry benzene, heated to reflux for 3 hours under nitrogen atmosphere. The reaction mixture, after cooling, is diluted with 1000 mL of dichloromethane, washed with saturated salt water, and dried with anhydrous sodium sulfate. The drying agent is removed by filtration, the solvent in the filtrate is removed on the rotary evaporator, and the resulting residue is purified by silica gel column chromatography to obtain pure product 6, which is a white, foamed solid.

Figure 4:
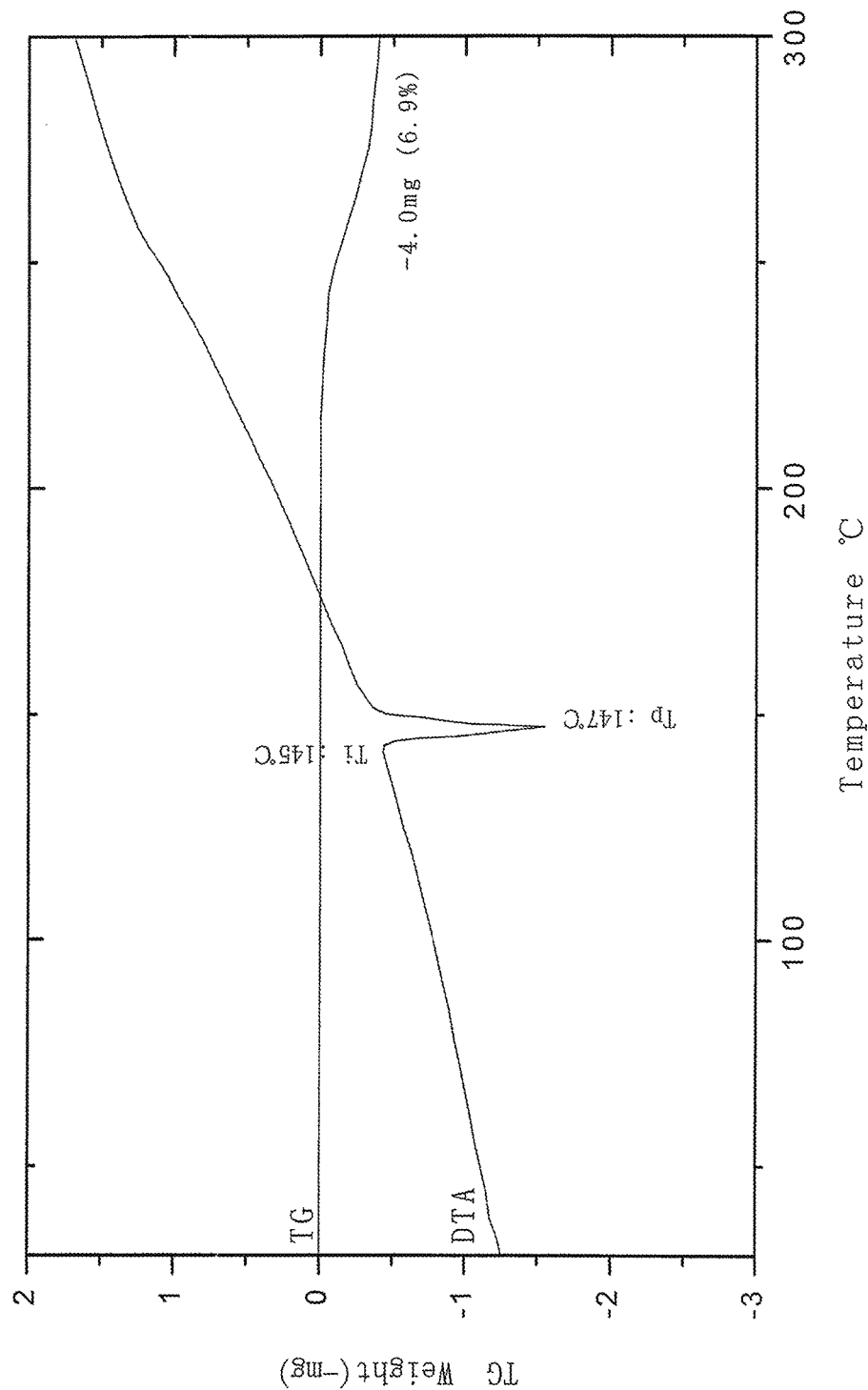
FIG. 4 illustrates the Differential Thermal Analysis (DTA) spectra of the I-D1-6 raw materials for preparing cocrystal.
Figure 5:
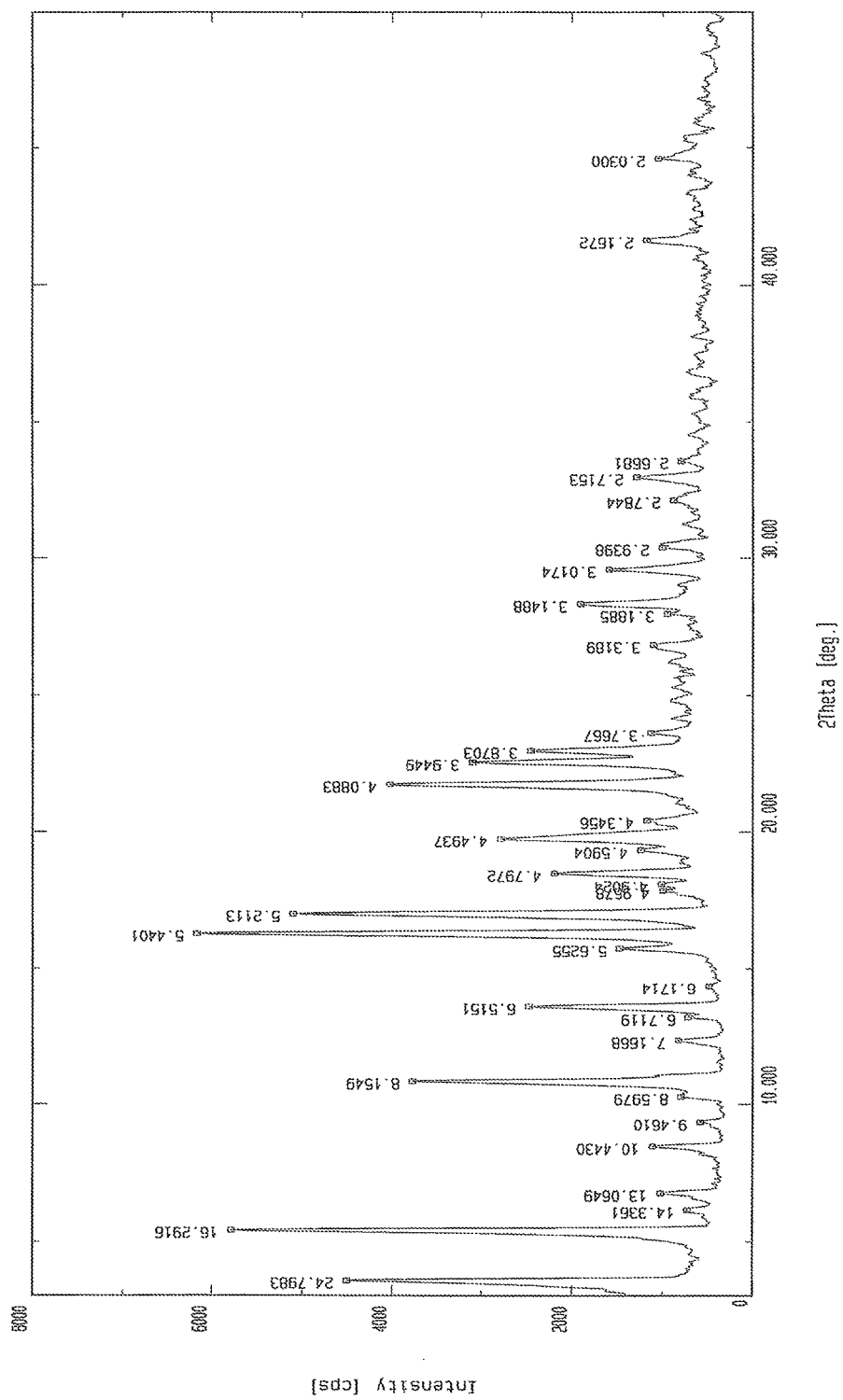
FIG. 5 illustrates the PXRD spectra of the I-D1-6 raw materials for preparing cocrystal.

To 100 mL of dry absolute methanol, 0.5 g of metallic sodium is added, stirred under the protection of nitrogen at room temperature, until the metallic sodium disappeared. After that, 5.2 g (10 mmol) of compound 6 is added, and stirred for another 3 hours at room temperature. To the reaction system, 5 g of strong acid cation exchange resin is added, stirred overnight at room temperature, until the reaction mixture's pH=7. The resin is removed by suction filtration, the filtrate is evaporated to dryness on the rotary evaporator, the resulting residue is further dried on the vacuum oil pump to obtain the product I-D1-6, which is a white, foamed solid. The DTA spectra is shown as FIG. 4, and the PXRD spectra is shown as FIG. 5.

Figure 6:
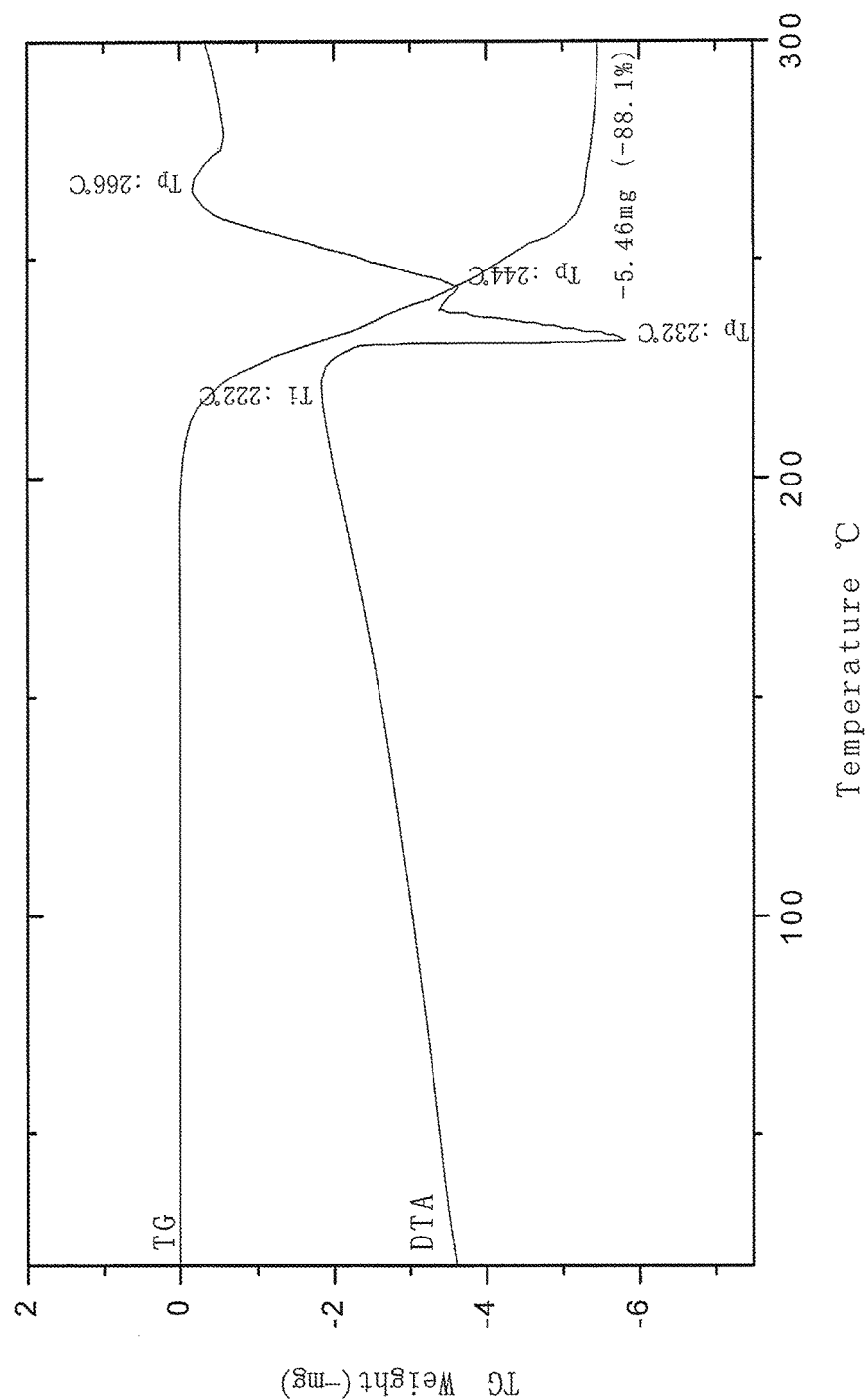
FIG. 6 illustrates the Differential Thermal Analysis (DTA) spectra of the cocrystal of L-proline for preparing cocrystal.
Figure 7:
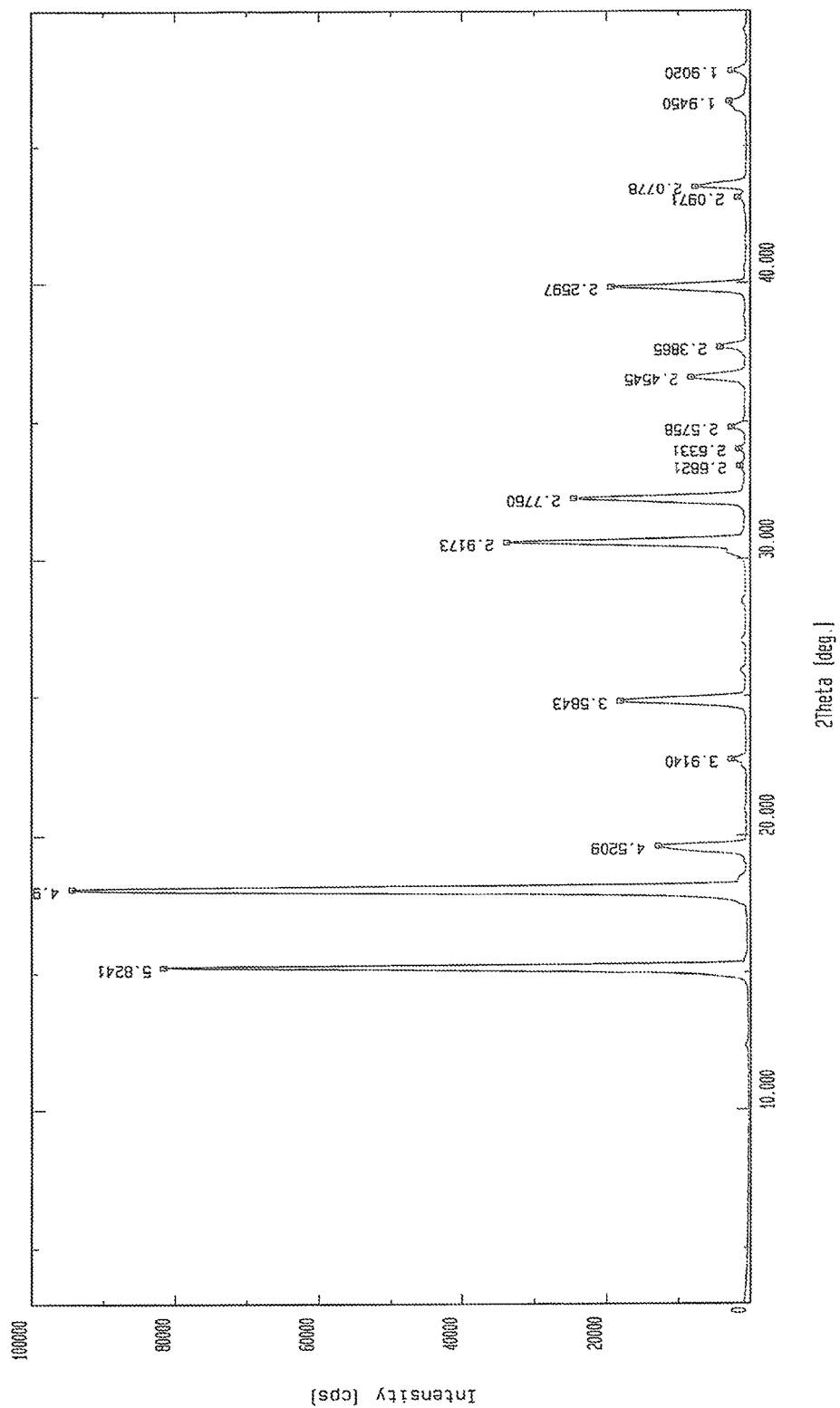
FIG. 7 illustrates the PXRD spectra of the L-proline for preparing cocrystal.

The DTA spectra and PXRD spectra of L-proline are as shown in FIG. 6, FIG. 7 respectively.

1.00 g (2.5 mmol) of compound I-D1-6 prepared according to the above method is dissolved in 20 mL of absolute ethanol under slightly heating to obtain the ethanol solution of I-D1-6. In addition, 0.60 g (5.2 mmol) of L-proline, 0.5 mL of water and 5 mL of absolute ethanol are added into a 50 mL of round-bottom flask, stirred at room temperature to obtain a clear mixture solution. The ethanol solution of I-D1-6 described above is added slowly into the said mixture solution containing L-proline under stirring to obtain a clear solution. This solution continues to be stirred at room temperature to obtain a white, crystal slurry system. The crystal is collected by suction filtration, and dried at 30° C. for 5 hours on the vacuum oil pump to obtain a white solid of 0.83 g.

Figure 2:
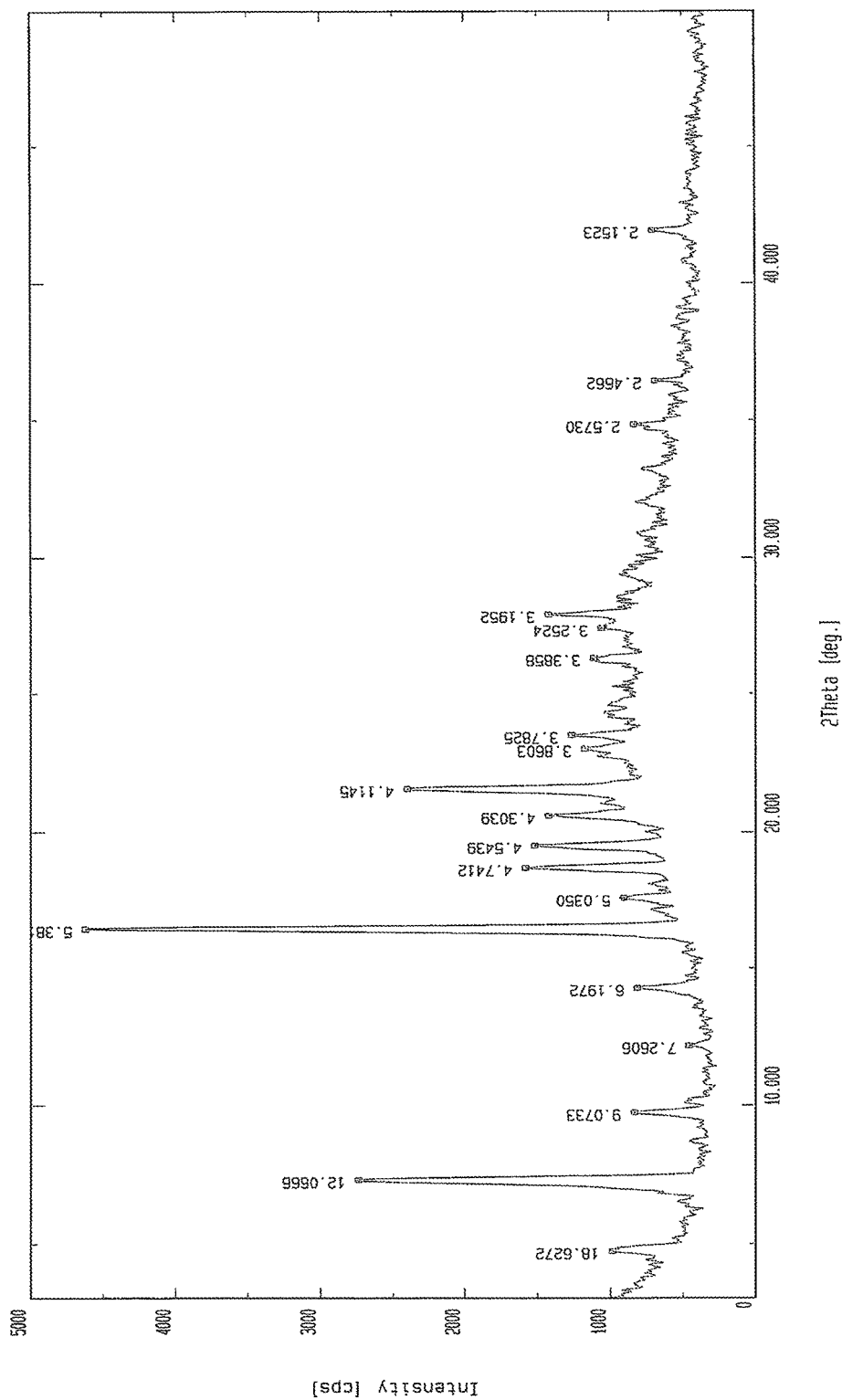
FIG. 2 illustrates the PXRD spectra of the cocrystal prepared in example 138.
Figure 3:
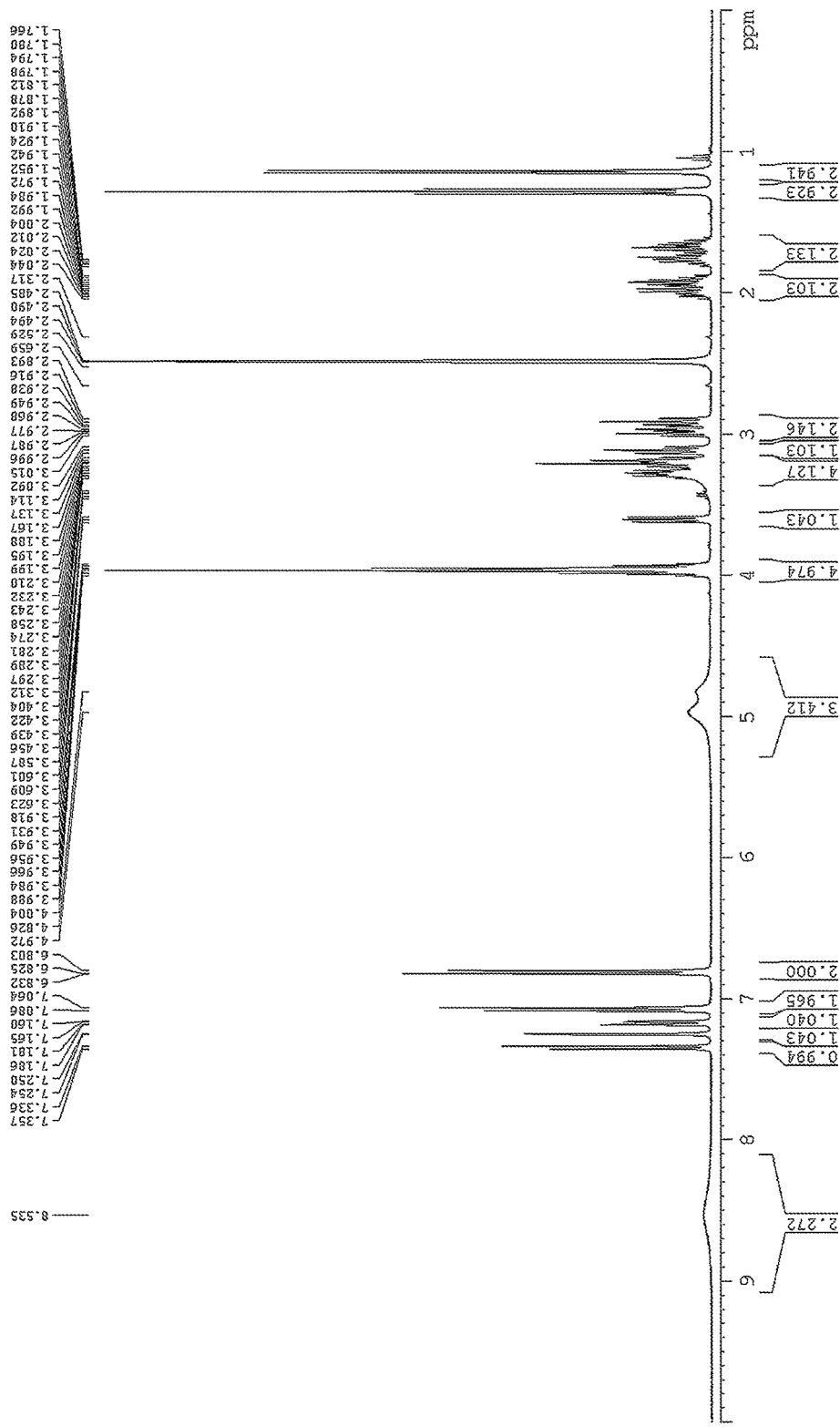
FIG. 3 illustrates the $^1$H NMR spectra of the cocrystal prepared in example 138.

The Differential Thermal Analysis (DTA) spectra and powder X-ray diffraction (PXRD) spectra of this white solid product (cocrystal) are shown as FIG. 1 and FIG. 2 respectively, the $^1$H NMR spectra is shown as FIG. 3. It can be determined that the white solid prepared in this Example is the cocrystal of I-D1-6 and L-proline of the present invention.

Example 139

This Example is used for illustrating the cocrystal of I-D1-6 and L-proline of the present invention and preparation process thereof.

Compound I-D1-6 is prepared as the raw material according to the same method as Example 138.

1.00 g (2.5 mmol) of compound I-D1-6 prepared above is dissolved in 20 mL of absolute ethanol under slightly heating to obtain the ethanol solution of I-D1-6. In addition, 0.40 g (3.5 mmol) of L-proline, 0.3 mL of water and 4 mL of absolute ethanol are added into a 50 mL round-bottom flask, stirred at room temperature to obtain a clear mixture solution. The ethanol solution of I-D1-6 described above is added slowly into said mixture solution containing L-proline under stirring to obtain a clear solution. This solution is further stirred at room temperature to obtain a white, crystal slurry system. The crystal is collected by suction filtration, and dried at 30° C. for 4 hours on the vacuum oil pump to obtain a white solid of 0.80 g.

It is determined by DTA and PXRD that the white solid is the cocrystal of I-D1-6 and L-proline. The DTA spectra has a absorption peak near 170° C.

Example 140

This Example is used for illustrating the cocrystal of I-D1-6 and L-proline of the present invention and preparation process thereof.

Compound I-D1-6 is prepared as the raw material according to the same method as Example 138.

1.00 g (2.5 mmol) of compound I-D1-6 prepared above is dissolved in 20 mL of absolute ethanol under slightly heating to obtain the ethanol solution of I-D1-6. In addition, 0.29 g (2.5 mmol) of L-proline, 0.3 mL of water and 4 mL of absolute ethanol are added into a 50 mL round-bottom flask, stirred at room temperature to obtain a clear mixture solution. The ethanol solution of I-D1-6 described above is added slowly into said mixture solution containing L-proline under stirring to obtain a clear solution. This solution is further stirred at room temperature to obtain a white, crystal slurry system. The crystal is collected by suction filtration, and dried at 30° C. for 5 hours on the vacuum oil pump to obtain a white solid of 0.79 g.

It is determined by DTA and PXRD that the white solid is the cocrystal of I-D1-6 and L-proline. The DTA spectra has a absorption peak near 170° C.

Example 141

This Example is used for illustrating the cocrystal of I-D1-6 and L-proline of the present invention and preparation process thereof.

Compound I-D1-6 is prepared as the raw material according to the same method as Example 138.

1.00 g (2.5 mmol) of compound I-D1-6 prepared above is dissolved in 20 mL of absolute ethanol under slightly heating to obtain the ethanol solution of I-D1-6. In addition, 0.40 g (3.5 mmol) of L-proline and 6 mL of absolute ethanol are added into a 50 mL round-bottom flask, stirred at 40° C. to obtain a clear mixture solution. The ethanol solution of I-D1-6 described above is added slowly into said mixture solution containing L-proline under stirring to obtain a clear solution. This solution is cooled naturally to room temperature and further stirred overnight to obtain a white, crystal slurry system. The crystal is collected by suction filtration, and dried at 30° C. for 8 hours on the vacuum oil pump to obtain a white solid of 0.80 g.

It is determined by DTA and PXRD that the white solid is the cocrystal of I-D1-6 and L-proline. The DTA spectra has a absorption peak near 170° C.

Example 142

This Example is used for illustrating the preparation of the tablet containing the cocrystal of I-D1-6 and L-proline of the present invention.

| Prescription | amount/tablet |
|---|---|
| sample prepared in Example 138 | 7 mg |
| microcrystalline cellulose | 80 mg |
| pregelatinized starch | 70 mg |
| polyvinyl pyrrolidone | 6 mg |
| sodium carboxymethyl starch | 5 mg |
| magnesium stearate | 2 mg |
| talc powders | 2 mg |

The sample cocrystal prepared in Example 138, pregelatinized starch and microcrystalline cellulose are sieved and mixed sufficiently in the prescription amount, and then prescription amount of polyvinyl pyrrolidone solution is added and mixed to make soft materials. The soft materials are sieved to make wet granules, which are dried at 40-50° C. Sodium carboxymethyl starch, magnesium stearate and talc powders are then pre-sieved, and added to granules described above in the prescription amount for tabletting, so as to obtain the tablet containing the cocrystal of I-D1-6 and L-proline.

Test Example 1

The $IC_{50}$ value of the inhibition of the cocrystal of I-D1-6 and L-proline prepared in Example 138 on SGLT2 and SGLT1 is measured according to the method recorded in the literature (Meng, W. et al, *J. Med. Chem.*, 2008, 51, 1145-1149). The results are as shown in Table 4 below:

TABLE 4

IC50 value of the inhibition of the cocrystal of I-D1-6 and L-proline on SGLT2 and SGLT1

| $IC_{50}$ (hSGLT2, nM) | $IC_{50}$ (hSGLT1, nM) | Selectivity $IC_{50}$ (hSGLT1)/ $IC_{50}$ (hSGLT2) |
|---|---|---|
| 0.69 | 259 | 375 |

It can be seen from the results of $IC_{50}$ value in the above Table that, the cocrystal of I-D1-6 and L-proline is a strong selective SGLT2 inhibitor.

Test Example 2

The purity of the cocrystal of I-D1-6 and L-proline prepared in Example 138 is measured by HPLC, which is 99.49%, and there are total of 3 small impurity peaks (0.27%, 0.07% and 0.17% respectively). Whereas the purity of the I-D1-6 raw materials used for preparing the cocrystal is measured as 99.11%, and there are total of 7 small impurity peaks (the impurities corresponding to the cocrystal are 0.32%, 0.08% and 0.19% respectively, there are 4 other extra impurities 0.11%, 0.10%, 0.03% and 0.06%). Thus it can be seen that the purity of the cocrystal is improved significantly, and it is more suitable for batch production of medicines.

Test Example 3

The cocrystal of I-D1-6 and L-proline prepared in Example 138 and the I-D1-6 raw materials serving as a contrast are tested for the influencing factors, and placed for two weeks (14 days) under the conditions of light (natural daylight, averages about 80000 Lx), higher temperature (45° C.) and higher humidity (30% relative humidity at 30° C.). The appearance, number of impurity and the amount of impurity (measured by HPLC) are compared with that of day 0. The test results are shown in Tables 5-7 respectively.

TABLE 5

Test data of light stability

| Time (day) | Sample | Appearance | Number of impurity | Total amount of impurity (%) | Crystal form |
|---|---|---|---|---|---|
| 0 | I-D1-6 raw materials | a white, foam-like solid | 7 | 0.89 | — |
|   | cocrystal | white crystalline powder | 3 | 0.51 | as shown in FIG. 2 |
| 7 | I-D1-6 raw materials | a white, foam-like solid | 7 | 0.93 | — |
|   | cocrystal | white crystalline powder | 3 | 0.51 | unchanged |
| 14 | I-D1-6 raw materials | a white, foam-like solid | 7 | 0.96 | — |
|   | cocrystal | white crystalline powder | 3 | 0.52 | unchanged |

TABLE 6

Test data of higher temperature stability

| Time (day) | Sample | Appearance | Number of impurity | Total amount of impurity (%) | Crystal form |
|---|---|---|---|---|---|
| 0 | I-D1-6 raw materials | white, foam-like solid | 7 | 0.89 | — |
|   | cocrystal | white crystalline powder | 3 | 0.51 | as shown in FIG. 2 |
| 7 | I-D1-6 raw materials | white, foam-like solid | 8 | 0.97 | — |
|   | cocrystal | white crystalline powder | 3 | 0.51 | unchanged |
| 14 | I-D1-6 raw materials | white, foam-like solid | 9 | 1.13 | — |
|   | cocrystal | white crystalline powder | 3 | 0.51 | unchanged |

TABLE 7

Test data of higher humidity stability

| Time (day) | Sample | Appearance | Number of impurity | Total amount of impurity (%) | Crystal form |
|---|---|---|---|---|---|
| 0 | I-D1-6 raw materials | white, foam-like solid | 7 | 0.89 | — |

TABLE 7-continued

Test data of higher humidity stability

| | | Investigation items | | | |
|---|---|---|---|---|---|
| Time (day) | Sample | Appearance | Number of impurity | Total amount of impurity (%) | Crystal form |
| | cocrystal | white crystalline powder | 3 | 0.51 | as shown in FIG. 2 |
| 7 | I-D1-6 raw materials | white foam-like solid | 7 | 0.93 | — |
| | cocrystal | white crystalline powder | 3 | 0.51 | unchanged |
| 14 | I-D1-6 raw materials | white foam-like solid | 8 | 1.08 | — |
| | cocrystal | white crystalline powder | 3 | 0.52 | unchanged |

It can be seen from Tables 5-7 that, in the two week stability test under the conditions of light, higher temperature, higher humidity condition, there is no visible change in the appearance of cocrystal of the present invention, the crystal form remains stable. In the meanwhile, the number of impurity and the total amount of impurity measured by HPLC did not increase significantly, and thus as compared with the I-D1-6 raw materials, the cocrystal has better storage stability, and may be a source of the I-D1-6 active pharmaceutical ingredient.

Test Example 4

The inhibiting activity of the cocrystal of I-D1-6 and L-proline on SGLT2 is measured by the model for rat urine glucose excretion.

The health SD rats are injected intraperitoneally with multiple low doses of streptozotocin for modeling (type 2 diabetes model) after feeding with high-fat and high-sucrose diet for one month, and the content of blood glucose is measured before and after modeling. After the modeling successful, the rats for modeling are randomly divided (8 rats/group) into one blank group (administering the same volume of 0.5% CMC sodium solution) and groups of tested compound (6 mg/kg) according to the content of 24-hour urine glucose and the body weight. Rats in each group are fasted for 16 hours before experiment. The experimental rats are administered intragastrically with the glucose (2 g/kg) at 0.5 h after intragastrical administration with the cocrystal of I-D1-6 and L-proline prepared in Example 138. The urine is collected at the time-period of 0-12 h after administration, and the urine glucose values are measured at each time-period by glucose-oxidase method. The experimental results show that the cocrystal is able to induce the production of 912 mg urine glucose/200 g body weight, indicating that the cocrystal has stronger ability of discharging urine glucose.

The invention claimed is:

1. A compound having one of the following structures or a pharmaceutically acceptable prodrug ester thereof:

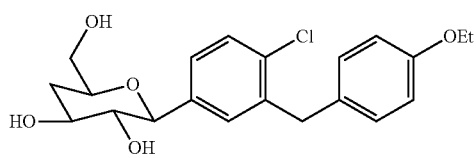

-continued

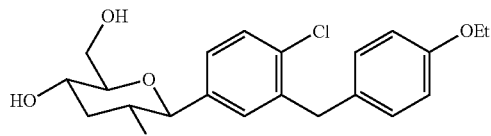

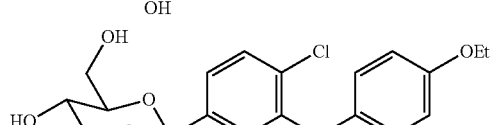

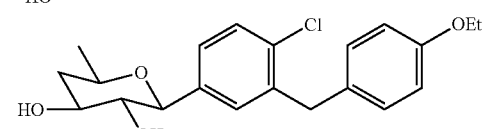

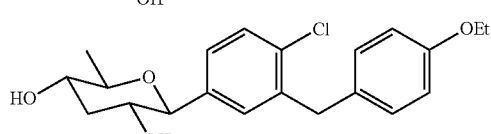

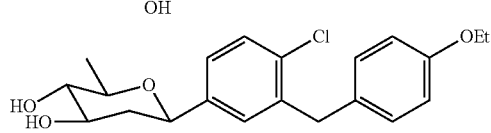

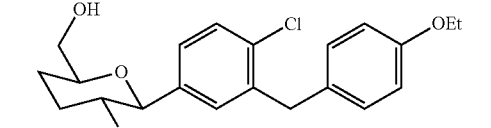

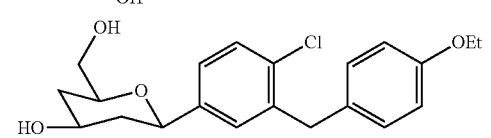

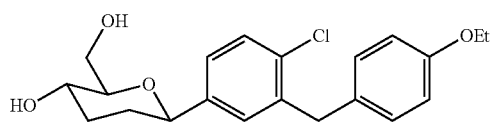

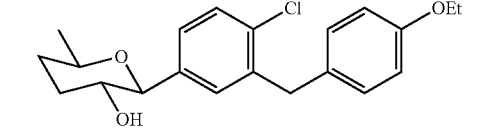

-continued
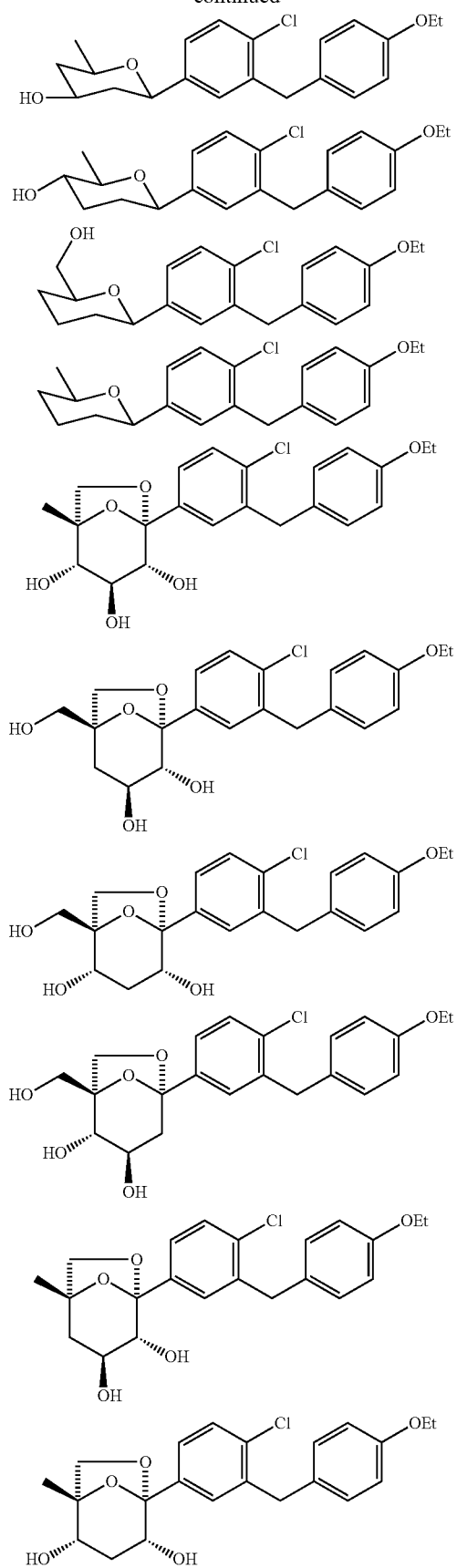
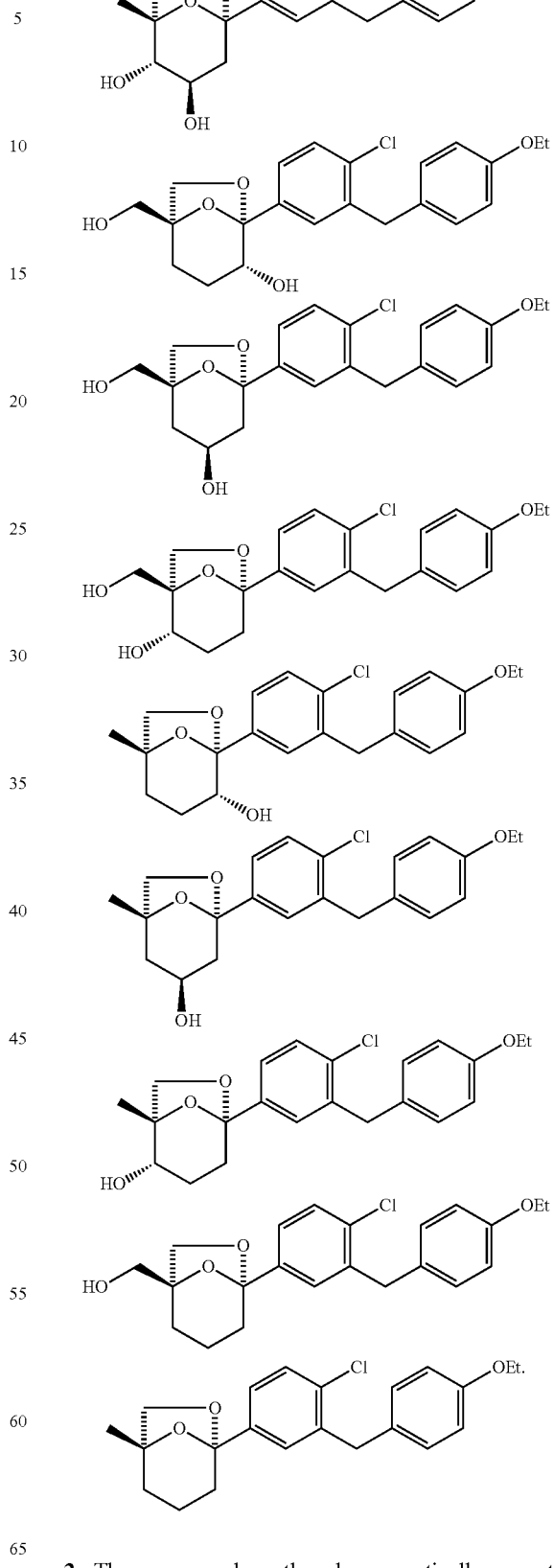
2. The compound or the pharmaceutically acceptable prodrug ester thereof according to claim 1, wherein the pharmaceutically acceptable prodrug ester includes an ester formed by one or more hydroxyl groups on the molecule of the compound having general formula I with acetyl, pivaloyl, phosphoryl, carbamoyl and/or alkoxycarbonyl.

3. A method for preparing a compound or a pharmaceutically acceptable prodrug ester thereof according to claim 1, the method comprising using an undeoxidized phenyl C-glucoside having the same structure as that of the target product as raw materials, when the target product is a fully deoxidized phenyl C-glucoside, the method comprises converting all the hydroxyl groups on the sugar ring into iodine with an iodizating reagent, and then removing the iodine on the sugar ring by reduction so as to obtain the target product;

when the target product is a partially deoxidized phenyl C-glucoside, the method comprises the following steps:
(1) hydroxyl protection: protecting the hydroxyl to be retained on the sugar ring with a hydroxyl protecting reagent;
(2) dehydroxylation: converting the hydroxyls to be removed on the sugar ring into iodine with an iodizating reagent, and then reducing the iodine on the sugar ring so as to remove the hydroxyls to be removed; and
(3) deprotection: removing the hydroxyl protecting group in the compound obtained in the above step so as to obtain the target product.

4. The method according to claim 3, wherein the iodizating reagent is $I_2$/triphenylphosphine/imidazole reagent.

5. The method according to claim 4, wherein the method for reducing in the step (2) is palladium-catalyzed hydrogenation or reducing with n-$Bu_3$SnH/AIBN reagent.

6. The method according to claim 5, wherein the hydroxyl-protecting reagent is selected from one or more of acetic anhydride, acetyl chloride, tert-butyldimethylsilyl chloride (TBDMSCl), tert-butyldiphenylsilyl chloride (TBDPSCl), benzoyl chloride, p-methyl benzoyl chloride, pivaloyl chloride, (dimethoxymethyl)benzene(PhCH(OMe)$_2$), benzoic acid, 1,1,2,2-tetramethoxy cyclohexane/trimethyl orthoformate, chloroacetyl chloride and bromoacetyl chloride.

7. The method according to claim 4, wherein the hydroxyl-protecting reagent is selected from one or more of acetic anhydride, acetyl chloride, tert-butyldimethylsilyl chloride (TBDMSCl), tert-butyldiphenylsilyl chloride (TBDPSCl), benzoyl chloride, p-methyl benzoyl chloride, pivaloyl chloride, (dimethoxymethyl)benzene(PhCH(OMe)$_2$), benzoic acid, 1,1,2,2-tetramethoxy cyclohexane/trimethyl orthoformate, chloroacetyl chloride and bromoacetyl chloride.

8. The method according to claim 3, wherein the method for reducing in the step (2) is palladium-catalyzed hydrogenation or reducing with n-$Bu_3$SnH/AIBN reagent.

9. The method according to claim 8, wherein the hydroxyl-protecting reagent is selected from one or more of acetic anhydride, acetyl chloride, tert-butyldimethylsilyl chloride (TBDMSCl), tert-butyldiphenylsilyl chloride (TBDPSCl), benzoyl chloride, p-methyl benzoyl chloride, pivaloyl chloride, (dimethoxymethyl)benzene(PhCH(OMe)$_2$), benzoic acid, 1,1,2,2-tetramethoxy cyclohexane/trimethyl orthoformate, chloroacetyl chloride and bromoacetyl chloride.

10. The method according to claim 3, wherein the hydroxyl-protecting reagent is selected from one or more of acetic anhydride, acetyl chloride, tert-butyldimethylsilyl chloride (TBDMSCl), tert-butyldiphenylsilyl chloride (TBDPSCl), benzoyl chloride, p-methyl benzoyl chloride, pivaloyl chloride, (dimethoxymethyl)benzene(PhCH(OMe)$_2$), benzoic acid, 1,1,2,2-tetramethoxy cyclohexane/trimethyl orthoformate, chloroacetyl chloride and bromoacetyl chloride.

11. A pharmaceutical composition, comprising a compound or a pharmaceutically acceptable prodrug ester thereof according to claim 1, and one or more pharmaceutically acceptable carriers, excipients or diluents.

12. The composition according to claim 11, wherein the pharmaceutically acceptable prodrug ester includes an ester formed by one or more hydroxyl groups on the molecule of the compound having general formula I with acetyl, pivaloyl, phosphoryl, carbamoyl and/or alkoxycarbonyl.

13. A method for inhibiting SGLT2 enzyme in a subject, the method comprising administering a compound or a pharmaceutically acceptable prodrug ester thereof according to claim 1 to a subject in an amount effective to inhibit SGLT2 enzyme.

14. A method for treating diabetes, the method comprising administering a therapeutically effective amount of a compound or a pharmaceutically acceptable prodrug ester thereof according to claim 1 to a patient in need of treatment.

* * * * *